US012788806B2

(12) United States Patent
Fairman et al.

(10) Patent No.: US 12,788,806 B2
(45) Date of Patent: Nov. 10, 2026

(54) GROUP A STREP IMMUNOGENIC COMPOSITIONS WITH POLYSACCHARIDE-PROTEIN CONJUGATES

(71) Applicant: Vaxcyte, Inc., San Carlos, CA (US)

(72) Inventors: Jeffery C. Fairman, Mountain View, CA (US); Neeraj Kapoor, Foster City, CA (US); Peter T. Davey, Foster City, CA (US); Angie A Sedra, Foster City, CA (US)

(73) Assignee: Vaxcyte, Inc., San Carlos, CA (US)

( * ) Notice: Subject to any disclaimer, the term of this patent is extended or adjusted under 35 U.S.C. 154(b) by 1026 days.

(21) Appl. No.: 17/820,554

(22) Filed: Aug. 17, 2022

(65) Prior Publication Data

US 2023/0293658 A1 Sep. 21, 2023

Related U.S. Application Data

(63) Continuation of application No. PCT/US2021/018402, filed on Feb. 17, 2021.

(60) Provisional application No. 63/123,293, filed on Dec. 9, 2020, provisional application No. 63/090,069, filed on Oct. 9, 2020, provisional application No. 63/013,924, filed on Apr. 22, 2020, provisional application No. 62/977,886, filed on Feb. 18, 2020.

(51) Int. Cl.

| | |
|---|---|
| ***A61K 39/09*** | (2006.01) |
| ***A61K 38/48*** | (2006.01) |
| ***A61K 39/00*** | (2006.01) |
| ***A61K 39/112*** | (2006.01) |
| ***A61K 39/116*** | (2006.01) |
| ***A61P 31/04*** | (2006.01) |

(52) U.S. Cl.

CPC .......... *A61K 39/092* (2013.01); *A61K 38/482* (2013.01); *A61K 39/0283* (2013.01); *A61K 39/116* (2013.01); *A61P 31/04* (2018.01); *C12Y 304/2111* (2013.01); *A61K 2039/58* (2013.01); *A61K 2039/6087* (2013.01); *A61K 2039/70* (2013.01)

(58) Field of Classification Search

None

See application file for complete search history.

(56) References Cited

U.S. PATENT DOCUMENTS

| | | | |
|---|---|---|---|
| 5,368,933 | A | 11/1994 | Aoki et al. |
| 5,512,492 | A | 4/1996 | Herron et al. |
| 5,770,461 | A | 6/1998 | Sakazume et al. |
| 5,846,743 | A | 12/1998 | Janmey et al. |
| 5,866,134 | A | 2/1999 | Fine et al. |
| 5,866,135 | A | 2/1999 | Blake et al. |
| 5,874,268 | A | 2/1999 | Meyer |
| 6,143,577 | A | 11/2000 | Bisconte Sconte De Saint Julien |
| 6,248,329 | B1 | 6/2001 | Chandrashekar et al. |
| 6,261,815 | B1 | 7/2001 | Meyer |
| 6,506,558 | B1 | 1/2003 | Fodor et al. |
| 6,589,503 | B1 | 7/2003 | Piwnica-Worms |
| 6,919,211 | B1 | 7/2005 | Fodor et al. |
| 7,109,034 | B2 | 9/2006 | Orwar et al. |
| 7,182,962 | B2 | 2/2007 | Hattori et al. |
| 7,223,592 | B2 | 5/2007 | Shea et al. |
| 7,303,924 | B2 | 12/2007 | Dugas et al. |
| 7,306,783 | B2 | 12/2007 | Piwnica-Worms |
| 7,357,936 | B1 | 4/2008 | Garcon |
| 7,399,523 | B2 | 7/2008 | Yamamoto et al. |
| 7,473,247 | B2 | 1/2009 | Mikszta et al. |
| 7,485,304 | B2 | 2/2009 | Rappuoli |
| 7,488,491 | B2 | 2/2009 | Tsuji et al. |
| 7,560,113 | B2 | 7/2009 | Christensen |
| 7,560,238 | B2 | 7/2009 | Miyamoto et al. |
| 7,622,273 | B2 | 11/2009 | Gibbs |
| 7,713,627 | B2 | 5/2010 | Tamori et al. |
| 7,759,074 | B2 | 7/2010 | Miyamoto et al. |
| 7,919,096 | B2 | 4/2011 | Christensen |
| 7,981,512 | B2 | 7/2011 | Tamori et al. |
| 7,985,340 | B2 | 7/2011 | Almaasbak et al. |
| 7,989,065 | B2 | 8/2011 | Winstead et al. |
| 7,989,614 | B2 | 8/2011 | Deggerdal et al. |
| 7,994,592 | B2 | 8/2011 | Tai et al. |
| 8,153,444 | B2 | 4/2012 | Kirkegaard et al. |
| 8,172,995 | B2 | 5/2012 | Iyengar |
| 8,177,716 | B2 | 5/2012 | Say et al. |
| 8,202,487 | B2 | 6/2012 | Lee |

(Continued)

FOREIGN PATENT DOCUMENTS

| | | |
|---|---|---|
| CN | 109045292 A | 12/2018 |
| WO | WO-96/08569 | 3/1996 |

(Continued)

OTHER PUBLICATIONS

Abdissa, A. et al. (2006). “High diversity of group A streptococcal emm types among healthy schoolchildren in Ethiopia,” Clin. Infect. Dis. 42:1362-1367.
Ayoub, E.M. et al. (1973). “Temperature-Dependent Variation in the Synthesis of Group-Specific Carbohydrate by Streptococcal Variant Strains. I. Immunochemical studies,” The Journal of Experimental Medicine 138:117-129.
Bensi, G. et al. (2012). “Multi High-Throughput Approach for Highly Selective Identification of Vaccine Candidates: The Group A Streptococcus Case,” Mol. Cell Proteomics 11:M111.
Bi, S. et al. (2019). “A multicomponent Vaccine Provides Immunity against Local and Systemic Infections by Group A Streptococcus across Serotypes,” *MBio.* 10:e02600-19.

(Continued)

*Primary Examiner* — Peter Johansen
(74) *Attorney, Agent, or Firm* — POLSINELLI PC; Ron Galant

(57) ABSTRACT

The present disclosure provides immunogenic compositions comprising Group A *Streptococcus* (GAS) polypeptide antigens and at least one polypeptide-polysaccharide conjugate. The present disclosure further provides methods of using such compositions to induce immune responses against GAS infections in subjects.

38 Claims, 57 Drawing Sheets

Specification includes a Sequence Listing.

(56) References Cited

U.S. PATENT DOCUMENTS

| | | | | |
|---|---|---|---|---|
| 8,206,661 | B2 | 6/2012 | Vallejo et al. | |
| 8,231,549 | B2 | 7/2012 | Douglas et al. | |
| 10,780,155 | B2 | 9/2020 | Nizet et al. | |
| 2001/0014332 | A1 | 8/2001 | Minetti et al. | |
| 2004/0062777 | A1* | 4/2004 | Cleary | C12N 9/6424 424/234.1 |
| 2004/0151766 | A1 | 8/2004 | Monahan et al. | |
| 2005/0136121 | A1 | 6/2005 | Kershman et al. | |
| 2006/0083737 | A1 | 4/2006 | Minomi et al. | |
| 2006/0148102 | A1 | 7/2006 | Guo et al. | |
| 2007/0042031 | A1 | 2/2007 | Maclachlan et al. | |
| 2007/0077286 | A1 | 4/2007 | Ishihara et al. | |
| 2007/0082042 | A1 | 4/2007 | Park et al. | |
| 2007/0110798 | A1 | 5/2007 | Drummond et al. | |
| 2007/0207454 | A1 | 9/2007 | Fischetti et al. | |
| 2009/0010948 | A1 | 1/2009 | Huang et al. | |
| 2009/0010998 | A1 | 1/2009 | Marchitto et al. | |
| 2009/0012494 | A1 | 1/2009 | Yeshurun et al. | |
| 2010/0158935 | A1* | 6/2010 | Bensi | A61P 31/04 435/69.3 |
| 2011/0117672 | A1 | 5/2011 | Legastelois et al. | |
| 2011/0318747 | A1 | 12/2011 | Akhavan-Tafti | |
| 2012/0031773 | A1 | 2/2012 | Miller | |
| 2012/0034624 | A1 | 2/2012 | Miller et al. | |
| 2012/0083044 | A1 | 4/2012 | Sturman et al. | |
| 2012/0135420 | A1 | 5/2012 | Koulchin et al. | |
| 2012/0164028 | A1 | 6/2012 | Lappalainen | |
| 2012/0181190 | A1 | 7/2012 | Feldman et al. | |
| 2012/0183442 | A1 | 7/2012 | Kloepfer et al. | |
| 2012/0193228 | A1 | 8/2012 | Hsu | |
| 2014/0294930 | A1 | 10/2014 | Nizet et al. | |
| 2015/0231232 | A1* | 8/2015 | Grandi | A61P 35/02 424/250.1 |
| 2018/0333484 | A1 | 11/2018 | Fairman et al. | |
| 2020/0054739 | A1 | 2/2020 | Fairman et al. | |
| 2021/0170012 | A1 | 6/2021 | Nizet et al. | |

FOREIGN PATENT DOCUMENTS

| | | | |
|---|---|---|---|
| WO | WO-2010/049806 | A1 | 5/2010 |
| WO | WO-2011/045316 | A1 | 4/2011 |
| WO | WO-2013/020090 | | 2/2013 |
| WO | WO-2018/126229 | | 7/2018 |
| WO | WO-2020/009993 | A1 | 1/2020 |
| WO | WO-2020/205584 | A1 | 10/2020 |
| WO | WO-2021/167996 | A1 | 8/2021 |
| WO | WO-2022/101434 | A1 | 5/2022 |
| WO | WO-2022/178015 | A1 | 8/2022 |

OTHER PUBLICATIONS

Brandt, E.R. et al. (2000). "New multi-determinant strategy for a group A streptococcal vaccine designed for the Australian Aboriginal population," Nat. Med. 6:455-459.

Brophy, T.R. et al. (1983). "Bioavailability of oral dexamethasone during high dose steroid therapy in neurological patients," Eur. J. Clin. Pharmacol. 24:103-108.

Caruthers, M.H. et al. (1980). "New chemical methods for synthesizing polynucleotides," Nucleic Acids Res. Symposium Series No. 7, pp. 215-223.

Coligan, J.E. et al. (1975). "Immunochemical and chemical studies on streptococcal group-specific carbohydrates," J. Immunol, 114:1654-1658.

Dale, J.B. (1999). "Multivalent group A streptococcal vaccine designed to optimize the immunogenicity of six tandem M protein fragments," Vaccine 17:193-200.

Dale, J.B. et al. (2011). "New 30-valent M protein-based vaccine evokes cross-opsonic antibodies against non-vaccine serotypes of group A streptococci," Vaccine 29:8175-8178.

Dale, J.B. et al. (2016). "Current Approaches to Group A Streptococcal Vaccine Development," Streptococcus pyogenes: Basic Biology to Clinical Manifestations [Internet]. Oklahoma City (OK): University of Oklahoma Health Sciences Center, 36 total pages.

Dallal, R.M. et al. (2000). "The dendritic cell and human cancer vaccines," Curr. Opin. Immunol. 12:583-588.

Di Benedetto, R. et al. (2020). "Rational Design of a Glycoconjugate Vaccine against Group A *Streptococcus*," Int. J. Mol. Sci. 21:8558.

Ellis, R.W. (1988). Chapter 29: New technologies for making vaccines, in *Vaccines*, Plotkin, S.A. et al. (eds) published by W. B. Saunders company (Philadelphia), pp. 568-575.

Feng, S. et al (1996). "P55, an immunogenic but nonprotective 55-kilodalton Borrelia burgdorferi protein in murine Lyme disease," Infect. Immun. 64:363-365.

Final Office Action mailed on Jun. 14, 2016, for U.S. Appl. No. 14/237,120, filed Jun. 9, 2014, 9 pages.

Final Office Action mailed on Dec. 3, 2018, for U.S. Appl. No. 15/265,800, filed Sep. 14, 2016, 5 pages.

Final Office Action mailed on Feb. 14, 2023, for U.S. Appl. No. 17/002,337, filed Aug. 25, 2020, 6 pages.

Fotherby, K. (1996). "Bioavailability of orally administered sex steroids used in oral contraception and hormone replacement therapy," Contraception 54:59-69.

Fritzer, A. et al. (2010). "Novel conserved group A streptococcal proteins identified by the antigenome technology as vaccine candidates for a non-M protein-based vaccine," Infect Immun. 78:4051-4067.

Gallotta, M. et al. (2014). "SpyAD, a moonlighting protein of group A Streptococcus contributing to bacterial division and host cell adhesion," Infect Immun.82:2890-2901.

Gao, N.J. et al. (Jun. 2021). "Site-specific conjugation of cell wall polyrhamnose to protein spyAD envisioning a safe universal group A streptococcal vaccine," Infectious Microbes and Diseases 3:87-100.

Goldstein, I. et al. (1967). "Immunological Relationship between Streptococcus A Polysaccharide and the Structural Glycoproteins of Heart Valve," Nature 213:44-47.

Groning, R. et al. (1996). "Three-dimensional solubility parameters and their use in characterising the permeation of drugs through the skin," Pharmazie 51:337-341.

Hall, M.A. et al. (2004). "Intranasal immunization with mullivalent group A streptococcal vaccines protects mice against intranasal challenge infections," Infect. Immun. 72:2507-2512.

Herbert et al eds. (1995). The Dictionary of Immunology, Academic Press, definition of "Vaccine," 1 total page.

Hidalgo-Aragones, M.I. et al. (1996). "Pharmacokinetics of Oestrone-3-O-sulphamate," J. Steroid Biochem. Mol. Biol.58:611-617.

Horn, T. et al. (1980). "Synthesis of oligonucleotides on cellulose. Part II: Design and synthetic strategy to the synthesis of 22 oligodeoxynucleotides coding for gastric inhibitory polypeptide (GIP)," Nucleic Acids Res. Symposium Series 7, pp. 225-232.

Hu, M.C. et al. (2002). "Immunogenicity of a 26-valent group A streptococcal vaccine," Infect. Immun. 70:2171-2177.

Ikebe, T. et al. (2007). "Distribution of erm genotypes among group A streptococcus isolates from patients with severe invasive streptococcal infections in Japan, 2001-2005," Epidemiol. Infect. 135:1227-1229.

International Search Report mailed on Jun. 8, 2021, for PCT Application No. PCT/US2021/018402, filed on Feb. 17, 2021, 7 pages.

International Search Report mailed on Feb. 28, 2013, for PCT Application No. PCT/US2012/049604, filed on Aug. 3, 2012, 4 pages.

International Search Report mailed on May 4, 2022, for PCT Application No. PCT/US2022/016630, filed on Feb. 16, 2022, 10 pages.

Johnson, M.E. et al. (1995). "Permeation of steroids through human skin," J. Pharm. Sci. 84:1144-1146.

Jones, LH. (2015). "Recent advances in the molecular design of synthetic vaccines," Nature Chemistry 7:952-960.

Jones, S. et al. (2018). "Development of an opsonophagocytic killing assay for group a streptococcus," Vaccine 36:3756-3763.

Kabanova, A. et al. (2011). "Evaluation of a group A Streptococcus synthetic oligosaccharide as vaccine candidate," Vaccine 29:104-114.

(56) References Cited

OTHER PUBLICATIONS

Kapoor, N. et al. (2022). "Non-Native Amino Acid Click Chemistry-Based Technology for Site-Specific Polysaccharide Conjugation to a Bacterial Protein Serving as Both Carrier and Vaccine Antigen," ACS Omega, 10 total pages.
Kapoor, N. et al. (2018). "Malaria Derived Glycosylphosphatidylinositol Anchor Enhances Anti-Pfs25 Functional Antibodies That Block Malaria Transmission," Biochemistry 57:516-519.
Kim, E. et al. (2019)." Biomedical applications of copper-free click chemistry: in vitro, in vivo, and ex vivo," Chemical Science 10:7835-7851.
Kotloff, K.L. et al. (2004). "Safety and immunogenicity of a recombinant multivalent group a streptococcal vaccine in healthy adults: phase 1 trial," JAMA 292:709-715.
McCarty, M. (1956). "Variation in the Group-Specific Carbohydrate of Group A Streptococci. II. Studies on the chemical basis for serological specificity of the carbohydrates.," Journal of Experimental Medicine 104:629-643.
McCarty, M. et al. (1955). "Variation in the group-specific carbohydrate of group a streptococci. I. Immunochemical studies on the carbohydrates of variant strains," JEMS 102:11-28.
McNeil, S.A. et al. (2005). "Safety and immunogenicity of 26-valent group a streptococcus vaccine in healthy adult volunteers," Clin. Infect. Dis. 41:1114-1122.
Merrifield, B. (1997). "Concept and early development of solid-phase peptide synthesis," Methods Enzymol. 289:3-13.
Nahm, M.H. et al. (2018). "Development, Interlaboratory Evaluations, and Application of a Simple, High-Throughput Shigella Serum Bactericidal Assay," mSphere 3:e00146-18.
Nir-Paz, R. et al. (2010)." Streptococcus pyogenes emm and T types within a decade, 1996-2005: implications for epidemiology and future vaccines," Epidemiol. Infect. 138:53-60.
Non-Final Office Action mailed on Dec. 30, 2015, for U.S. Appl. No. 14/237,120, filed Jun. 9, 2014, 11 pages.
Non-Final Office Action mailed on Jun. 8, 2018, for U.S. Appl. No. 15/265,800, filed Sep. 14, 2016, 12 pages.
Non-Final Office Action mailed on Jul. 25, 2022, for U.S. Appl. No. 17/002,337, filed Aug. 25, 2020, 11 pages.
Notice of Allowance mailed on May 21, 2020, for U.S. Appl. No. 15/265,800, filed Sep. 14, 2016, 5 pages.
O'Loughlin, R.E. et al. (2007). "The epidemiology of invasive group A streptococcal infection and potential vaccine implications: United States, 2000-2004," Clin. Infect. Dis. 45:853-862.
Osterland, K. et al. (1996). "Characteristics of streptococcal group-specific antibody isolated from hyperimmune rabbits," J. Exp Med. 123:599-614.
Reglinski, M. et al. (2016). "Development of a multicomponent vaccine for *Streptococcus pyogenes* based on the antigenic targets of IVIG," *J Infect*. 72:450-459.
Rivera-Hernandez, T. et al. (2019). "An Experimental Group A Streptococcus Vaccine That Reduces pharyngitis and Tonsillitis in a nonhuman primate model," MBio. 10:e00693-19.
Rivera-Hernandez, T. et al. (2016). "Differing Efficacies of Lead Group A Streptococcal Vaccine Candidates and Full-Length M Protein in Cutaneous and Invasive Disease Models," mBio 7:e00618-16, 9 total pages.
Roberge, J.Y. et al. (1995). "A strategy for a convergent synthesis of N-linked glycopeptides on a solid support," Science 269:202-204.
Rohatagi, S. et al. (1995). "Pharmacokinetic interaction between endogenous cortisol and exogenous corticosteroids," Pharmazie 50:610-613.
Sabharwal, H. et al. (2006). "Group A streptococcus (GAS) carbohydrate as an immunogen for protection against GAS infection," J. Infect. Dis. 193:129-135.
Salvadori, L.G. et al. (1995). "Group A streptococcus-liposome ELISA antibody titers to group A polysaccharide and opsonophagocytic capabilities of the antibodies," J. Infect. Dis. 171:593-600.
Schuler, G. (2003). "The use of dendritic cells in cancer immunotherapy," Curr. Opin. Imnmnol. 15:138-147.
Shikhman, A.R. et al. (1993). "A subset of mouse monoclonal antibodies cross-reactive with cytoskeletal proteins and group A Streptococcal M proteins recognizes N-acetyl-ß -d-glucosamine," Journal of Immunology 151:3902-3913.
Steer, A.C. et al. (2009). "Global emm type distribution of group A streptococci: systematic review and implications for vaccine development," Lancet Infect. Dis. 9:611-616.
Steinman, R.M. et al. (2001). "Active immunization against cancer with dendritic cells: The near future," Int J. Cancer. 94:459-473.
van Sorge, N.M. et al. (2014). "The classical lancefield antigen of group a Streptococcus is a virulence determinant with implications for vaccine design," Cell Host Microbe. 15:729-740.
Wang S. et al. (2020). "Group A Streptococcus Cell Wall Oligosaccharide-Streptococcal C5a Peptidase Conjugates as Effective Antibacterial Vaccines," ACS Infect. Dis. 6:281-290.
Written Opinion of the International Searching Authority mailed on Jun. 8, 2021, for PCT Application No. PCT/US2021/018402, filed on Feb. 17, 2021, 10 pages.
Written Opinion of the International Searching Authority mailed on Feb. 28, 2013, for PCT Application No. PCT/US2012/049604, filed on Aug. 3, 2012, 6 pages.
Written Opinion of the International Searching Authority mailed on May 4, 2022, for PCT Application No. PCT/US2022/016630, filed on Feb. 16, 2022, 9 pages.
Zhao, Y. et al. (2019). "Synthesis and immunological studies of a Group A Streptococcus cell-wall oligosaccharide—streptococcal C5a peptidase conjugates as bivalent vaccines," Org. Chem. Front.
Zimmerman, E.S. et al. (2014). "Production of site-specific antibody-drug conjugates using optimized non-natural amino acids in a cell-free expression system," Bioconjugate Chemistry 25:351-361.

* cited by examiner

T = Total Protein S = Soluble Protein

FIG. 28

Incubate DBCO derivatized GAC with SLO variants for conjugated at 25C overnight

| Reaction | 1 | 2 | 3 | 4 | 5 | 6 | 7 | 8 | 9 | 10 | |
|---|---|---|---|---|---|---|---|---|---|---|---|
| Protein | 60.0 | 48.0 | 80.0 | 48.0 | 40.0 | 17.8 | 20.9 | 48.0 | 21.8 | 30.0 | |
| PS-DBCO | 42.5 | 42.5 | 42.5 | 42.5 | 42.5 | 42.5 | 42.5 | 42.5 | 42.5 | 42.5 | 424.8 |
| Buffer (10x PBS) | 6.0 | 12.0 | 6.0 | 12.0 | 12.0 | 12.0 | 12.0 | 12.0 | 12.0 | 12.0 | |
| Water | 11.5 | 17.5 | -8.5 | 17.5 | 25.5 | 47.7 | 44.7 | 17.5 | 43.7 | 35.5 | |
| Total | 120.0 | 120.0 | 120.0 | 120.0 | 120.0 | 120.0 | 120.0 | 120.0 | 120.0 | 120.0 | |

| Protein Stock | var1 | var2 | var3 | var4 | var5 | var6 | var7 | var8 | var9 | var10 | mg/ml |
|---|---|---|---|---|---|---|---|---|---|---|---|
| | 0.8 | 1.0 | 0.6 | 1.0 | 1.2 | 2.7 | 2.3 | 1.0 | 2.2 | 1.6 | |

| | | | | | | | | | | | |
|---|---|---|---|---|---|---|---|---|---|---|---|
| PS-DBCO stock | 1.13 | 1.13 | 1.13 | 1.13 | 1.13 | 1.13 | 1.13 | 1.13 | 1.13 | 1.13 | mg/ml |

| Sample ID | Mw (kDa) |
|---|---|
| SLO 1 - GAC CNJ | 97.1 |
| SLO 2 - GAC CNJ | 78.5 |
| SLO 3 - GAC CNJ | 90.4 |
| SLO 4 - GAC CNJ | 79.1 |
| SLO 5 - GAC CNJ | 116 |
| GAC DER DBCO | 6.2 |
| GAC-DBCO | 6.6 |

| Sample ID | Mw (kDa) |
|---|---|
| SLO 6 - GAC CNJ | 67.4 |
| SLO 7 - GAC CNJ | 72.6 |
| SLO 8 - GAC CNJ | 62.6 |
| SLO 9 - GAC CNJ | 69.6 |
| SLO 10 - GAC CNJ | 73.3 |
| GAC DER DBCO | 6.6 |
| GAC-Mut no Der | 6.9 |

| Sample ID | Mw (kDa) |
|---|---|
| 426507SLO(ΔC101)-GAC conjugate | 161.1 |
| 426508 SLO(ΔC101)-GAC conjugate | 162.2 |
| 426510 SLO(ΔC101)-GAC conjugate | 159.1 |
| 4265011 SLO(ΔC101)-GAC conjugate | 208.9 |

SEQUENCE LISTING

```
Sequence total quantity: 76
SEQ ID NO: 1           moltype = AA  length = 962
FEATURE                Location/Qualifiers
REGION                 1..962
                       note = C5a [90-1035 fragment] - WT w/ leader
source                 1..962
                       mol_type = protein
                       organism = synthetic construct
SEQUENCE: 1
MHHHHHHGSG ENLYFQGKTA DTPVTSKATI RDLNDPSQVK TLQEKAGKGA GTVVAVIDAG  60
FDKNHEAWRL TDKTKARYQS KEDLEKAKKE HGITYGEWVN DKVAYYHDYS KDGKTAVDQE  120
HGTHVSGILS GNAPSETKEP YRLEGAMPEA QLLLMRVEIV NGLADYARNY AQAIRDAVNL  180
GAKVINMSFG NAALAYANLP DETKKAFDYA KSKGVSIVTS AGNDSSFGGK TRLPLADHPD  240
YGVVGTPAAA DSTLTVASYS PDKQLTETAT VKTADKQDKE MPVLSTNRFE PNKAYDYAYA  300
NRGMKEDDFK DVKGKIALIE RGDIDFKDKI ANAKKAGAVG VLIYDNQDKG FPIELPNVDQ  360
MPAAFISRKD GLLLKDNPKK TITFNATPKV LPTASGTKLS RFSSWGLTAD GNIKPDIAAP  420
GQDILSSVAN NKYAKLSGTS MSAPLVAGIM GLLQKQYETQ YPDMTPSERL DLAKKVLMSS  480
ATALYDEDEK AYFSPRQQGA GAVDAKKASA ATMYVTDKDN TSSKVHLNNV SDTFEVTVTV  540
HNKSDKPQEL YYQATVQTDK VDGKHFALAP KALYETSWQK ITIPANSSKQ VTVPIDASRF  600
SKDLLAQMKN GYFLEGFVRF KQDPTKEELM SIPYIGFRGD FGNLSALEKP IYDSKDGSSY  660
YHEANSDAKD QLDGDGLQFY ALKNNFTALT TESNPWTIIK AVKEGVENIE DIESSEITET  720
IFAGTFAKQD DDSHYYIHRH ANGKPYAAIS PNGDGNRDYV QFQGTFLRNA KNLVAEVLDK  780
EGNVVWTSEV TEQVVKNYNN DLASTLGSTR FEKTRWDGKD KDGKVVANGT YTYRVRYTPI  840
SSGAKEQHTD FDVIVDNTTP EVATSATFST EDRRLTLASK PKTSQPVYRE RIAYTYMDED  900
LPTTEYISPN EDGTFTLPEE AETMEGATVP LKMSDFTYVV EDMAGNITYT PVTKLLEGHS  960
NK                                                                962

SEQ ID NO: 2           moltype = AA  length = 945
FEATURE                Location/Qualifiers
source                 1..945
                       mol_type = protein
```

-continued

```
                         organism = Streptococcus pyogenes
SEQUENCE: 2
KTADTPVTSK ATIRDLNDPS QVKTLQEKAG KGAGTVVAVI DAGFDKNHEA WRLTDKTKAR  60
YQSKEDLEKA KKEHGITYGE WVNDKVAYYH DYSKDGKTAV DQEHGTHVSG ILSGNAPSET  120
KEPYRLEGAM PEAQLLLMRV EIVNGLADYA RNYAQAIRDA VNLGAKVINM SFGNAALAYA  180
NLPDETKKAF DYAKSKGVSI VTSAGNDSSF GGKTRLPLAD HPDYGVVGTP AAADSTLTVA  240
SYSPDKQLTE TATVKTADKQ DKEMPVLSTN RFEPNKAYDY AYANRGMKED DFKDVKGKIA  300
LIERGDIDFK DKIANAKKAG AVGVLIYDNQ DKGFPIELPN VDQMPAAFIS RKDGLLLKDN  360
PKKTITFNAT PKVLPTASGT KLSRFSSWGL TADGNIKPDI AAPGQDILSS VANNKYAKLS  420
GTSMSAPLVA GIMGLLQKQY ETQYPDMTPS ERLDLAKKVL MSSATALYDE DEKAYFSPRQ  480
QGAGAVDAKK ASAATMYVTD KDNTSSKVHL NNVSDTFEVT VTVHNKSDKP QELYYQATVQ  540
TDKVDGKHFA LAPKALYETS WQKITIPANS SKQVTVPIDA SRFSKDLLAQ MKNGYFLEGF  600
VRFKQDPTKE ELMSIPYIGF RGDFGNLSAL EKPIYDSKDG SSYYHEANSD AKDQLDGDGL  660
QFYALKNNFT ALTTESNPWT IIKAVKEGVE NIEDIESSEI TETIFAGTFA KQDDDSHYYI  720
HRHANGKPYA AISPNGDGNR DYVQFQGTFL RNAKNLVAEV LDKEGNVVWT SEVTEQVVKN  780
YNNDLASTLG STRFEKTRWD GKDKDGKVVA NGTYTYRVRY TPISSGAKEQ HTDFDVIVDN  840
TTPEVATSAT FSTEDRRLTL ASKPKTSQPV YRERIAYTYM DEDLPTTEYI SPNEDGTFTL  900
PEEAETMEGA TVPLKMSDFT YVVEDMAGNI TYTPVTKLLE GHSNK                945

SEQ ID NO: 3             moltype = AA  length = 962
FEATURE                  Location/Qualifiers
REGION                   1..962
                         note = C5a [90-1035 fragment] D131A/S513A mutant w/ leader
source                   1..962
                         mol_type = protein
                         organism = synthetic construct
SEQUENCE: 3
MHHHHHHGSG ENLYFQGKTA DTPVTSKATI RDLNDPSQVK TLQEKAGKGA GTVVAVIAAG  60
FDKNHEAWRL TDKTKARYQS KEDLEKAKKE HGITYGEWVN DKVAYYHDYS KDGKTAVDQE  120
HGTHVSGILS GNAPSETKEP YRLEGAMPEA QLLLMRVEIV NGLADYARNY AQAIRDAVNL  180
GAKVINMSFG NAALAYANLP DETKKAFDYA KSKGVSIVTS AGNDSSFGGK TRLPLADHPD  240
YGVVGTPAAA DSTLTVASYS PDKQLTETAT VKTADKQDKE MPVLSTNRFE PNKAYDYAYA  300
NRGMKEDDFK DVKGKIALIE RGDIDFKDKI ANAKKAGAVG VLIYDNQDKG FPIELPNVDQ  360
MPAAFISRKD GLLLKDNPKK TITFNATPKV LPTASGTKLS RFSSWGLTAD GNIKPDIAAP  420
GQDILSSVAN NKYAKLSGTA MSAPLVAGIM GLLQKQYETQ YPDMTPSERL DLAKKVLMSS  480
ATALYDEDEK AYFSPRQQGA GAVDAKKASA ATMYVTDKDN TSSKVHLNNV SDTFEVTVTV  540
HNKSDKPQEL YYQATVQTDK VDGKHFALAP KALYETSWQK ITIPANSSKQ VTVPIDASRF  600
SKDLLAQMKN GYFLEGFVRF KQDPTKEELM SIPYIGFRGD FGNLSALEKP IYDSKDGSSY  660
YHEANSDAKD QLDGDGLQFY ALKNNFTALT TESNPWTIIK AVKEGVENIE DIESSEITET  720
IFAGTFAKQD DDSHYYIHRH ANGKPYAAIS PNGDGNRDYV QFQGTFLRNA KNLVAEVLDK  780
EGNVVWTSEV TEQVVKNYNN DLASTLGSTR FEKTRWDGKD KDGKVVANGT YTYRVRYTPI  840
SSGAKEQHTD FDVIVDNTTP EVATSATFST EDRRLTLASK PKTSQPVYRE RIAYTYMDED  900
LPTTEYISPN EDGTFTLPEE AETMEGATVP LKMSDFTYVV EDMAGNITYT PVTKLLEGHS  960
NK                                                               962

SEQ ID NO: 4             moltype = AA  length = 945
FEATURE                  Location/Qualifiers
REGION                   1..945
                         note = C5a [90-1035 fragment] D131A/S513A mutant w/o leader
source                   1..945
                         mol_type = protein
                         organism = synthetic construct
SEQUENCE: 4
KTADTPVTSK ATIRDLNDPS QVKTLQEKAG KGAGTVVAVI AAGFDKNHEA WRLTDKTKAR  60
YQSKEDLEKA KKEHGITYGE WVNDKVAYYH DYSKDGKTAV DQEHGTHVSG ILSGNAPSET  120
KEPYRLEGAM PEAQLLLMRV EIVNGLADYA RNYAQAIRDA VNLGAKVINM SFGNAALAYA  180
NLPDETKKAF DYAKSKGVSI VTSAGNDSSF GGKTRLPLAD HPDYGVVGTP AAADSTLTVA  240
SYSPDKQLTE TATVKTADKQ DKEMPVLSTN RFEPNKAYDY AYANRGMKED DFKDVKGKIA  300
LIERGDIDFK DKIANAKKAG AVGVLIYDNQ DKGFPIELPN VDQMPAAFIS RKDGLLLKDN  360
PKKTITFNAT PKVLPTASGT KLSRFSSWGL TADGNIKPDI AAPGQDILSS VANNKYAKLS  420
GTAMSAPLVA GIMGLLQKQY ETQYPDMTPS ERLDLAKKVL MSSATALYDE DEKAYFSPRQ  480
QGAGAVDAKK ASAATMYVTD KDNTSSKVHL NNVSDTFEVT VTVHNKSDKP QELYYQATVQ  540
TDKVDGKHFA LAPKALYETS WQKITIPANS SKQVTVPIDA SRFSKDLLAQ MKNGYFLEGF  600
VRFKQDPTKE ELMSIPYIGF RGDFGNLSAL EKPIYDSKDG SSYYHEANSD AKDQLDGDGL  660
QFYALKNNFT ALTTESNPWT IIKAVKEGVE NIEDIESSEI TETIFAGTFA KQDDDSHYYI  720
HRHANGKPYA AISPNGDGNR DYVQFQGTFL RNAKNLVAEV LDKEGNVVWT SEVTEQVVKN  780
YNNDLASTLG STRFEKTRWD GKDKDGKVVA NGTYTYRVRY TPISSGAKEQ HTDFDVIVDN  840
TTPEVATSAT FSTEDRRLTL ASKPKTSQPV YRERIAYTYM DEDLPTTEYI SPNEDGTFTL  900
PEEAETMEGA TVPLKMSDFT YVVEDMAGNI TYTPVTKLLE GHSNK                945

SEQ ID NO: 5             moltype = AA  length = 510
FEATURE                  Location/Qualifiers
REGION                   1..510
                         note = SLO [79-571] fragment w/ leader
source                   1..510
                         mol_type = protein
                         organism = synthetic construct
SEQUENCE: 5
MHHHHHHGSG ENLYFQGAPK EMPLESAEKE EKKSEDKKKS EEDHTEEIND KIYSLNYNEL  60
```

-continued

```
EVLAKNGETI ENFVPKEGVK KADKFIVIER KKKNINTTPV DISIIDSVTD RTYPAALQLA  120
NKGFTENKPD AVVTKRNPQK IHIDLPGMGD KATVEVNDPT YANVSTAIDN LVNQWHDNYS  180
GGNTLPARTQ YTESMVYSKS QIEAALNVNS KILDGTLGID FKSISKGEKK VMIAAYKQIF  240
YTVSANLPNN PADVFDKSVT FKELQRKGVS NEAPPLFVSN VAYGRTVFVK LETSSKSNDV  300
EAAFSAALKG TDVKTNGKYS DILENSSFTA VVLGGDAAEH NKVVTKDFDV IRNVIKDNAT  360
FSRKNPAYPI SYTSVFLKNN KIAGVNNRTE YVETTSTEYT SGKINLSHQG AYVAQYEILW  420
DEINYDDKGK EVITKRRWDN NWYSKTSPFS TVIPLGANSR NIRIMARECT GLAWEWWRKV  480
IDERDVKLSK EINVNISGST LSPYGSITYK                                   510

SEQ ID NO: 6           moltype = AA  length = 493
FEATURE                Location/Qualifiers
source                 1..493
                       mol_type = protein
                       organism = Streptococcus pyogenes
SEQUENCE: 6
APKEMPLESA EKEEKKSEDK KKSEEDHTEE INDKIYSLNY NELEVLAKNG ETIENFVPKE  60
GVKKADKFIV IERKKKNINT TPVDISIIDS VTDRTYPAAL QLANKGFTEN KPDAVVTKRN  120
PQKIHIDLPG MGDKATVEVN DPTYANVSTA IDNLVNQWHD NYSGGNTLPA RTQYTESMVY  180
SKSQIEAALN VNSKILDGTL GIDFKSISKG EKKVMIAAYK QIFYTVSANL PNNPADVFDK  240
SVTFKELQRK GVSNEAPPLF VSNVAYGRTV FVKLETSSKS NDVEAAFSAA LKGTDVKTNG  300
KYSDILENSS FTAVVLGGDA AEHNKVVTKD FDVIRNVIKD NATFSRKNPA YPISYTSVFL  360
KNNKIAGVNN RTEYVETTST EYTSGKINLS HQGAYVAQYE ILWDEINYDD KGKEVITKRR  420
WDNNWYSKTS PFSTVIPLGA NSRNIRIMAR ECTGLAWEWW RKVIDERDVK LSKEINVNIS  480
GSTLSPYGSI TYK                                                     493

SEQ ID NO: 7           moltype = AA  length = 510
FEATURE                Location/Qualifiers
REGION                 1..510
                       note = SLO [79-571 fragment] - W535 mutant w/ leader
source                 1..510
                       mol_type = protein
                       organism = synthetic construct
SEQUENCE: 7
MHHHHHHGSG ENLYFQGAPK EMPLESAEKE EKKSEDKKKS EEDHTEEIND KIYSLNYNEL  60
EVLAKNGETI ENFVPKEGVK KADKFIVIER KKKNINTTPV DISIIDSVTD RTYPAALQLA  120
NKGFTENKPD AVVTKRNPQK IHIDLPGMGD KATVEVNDPT YANVSTAIDN LVNQWHDNYS  180
GGNTLPARTQ YTESMVYSKS QIEAALNVNS KILDGTLGID FKSISKGEKK VMIAAYKQIF  240
YTVSANLPNN PADVFDKSVT FKELQRKGVS NEAPPLFVSN VAYGRTVFVK LETSSKSNDV  300
EAAFSAALKG TDVKTNGKYS DILENSSFTA VVLGGDAAEH NKVVTKDFDV IRNVIKDNAT  360
FSRKNPAYPI SYTSVFLKNN KIAGVNNRTE YVETTSTEYT SGKINLSHQG AYVAQYEILW  420
DEINYDDKGK EVITKRRWDN NWYSKTSPFS TVIPLGANSR NIRIMARECT GLAAEWWRKV  480
IDERDVKLSK EINVNISGST LSPYGSITYK                                   510

SEQ ID NO: 8           moltype = AA  length = 493
FEATURE                Location/Qualifiers
REGION                 1..493
                       note = SLO [79-571 fragment] - W535 mutant w/o leader
source                 1..493
                       mol_type = protein
                       organism = synthetic construct
SEQUENCE: 8
APKEMPLESA EKEEKKSEDK KKSEEDHTEE INDKIYSLNY NELEVLAKNG ETIENFVPKE  60
GVKKADKFIV IERKKKNINT TPVDISIIDS VTDRTYPAAL QLANKGFTEN KPDAVVTKRN  120
PQKIHIDLPG MGDKATVEVN DPTYANVSTA IDNLVNQWHD NYSGGNTLPA RTQYTESMVY  180
SKSQIEAALN VNSKILDGTL GIDFKSISKG EKKVMIAAYK QIFYTVSANL PNNPADVFDK  240
SVTFKELQRK GVSNEAPPLF VSNVAYGRTV FVKLETSSKS NDVEAAFSAA LKGTDVKTNG  300
KYSDILENSS FTAVVLGGDA AEHNKVVTKD FDVIRNVIKD NATFSRKNPA YPISYTSVFL  360
KNNKIAGVNN RTEYVETTST EYTSGKINLS HQGAYVAQYE ILWDEINYDD KGKEVITKRR  420
WDNNWYSKTS PFSTVIPLGA NSRNIRIMAR ECTGLAAEWW RKVIDERDVK LSKEINVNIS  480
GSTLSPYGSI TYK                                                     493

SEQ ID NO: 9           moltype = AA  length = 834
FEATURE                Location/Qualifiers
REGION                 1..834
                       note = SpyAD [33-849 fragment] WT w/ leader
source                 1..834
                       mol_type = protein
                       organism = synthetic construct
SEQUENCE: 9
MHHHHHHGSG ENLYFQGQVK ADDRASGETK ASNTHDDSLP KPETIQEAKA TIDAVEKTLS  60
QQKAELTELA TALTKTTAEI NHLKEQQDNE QKALTSAQEI YTNTLASSEE TLLAQGAEHQ  120
RELTATETEL HNAQADQHSK ETALSEQKAS ISAETTRAQD LVEQVKTSEQ NIAKLNAMIS  180
NPDAITKAAQ TANDNTKALS SELEKAKADL ENQKAKVKKQ LTEELAAQKA ALAEKEAELS  240
RLKSSAPSTQ DSIVGNNTMK APQGYPLEEL KKLEASGYIG SASYNNYYKE HADQIIAKAS  300
PGNQLNQYQD IPADRNRFVD PDNLTPEVQN ELAQFAAHMI NSVRRQLGLP PVTVTAGSQE  360
FARLLSTSYK KTHGNTRPSF VYGQPGVSGH YGVGPHDKTI IEDSAGASGL IRNDDNMYEN  420
IGAFNDVHTV NGIKRGIYDS IKYMLFTDHL HGNTYGHAIN FLRVDKHNPN APVYLGFSTS  480
NVGSLNEHFV MFPESNIANH QRFNKTPIKA VGSTKDYAQR VGTVSDTIAA IKGKVSSLEN  540
RLSAIHQEAD IMAAQAKVSQ LQGKLASTLK QSDSLNLQVR QLNDTKGSLR TELLAAKAKQ  600
```

```
AQLEATRDQS LAKLASLKAA LHQTEALAEQ AAARVTALVA KKAHLQYLRD FKLNPNRLQV  660
IRERIDNTKQ DLAKTTSSLL NAQEALAALQ AKQSSLEATI ATTEHQLTLL KTLANEKEYR  720
HLDEDIATVP DLQVAPPLTG VKPLSYSKID TTPLVQEMVK ETKQLLEASA RLAAENTSLV  780
AEALVGQTSE MVASNAIVSK ITSSITQPSS KTSYGSGSST TSNLISDVDE STQR        834

SEQ ID NO: 10           moltype = AA  length = 817
FEATURE                 Location/Qualifiers
source                  1..817
                        mol_type = protein
                        organism = Streptococcus pyogenes
SEQUENCE: 10
QVKADDRASG ETKASNTHDD SLPKPETIQE AKATIDAVEK TLSQQKAELT ELATALTKTT  60
AEINHLKEQQ DNEQKALTSA QEIYTNTLAS SEETLLAQGA EHQRELTATE TELHNAQADQ  120
HSKETALSEQ KASISAETTR AQDLVEQVKT SEQNIAKLNA MISNPDAITK AAQTANDNTK  180
ALSSELEKAK ADLENQKAKV KKQLTEELAA QKAALAEKEA ELSRLKSSAP STQDSIVGNN  240
TMKAPQGYPL EELKKLEASG YIGSASYNNY YKEHADQIIA KASPGNQLNQ YQDIPADRNR  300
FVDPDNLTPE VQNELAQFAA HMINSVRRQL GLPPVTVTAG SQEFARLLST SYKKTHGNTR  360
PSFVYGQPGV SGHYGVGPHD KTIIEDSAGA SGLIRNDDNM YENIGAFNDV HTVNGIKRGI  420
YDSIKYMLFT DHLHGNTYGH AINFLRVDKH NPNAPVYLGF STSNVGSLNE HFVMFPESNI  480
ANHQRFNKTP IKAVGSTKDY AQRVGTVSDT IAAIKGKVSS LENRLSAIHQ EADIMAAQAK  540
VSQLQGKLAS TLKQSDSLNL QVRQLNDTKG SLRTELLAAK AKQAQLEATR DQSLAKLASL  600
KAALHQTEAL AEQAAARVTA LVAKKAHLQY LRDFKLNPNR LQVIRERIDN TKQDLAKTTS  660
SLLNAQEALA ALQAKQSSLE ATIATTEHQL TLLKTLANEK EYRHLDEDIA TVPDLQVAPP  720
LTGVKPLSYS KIDTTPLVQE MVKETKQLLE ASARLAAENT SLVAEALVGQ TSEMVASNAI  780
VSKITSSITQ PSSKTSYGSG SSTTSNLISD VDESTQR                           817

SEQ ID NO: 11           moltype = AA  length = 834
FEATURE                 Location/Qualifiers
REGION                  1..834
                        note = SpyAD [33-849 fragment] non-natural Amino Acid (e.g.
                         pAMF) K64/K287/K386/K657mutant w/ leader
VARIANT                 49
                        note = non-natural Amino Acid (e.g pAMF)
VARIANT                 272
                        note = non-natural Amino Acid (e.g pAMF)
VARIANT                 371
                        note = non-natural Amino Acid (e.g pAMF)
VARIANT                 642
                        note = non-natural Amino Acid (e.g pAMF)
source                  1..834
                        mol_type = protein
                        organism = synthetic construct
SEQUENCE: 11
MHHHHHHGSG ENLYFQGQVK ADDRASGETK ASNTHDDSLP KPETIQEAXA TIDAVEKTLS  60
QQKAELTELA TALTKTTAEI NHLKEQQDNE QKALTSAQEI YTNTLASSEE TLLAQGAEHQ  120
RELTATETEL HNAQADQHSK ETALSEQKAS ISAETTRAQD LVEQVKTSEQ NIAKLNAMIS  180
NPDAITKAAQ TANDNTKALS SELEKAKADL ENQKAKVKKQ LTEELAAQKA ALAEKEAELS  240
RLKSSAPSTQ DSIVGNNTMK APQGYPLEEL KXLEASGYIG SASYNNYYKE HADQIIAKAS  300
PGNQLNQYQD IPADRNRFVD PDNLTPEVQN ELAQFAAHMI NSVRRQLGLP PVTVTAGSQE  360
FARLLSTSYK XTHGNTRPSF VYGQPGVSGH YGVGPHDKTI IEDSAGASGL IRNDDNMYEN  420
IGAFNDVHTV NGIKRGIYDS IKYMLFTDHL HGNTYGHAIN FLRVDKHNPN APVYLGFSTS  480
NVGSLNEHFV MFPESNIANH QRFNKTPIKA VGSTKDYAQR VGTVSDTIAA IKGKVSSLEN  540
RLSAIHQEAD IMAAQAKVSQ LQGKLASTLK QSDSLNLQVR QLNDTKGSLR TELLAAKAKQ  600
AQLEATRDQS LAKLASLKAA LHQTEALAEQ AAARVTALVA KXAHLQYLRD FKLNPNRLQV  660
IRERIDNTKQ DLAKTTSSLL NAQEALAALQ AKQSSLEATI ATTEHQLTLL KTLANEKEYR  720
HLDEDIATVP DLQVAPPLTG VKPLSYSKID TTPLVQEMVK ETKQLLEASA RLAAENTSLV  780
AEALVGQTSE MVASNAIVSK ITSSITQPSS KTSYGSGSST TSNLISDVDE STQR        834

SEQ ID NO: 12           moltype = AA  length = 817
FEATURE                 Location/Qualifiers
REGION                  1..817
                        note = SpyAD [33-849 fragment] non-natural Amino Acid (e.g.
                         pAMF)K64/K287/K386/K657mutant w/o leader
VARIANT                 31
                        note = non-natural Amino Acid (e.g pAMF)
VARIANT                 32
                        note = any naturally occurring amino acid
VARIANT                 255
                        note = non-natural Amino Acid (e.g pAMF)
VARIANT                 354
                        note = non-natural Amino Acid (e.g pAMF)
VARIANT                 625
                        note = non-natural Amino Acid (e.g pAMF)
source                  1..817
                        mol_type = protein
                        organism = synthetic construct
SEQUENCE: 12
QVKADDRASG ETKASNTHDD SLPKPETIQE AXATIDAVEK TLSQQKAELT ELATALTKTT  60
AEINHLKEQQ DNEQKALTSA QEIYTNTLAS SEETLLAQGA EHQRELTATE TELHNAQADQ  120
```

-continued

```
HSKETALSEQ KASISAETTR AQDLVEQVKT SEQNIAKLNA MISNPDAITK AAQTANDNTK  180
ALSSELEKAK ADLENQKAKV KKQLTEELAA QKAALAEKEA ELSRLKSSAP STQDSIVGNN  240
TMKAPQGYPL EELKXLEASG YIGSASYNNY YKEHADQIIA KASPGNQLNQ YQDIPADRNR  300
FVDPDNLTPE VQNELAQFAA HMINSVRRQL GLPPVTVTAG SQEFARLLST SYKXTHGNTR  360
PSFVYGQPGV SGHYGVGPHD KTIIEDSAGA SGLIRNDDNM YENIGAFNDV HTVNGIKRGI  420
YDSIKYMLFT DHLHGNTYGH AINFLRVDKH NPNAPVYLGF STSNVGSLNE HFVMFPESNI  480
ANHQRFNKTP IKAVGSTKDY AQRVGTVSDT IAAIKGKVSS LENRLSAIHQ EADIMAAQAK  540
VSQLQGKLAS TLKQSDSLNL QVRQLNDTKG SLRTELLAAK AKQAQLEATR DQSLAKLASL  600
KAALHQTEAL AEQAAARVTA LVAKXAHLQY LRDFKLNPNR LQVIRERIDN TKQDLAKTTS  660
SLLNAQEALA ALQAKQSSLE ATIATTEHQL TLLKTLANEK EYRHLDEDIA TVPDLQVAPP  720
LTGVKPLSYS KIDTTPLVQE MVKETKQLLE ASARLAAENT SLVAEALVGQ TSEMVASNAI  780
VSKITSSITQ PSSKTSYGSG SSTTSNLISD VDESTQR                           817

SEQ ID NO: 13          moltype = AA  length = 427
FEATURE                Location/Qualifiers
REGION                 1..427
                       note = ADI [full length] WT w/ leader
source                 1..427
                       mol_type = protein
                       organism = synthetic construct
SEQUENCE: 13
MHHHHHHGSG ENLYFQGTAQ TPIHVYSEIG KLKKVLLHRP GKEIENLMPD YLERLLFDDI  60
PFLEDAQKEH DAFAQALRDE GIEVLYLETL AAESLVTPEI REAFIDEYLS EANIRGRATK  120
KAIRELLMAI EDNQELIEKT MAGVQKSELP EIPASEKGLT DLVESNYPFA IDPMPNLYFT  180
RDPFATIGTG VSLNHMFSET RNRETLYGKY IFTHHPIYGG GKVPMVYDRN ETTRIEGGDE  240
LVLSKDVLAV GISQRTDAAS IEKLLVNIFK QNLGFKKVLA FEFANNRKFM HLDTVFTMVD  300
YDKFTIHPEI EGDLRVYSVT YDNEELHIVE EKGDLAELLA ANLGVEKVDL IRCGGDNLVA  360
AGREQWNDGS NTLTIAPGVV VVYNRNTITN AILESKGLKL IKIHGSELVR GRGGPRCMSM  420
PFEREDI                                                           427

SEQ ID NO: 14          moltype = AA  length = 410
FEATURE                Location/Qualifiers
source                 1..410
                       mol_type = protein
                       organism = Streptococcus pyogenes
SEQUENCE: 14
TAQTPIHVYS EIGKLKKVLL HRPGKEIENL MPDYLERLLF DDIPFLEDAQ KEHDAFAQAL  60
RDEGIEVLYL ETLAAESLVT PEIREAFIDE YLSEANIRGR ATKKAIRELL MAIEDNQELI  120
EKTMAGVQKS ELPEIPASEK GLTDLVESNY PFAIDPMPNL YFTRDPFATI GTGVSLNHMF  180
SETRNRETLY GKYIFTHHPI YGGGKVPMVY DRNETTRIEG GDELVLSKDV LAVGISQRTD  240
AASIEKLLVN IFKQNLGFKK VLAFEFANNR KFMHLDTVFT MVDYDKFTIH PEIEGDLRVY  300
SVTYDNEELH IVEEKGDLAE LLAANLGVEK VDLIRCGGDN LVAAGREQWN DGSNTLTIAP  360
GVVVVYNRNT ITNAILESKG LKLIKIHGSE LVRGRGGPRC MSMPFEREDI            410

SEQ ID NO: 15          moltype = AA  length = 427
FEATURE                Location/Qualifiers
REGION                 1..427
                       note = ADI [full length] D277A mut w/ leader
source                 1..427
                       mol_type = protein
                       organism = synthetic construct
SEQUENCE: 15
MHHHHHHGSG ENLYFQGTAQ TPIHVYSEIG KLKKVLLHRP GKEIENLMPD YLERLLFDDI  60
PFLEDAQKEH DAFAQALRDE GIEVLYLETL AAESLVTPEI REAFIDEYLS EANIRGRATK  120
KAIRELLMAI EDNQELIEKT MAGVQKSELP EIPASEKGLT DLVESNYPFA IDPMPNLYFT  180
RDPFATIGTG VSLNHMFSET RNRETLYGKY IFTHHPIYGG GKVPMVYDRN ETTRIEGGDE  240
LVLSKDVLAV GISQRTDAAS IEKLLVNIFK QNLGFKKVLA FEFANNRKFM HLATVFTMVD  300
YDKFTIHPEI EGDLRVYSVT YDNEELHIVE EKGDLAELLA ANLGVEKVDL IRCGGDNLVA  360
AGREQWNDGS NTLTIAPGVV VVYNRNTITN AILESKGLKL IKIHGSELVR GRGGPRCMSM  420
PFEREDI                                                           427

SEQ ID NO: 16          moltype = AA  length = 410
FEATURE                Location/Qualifiers
REGION                 1..410
                       note = ADI [full length] D277A mut w/o leader
source                 1..410
                       mol_type = protein
                       organism = synthetic construct
SEQUENCE: 16
TAQTPIHVYS EIGKLKKVLL HRPGKEIENL MPDYLERLLF DDIPFLEDAQ KEHDAFAQAL  60
RDEGIEVLYL ETLAAESLVT PEIREAFIDE YLSEANIRGR ATKKAIRELL MAIEDNQELI  120
EKTMAGVQKS ELPEIPASEK GLTDLVESNY PFAIDPMPNL YFTRDPFATI GTGVSLNHMF  180
SETRNRETLY GKYIFTHHPI YGGGKVPMVY DRNETTRIEG GDELVLSKDV LAVGISQRTD  240
AASIEKLLVN IFKQNLGFKK VLAFEFANNR KFMHLATVFT MVDYDKFTIH PEIEGDLRVY  300
SVTYDNEELH IVEEKGDLAE LLAANLGVEK VDLIRCGGDN LVAAGREQWN DGSNTLTIAP  360
GVVVVYNRNT ITNAILESKG LKLIKIHGSE LVRGRGGPRC MSMPFEREDI            410

SEQ ID NO: 17          moltype = AA  length = 427
FEATURE                Location/Qualifiers
```

-continued

```
REGION                  1..427
                        note = ADI [full length] WT non-natural Amino Acid (e.g.
                         pAMF) K15/K193/K316 w/ leader
VARIANT                 31
                        note = non-natural Amino Acid (e.g pAMF)
VARIANT                 209
                        note = non-natural Amino Acid (e.g pAMF)
VARIANT                 332
                        note = non-natural Amino Acid (e.g pAMF)
source                  1..427
                        mol_type = protein
                        organism = synthetic construct
SEQUENCE: 17
MHHHHHHGSG ENLYFQGTAQ TPIHVYSEIG XLKKVLLHRP GKEIENLMPD YLERLLFDDI  60
PFLEDAQKEH DAFAQALRDE GIEVLYLETL AAESLVTPEI REAFIDEYLS EANIRGRATK  120
KAIRELLMAI EDNQELIEKT MAGVQKSELP EIPASEKGLT DLVESNYPFA IDPMPNLYFT  180
RDPFATIGTG VSLNHMFSET RNRETLYGXY IFTHHPIYGG GKVPMVYDRN ETTRIEGGDE  240
LVLSKDVLAV GISQRTDAAS IEKLLVNIFK QNLGFKKVLA FEFANNRKFM HLDTVFTMVD  300
YDKFTIHPEI EGDLRVYSVT YDNEELHIVE EXGDLAELLA ANLGVEKVDL IRCGGDNLVA  360
AGREQWNDGS NTLTIAPGVV VVYNRNTITN AILESKGLKL IKIHGSELVR GRGGPRCMSM  420
PFEREDI                                                            427

SEQ ID NO: 18           moltype = AA  length = 410
FEATURE                 Location/Qualifiers
REGION                  1..410
                        note = ADI [full length] WT non-natural Amino Acid (e.g.
                         pAMF) K15/K193/K316 w/o leader
VARIANT                 14
                        note = non-natural Amino Acid (e.g pAMF)
VARIANT                 192
                        note = non-natural Amino Acid (e.g pAMF)
VARIANT                 315
                        note = non-natural Amino Acid (e.g pAMF)
source                  1..410
                        mol_type = protein
                        organism = synthetic construct
SEQUENCE: 18
TAQTPIHVYS EIGXLKKVLL HRPGKEIENL MPDYLERLLF DDIPFLEDAQ KEHDAFAQAL  60
RDEGIEVLYL ETLAAESLVT PEIREAFIDE YLSEANIRGR ATKKAIRELL MAIEDNQELI  120
EKTMAGVQKS ELPEIPASEK GLTDLVESNY PFAIDPMPNL YFTRDPFATI GTGVSLNHMF  180
SETRNRETLY GXYIFTHHPI YGGGKVPMVY DRNETTRIEG GDELVLSKDV LAVGISQRTD  240
AASIEKLLVN IFKQNLGFKK VLAFEFANNR KFMHLDTVFT MVDYDKFTIH PEIEGDLRVY  300
SVTYDNEELH IVEEXGDLAE LLAANLGVEK VDLIRCGGDN LVAAGREQWN DGSNTLTIAP  360
GVVVVYNRNT ITNAILESKG LKLIKIHGSE LVRGRGGPRC MSMPFEREDI             410

SEQ ID NO: 19           moltype = AA  length = 427
FEATURE                 Location/Qualifiers
REGION                  1..427
                        note = ADI [full length] D277A non-natural Amino Acid (e.g.
                         pAMF) K15/K193/K316 w/ leader
VARIANT                 31
                        note = non-natural Amino Acid (e.g pAMF)
VARIANT                 209
                        note = non-natural Amino Acid (e.g pAMF)
VARIANT                 332
                        note = non-natural Amino Acid (e.g pAMF)
source                  1..427
                        mol_type = protein
                        organism = synthetic construct
SEQUENCE: 19
MHHHHHHGSG ENLYFQGTAQ TPIHVYSEIG XLKKVLLHRP GKEIENLMPD YLERLLFDDI  60
PFLEDAQKEH DAFAQALRDE GIEVLYLETL AAESLVTPEI REAFIDEYLS EANIRGRATK  120
KAIRELLMAI EDNQELIEKT MAGVQKSELP EIPASEKGLT DLVESNYPFA IDPMPNLYFT  180
RDPFATIGTG VSLNHMFSET RNRETLYGXY IFTHHPIYGG GKVPMVYDRN ETTRIEGGDE  240
LVLSKDVLAV GISQRTDAAS IEKLLVNIFK QNLGFKKVLA FEFANNRKFM HLATVFTMVD  300
YDKFTIHPEI EGDLRVYSVT YDNEELHIVE EXGDLAELLA ANLGVEKVDL IRCGGDNLVA  360
AGREQWNDGS NTLTIAPGVV VVYNRNTITN AILESKGLKL IKIHGSELVR GRGGPRCMSM  420
PFEREDI                                                            427

SEQ ID NO: 20           moltype = AA  length = 410
FEATURE                 Location/Qualifiers
REGION                  1..410
                        note = ADI [full length] D277A non-natural Amino Acid (e.g.
                         pAMF) K15/K193/K316 w/o leader
VARIANT                 14
                        note = non-natural Amino Acid (e.g pAMF)
VARIANT                 192
                        note = non-natural Amino Acid (e.g pAMF)
VARIANT                 315
```

```
                          note = non-natural Amino Acid (e.g pAMF)
source                    1..410
                          mol_type = protein
                          organism = synthetic construct
SEQUENCE: 20
TAQTPIHVYS EIGXLKKVLL HRPGKEIENL MPDYLERLLF DDIPFLEDAQ KEHDAFAQAL  60
RDEGIEVLYL ETLAAESLVT PEIREAFIDE YLSEANIRGR ATKKAIRELL MAIEDNQELI  120
EKTMAGVQKS ELPEIPASEK GLTDLVESNY PFAIDPMPNL YFTRDPFATI GTGVSLNHMF  180
SETRNRETLY GXYIFTHHPI YGGGKVPMVY DRNETTRIEG GDELVLSKDV LAVGISQRTD  240
AASIEKLLVN IFKQNLGFKK VLAFEFANNR KFMHLATVFT MVDYDKFTIH PEIEGDLRVY  300
SVTYDNEELH IVEEXGDLAE LLAANLGVEK VDLIRCGGDN LVAAGREQWN DGSNTLTIAP  360
GVVVVYNRNT ITNAILESKG LKLIKIHGSE LVRGRGGPRC MSMPFEREDI              410

SEQ ID NO: 21             moltype = AA  length = 184
FEATURE                   Location/Qualifiers
REGION                    1..184
                          note = hFerritin [full length] WT w/ leader
source                    1..184
                          mol_type = protein
                          organism = synthetic construct
SEQUENCE: 21
MHHHHHHGSG SSQIRQNYST DVEAAVNSLV NLYLQASYTY LSLGFYFDRD DVALEGVSHF  60
FRELAEEKRE GYERLLKMQN QRGGRALFQD IKKPAEDEWG KTPDAMKAAM ALEKKLNQAL  120
LDLHALGSAR TDPHLCDFLE THFLDEEVKL IKKMGDHLTN LHRLGGPEAG LGEYLFERLT  180
LKHD                                                                184

SEQ ID NO: 22             moltype = AA  length = 174
FEATURE                   Location/Qualifiers
source                    1..174
                          mol_type = protein
                          organism = Homo sapiens
SEQUENCE: 22
SSQIRQNYST DVEAAVNSLV NLYLQASYTY LSLGFYFDRD DVALEGVSHF FRELAEEKRE  60
GYERLLKMQN QRGGRALFQD IKKPAEDEWG KTPDAMKAAM ALEKKLNQAL LDLHALGSAR  120
TDPHLCDFLE THFLDEEVKL IKKMGDHLTN LHRLGGPEAG LGEYLFERLT LKHD        174

SEQ ID NO: 23             moltype = AA  length = 184
FEATURE                   Location/Qualifiers
REGION                    1..184
                          note = hFerritin [full length] non-natural Amino Acid (e.g.
                           pAMF) mutant I5 w/ leader
VARIANT                   14
                          note = non-natural Amino Acid (e.g pAMF)
source                    1..184
                          mol_type = protein
                          organism = synthetic construct
SEQUENCE: 23
MHHHHHHGSG SSQXRQNYST DVEAAVNSLV NLYLQASYTY LSLGFYFDRD DVALEGVSHF  60
FRELAEEKRE GYERLLKMQN QRGGRALFQD IKKPAEDEWG KTPDAMKAAM ALEKKLNQAL  120
LDLHALGSAR TDPHLCDFLE THFLDEEVKL IKKMGDHLTN LHRLGGPEAG LGEYLFERLT  180
LKHD                                                                184

SEQ ID NO: 24             moltype = AA  length = 174
FEATURE                   Location/Qualifiers
REGION                    1..174
                          note = hFerritin [full length] non-natural Amino Acid (e.g.
                           pAMF) mutant I5 w/o leader
VARIANT                   4
                          note = non-natural Amino Acid (e.g pAMF)
source                    1..174
                          mol_type = protein
                          organism = synthetic construct
SEQUENCE: 24
SSQXRQNYST DVEAAVNSLV NLYLQASYTY LSLGFYFDRD DVALEGVSHF FRELAEEKRE  60
GYERLLKMQN QRGGRALFQD IKKPAEDEWG KTPDAMKAAM ALEKKLNQAL LDLHALGSAR  120
TDPHLCDFLE THFLDEEVKL IKKMGDHLTN LHRLGGPEAG LGEYLFERLT LKHD        174

SEQ ID NO: 25             moltype = AA  length = 536
FEATURE                   Location/Qualifiers
REGION                    1..536
                          note = eCRM - non-natural Amino Acid (e.g. pAMF) mutant
VARIANT                   34
                          note = non-natural Amino Acid (e.g pAMF)
VARIANT                   213
                          note = non-natural Amino Acid (e.g pAMF)
VARIANT                   245
                          note = non-natural Amino Acid (e.g pAMF)
VARIANT                   265
                          note = non-natural Amino Acid (e.g pAMF)
```

-continued

```
VARIANT                386
                       note = non-natural Amino Acid (e.g pAMF)
VARIANT                527
                       note = non-natural Amino Acid (e.g pAMF)
source                 1..536
                       mol_type = protein
                       organism = synthetic construct
SEQUENCE: 25
MGADDVVDSS KSFVMENFSS YHGTKPGYVD SIQXGIQKPK SGTQGNYDDD WKEFYSTDNK  60
YDAAGYSVDN ENPLSGKAGG VVKVTYPGLT KVLALKVDNA ETIKKELGLS LTEPLMEQVG  120
TEEFIKRFGD GASRVVLSLP FAEGSSSVEY INNWEQAKAL SVELEINFET RGKRGQDAMY  180
EYMAQACAGN RVRNSVGSSL SCINLDWDVI RDXTKTKIES LKEHGPIKNK MSESPNKTVS  240
EEKAXQYLEE FHQTALEHPE LSELXTVTGT NPVFAGANYA AWAVNVAQVI DSETADNLEK  300
TTAALSILPG IGSVMGIADG AVHHNTEEIV AQSIALSSLM VAQAIPLVGE LVDIGFAAYN  360
FVESIINLFQ VVHNSYNRPA YSPGHXTQPF LHDGYAVSWN TVEDSIIRTG FQGESGHDIK  420
ITAENTPLPI AGVLLPTIPG KLDVNKSKTH ISVNGRKIRM RCRAIDGDVT FCRPKSPVYV  480
GNGVHANLHV AFHRSSSEKI HSNEISSDSI GVLGYQKTVD HTKVNSXLSL FFEIKS      536

SEQ ID NO: 26          moltype = AA  length = 427
FEATURE                Location/Qualifiers
REGION                 1..427
                       note = ADI (mut2) [full length] D277A non-natural Amino
                        Acid (e.g. pAMF) mutant w/ leader
VARIANT                139
                       note = non-natural Amino Acid (e.g pAMF)
VARIANT                263
                       note = non-natural Amino Acid (e.g pAMF)
VARIANT                332
                       note = non-natural Amino Acid (e.g pAMF)
source                 1..427
                       mol_type = protein
                       organism = synthetic construct
SEQUENCE: 26
MHHHHHHGSG ENLYFQGTAQ TPIHVYSEIG KLKKVLLHRP GKEIENLMPD YLERLLFDDI  60
PFLEDAQKEH DAFAQALRDE GIEVLYLETL AAESLVTPEI REAFIDEYLS EANIRGRATK  120
KAIRELLMAI EDNQELIEXT MAGVQKSELP EIPASEKGLT DLVESNYPFA IDPMPNLYFT  180
RDPFATIGTG VSLNHMFSET RNRETLYGKY IFTHHPIYGG GKVPMVYDRN ETTRIEGGDE  240
LVLSKDVLAV GISQRTDAAS IEXLLVNIFK QNLGFKKVLA FEFANNRKFM HLATVFTMVD  300
YDKFTIHPEI EGDLRVYSVT YDNEELHIVE EXGDLAELLA ANLGVEKVDL IRCGGDNLVA  360
AGREQWNDGS NTLTIAPGVV VVYNRNTITN AILESKGLKL IKIHGSELVR GRGGPRCMSM  420
PFEREDI                                                          427

SEQ ID NO: 27          moltype = AA  length = 411
FEATURE                Location/Qualifiers
REGION                 1..411
                       note = ADI (mut2) [full length] D277A non-natural Amino
                        Acid (e.g. pAMF) mutant w/oleader, with G overhang from
                        cleavage
VARIANT                123
                       note = non-natural Amino Acid (e.g pAMF)
VARIANT                247
                       note = non-natural Amino Acid (e.g pAMF)
VARIANT                316
                       note = non-natural Amino Acid (e.g pAMF)
source                 1..411
                       mol_type = protein
                       organism = synthetic construct
SEQUENCE: 27
GTAQTPIHVY SEIGKLKKVL LHRPGKEIEN LMPDYLERLL FDDIPFLEDA QKEHDAFAQA  60
LRDEGIEVLY LETLAAESLV TPEIREAFID EYLSEANIRG RATKKAIREL LMAIEDNQEL  120
IEXTMAGVQK SELPEIPASE KGLTDLVESN YPFAIDPMPN LYFTRDPFAT IGTGVSLNHM  180
FSETRNRETL YGKYIFTHHP IYGGGKVPMV YDRNETTRIE GGDELVLSKD VLAVGISQRT  240
DAASIEXLLV NIFKQNLGFK KVLAFEFANN RKFMHLATVF TMVDYDKFTI HPEIEGDLRV  300
YSVTYDNEEL HIVEEXGDLA ELLAANLGVE KVDLIRCGGD NLVAAGREQW NDGSNTLTIA  360
PGVVVVYNRN TITNAILESK GLKLIKIHGS ELVRGRGGPR CMSMPFERED I         411

SEQ ID NO: 28          moltype = AA  length = 157
FEATURE                Location/Qualifiers
REGION                 1..157
                       note = Sfb1 repeat region with leader
source                 1..157
                       mol_type = protein
                       organism = synthetic construct
SEQUENCE: 28
MHHHHHHGSG VETEDTKEPG VLMGGQSESV EFTKDTQTGM SGQTTPQVET EDTKEPGVLM  60
GGQSESVEFT KDTQTGMSGQ TASQVETEDT KEPGVLMGGQ SESVEFTKDT QTGMSGQTTP  120
QVETEDTKEP GVLMGGQSES VEFTKDTQTG MSGFSET                         157

SEQ ID NO: 29          moltype = AA  length = 946
```

```
FEATURE                Location/Qualifiers
REGION                 1..946
                       note = C5a [90-1035 fragment] WT w/o leader, with G
                        overhang fromcleavage
source                 1..946
                       mol_type = protein
                       organism = synthetic construct
SEQUENCE: 29
GKTADTPVTS KATIRDLNDP SQVKTLQEKA GKGAGTVVAV IDAGFDKNHE AWRLTDKTKA  60
RYQSKEDLEK AKKEHGITYG EWVNDKVAYY HDYSKDGKTA VDQEHGTHVS GILSGNAPSE  120
TKEPYRLEGA MPEAQLLLMR VEIVNGLADY ARNYAQAIRD AVNLGAKVIN MSFGNAALAY  180
ANLPDETKKA FDYAKSKGVS IVTSAGNDSS FGGKTRLPLA DHPDYGVVGT PAAADSTLTV  240
ASYSPDKQLT ETATVKTADK QDKEMPVLST NRFEPNKAYD YAYANRGMKE DDFKDVKGKI  300
ALIERGDIDF KDKIANAKKA GAVGVLIYDN QDKGFPIELP NVDQMPAAFI SRKDGLLLKD  360
NPKKTITFNA TPKVLPTASG TKLSRFSSWG LTADGNIKPD IAAPGQDILS SVANNKYAKL  420
SGTSMSAPLV AGIMGLLQKQ YETQYPDMTP SERLDLAKKV LMSSATALYD EDEKAYFSPR  480
QQGAGAVDAK KASAATMYVT DKDNTSSKVH LNNVSDTFEV TVTVHNKSDK PQELYYQATV  540
QTDKVDGKHF ALAPKALYET SWQKITIPAN SSKQVTVPID ASRFSKDLLA QMKNGYFLEG  600
FVRFKQDPTK EELMSIPYIG FRGDFGNLSA LEKPIYDSKD GSSYYHEANS DAKDQLDGDG  660
LQFYALKNNF TALTTESNPW TIIKAVKEGV ENIEDIESSE ITETIFAGTF AKQDDDSHYY  720
IHRHANGKPY AAISPNGDGN RDYVQFQGTF LRNAKNLVAE VLDKEGNVVW TSEVTEQVVK  780
NYNNDLASTL GSTRFEKTRW DGKDKDGKVV ANGTYTYRVR YTPISSGAKE QHTDFDVIVD  840
NTTPEVATSA TFSTEDRRLT LASKPKTSQP VYRERIAYTY MDEDLPTTEY ISPNEDGTFT  900
LPEEAETMEG ATVPLKMSDF TYVVEDMAGN ITYTPVTKLL EGHSNK                946

SEQ ID NO: 30          moltype = AA  length = 946
FEATURE                Location/Qualifiers
REGION                 1..946
                       note = C5a [90-1035 fragment] D131A/S513A w/o leader, with
                        G overhangfrom cleavage
source                 1..946
                       mol_type = protein
                       organism = synthetic construct
SEQUENCE: 30
GKTADTPVTS KATIRDLNDP SQVKTLQEKA GKGAGTVVAV IAAGFDKNHE AWRLTDKTKA  60
RYQSKEDLEK AKKEHGITYG EWVNDKVAYY HDYSKDGKTA VDQEHGTHVS GILSGNAPSE  120
TKEPYRLEGA MPEAQLLLMR VEIVNGLADY ARNYAQAIRD AVNLGAKVIN MSFGNAALAY  180
ANLPDETKKA FDYAKSKGVS IVTSAGNDSS FGGKTRLPLA DHPDYGVVGT PAAADSTLTV  240
ASYSPDKQLT ETATVKTADK QDKEMPVLST NRFEPNKAYD YAYANRGMKE DDFKDVKGKI  300
ALIERGDIDF KDKIANAKKA GAVGVLIYDN QDKGFPIELP NVDQMPAAFI SRKDGLLLKD  360
NPKKTITFNA TPKVLPTASG TKLSRFSSWG LTADGNIKPD IAAPGQDILS SVANNKYAKL  420
SGTAMSAPLV AGIMGLLQKQ YETQYPDMTP SERLDLAKKV LMSSATALYD EDEKAYFSPR  480
QQGAGAVDAK KASAATMYVT DKDNTSSKVH LNNVSDTFEV TVTVHNKSDK PQELYYQATV  540
QTDKVDGKHF ALAPKALYET SWQKITIPAN SSKQVTVPID ASRFSKDLLA QMKNGYFLEG  600
FVRFKQDPTK EELMSIPYIG FRGDFGNLSA LEKPIYDSKD GSSYYHEANS DAKDQLDGDG  660
LQFYALKNNF TALTTESNPW TIIKAVKEGV ENIEDIESSE ITETIFAGTF AKQDDDSHYY  720
IHRHANGKPY AAISPNGDGN RDYVQFQGTF LRNAKNLVAE VLDKEGNVVW TSEVTEQVVK  780
NYNNDLASTL GSTRFEKTRW DGKDKDGKVV ANGTYTYRVR YTPISSGAKE QHTDFDVIVD  840
NTTPEVATSA TFSTEDRRLT LASKPKTSQP VYRERIAYTY MDEDLPTTEY ISPNEDGTFT  900
LPEEAETMEG ATVPLKMSDF TYVVEDMAGN ITYTPVTKLL EGHSNK                946

SEQ ID NO: 31          moltype = AA  length = 494
FEATURE                Location/Qualifiers
REGION                 1..494
                       note = SLO [79-571 fragment] WT w/o leader, with G overhang
                        fromcleavage
source                 1..494
                       mol_type = protein
                       organism = synthetic construct
SEQUENCE: 31
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPFSTVIPLG ANSRNIRIMA RECTGLAWEW WRKVIDERDV KLSKEINVNI  480
SGSTLSPYGS ITYK                                                   494

SEQ ID NO: 32          moltype = AA  length = 494
FEATURE                Location/Qualifiers
REGION                 1..494
                       note = SLO [79-571 fragment] W535A w/o leader, with G
                        overhang fromcleavage
source                 1..494
                       mol_type = protein
                       organism = synthetic construct
SEQUENCE: 32
```

-continued

```
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPFSTVIPLG ANSRNIRIMA RECTGLAAEW WRKVIDERDV KLSKEINVNI  480
SGSTLSPYGS ITYK                                                  494

SEQ ID NO: 33          moltype = AA  length = 818
FEATURE                Location/Qualifiers
REGION                 1..818
                       note = SpyAD [33-849 fragment] WT w/o leader, with G
                        overhang fromcleavage
source                 1..818
                       mol_type = protein
                       organism = synthetic construct
SEQUENCE: 33
GQVKADDRAS GETKASNTHD DSLPKPETIQ EAKATIDAVE KTLSQQKAEL TELATALTKT  60
TAEINHLKEQ QDNEQKALTS AQEIYTNTLA SSEETLLAQG AEHQRELTAT ETELHNAQAD  120
QHSKETALSE QKASISAETT RAQDLVEQVK TSEQNIAKLN AMISNPDAIT KAAQTANDNT  180
KALSSELEKA KADLENQKAK VKKQLTEELA AQKAALAEKE AELSRLKSSA PSTQDSIVGN  240
NTMKAPQGYP LEELKKLEAS GYIGSASYNN YYKEHADQII AKASPGNQLN QYQDIPADRN  300
RFVDPDNLTP EVQNELAQFA AHMINSVRRQ LGLPPVTVTA GSQEFARLLS TSYKKTHGNT  360
RPSFVYGQPG VSGHYGVGPH DKTIIEDSAG ASGLIRNDDN MYENIGAFND VHTVNGIKRG  420
IYDSIKYMLF TDHLHGNTYG HAINFLRVDK HNPNAPVYLG FSTSNVGSLN EHFVMFPESN  480
IANHQRFNKT PIKAVGSTKD YAQRVGTVSD TIAAIKGKVS SLENRLSAIH QEADIMAAQA  540
KVSQLQGKLA STLKQSDSLN LQVRQLNDTK GSLRTELLAA KAKQAQLEAT RDQSLAKLAS  600
LKAALHQTEA LAEQAAARVT ALVAKKAHLQ YLRDFKLNPN RLQVIRERID NTKQDLAKTT  660
SSLLNAQEAL AALQAKQSSL EATIATTEHQ LTLLKTLANE KEYRHLDEDI ATVPDLQVAP  720
PLTGVKPLSY SKIDTTPLVQ EMVKETKQLL EASARLAAEN TSLVAEALVG QTSEMVASNA  780
IVSKITSSIT QPSSKTSYGS GSSTTSNLIS DVDESTQR                        818

SEQ ID NO: 34          moltype = AA  length = 818
FEATURE                Location/Qualifiers
REGION                 1..818
                       note = SpyAD [33-849 fragment] non-natural Amino Acid (e.g.
                        pAMF) mutant w/o leader, withG overhang from cleavage
VARIANT                33
                       note = non-natural Amino Acid (e.g pAMF)
VARIANT                256
                       note = non-natural Amino Acid (e.g pAMF)
VARIANT                355
                       note = non-natural Amino Acid (e.g pAMF)
VARIANT                626
                       note = non-natural Amino Acid (e.g pAMF)
source                 1..818
                       mol_type = protein
                       organism = synthetic construct
SEQUENCE: 34
GQVKADDRAS GETKASNTHD DSLPKPETIQ EAXATIDAVE KTLSQQKAEL TELATALTKT  60
TAEINHLKEQ QDNEQKALTS AQEIYTNTLA SSEETLLAQG AEHQRELTAT ETELHNAQAD  120
QHSKETALSE QKASISAETT RAQDLVEQVK TSEQNIAKLN AMISNPDAIT KAAQTANDNT  180
KALSSELEKA KADLENQKAK VKKQLTEELA AQKAALAEKE AELSRLKSSA PSTQDSIVGN  240
NTMKAPQGYP LEELKXLEAS GYIGSASYNN YYKEHADQII AKASPGNQLN QYQDIPADRN  300
RFVDPDNLTP EVQNELAQFA AHMINSVRRQ LGLPPVTVTA GSQEFARLLS TSYKXTHGNT  360
RPSFVYGQPG VSGHYGVGPH DKTIIEDSAG ASGLIRNDDN MYENIGAFND VHTVNGIKRG  420
IYDSIKYMLF TDHLHGNTYG HAINFLRVDK HNPNAPVYLG FSTSNVGSLN EHFVMFPESN  480
IANHQRFNKT PIKAVGSTKD YAQRVGTVSD TIAAIKGKVS SLENRLSAIH QEADIMAAQA  540
KVSQLQGKLA STLKQSDSLN LQVRQLNDTK GSLRTELLAA KAKQAQLEAT RDQSLAKLAS  600
LKAALHQTEA LAEQAAARVT ALVAKXAHLQ YLRDFKLNPN RLQVIRERID NTKQDLAKTT  660
SSLLNAQEAL AALQAKQSSL EATIATTEHQ LTLLKTLANE KEYRHLDEDI ATVPDLQVAP  720
PLTGVKPLSY SKIDTTPLVQ EMVKETKQLL EASARLAAEN TSLVAEALVG QTSEMVASNA  780
IVSKITSSIT QPSSKTSYGS GSSTTSNLIS DVDESTQR                        818

SEQ ID NO: 35          moltype = AA  length = 411
FEATURE                Location/Qualifiers
REGION                 1..411
                       note = ADI [full length] WT w/o leader, with G overhang
                        from cleavage
source                 1..411
                       mol_type = protein
                       organism = synthetic construct
SEQUENCE: 35
GTAQTPIHVY SEIGKLKKVL LHRPGKEIEN LMPDYLERLL FDDIPFLEDA QKEHDAFAQA  60
LRDEGIEVLY LETLAAESLV TPEIREAFID EYLSEANIRG RATKKAIREL LMAIEDNQEL  120
IEKTMAGVQK SELPEIPASE KGLTDLVESN YPFAIDPMPN LYFTRDPFAT IGTGVSLNHM  180
FSETRNRETL YGKYIFTHHP IYGGGKVPMV YDRNETTRIE GGDELVLSKD VLAVGISQRT  240
```

-continued

```
DAASIEKLLV NIFKQNLGFK KVLAFEFANN RKFMHLDTVF TMVDYDKFTI HPEIEGDLRV  300
YSVTYDNEEL HIVEEKGDLA ELLAANLGVE KVDLIRCGGD NLVAAGREQW NDGSNTLTIA  360
PGVVVVYNRN TITNAILESK GLKLIKIHGS ELVRGRGGPR CMSMPFERED I           411

SEQ ID NO: 36          moltype = AA  length = 411
FEATURE                Location/Qualifiers
REGION                 1..411
                       note = DI [full length] D277A w/o leader, with G overhang
                        from cleavage
source                 1..411
                       mol_type = protein
                       organism = synthetic construct
SEQUENCE: 36
GTAQTPIHVY SEIGKLKKVL LHRPGKEIEN LMPDYLERLL FDDIPFLEDA QKEHDAFAQA  60
LRDEGIEVLY LETLAAESLV TPEIREAFID EYLSEANIRG RATKKAIREL LMAIEDNQEL  120
IEKTMAGVQK SELPEIPASE KGLTDLVESN YPFAIDPMPN LYFTRDPFAT IGTGVSLNHM  180
FSETRNRETL YGKYIFTHHP IYGGGKVPMV YDRNETTRIE GGDELVLSKD VLAVGISQRT  240
DAASIEKLLV NIFKQNLGFK KVLAFEFANN RKFMHLATVF TMVDYDKFTI HPEIEGDLRV  300
YSVTYDNEEL HIVEEKGDLA ELLAANLGVE KVDLIRCGGD NLVAAGREQW NDGSNTLTIA  360
PGVVVVYNRN TITNAILESK GLKLIKIHGS ELVRGRGGPR CMSMPFERED I           411

SEQ ID NO: 37          moltype = AA  length = 411
FEATURE                Location/Qualifiers
REGION                 1..411
                       note = ADI [full length] non-natural Amino Acid (e.g. pAMF)
                        mutant w/o leader, with Goverhang from cleavage
VARIANT                15
                       note = non-natural Amino Acid (e.g pAMF)
VARIANT                193
                       note = non-natural Amino Acid (e.g pAMF)
VARIANT                316
                       note = non-natural Amino Acid (e.g pAMF)
source                 1..411
                       mol_type = protein
                       organism = synthetic construct
SEQUENCE: 37
GTAQTPIHVY SEIGXLKKVL LHRPGKEIEN LMPDYLERLL FDDIPFLEDA QKEHDAFAQA  60
LRDEGIEVLY LETLAAESLV TPEIREAFID EYLSEANIRG RATKKAIREL LMAIEDNQEL  120
IEKTMAGVQK SELPEIPASE KGLTDLVESN YPFAIDPMPN LYFTRDPFAT IGTGVSLNHM  180
FSETRNRETL YGXYIFTHHP IYGGGKVPMV YDRNETTRIE GGDELVLSKD VLAVGISQRT  240
DAASIEKLLV NIFKQNLGFK KVLAFEFANN RKFMHLDTVF TMVDYDKFTI HPEIEGDLRV  300
YSVTYDNEEL HIVEEXGDLA ELLAANLGVE KVDLIRCGGD NLVAAGREQW NDGSNTLTIA  360
PGVVVVYNRN TITNAILESK GLKLIKIHGS ELVRGRGGPR CMSMPFERED I           411

SEQ ID NO: 38          moltype = AA  length = 411
FEATURE                Location/Qualifiers
REGION                 1..411
                       note = ADI (mut5) [full length] D277A non-natural Amino
                        Acid (e.g. pAMF) mutant w/oleader, with G overhang from
                        cleavage
VARIANT                15
                       note = non-natural Amino Acid (e.g pAMF)
VARIANT                193
                       note = non-natural Amino Acid (e.g pAMF)
VARIANT                316
                       note = non-natural Amino Acid (e.g pAMF)
source                 1..411
                       mol_type = protein
                       organism = synthetic construct
SEQUENCE: 38
GTAQTPIHVY SEIGXLKKVL LHRPGKEIEN LMPDYLERLL FDDIPFLEDA QKEHDAFAQA  60
LRDEGIEVLY LETLAAESLV TPEIREAFID EYLSEANIRG RATKKAIREL LMAIEDNQEL  120
IEKTMAGVQK SELPEIPASE KGLTDLVESN YPFAIDPMPN LYFTRDPFAT IGTGVSLNHM  180
FSETRNRETL YGXYIFTHHP IYGGGKVPMV YDRNETTRIE GGDELVLSKD VLAVGISQRT  240
DAASIEKLLV NIFKQNLGFK KVLAFEFANN RKFMHLATVF TMVDYDKFTI HPEIEGDLRV  300
YSVTYDNEEL HIVEEXGDLA ELLAANLGVE KVDLIRCGGD NLVAAGREQW NDGSNTLTIA  360
PGVVVVYNRN TITNAILESK GLKLIKIHGS ELVRGRGGPR CMSMPFERED I           411

SEQ ID NO: 39          moltype = AA  length = 184
FEATURE                Location/Qualifiers
REGION                 1..184
                       note = hFL [full length] WT w/ leader
source                 1..184
                       mol_type = protein
                       organism = synthetic construct
SEQUENCE: 39
MHHHHHHGSG SSQIRQNYST DVEAAVNSLV NLYLQASYTY LSLGFYFDRD DVALEGVSHF  60
FRELAEEKRE GYERLLKMQN QRGGRALFQD IKKPAEDEWG KTPDAMKAAM ALEKKLNQAL  120
LDLHALGSAR TDPHLCDFLE THFLDEEVKL IKKMGDHLTN LHRLGGPEAG LGEYLFERLT  180
```

-continued

```
LKHD                                                          184

SEQ ID NO: 40          moltype = AA  length = 174
FEATURE                Location/Qualifiers
source                 1..174
                       mol_type = protein
                       organism = Homo sapiens
SEQUENCE: 40
SSQIRQNYST DVEAAVNSLV NLYLQASYTY LSLGFYFDRD DVALEGVSHF FRELAEEKRE  60
GYERLLKMQN QRGGRALFQD IKKPAEDEWG KTPDAMKAAM ALEKKLNQAL LDLHALGSAR  120
TDPHLCDFLE THFLDEEVKL IKKMGDHLTN LHRLGGPEAG LGEYLFERLT LKHD        174

SEQ ID NO: 41          moltype = AA  length = 184
FEATURE                Location/Qualifiers
REGION                 1..184
                       note = hFL [full length] non-natural Amino Acid (e.g. pAMF)
                        mutant w/ leader
VARIANT                14
                       note = non-natural Amino Acid (e.g pAMF)
source                 1..184
                       mol_type = protein
                       organism = synthetic construct
SEQUENCE: 41
MHHHHHHGSG SSQXRQNYST DVEAAVNSLV NLYLQASYTY LSLGFYFDRD DVALEGVSHF  60
FRELAEEKRE GYERLLKMQN QRGGRALFQD IKKPAEDEWG KTPDAMKAAM ALEKKLNQAL  120
LDLHALGSAR TDPHLCDFLE THFLDEEVKL IKKMGDHLTN LHRLGGPEAG LGEYLFERLT  180
LKHD                                                          184

SEQ ID NO: 42          moltype = AA  length = 174
FEATURE                Location/Qualifiers
REGION                 1..174
                       note = hFL [full length] non-natural Amino Acid (e.g. pAMF)
                        mutant w/o leader
VARIANT                4
                       note = non-natural Amino Acid (e.g pAMF)
source                 1..174
                       mol_type = protein
                       organism = synthetic construct
SEQUENCE: 42
SSQXRQNYST DVEAAVNSLV NLYLQASYTY LSLGFYFDRD DVALEGVSHF FRELAEEKRE  60
GYERLLKMQN QRGGRALFQD IKKPAEDEWG KTPDAMKAAM ALEKKLNQAL LDLHALGSAR  120
TDPHLCDFLE THFLDEEVKL IKKMGDHLTN LHRLGGPEAG LGEYLFERLT LKHD        174

SEQ ID NO: 43          moltype = AA  length = 535
FEATURE                Location/Qualifiers
REGION                 1..535
                       note = eCRM-non-natural Amino Acid (e.g. pAMF) mutant
VARIANT                33
                       note = non-natural Amino Acid (e.g pAMF)
VARIANT                212
                       note = non-natural Amino Acid (e.g pAMF)
VARIANT                244
                       note = non-natural Amino Acid (e.g pAMF)
VARIANT                264
                       note = non-natural Amino Acid (e.g pAMF)
VARIANT                385
                       note = non-natural Amino Acid (e.g pAMF)
VARIANT                526
                       note = non-natural Amino Acid (e.g pAMF)
source                 1..535
                       mol_type = protein
                       organism = synthetic construct
SEQUENCE: 43
GADDVVDSSK SFVMENFSSY HGTKPGYVDS IQXGIQKPKS GTQGNYDDDW KEFYSTDNKY  60
DAAGYSVDNE NPLSGKAGGV VKVTYPGLTK VLALKVDNAE TIKKELGLSL TEPLMEQVGT  120
EEFIKRFGDG ASRVVLSLPF AEGSSSVEYI NNWEQAKALS VELEINFETR GKRGQDAMYE  180
YMAQACAGNR VRNSVGSSLS CINLDWDVIR DXTKTKIESL KEHGPIKNKM SESPNKTVSE  240
EKAXQYLEEF HQTALEHPEL SELXTVTGTN PVFAGANYAA WAVNVAQVID SETADNLEKT  300
TAALSILPGI GSVMGIADGA VHHNTEEIVA QSIALSSLMV AQAIPLVGEL VDIGFAAYNF  360
VESIINLFQV VHNSYNRPAY SPGHXTQPFL HDGYAVSWNT VEDSIIRTGF QGESGHDIKI  420
TAENTPLPIA GVLLPTIPGK LDVNKSKTHI SVNGRKIRMR CRAIDGDVTF CRPKSPVYVG  480
NGVHANLHVA FHRSSSEKIH SNEISSDSIG VLGYQKTVDH TKVNSXLSLF FEIKS       535

SEQ ID NO: 44          moltype = AA  length = 483
FEATURE                Location/Qualifiers
REGION                 1..483
                       note = SLO(deltaC11) W535A w/o leader, with G overhang from
                        cleavage
source                 1..483
```

```
                        mol_type = protein
                        organism = synthetic construct
SEQUENCE: 44
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPFSTVIPLG ANSRNIRIMA RECTGLAAEW WRKVIDERDV KLSKEINVNI  480
SGS                                                               483

SEQ ID NO: 45           moltype = AA  length = 473
FEATURE                 Location/Qualifiers
REGION                  1..473
                        note = SLO(deltaC21) fragment W535A w/o leader, with G
                         overhang fromcleavage
source                  1..473
                        mol_type = protein
                        organism = synthetic construct
SEQUENCE: 45
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPFSTVIPLG ANSRNIRIMA RECTGLAAEW WRKVIDERDV KLS         473

SEQ ID NO: 46           moltype = AA  length = 463
FEATURE                 Location/Qualifiers
REGION                  1..463
                        note = SLO(deltaC31) fragment W535A w/o leader, with G
                         overhang fromcleavage
source                  1..463
                        mol_type = protein
                        organism = synthetic construct
SEQUENCE: 46
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPFSTVIPLG ANSRNIRIMA RECTGLAAEW WRK                   463

SEQ ID NO: 47           moltype = AA  length = 453
FEATURE                 Location/Qualifiers
REGION                  1..453
                        note = SLO(deltaC41) fragment W535A w/o leader, with G
                         overhang fromcleavage
source                  1..453
                        mol_type = protein
                        organism = synthetic construct
SEQUENCE: 47
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPFSTVIPLG ANSRNIRIMA REC                               453

SEQ ID NO: 48           moltype = AA  length = 443
FEATURE                 Location/Qualifiers
REGION                  1..443
                        note = SLO(deltaC51) fragment W535A w/o leader, with G
                         overhang fromcleavage
source                  1..443
                        mol_type = protein
                        organism = synthetic construct
SEQUENCE: 48
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
```

```
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPFSTVIPLG ANS                                         443

SEQ ID NO: 49          moltype = AA  length = 433
FEATURE                Location/Qualifiers
REGION                 1..433
                       note = SLO(deltaC61) fragment W535A w/o leader, with G
                        overhang fromcleavage
source                 1..433
                       mol_type = protein
                       organism = synthetic construct
SEQUENCE: 49
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWDNNWYSKT SPF                                                    433

SEQ ID NO: 50          moltype = AA  length = 423
FEATURE                Location/Qualifiers
REGION                 1..423
                       note = SLO(deltaC71) fragment W535A w/o leader, with G
                        overhang fromcleavage
source                 1..423
                       mol_type = protein
                       organism = synthetic construct
SEQUENCE: 50
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKGKEVITKR  420
RWD                                                               423

SEQ ID NO: 51          moltype = AA  length = 413
FEATURE                Location/Qualifiers
REGION                 1..413
                       note = SLO(deltaC81) fragment W535A w/o leader, with G
                        overhang fromcleavage
source                 1..413
                       mol_type = protein
                       organism = synthetic construct
SEQUENCE: 51
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EILWDEINYD DKG         413

SEQ ID NO: 52          moltype = AA  length = 403
FEATURE                Location/Qualifiers
REGION                 1..403
                       note = SLO(deltaC91) fragment W535A w/o leader, with G
                        overhang fromcleavage
source                 1..403
                       mol_type = protein
                       organism = synthetic construct
SEQUENCE: 52
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQGAYVAQY EIL                   403

SEQ ID NO: 53          moltype = AA  length = 393
FEATURE                Location/Qualifiers
REGION                 1..393
```

-continued

```
                      note = SLO(deltaC101) fragment W535A w/o leader, with G
                       overhang fromcleavage
source                1..393
                      mol_type = protein
                      organism = synthetic construct
SEQUENCE: 53
GAPKEMPLES AEKEEKKSED KKKSEEDHTE EINDKIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                              393

SEQ ID NO: 54         moltype = AA  length = 393
FEATURE               Location/Qualifiers
REGION                1..393
                      note = SLO(deltaC101) fragment W535A w/o leader, with G
                       overhang fromcleavage
VARIANT               21
                      note = non-natural Amino Acid (e.g pAMF)
VARIANT               35
                      note = non-natural Amino Acid (e.g pAMF)
VARIANT               74
                      note = non-natural Amino Acid (e.g pAMF)
VARIANT               112
                      note = non-natural Amino Acid (e.g pAMF)
VARIANT               195
                      note = non-natural Amino Acid (e.g pAMF)
VARIANT               246
                      note = non-natural Amino Acid (e.g pAMF)
VARIANT               280
                      note = non-natural Amino Acid (e.g pAMF)
VARIANT               298
                      note = non-natural Amino Acid (e.g pAMF)
VARIANT               330
                      note = non-natural Amino Acid (e.g pAMF)
VARIANT               387
                      note = non-natural Amino Acid (e.g pAMF)
source                1..393
                      mol_type = protein
                      organism = synthetic construct
SEQUENCE: 54
GAPKEMPLES AEKEEKKSED XKKSEEDHTE EINDXIYSLN YNELEVLAKN GETIENFVPK  60
EGVKKADKFI VIEXKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFXELQR KGVSNEAPPL FVSNVAYGRT VFVKLETSSX SNDVEAAFSA ALKGTDVXTN  300
GKYSDILENS SFTAVVLGGD AAEHNKVVTX DFDVIRNVIK DNATFSRKNP AYPISYTSVF  360
LKNNKIAGVN NRTEYVETTS TEYTSGXINL SHQ                              393

SEQ ID NO: 55         moltype = AA  length = 393
FEATURE               Location/Qualifiers
REGION                1..393
                      note = SLO(deltaC101) fragment W535A - non-natural Amino
                       Acid (e.g. pAMF) mutant 1 -w/oleader, with G overhang from
                       cleavage
VARIANT               21
                      note = non-natural Amino Acid (e.g pAMF)
VARIANT               74
                      note = non-natural Amino Acid (e.g pAMF)
VARIANT               195
                      note = non-natural Amino Acid (e.g pAMF)
VARIANT               280
                      note = non-natural Amino Acid (e.g pAMF)
source                1..393
                      mol_type = protein
                      organism = synthetic construct
SEQUENCE: 55
GAPKEMPLES AEKEEKKSED XKKSEEDHTE EINDKIYSLN YNELEVLAKN GETIENFVPK  60
EGVKKADKFI VIEXKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                              393

SEQ ID NO: 56         moltype = AA  length = 393
FEATURE               Location/Qualifiers
```

```
REGION                  1..393
                        note = SLO(deltaC101) fragment W535A - non-natural Amino
                         Acid (e.g. pAMF) mutant 2 -w/oleader, with G overhang from
                         cleavage
VARIANT                 35
                        note = non-natural Amino Acid (e.g pAMF)
VARIANT                 112
                        note = non-natural Amino Acid (e.g pAMF)
VARIANT                 246
                        note = non-natural Amino Acid (e.g pAMF)
VARIANT                 298
                        note = non-natural Amino Acid (e.g pAMF)
source                  1..393
                        mol_type = protein
                        organism = synthetic construct
SEQUENCE: 56
GAPKEMPLES AEKEEKKSED KKKSEEDHTE EINDXIYSLN YNELEVLAKN GETIENFVPK  60
EGVKKADKFI VIERKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFXELQR KGVSNEAPPL FVSNVAYGRT VFVKLETSSK SNDVEAAFSA ALKGTDVXTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                              393

SEQ ID NO: 57           moltype = AA  length = 393
FEATURE                 Location/Qualifiers
REGION                  1..393
                        note = SLO(deltaC101) fragment W535A - non-natural Amino
                         Acid (e.g. pAMF) mutant 3 -w/oleader, with G overhang from
                         cleavage
VARIANT                 74
                        note = non-natural Amino Acid (e.g pAMF)
VARIANT                 195
                        note = non-natural Amino Acid (e.g pAMF)
VARIANT                 280
                        note = non-natural Amino Acid (e.g pAMF)
VARIANT                 330
                        note = non-natural Amino Acid (e.g pAMF)
source                  1..393
                        mol_type = protein
                        organism = synthetic construct
SEQUENCE: 57
GAPKEMPLES AEKEEKKSED KKKSEEDHTE EINDKIYSLN YNELEVLAKN GETIENFVPK  60
EGVKKADKFI VIEXKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTX DFDVIRNVIK DNATFSRKNP AYPISYTSVF  360
LKNNKIAGVN NRTEYVETTS TEYTSGKINL SHQ                              393

SEQ ID NO: 58           moltype = AA  length = 393
FEATURE                 Location/Qualifiers
REGION                  1..393
                        note = SLO(deltaC101) fragment W535A - non-natural Amino
                         Acid (e.g. pAMF) mutant 4 -w/oleader, with G overhang from
                         cleavage
VARIANT                 74
                        note = non-natural Amino Acid (e.g pAMF)
VARIANT                 195
                        note = non-natural Amino Acid (e.g pAMF)
VARIANT                 298
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 58
GAPKEMPLES AEKEEKKSED KKKSEEDHTE EINDKIYSLN YNELEVLAKN GETIENFVPK  60
EGVKKADKFI VIEXKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVXTN  300
GKYSDILENS SFTAVVLGGD AAEHNKVVTK DFDVIRNVIK DNATFSRKNP AYPISYTSVF  360
LKNNKIAGVN NRTEYVETTS TEYTSGXINL SHQ                              393

SEQ ID NO: 59           moltype = AA  length = 393
FEATURE                 Location/Qualifiers
REGION                  1..393
```

```
                        note = SLO(deltaC101) fragment W535A - non-natural Amino
                         Acid (e.g. pAMF) mutant 5 -w/oleader, with G overhang from
                         cleavage
VARIANT                 35
                        note = non-natural Amino Acid (e.g pAMF)
VARIANT                 195
                        note = non-natural Amino Acid (e.g pAMF)
VARIANT                 280
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 59
GAPKEMPLES AEKEEKKSED KKKSEEDHTE EINDXIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGXINL SHQ                                393

SEQ ID NO: 60           moltype = AA  length = 393
FEATURE                 Location/Qualifiers
REGION                  1..393
                        note = SLO(deltaC101) fragment W535A - non-natural Amino
                         Acid (e.g. pAMF) mutant 6 -w/oleader, with G overhang from
                         cleavage
VARIANT                 21
                        note = non-natural Amino Acid (e.g pAMF)
VARIANT                 112
                        note = non-natural Amino Acid (e.g pAMF)
VARIANT                 280
                        note = non-natural Amino Acid (e.g pAMF)
source                  1..393
                        mol_type = protein
                        organism = synthetic construct
SEQUENCE: 60
GAPKEMPLES AEKEEKKSED XKKSEEDHTE EINDKIYSLN YNELEVLAKN GETIENFVPK  60
EGVKKADKFI VIERKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                                393

SEQ ID NO: 61           moltype = AA  length = 393
FEATURE                 Location/Qualifiers
REGION                  1..393
                        note = SLO(deltaC101) fragment W535A - non-natural Amino
                         Acid (e.g. pAMF) mutant 7 -w/oleader, with G overhang from
                         cleavage
VARIANT                 21
                        note = non-natural Amino Acid (e.g pAMF)
VARIANT                 35
                        note = non-natural Amino Acid (e.g pAMF)
VARIANT                 112
                        note = non-natural Amino Acid (e.g pAMF)
VARIANT                 246
                        note = non-natural Amino Acid (e.g pAMF)
source                  1..393
                        mol_type = protein
                        organism = synthetic construct
SEQUENCE: 61
GAPKEMPLES AEKEEKKSED XKKSEEDHTE EINDXIYSLN YNELEVLAKN GETIENFVPK  60
EGVKKADKFI VIERKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFXELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                                393

SEQ ID NO: 62           moltype = AA  length = 393
FEATURE                 Location/Qualifiers
REGION                  1..393
                        note = SLO(deltaC101) fragment W535A - non-natural Amino
                         Acid (e.g. pAMF) mutant 8 -w/oleader, with G overhang from
                         cleavage
```

-continued

```
VARIANT                21
                       note = non-natural Amino Acid (e.g pAMF)
VARIANT                74
                       note = non-natural Amino Acid (e.g pAMF)
VARIANT                195
                       note = non-natural Amino Acid (e.g pAMF)
source                 1..393
                       mol_type = protein
                       organism = synthetic construct
SEQUENCE: 62
GAPKEMPLES AEKEEKKSED XKKSEEDHTE EINDKIYSLN YNELEVLAKN GETIENFVPK  60
EGVKKADKFI VIEXKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVKTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                               393

SEQ ID NO: 63          moltype = AA  length = 393
FEATURE                Location/Qualifiers
REGION                 1..393
                       note = SLO(deltaC101) fragment W535A - non-natural Amino
                        Acid (e.g. pAMF) mutant 9 -w/oleader, with G overhang from
                        cleavage
VARIANT                35
                       note = non-natural Amino Acid (e.g pAMF)
VARIANT                195
                       note = non-natural Amino Acid (e.g pAMF)
VARIANT                298
                       note = non-natural Amino Acid (e.g pAMF)
source                 1..393
                       mol_type = protein
                       organism = synthetic construct
SEQUENCE: 63
GAPKEMPLES AEKEEKKSED KKKSEEDHTE EINDXIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSK SNDVEAAFSA ALKGTDVXTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                               393

SEQ ID NO: 64          moltype = AA  length = 393
FEATURE                Location/Qualifiers
REGION                 1..393
                       note = SLO(deltaC101) fragment W535A - non-natural Amino
                        Acid (e.g. pAMF) mutant 10 -w/oleader, with G overhang
                        from cleavage
VARIANT                35
                       note = non-natural Amino Acid (e.g pAMF)
VARIANT                246
                       note = non-natural Amino Acid (e.g pAMF)
VARIANT                330
                       note = non-natural Amino Acid (e.g pAMF)
source                 1..393
                       mol_type = protein
                       organism = synthetic construct
SEQUENCE: 64
GAPKEMPLES AEKEEKKSED KKKSEEDHTE EINDXIYSLN YNELEVLAKN GETIENFVPK  60
EGVKKADKFI VIERKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFXELQR KGVSNEAPPL FVSNVAYGRT VFVKLETSSK SNDVEAAFSA ALKGTDVKTN  300
GKYSDILENS SFTAVVLGGD AAEHNKVVTX DFDVIRNVIK DNATFSRKNP AYPISYTSVF  360
LKNNKIAGVN NRTEYVETTS TEYTSGKINL SHQ                               393

SEQ ID NO: 65          moltype = AA  length = 393
FEATURE                Location/Qualifiers
REGION                 1..393
                       note = SLO(deltaC101) fragment W535A - non-natural Amino
                        Acid (e.g. pAMF) mutant 10 -w/oleader, with G overhang
                        from cleavage
VARIANT                21
                       note = non-natural Amino Acid (e.g pAMF)
VARIANT                74
                       note = non-natural Amino Acid (e.g pAMF)
VARIANT                195
                       note = non-natural Amino Acid (e.g pAMF)
VARIANT                280
```

```
                     note = non-natural Amino Acid (e.g pAMF)
VARIANT              330
                     note = non-natural Amino Acid (e.g pAMF)
source               1..393
                     mol_type = protein
                     organism = synthetic construct
SEQUENCE: 65
GAPKEMPLES AEKEEKKSED XKKSEEDHTE EINDKIYSLN YNELEVLAKN GETIENFVPK  60
EGVKKADKFI VIEXKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTX DFDVIRNVIK DNATFSRKNP AYPISYTSVF  360
LKNNKIAGVN NRTEYVETTS TEYTSGKINL SHQ                               393

SEQ ID NO: 66        moltype = AA  length = 393
FEATURE              Location/Qualifiers
REGION               1..393
                     note = SLO(deltaC101) fragment W535A - non-natural Amino
                      Acid (e.g. pAMF) mutant 10 -w/oleader, with G overhang
                      from cleavage
VARIANT              35
                     note = non-natural Amino Acid (e.g pAMF)
VARIANT              112
                     note = non-natural Amino Acid (e.g pAMF)
VARIANT              246
                     note = non-natural Amino Acid (e.g pAMF)
VARIANT              298
                     note = non-natural Amino Acid (e.g pAMF)
VARIANT              387
                     note = non-natural Amino Acid (e.g pAMF)
source               1..393
                     mol_type = protein
                     organism = synthetic construct
SEQUENCE: 66
GAPKEMPLES AEKEEKKSED KKKSEEDHTE EINDXIYSLN YNELEVLAKN GETIENFVPK  60
EGVKKADKFI VIERKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFXELQR KGVSNEAPPL FVSNVAYGRT VFVKLETSSK SNDVEAAFSA ALKGTDVXTN  300
GKYSDILENS SFTAVVLGGD AAEHNKVVTK DFDVIRNVIK DNATFSRKNP AYPISYTSVF  360
LKNNKIAGVN NRTEYVETTS TEYTSGXINL SHQ                               393

SEQ ID NO: 67        moltype = AA  length = 393
FEATURE              Location/Qualifiers
REGION               1..393
                     note = SLO(deltaC101) fragment W535A - non-natural Amino
                      Acid (e.g. pAMF) mutant 10 -w/oleader, with G overhang
                      from cleavage
VARIANT              35
                     note = non-natural Amino Acid (e.g pAMF)
VARIANT              74
                     note = non-natural Amino Acid (e.g pAMF)
VARIANT              195
                     note = non-natural Amino Acid (e.g pAMF)
VARIANT              280
                     note = non-natural Amino Acid (e.g pAMF)
VARIANT              330
                     note = non-natural Amino Acid (e.g pAMF)
source               1..393
                     mol_type = protein
                     organism = synthetic construct
SEQUENCE: 67
GAPKEMPLES AEKEEKKSED KKKSEEDHTE EINDXIYSLN YNELEVLAKN GETIENFVPK  60
EGVKKADKFI VIEXKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTX DFDVIRNVIK DNATFSRKNP AYPISYTSVF  360
LKNNKIAGVN NRTEYVETTS TEYTSGKINL SHQ                               393

SEQ ID NO: 68        moltype = AA  length = 393
FEATURE              Location/Qualifiers
REGION               1..393
                     note = SLO(deltaC101) fragment W535A - non-natural Amino
                      Acid (e.g. pAMF) mutant 10 -w/oleader, with G overhang
                      from cleavage
VARIANT              21
                     note = non-natural Amino Acid (e.g pAMF)
```

-continued

```
VARIANT                 74
                        note = non-natural Amino Acid (e.g pAMF)
VARIANT                 195
                        note = non-natural Amino Acid (e.g pAMF)
VARIANT                 280
                        note = non-natural Amino Acid (e.g pAMF)
VARIANT                 330
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 68
GAPKEMPLES AEKEEKKSED XKKSEEDHTE EINDKIYSLN YNELEVLAKN GETIENFVPK  60
EGVKKADKFI VIEXKKKNIN TTPVDISIID SVTDRTYPAA LQLANKGFTE NKPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTX DFDVIRNVIK DNATFSRKNP AYPISYTSVF  360
LKNNKIAGVN NRTEYVETTS TEYTSGXINL SHQ                               393

SEQ ID NO: 69           moltype = AA  length = 393
FEATURE                 Location/Qualifiers
REGION                  1..393
                        note = SLO(deltaC101) fragment W535A - non-natural Amino
                         Acid (e.g. pAMF) mutant 10 -w/oleader, with G overhang
                         from cleavage
VARIANT                 35
                        note = non-natural Amino Acid (e.g pAMF)
VARIANT                 74
                        note = non-natural Amino Acid (e.g pAMF)
VARIANT                 112
                        note = non-natural Amino Acid (e.g pAMF)
VARIANT                 246
                        note = non-natural Amino Acid (e.g pAMF)
VARIANT                 298
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 69
GAPKEMPLES AEKEEKKSED KKKSEEDHTE EINDXIYSLN YNELEVLAKN GETIENFVPK  60
EGVKKADKFI VIEXKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFXELQR KGVSNEAPPL FVSNVAYGRT VFVKLETSSK SNDVEAAFSA ALKGTDVXTN  300
GKYSDILENS SFTAVVLGGD AAEHNKVVTK DFDVIRNVIK DNATFSRKNP AYPISYTSVF  360
LKNNKIAGVN NRTEYVETTS TEYTSGXINL SHQ                               393

SEQ ID NO: 70           moltype = AA  length = 393
FEATURE                 Location/Qualifiers
REGION                  1..393
                        note = SLO(deltaC101) fragment W535A - non-natural Amino
                         Acid (e.g. pAMF) mutant 10 -w/oleader, with G overhang
                         from cleavage
VARIANT                 21
                        note = non-natural Amino Acid (e.g pAMF)
VARIANT                 35
                        note = non-natural Amino Acid (e.g pAMF)
VARIANT                 112
                        note = non-natural Amino Acid (e.g pAMF)
VARIANT                 246
                        note = non-natural Amino Acid (e.g pAMF)
VARIANT                 298
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 70
GAPKEMPLES AEKEEKKSED XKKSEEDHTE EINDXIYSLN YNELEVLAKN GETIENFVPK  60
EGVKKADKFI VIERKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFXELQR KGVSNEAPPL FVSNVAYGRT VFVKLETSSK SNDVEAAFSA ALKGTDVXTN  300
```

```
GKYSDILENS SFTAVVLGGD AAEHNKVVTK DFDVIRNVIK DNATFSRKNP AYPISYTSVF  360
LKNNKIAGVN NRTEYVETTS TEYTSGXINL SHQ                               393

SEQ ID NO: 71           moltype = AA  length = 393
FEATURE                 Location/Qualifiers
REGION                  1..393
                        note = SLO(deltaC101) fragment W535A - non-natural Amino
                         Acid (e.g. pAMF) mutant 10 -w/oleader, with G overhang
                         from cleavage
VARIANT                 35
                        note = non-natural Amino Acid (e.g pAMF)
VARIANT                 74
                        note = non-natural Amino Acid (e.g pAMF)
VARIANT                 112
                        note = non-natural Amino Acid (e.g pAMF)
VARIANT                 195
                        note = non-natural Amino Acid (e.g pAMF)
VARIANT                 280
                        note = non-natural Amino Acid (e.g pAMF)
VARIANT                 330
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 71
GAPKEMPLES AEKEEKKSED KKKSEEDHTE EINDXIYSLN YNELEVLAKN GETIENFVPK  60
EGVKKADKFI VIEXKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVKTN  300
GKYSDILENS SFTAVVLGGD AAEHNKVVTX DFDVIRNVIK DNATFSRKNP AYPISYTSVF  360
LKNNKIAGVN NRTEYVETTS TEYTSGXINL SHQ                               393

SEQ ID NO: 72           moltype = AA  length = 393
FEATURE                 Location/Qualifiers
REGION                  1..393
                        note = SLO(deltaC101) fragment W535A - non-natural Amino
                         Acid (e.g. pAMF) mutant 10 -w/oleader, with G overhang
                         from cleavage
VARIANT                 21
                        note = non-natural Amino Acid (e.g pAMF)
VARIANT                 74
                        note = non-natural Amino Acid (e.g pAMF)
VARIANT                 112
                        note = non-natural Amino Acid (e.g pAMF)
VARIANT                 246
                        note = non-natural Amino Acid (e.g pAMF)
VARIANT                 298
                        note = non-natural Amino Acid (e.g pAMF)
VARIANT                 330
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 72
GAPKEMPLES AEKEEKKSED XKKSEEDHTE EINDKIYSLN YNELEVLAKN GETIENFVPK  60
EGVKKADKFI VIEXKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSKILDGT LGIDFKSISK GEKKVMIAAY KQIFYTVSAN LPNNPADVFD  240
KSVTFXELQR KGVSNEAPPL FVSNVAYGRT VFVKLETSSK SNDVEAAFSA ALKGTDVXTN  300
GKYSDILENS SFTAVVLGGD AAEHNKVVTX DFDVIRNVIK DNATFSRKNP AYPISYTSVF  360
LKNNKIAGVN NRTEYVETTS TEYTSGXINL SHQ                               393

SEQ ID NO: 73           moltype = AA  length = 393
FEATURE                 Location/Qualifiers
REGION                  1..393
                        note = SLO(deltaC101) fragment W535A - non-natural Amino
                         Acid (e.g. pAMF) mutant 10 -w/oleader, with G overhang
                         from cleavage
VARIANT                 35
                        note = non-natural Amino Acid (e.g pAMF)
VARIANT                 112
                        note = non-natural Amino Acid (e.g pAMF)
VARIANT                 195
                        note = non-natural Amino Acid (e.g pAMF)
```

-continued

```
VARIANT                 280
                        note = non-natural Amino Acid (e.g pAMF)
VARIANT                 298
                        note = any naturally occurring amino acid
VARIANT                 330
                        note = non-natural Amino Acid (e.g pAMF)
VARIANT                 387
                        note = non-natural Amino Acid (e.g pAMF)
source                  1..393
                        mol_type = protein
                        organism = synthetic construct
SEQUENCE: 73
GAPKEMPLES AEKEEKKSED KKKSEEDHTE EINDXIYSLN YNELEVLAKN GETIENFVPK  60
EGVKKADKFI VIERKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFKELQR KGVSNEAPPL FVSNVAYGRT VFVKLETSSX SNDVEAAFSA ALKGTDVXTN  300
GKYSDILENS SFTAVVLGGD AAEHNKVVTX DFDVIRNVIK DNATFSRKNP AYPISYTSVF  360
LKNNKIAGVN NRTEYVETTS TEYTSGXINL SHQ                               393

SEQ ID NO: 74           moltype = AA  length = 393
FEATURE                 Location/Qualifiers
REGION                  1..393
                        note = SLO(deltaC101) fragment W535A - non-natural Amino
                         Acid (e.g. pAMF) mutant 10 -w/oleader, with G overhang
                         from cleavage
VARIANT                 21
                        note = non-natural Amino Acid (e.g pAMF)
VARIANT                 35
                        note = non-natural Amino Acid (e.g pAMF)
VARIANT                 74
                        note = non-natural Amino Acid (e.g pAMF)
VARIANT                 112
                        note = non-natural Amino Acid (e.g pAMF)
VARIANT                 195
                        note = non-natural Amino Acid (e.g pAMF)
VARIANT                 246
                        note = non-natural Amino Acid (e.g pAMF)
VARIANT                 280
                        note = non-natural Amino Acid (e.g pAMF)
VARIANT                 298
                        note = non-natural Amino Acid (e.g pAMF)
source                  1..393
                        mol_type = protein
                        organism = synthetic construct
SEQUENCE: 74
GAPKEMPLES AEKEEKKSED XKKSEEDHTE EINDXIYSLN YNELEVLAKN GETIENFVPK  60
EGVKKADKFI VIEXKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFXELQR KGVSNEAPPL FVSNVAYGRT VFVKLETSSX SNDVEAAFSA ALKGTDVXTN  300
GKYSDILENS SFTAVVLGGD AAEHNKVVTK DFDVIRNVIK DNATFSRKNP AYPISYTSVF  360
LKNNKIAGVN NRTEYVETTS TEYTSGKINL SHQ                               393

SEQ ID NO: 75           moltype = AA  length = 393
FEATURE                 Location/Qualifiers
REGION                  1..393
                        note = SLO(deltaC101) fragment W535A - non-natural Amino
                         Acid (e.g. pAMF) mutant 10 -w/oleader, with G overhang
                         from cleavage
VARIANT                 21
                        note = non-natural Amino Acid (e.g pAMF)
VARIANT                 74
                        note = non-natural Amino Acid (e.g pAMF)
VARIANT                 112
                        note = non-natural Amino Acid (e.g pAMF)
VARIANT                 195
                        note = non-natural Amino Acid (e.g pAMF)
VARIANT                 246
                        note = non-natural Amino Acid (e.g pAMF)
VARIANT                 280
                        note = non-natural Amino Acid (e.g pAMF)
VARIANT                 330
                        note = non-natural Amino Acid (e.g pAMF)
VARIANT                 387
                        note = non-natural Amino Acid (e.g pAMF)
source                  1..393
                        mol_type = protein
                        organism = synthetic construct
```

-continued

```
SEQUENCE: 75
GAPKEMPLES AEKEEKKSED XKKSEEDHTE EINDKIYSLN YNELEVLAKN GETIENFVPK  60
EGVKKADKFI VIEXKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFXELQR KGVSNEAPPL FVSNVAYGRT VFVKLETSSX SNDVEAAFSA ALKGTDVKTN  300
GKYSDILENS SFTAVVLGGD AAEHNKVVTX DFDVIRNVIK DNATFSRKNP AYPISYTSVF  360
LKNNKIAGVN NRTEYVETTS TEYTSGXINL SHQ                               393

SEQ ID NO: 76          moltype = AA  length = 393
FEATURE                Location/Qualifiers
REGION                 1..393
                       note = SLO(deltaC101) fragment W535A - non-natural Amino
                        Acid (e.g. pAMF) mutant 10 -w/oleader, with G overhang
                        from cleavage
VARIANT                35
                       note = non-natural Amino Acid (e.g pAMF)
VARIANT                112
                       note = non-natural Amino Acid (e.g pAMF)
VARIANT                195
                       note = non-natural Amino Acid (e.g pAMF)
VARIANT                246
                       note = non-natural Amino Acid (e.g pAMF)
VARIANT                280
                       note = non-natural Amino Acid (e.g pAMF)
VARIANT                298
                       note = non-natural Amino Acid (e.g pAMF)
VARIANT                330
                       note = non-natural Amino Acid (e.g pAMF)
VARIANT                387
                       note = non-natural Amino Acid (e.g pAMF)
source                 1..393
                       mol_type = protein
                       organism = synthetic construct
SEQUENCE: 76
GAPKEMPLES AEKEEKKSED KKKSEEDHTE EINDXIYSLN YNELEVLAKN GETIENFVPK  60
EGVKKADKFI VIERKKKNIN TTPVDISIID SVTDRTYPAA LQLANKGFTE NXPDAVVTKR  120
NPQKIHIDLP GMGDKATVEV NDPTYANVST AIDNLVNQWH DNYSGGNTLP ARTQYTESMV  180
YSKSQIEAAL NVNSXILDGT LGIDFKSISK GEKKVMIAAY KQIFYTVSAN LPNNPADVFD  240
KSVTFXELQR KGVSNEAPPL FVSNVAYGRT VFVKLETSSX SNDVEAAFSA ALKGTDVXTN  300
GKYSDILENS SFTAVVLGGD AAEHNKVVTX DFDVIRNVIK DNATFSRKNP AYPISYTSVF  360
LKNNKIAGVN NRTEYVETTS TEYTSGXINL SHQ                               393
```

GROUP A STREP IMMUNOGENIC COMPOSITIONS WITH POLYSACCHARIDE-PROTEIN CONJUGATES

CROSS-REFERENCE TO RELATED APPLICATIONS

This application is a continuation of International Application No. PCT/US2021/018402, filed Feb. 17, 2021, which claims the benefit of U.S. Provisional Application No. 62/977,886, filed Feb. 18, 2020; U.S. Provisional Application No. 63/013,924, filed Apr. 22, 2020; U.S. Provisional Application No. 63/090,069, filed Oct. 9, 2020; and U.S. Provisional Application No. 63/123,293, filed Dec. 9, 2020, the disclosure of each of which is hereby incorporated by reference in its entirety.

STATEMENT OF GOVERNMENT INTEREST

This invention was made with the support of the United States government under grant number 93.360, subaward 4500003905, awarded by the Health and Human Services Office of the Assistant Secretary for Preparedness and Response (HHS/ASPR) under the CARB-X Pass Through Entity. The government has certain rights in the invention.

DESCRIPTION OF THE TEXT FILE SUBMITTED ELECTRONICALLY

The sequence listing XML associated with this application is provided in XML file format and is hereby incorporated by reference into the specification. The name of the XML file containing the sequence listing XML is STRO_011_04US_ST26.xml. The XML file is 202,126 bytes, was created on Aug. 17, 2022, and is being submitted electronically via USPTO Patent Center.

FIELD

The present application relates to the fields of microbiology and vaccine development.

BACKGROUND

Group A *Streptococcus* (GAS) is a preeminent human pathogen causing 700 million cases of pharyngitis ('strep throat') annually worldwide and increasing cases of severe invasive infections, sepsis, necrotizing fasciitis, otitis media, and toxic shock syndrome. Pharyngitis is highly prevalent in school-age children and a major source of antibiotic prescriptions worldwide; driving selective pressure for resistance throughout the human microflora. GAS is also responsible for post-infectious immune-mediated rheumatic heart disease (RHD), a leading cause of mortality in the developing world. Some 30 million people are currently affected by RHD, with over 300,000 deaths annually (60%<age 70) and 11.5 million disability-adjusted life years lost.

BRIEF SUMMARY

In some embodiments, the present disclosure provides an immunogenic composition comprising a first Group A *Streptococcus* (GAS) polypeptide antigen; a second GAS polypeptide antigen; and at least one polypeptide-polysaccharide conjugate, wherein the conjugate polypeptide is a third GAS polypeptide antigen or a non-GAS carrier polypeptide and comprises at least one non-natural amino acid (nnAA), and wherein the conjugate polysaccharide is a GAS polysaccharide or a variant thereof that lacks an immunodominant N-acetyl Glucosamine (GlcNAc) side chain.

In some embodiments, at least one of the GAS polypeptide antigens is a full length GAS antigen. In some embodiments, at least one of the GAS polypeptide antigens is a peptide fragment of a full length GAS antigen. In some embodiments, the first and second GAS polypeptide antigens are independently selected from C5a peptidase, streptolysin O (SLO), Sib35, and Sfb1. In some embodiments, the first and second GAS polypeptide antigens are C5a peptidase and SLO.

In some embodiments, the C5a peptidase polypeptide antigen comprises an amino acid sequence that is at least 95% identical to SEQ ID NO: 1 or SEQ ID NO: 3. In some embodiments, the C5a peptidase polypeptide antigen comprises the amino acid sequence of SEQ ID NO: 1 or SEQ ID NO: 3. In some embodiments, the C5a peptidase polypeptide antigen comprises the amino acid sequence of SEQ ID NO: 29 or SEQ ID NO: 30.

In some embodiments, the SLO polypeptide antigen comprises an amino acid sequence that is at least 95% identical to SEQ ID NO: 5 or SEQ ID NO: 7. In some embodiments, the SLO polypeptide antigen comprises the amino acid sequence of SEQ ID NO: 5 or SEQ ID NO: 7. In some embodiments, the SLO polypeptide antigen comprises an amino acid sequence that is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53. In some embodiments, the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53. In some embodiments, the SLO polypeptide antigen comprises an amino acid sequence that is at least 95% identical to SEQ ID NO: SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, or SEQ ID NO: 64. In some embodiments, the SLO polypeptide antigen comprises the amino acid sequence of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, or SEQ ID NO: 64.

In some embodiments, the non-GAS carrier polypeptide is ferritin. In some embodiments, the third GAS polypeptide antigen or non-GAS carrier polypeptide is selected from *Streptococcus pyogenes* Adhesion and Division (SpyAD) polypeptide, arginine deiminase (ADI), SEQ ID NO: 25, and Protein D. In some embodiments, the third GAS polypeptide antigen is SLO.

In some embodiments, the at least one nnAA is substituted for a lysine, a leucine, or an isoleucine in the conjugate polypeptide. In some embodiments, the at least one nnAA is substituted for a lysine, a leucine, an arginine, or an isoleucine in the conjugate polypeptide. In some embodiments, the nnAA comprises a click chemistry reactive group. In some embodiments, the nnAA is selected from 2-amino-3-(4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl) propanoic acid (pAMF), 2-amino-3-(5-(azidomethyl) pyridin-2-yl)propanoic acid, 2-amino-3-(4-(azidomethyl) pyridin-2-yl)propanoic acid, 2-amino-3-(6-(azidomethyl)

pyridin-3-yl)propanoic acid, and 2-amino-5-azidopentanoic acid. In some embodiments, the nnAA is pAMF.

In some embodiments, the conjugate polypeptide is a third GAS protein, which is a SpyAD polypeptide and comprises an amino acid sequence that is at least 95% identical to SEQ ID NO: 9. In some embodiments, the Spy AD polypeptide comprises a pAMF substitution at positions K64, K287, K386, and K657 of SEQ ID NO: 9. In some embodiments, the Spy AD polypeptide comprises the amino acid sequence of SEQ ID NO: 9 or SEQ ID NO: 11. In some embodiments, the conjugate polypeptide is a third GAS protein, which is a Spy AD polypeptide and comprises an amino acid sequence that is at least 95% identical to SEQ ID NO: 33. In some embodiments, the Spy AD polypeptide comprises a pAMF substitution at positions K64, K287, K386, and K657 of SEQ ID NO: 33. In some embodiments, the Spy AD polypeptide comprises the amino acid sequence of SEQ ID NO: 33 or SEQ ID NO: 34.

In some embodiments, the conjugate polypeptide is a third GAS polypeptide, which is an ADI polypeptide and comprises an amino acid sequence that is at least 95% identical to SEQ ID NO: 13 or SEQ ID NO: 15. In some embodiments, the ADI polypeptide comprises a pAMF substitution at positions K15, K193, and K316 of SEQ ID NO: 13 or SEQ ID NO: 15. In some embodiments, the ADI polypeptide comprises the amino acid sequence of SEQ ID NO: 17 or SEQ ID NO: 19. In some embodiments, the conjugate polypeptide is a third GAS polypeptide, which is an ADI polypeptide and comprises an amino acid sequence that is at least 95% identical to SEQ ID NO: 35 or SEQ ID NO: 36. In some embodiments, the ADI polypeptide comprises a pAMF substitution at positions K15, K193, and K316 of SEQ ID NO: 35 or SEQ ID NO: 36. In some embodiments, the ADI polypeptide comprises the amino acid sequence of SEQ ID NO: 35 or SEQ ID NO: 36.

In some embodiments, the conjugate polypeptide is a ferritin polypeptide and comprises an amino acid sequence that is at least 95% identical to SEQ ID NO: 21. In some embodiments, the ferritin polypeptide comprises a pAMF substitution at position 15 of SEQ ID NO: 21. In some embodiments, the ferritin polypeptide comprises the amino acid sequence of SEQ ID NO: 23.

In some embodiments, the conjugate polysaccharide comprises a polyrhamnose core. In some embodiments, the conjugate polysaccharide has an average molecular weight of about 5 kDa to about 7 kDa. In some embodiments, the conjugate polysaccharide is a tetramer, a hexamer, an octamer, or a decamer polysaccharide. In some embodiments, the conjugate polysaccharide has an average molecular weight of about 10 kDa to 40 kDa.

In some embodiments, the present disclosure provides an immunogenic composition comprising a Group A *Streptococcus* (GAS) C5a peptidase polypeptide antigen; a GAS streptolysin O (SLO) polypeptide antigen; and a polypeptide-polysaccharide conjugate comprising a *Streptococcus pyogenes* Adhesion and Division (SpyAD) conjugate polypeptide and a GAS conjugate polysaccharide or a variant thereof that lacks an immunodominant N-acetyl Glucosamine (GlcNAc) side chain. In some embodiments, the SpyAD protein comprises an amino acid sequence that is at least 95% identical to SEQ ID NO: 9 and comprises a pAMF substitution at positions K64, K287, K386, and K657. In some embodiments, the SpyAD protein comprises the amino acid sequence of SEQ ID NO: 9 or SEQ ID NO: 11. In some embodiments, the SpyAD protein comprises an amino acid sequence that is at least 95% identical to SEQ ID NO: 33 and comprises a pAMF substitution at positions K64, K287, K386, and K657. In some embodiments, the SpyAD protein comprises the amino acid sequence of SEQ ID NO: 33 or SEQ ID NO: 34. In some embodiments, the SpyAD protein comprises the amino acid sequence of SEQ ID NO: 9 or SEQ ID NO: 34

In some embodiments, the present disclosure provides an immunogenic composition comprising a Group A *Streptococcus* (GAS) C5a peptidase polypeptide antigen; a GAS streptolysin O (SLO) polypeptide antigen; and a polypeptide-polysaccharide conjugate comprising an arginine deiminase (ADI) conjugate polypeptide and a GAS conjugate polysaccharide or a variant thereof that lacks an immunodominant N-acetyl Glucosamine (GlcNAc) side chain. In some embodiments, the ADI polypeptide comprises an amino acid sequence that is at least 95% identical to SEQ ID NO: 13 or SEQ ID NO: 15 and comprises a pAMF substitution at positions K15, K193, and K316. In some embodiments, the ADI polypeptide comprises the amino acid sequence of SEQ ID NO: 17 or SEQ ID NO: 19. In some embodiments, the ADI polypeptide comprises an amino acid sequence that is at least 95% identical to SEQ ID NO: 35 or SEQ ID NO: 36 and comprises a pAMF substitution at positions K15, K193, and K316. In some embodiments, the ADI polypeptide comprises the amino acid sequence of SEQ ID NO: 37 or SEQ ID NO: 38

In some embodiments, the present disclosure provides an immunogenic composition comprising a Group A *Streptococcus* (GAS) C5a peptidase polypeptide antigen; a GAS streptolysin O (SLO) polypeptide antigen; and a polypeptide-polysaccharide conjugate comprising a ferritin polypeptide and a GAS conjugate polysaccharide or a variant thereof that lacks an immunodominant N-acetyl Glucosamine (GlcNAc) side chain. In some embodiments, the ferritin protein comprises an amino acid sequence that is at least 95% identical to SEQ ID NO: 21 and comprises a pAMF substitution at position 15. In some embodiments, the ferritin protein comprises the amino acid sequence of SEQ ID NO: 23.

In some embodiments, the composition comprises about 10% to about 50% of the first GAS antigen, about 10% to about 50% of the second GAS antigen, and about 10% to about 50% of the polypeptide-polysaccharide conjugate. In some embodiments, the composition further comprises one or more adjuvants selected from alum, saponin, monophosphoryl lipid A (MPL), or combinations thereof. In some embodiments, the composition comprises Alhydogel.

In some embodiments, the present disclosure provides a method of inducing a protective immune response against a Group A *Streptococcus* (GAS) bacterium in a subject comprising administering an immunogenic composition described herein to the subject.

In some embodiments, the subject is 18 years or older. In some embodiments, the subject is less than 18 years old. In some embodiments, the subject is between 5 years and 17 years old, between 6 months and 9 years old, or between 5 years and 9 years old.

In some embodiments, the GAS bacterium is of a serotype selected from M1, M2, M3, M4, M6, M11, M12, M22, M28, M75, and M89. In some embodiments, the GAS bacterium is a serotype selected from M1, M3, M5, M9, M12, M18, M22, M25, M28, M71, M72, and M74. In some embodiments, the GAS bacterium is a serotype selected from M1, M4, M6, M11, M12, M22, M44, M75, M77, M77, and M81. In some embodiments, the GAS bacterium is a serotype selected from M1, M2, M3, M4, M6, M9, M12, M18, M22, M75, M77, M89, and M92. In some embodiments, the GAS bacterium is a serotype selected from M1, M2, M3, M4, M5, M6, M9, M11, M12, M13, M28, M62, and M89. In some embodiments, the GAS bacterium is a serotype selected from M1, M2, M3, M4, M6, M12, M22, M28, M49, M53, M68, M77, M80, M83, M87, M89, and M92.

In some embodiments, the immunogenic composition induces an antibody response in the subject against the Group A *Streptococcus* (GAS) bacterium and does not induce an antibody response in the subject against human tissue. In some embodiments, the immunogenic composition induces a protective immune response against a *Shigella* bacterium in the subject, wherein the *Shigella* bacterium comprises a polysaccharide with a polyrhmanose backbone.

In some embodiments, the present disclosure provides a method of inducing a protective immune response against a *Shigella* bacterium in a subject comprising administering an immunogenic composition described herein to the subject. In some embodiments, the present disclosure provides a use of an immunogenic composition described herein for inducing a protective immune response against a *Shigella* bacterium in a subject. In some embodiments, the present disclosure provides a use of an immunogenic composition described herein in the manufacture of a medicament for inducing a protective immune response against a *Shigella* bacterium in a subject. In some embodiments, the subject is 18 years or older. In some embodiments, the subject is less than 18 years old. In some embodiments, the subject is between 5 years and 17 years old, between 6 months and 9 years old, or between 5 years and 9 years old.

BRIEF DESCRIPTION OF THE DRAWINGS

FIG. 28 shows conditions for the conjugation of SLO variants to DBCO-GAC.

DETAILED DESCRIPTION

Overview

Figure 1A:
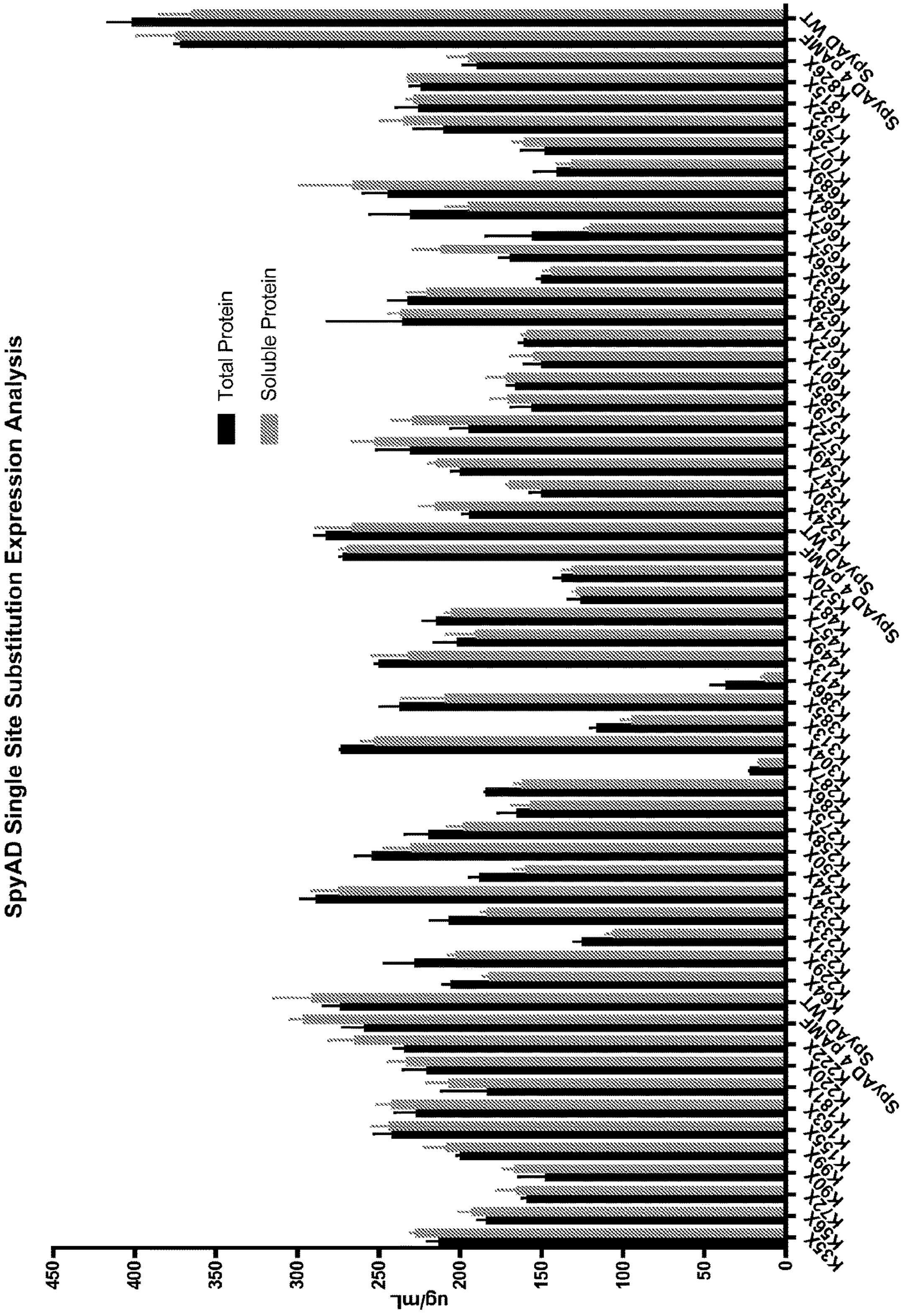
FIG. 1A and FIG. 1B show the expression levels of native polypeptide antigens and non-natural amino acids containing polypeptide antigens used for making conjugates with GAS polysaccharide.

Despite high global demand, there is no safe and efficacious commercial vaccine against GAS. Features of the pathogen pose particular challenges to vaccination, including its invariant capsule of hyaluronic acid, an immunologically inert carbohydrate ubiquitous in connective tissues. Furthermore, the immunodominant surface-anchored GAS M proteins are highly polymorphic (>200 emm types), and regions of their dimeric coiled-coil structure may provoke an autoimmune response against cardiac tissue in rheumatic heart disease (RHD). The World Health Organization, International Vaccine Institute, Wellcome Trust, Gates Foundation and others have recently convened in advisories on GAS vaccine development to address these significant scientific challenges and meet this paramount global health need.

Group A *Streptococcus*

Group A *streptococcus* (GAS) bacteria is a Gram positive, beta-hemolytic coccus in chains. It is responsible for a range of diseases in humans. These diseases include strep throat (acute pharyngitis), otitis media, and skin and soft tissue infections such impetigo and cellulitis. These can also include rare cases of invasive (serious) illnesses such as necrotizing fasciitis (flesh eating disease) and toxic shock syndrome (TSS). Several virulence factors contribute to the pathogenesis of GAS, such as M protein, hemolysins, and extracellular enzymes.

GAS vaccinology has been focused largely on the cell wall-anchored M protein. Historical studies administered crude whole M protein preparations to human volunteers, which was followed by challenge with live GAS bacteria in the pharynx. While these preparations decreased GAS colonization, an increased incidence of acute rheumatic fever (ARF) was reported for some of the immunized subjects. Two N-terminal M protein vaccine preparations have reached human clinical trials to date: a hexavalent preparation (Dale J B. 1999. Vaccine, 17:193-200; Kotloff et al, 2004. JAMA 292:709-715; Hall et al., 2004. Infect. Immun. 72:2507-2512) and a 26-valent preparation (Hu et al., 2002. Infect. Immun. 70:2171-2177; McNeil et al., 2005. Clin. Infect. Dis. 41:1114-1122). These preparations were well tolerated in adult volunteers. More recently, a similar multivalent vaccine was developed, which includes N-terminal peptides representing 30 GAS serotypes (Dale et al., 2011. Vaccine 29:8175-8178.). Sera raised against this experimental vaccine exhibited bactericidal activity against all 30 vaccine serotypes as well as 24 (of 40 tested) nonvaccine serotypes. While such preparations have been shown to have the capacity to protect against select nonvaccine serotypes, they do not protect against all globally circulating serotypes (Abdissa et al., 2006. Clin. Infect. Dis. 42:1362-1367; Ikebe et al., Working Group for Beta-Haemolytic Streptococci in Japan. 2007. 2001-2005. Epidemiol. Infect. 135:1227-1229; Nir-Paz et al., 2010. Epidemiol. Infect. 138:53-60; Steer et al., 2009. Lancet Infect. Dis. 9:611-616; O'Loughlin et al., 2007. Clin. Infect. Dis. 45:853-862). The 30 serotypes included are based on those prevalent in North America and Europe (Dale J B et al., 2011. Vaccine 29:8175-8178.), which often differ from the diverse serotypes isolated in regions of endemicity. The use of GAS proteins and Protein-GAC conjugates as vaccines has been recently reported (Di Benedetto, R. et al., 2020. J. Mol. Sci. no 22:8558), although these use non-specific conjugation methods that can disrupt both the B/T-cell epitopes on the carrier protein and the PS backbone. Furthermore, these conjugates were also made with thenative GAC, which harbors potentially cross-reactive GlcNAc immunodominant epitope.

Thus, there is a need in the art for improved vaccines against GAS.

Combination Vaccines

In some embodiments, the present disclosure provides an immunogenic composition comprising two or more GAS polypeptide antigens and a polypeptide-polysaccharide conjugate. For clarity, in compositions described herein, each polypeptide is different. For example, in compositions comprising a first, a second, and a third polypeptide antigen or polypeptide-polysaccharide conjugate, the first, second, and third polypeptides have different sequences.

GAS Antigens

In some embodiments, the immunogenic compositions of the present disclosure comprise two or more GAS polypeptide antigens. In some embodiments, the GAS polypeptide antigens are selected from C5a peptidase, streptolysin O (SLO), streptococcal immunoglobulin-binding protein 35 (Sib35), and Fibronectin binding protein F1 (Sfb1). In some embodiments, the GAS polypeptide antigens are selected from C5a peptidase, streptolysin O (SLO), streptococcal immunoglobulin-binding protein 35 (Sib35), Fibronectin binding protein F1 (Sfb1), and Adhesion and Division polypeptide (SpyAD). UniProt Reference Identifiers for each of these GAS antigens are provided in Table 1 below.

TABLE 1

UniProt References for exemplary GAS antigens

| Antigen | UniProt Ref |
|---|---|
| C5a | P15926 |
| SLO | P0C0I3 |
| Sib35 | Q1XG74 |
| Sfb1 | Q48VN7 |

In some embodiments, the GAS polypeptide antigens comprise the full length polypeptide antigen sequence. In some embodiments, the GAS polypeptide antigens comprise a fragment of the full length polypeptide antigen sequence. For example, in some embodiments, the immunogenic composition comprises a C5a GAS polypeptide antigen, wherein the C5a polypeptide is a fragment of the full length C5a polypeptide. In some embodiments, the C5a fragment comprises amino acids 90-1035 of the full length protein (e.g., comprises SEQ ID NO: 1, SEQ ID NO: 2, SEQ ID NO: 29, or SEQ ID NO: 30). In some embodiments, the immunogenic composition comprises an SLO GAS polypeptide antigen, wherein the SLO polypeptide is a fragment of the full length SLO polypeptide. In some embodiments, the SLO fragment comprises amino acids 79-571 of the full length protein (e.g., comprises SEQ ID NO: 5, SEQ ID NO: 6, SEQ ID NO: 31, or SEQ ID NO: 32).

In some embodiments, the GAS polypeptide antigens comprise one or more amino acid mutations in the wild-type amino acid sequence. For example, in some embodiments, the immunogenic composition comprises a C5a GAS polypeptide antigen, wherein the C5a polypeptide comprises one or more amino acid mutations. In some embodiments, the amino acid mutations are D131A and S513A (e.g., SEQ ID NO: 3, SEQ ID NO: 4, or SEQ ID NO: 30). In some embodiments, the immunogenic composition comprises an SLO GAS polypeptide antigen, wherein the SLO polypeptide comprises one or more amino acid mutations. In some embodiments, the amino acid mutation is W535A (e.g., SEQ ID NO: 7, SEQ ID NO: 8, or SEQ ID NO: 32).

Amino acid sequences of exemplary GAS antigen are provided below in Table 2. Mutated amino acids are indicated in bolded text. In some embodiments, the underlined and italicized amino acids are cleaved from the mature GAS antigens.

TABLE 2

Exemplary GAS Antigens

| Antigen | Amino Acid Sequence | SEQ ID: |
|---|---|---|
| SLO [79-571 fragment] WT w/ His tag and TEV sequence | *MHHHHHHGSGENLYFQG*APKEMPLESAEKEEKKSEDKKKSEEDHTE<br>EINDKIYSLNYNELEVLAKNGETIENFVPKEGVKKADKFIVIERKK<br>KNINTTPVDISIIDSVTDRTYPAALQLANKGFTENKPDAVVTKRNP<br>QKIHIDLPGMGDKATVEVNDPTYANVSTAIDNLVNQWHDNYSGGNT<br>LPARTQYTESMVYSKSQIEAALNVNSKILDGTLGIDEKSISKGEKK<br>VMIAAYKQIFYTVSANLPNNPADVEDKSVTFKELQRKGVSNEAPPL<br>FVSNVAYGRTVFVKLETSSKSNDVEAAFSAALKGTDVKINGKYSDI<br>LENSSFTAVVLGGDAAEHNKVVTKDEDVIRNVIKDNATFSRKNPAY<br>PISYTSVELKNNKIAGVNNRTEYVETTSTEYTSGKINLSHQGAYVA<br>QYEILWDEINYDDKGKEVITKRRWDNNWYSKTSPFSTVIPLGANSR<br>NIRIMARECTGLAWEWWRKVIDERDVKLSKEINVNISGSTLSPYGS<br>ITYK | 5 |
| SLO [79-571 fragment] W535A w/ leader | *MHHHHHHGSGENLYFQG*APKEMPLESAEKEEKKSEDKKKSEEDHTE<br>EINDKIYSLNYNELEVLAKNGETIENFVPKEGVKKADKFIVIERKK<br>KNINTTPVDISIIDSVTDRTYPAALQLANKGFTENKPDAVVTKRNP<br>QKIHIDLPGMGDKATVEVNDPTYANVSTAIDNLVNQWHDNYSGGNT<br>LPARTQYTESMVYSKSQIEAALNVNSKILDGTLGIDEKSISKGEKK<br>VMIAAYKQIFYTVSANLPNNPADVEDKSVTEKELQRKGVSNEAPPL<br>FVSNVAYGRTVFVKLETSSKSNDVEAAFSAALKGTDVKINGKYSDI<br>LENSSFTAVVLGGDAAEHNKVVTKDEDVIRNVIKDNATESRKNPAY<br>PISYTSVFLKNNKIAGVNNRTEYVETTSTEYTSGKINLSHQGAYVA<br>QYEILWDEINYDDKGKEVITKRRWDNNWYSKTSPESTVIPLGANSR<br>NIRIMARECTGLA**A**EWWRKVIDERDVKLSKEINVNISGSTLSPYGS<br>ITYK | 7 |
| SLO(ΔC101) fragment W535A w/o leader, with G overhang from cleavage | GAPKEMPLESAEKEEKKSEDKKKSEEDHTEEINDKIYSLNYN<br>ELEVLAKNGETIENFVPKEGVKKADKFIVIERKKKNINTTPV<br>DISIIDSVTDRTYPAALQLANKGFTENKPDAVVTKRNPQKIH<br>IDLPGMGDKATVEVNDPTYANVSTAIDNLVNQWHDNYSGGNT<br>LPARTQYTESMVYSKSQIEAALNVNSKILDGTLGIDFKSISK<br>GEKKVMIAAYKQIFYTVSANLPNNPADVEDKSVTFKELQRKG<br>VSNEAPPLFVSNVAYGRTVFVKLETSSKSNDVEAAFSAALKG<br>TDVKTNGKYSDILENSSFTAVVLGGDAAEHNKVVTKDEDVIR<br>NVIKDNATFSRKNPAYPISYTSVFLKNNKIAGVNNRTEYVET<br>TSTEYTSGKINLSHQ | 53 |
| C5a [90-1035 fragment] WT w/ leader | *MHHHHHHGSGENLYFQG*KTADTPVTSKATIRDLNDPSQVKTLQEKA<br>GKGAGTVVAVIDAGEDKNHEAWRLTDKTKARYQSKEDLEKAKKEHG<br>ITYGEWVNDKVAYYHDYSKDGKTAVDQEHGTHVSGILSGNAPSETK<br>EPYRLEGAMPEAQLLLMRVEIVNGLADYARNYAQAIRDAVNLGAKV<br>INMSFGNAALAYANLPDETKKAFDYAKSKGVSIVTSAGNDSSEGGK<br>TRLPLADHPDYGVVGTPAAADSTLTVASYSPDKQLTETATVKTADK<br>QDKEMPVLSTNRFEPNKAYDYAYANRGMKEDDEKDVKGKIALIERG<br>DIDFKDKIANAKKAGAVGVLIYDNQDKGFPIELPNVDQMPAAFISR<br>KDGLLLKDNPKKTITFNATPKVLPTASGTKLSRESSWGLTADGNIK<br>PDIAAPGQDILSSVANNKYAKLSGTSMSAPLVAGIMGLLQKQYETQ<br>YPDMTPSERLDLAKKVLMSSATALYDEDEKAYESPRQQGAGAVDAK<br>KASAATMYVTDKDNTSSKVHLNNVSDTFEVTVTVHNKSDKPQELYY<br>QATVQTDKVDGKHFALAPKALYETSWQKITIPANSSKQVTVPIDAS<br>RFSKDLLAQMKNGYFLEGFVRFKQDPTKEELMSIPYIGERGDEGNL<br>SALEKPIYDSKDGSSYYHEANSDAKDQLDGDGLQFYALKNNFTALT<br>TESNPWTIIKAVKEGVENIEDIESSEITETIFAGTFAKQDDDSHYY<br>IHRHANGKPYAAISPNGDGNRDYVQFQGTFLRNAKNLVAEVLDKEG<br>NVVWTSEVTEQVVKNYNNDLASTLGSTRFEKTRWDGKDKDGKVVAN<br>GTYTYRVRYTPISSGAKEQHTDEDVIVDNTTPEVATSATESTEDRR<br>LTLASKPKTSQPVYRERIAYTYMDEDLPTTEYISPNEDGTFTLPEE<br>AETMEGATVPLKMSDFTYVVEDMAGNITYTPVTKLLEGHSNK | 1 |

TABLE 2-continued

Exemplary GAS Antigens

| Antigen | Amino Acid Sequence | SEQ ID: |
|---|---|---|
| C5a [90-1035 fragment] D131A/S513A w/ leader | *MHHHHHHGSGENLYFQ*GKTADTPVTSKATIRDLNDPSQVKTLQEKA<br>GKGAGTVVAVI**A**AGEDKNHEAWRLTDKTKARYQSKEDLEKAKKEHG<br>ITYGEWVNDKVAYYHDYSKDGKTAVDQEHGTHVSGILSGNAPSETK<br>EPYRLEGAMPEAQLLLMRVEIVNGLADYARNYAQAIRDAVNLGAKV<br>INMSFGNAALAYANLPDETKKAFDYAKSKGVSIVTSAGNDSSEGGK<br>TRLPLADHPDYGVVGTPAAADSTLTVASYSPDKQLTETATVKTADK<br>QDKEMPVLSTNRFEPNKAYDYAYANRGMKEDDEKDVKGKIALIERG<br>DIDFKDKIANAKKAGAVGVLIYDNQDKGFPIELPNVDQMPAAFISR<br>KDGLLLKDNPKKTITFNATPKVLPTASGTKLSRESSWGLTADGNIK<br>PDIAAPGQDILSSVANNKYAKLSGT**A**MSAPLVAGIMGLLQKQYETQ<br>YPDMTPSERLDLAKKVLMSSATALYDEDEKAYESPRQQGAGAVDAK<br>KASAATMYVTDKDNTSSKVHLNNVSDTFEVTVTVHNKSDKPQELYY<br>QATVQTDKVDGKHFALAPKALYETSWQKITIPANSSKQVTVPIDAS<br>RFSKDLLAQMKNGYFLEGFVRFKQDPTKEELMSIPYIGERGDEGNL<br>SALEKPIYDSKDGSSYYHEANSDAKDQLDGDGLQFYALKNNFTALT<br>TESNPWTIIKAVKEGVENIEDIESSEITETIFAGTFAKQDDDSHYY<br>IHRHANGKPYAAISPNGDGNRDYVQFQGTFLRNAKNLVAEVLDKEG<br>NVVWTSEVTEQVVKNYNNDLASTLGSTRFEKTRWDGKDKDGKVVAN<br>GTYTYRVRYTPISSGAKEQHTDEDVIVDNTTPEVATSATESTEDRR<br>LTLASKPKTSQPVYRERIAYTYMDEDLPTTEYISPNEDGTFTLPEE<br>AETMEGATVPLKMSDFTYVVEDMAGNITYTPVTKLLEGHSNK | 3 |

Residue positions in Table 2, above, and elsewhere in this disclosure, refer to the residue numbering according to the residue position in the full length sequences (e.g., as identified in Tables 1 and 3 by reference to the UniProt sequence database) for identifying the fragments and/or lysine residues modified by nnAA (e.g., pAMF replacements of certain lysine residues).

In some embodiments, the immunogenic composition comprises a C5a GAS polypeptide antigen comprising or consisting of an amino acid sequence that is at least 95%, 95%, 97%, 98%, or 99% identical to any one of SEQ ID NOs: 1-4. In some embodiments, the immunogenic composition comprises a C5a GAS polypeptide antigen comprising or consisting of an amino acid sequence that is at least 95%, 95%, 97%, 98%, or 99% identical to any one of SEQ ID NOs: 29-30. In some embodiments, the immunogenic composition comprises a C5a GAS polypeptide antigen comprising or consisting of the amino acid sequence of any one of SEQ ID NOs: 1-4. In some embodiments, the immunogenic composition comprises a C5a GAS polypeptide antigen comprising or consisting of the amino acid sequence of any one of SEQ ID NOs: 29-30. In some embodiments, the immunogenic composition comprises an SLO GAS polypeptide antigen comprising or consisting of an amino acid sequence that is at least 95%, 95%, 97%, 98%, or 99% identical to any one of SEQ ID NOs: 5-8. In some embodiments, the immunogenic composition comprises an SLO GAS polypeptide antigen comprising or consisting of an amino acid sequence that is at least 95%, 95%, 97%, 98%, or 99% identical to any one of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53. In some embodiments, the immunogenic composition comprises an SLO GAS polypeptide antigen comprising or consisting of the amino acid sequence of any one of SEQ ID NOs: 5-8. In some embodiments, the immunogenic composition comprises an SLO GAS polypeptide antigen comprising or consisting of the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53. In some embodiments, the immunogenic composition comprises a SpyAD GAS polypeptide antigen comprising or consisting of an amino acid sequence that is at least 95%, 95%, 97%, 98%, or 99% identical to SEQ ID NO: 10 or 33. In some embodiments, the immunogenic composition comprises a SpyAD GAS polypeptide antigen comprising or consisting of the amino acid sequence of SEQ ID NO: 10 or 33.

Polypeptide-Polysaccharide Conjugates

In some embodiments, immunogenic compositions described herein comprise at least one polypeptide-polysaccharide conjugate. The polypeptide-polysaccharide conjugates comprise a conjugate polypeptide (also referred to as a carrier protein) and a polysaccharide conjugated to the conjugate polypeptide at one or more amino acid positions. In some embodiments, the conjugate polypeptide is selected from SpyAD, ADI, SEQ ID NO: 25, ferritin, and Protein D. UniProt Reference Identifiers for exemplary conjugate polypeptides are provided in Table 3 below.

TABLE 3

UniProt and CAS References for exemplary conjugate polypeptides

| Antigen | UniProt (or CAS) Ref |
|---|---|
| SpyAD | Q9A1H3 |
| ADI | P0C0B3 |
| Protein D | R4R7Q5 |
| ferritin | P02792 |
| CRM197 | (CAS: 1272033-67-6) |

In some embodiments, the conjugate polypeptides comprise the full length polypeptide antigen sequence. In some embodiments, the conjugate polypeptides comprise a fragment of the full length polypeptide sequence. For example, in some embodiments, the immunogenic composition comprises a polypeptide-polysaccharide conjugate wherein the conjugate polypeptide is SpyAD and is a fragment of the full length SpyAD polypeptide (e.g., SEQ ID NO: 9 or SEQ ID NO: 10). In some embodiments, the SpyAD fragment comprises amino acids 33-849 of the full length protein (e.g., comprises SEQ ID NO: 9 or SEQ ID NO: 10). In some embodiments, the immunogenic composition comprises a polypeptide-polysaccharide conjugate wherein the conjugate polypeptide is ADI and is a fragment of the full length ADI polypeptide (e.g., comprises SEQ ID NO: 13 or SEQ ID NO: 14). In some embodiments, the immunogenic composition comprises a polypeptide-polysaccharide conjugate wherein the conjugate polypeptide is ferritin and is a fragment of the full length ferritin polypeptide (e.g., SEQ ID NO: 21 or SEQ ID NO: 22).

In some embodiments, the conjugate polypeptide comprises one or more amino acid mutations in the wild-type amino acid sequence. For example, in some embodiments, the conjugate polypeptide is SpyAD, wherein the SpyAD polypeptide comprises one or more amino acid mutations. In some embodiments, the conjugate polypeptide is ADI, wherein the ADI polypeptide comprises one or more amino acid mutations. In some embodiments, the amino acid mutation is D277A (e.g., SEQ ID NO: 15 or SEQ ID NO: 16).

In some embodiments, the conjugate polypeptide comprises one or more non-natural amino acids (nnAA). In some embodiments, the one or more nnAA comprise a click chemistry reactive group. Herein, a "click chemistry reactive group" refers to a moiety, such as an azide or an alkyne, capable of undergoing a click chemistry reaction with a second click chemistry reactive group. In some embodiments, one click chemistry reactive group reacts with a second click chemistry reactive group to form a substituted triazole. Examples of this type of click reaction can be found, for instance, in International PCT Publication No. WO 2018/126229. General examples of metal-free click reactions used in biomedical applications can be found, for instance, in Kim, et al., Chemical Science, 2019, 10, 7835-7851. Examples of nnAAs comprising click chemistry reactive groups include 2-amino-3-(4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl) propanoic acid, 2-amino-3-(6-(azidomethyl)pyridin-3-yl)propanoic acid, and 2-amino-5-azidopentanoic acid. In some embodiments, the conjugate polypeptide comprises one or more nnAAs, wherein each of the nnAAs are pAMF.

Amino acid sequences of exemplary conjugate polypeptides are provided in Table 4 below. Sites suitable for substitution with an nnAA are indicated in bolded and underlined text. In some embodiments, the underlined and italicized amino acids are cleaved from the mature protein during production.

TABLE 4

Exemplary Carrier Proteins

| Protein | Amino Acid Sequence | SEQ ID: |
|---|---|---|
| ADI [full length] WT w/ leader | *MHHHHHHGSGENLYFQG*TAQTPIHVYSEIG**K**LKKVLLHRPG<br>KEIENLMPDYLERLLEDDIPFLEDAQKEHDAFAQALRDEGIEVLYL<br>ETLAAESLVTPEIREAFIDEYLSEANIRGRATKKAIRELLMAIEDN<br>QELIEKTMAGVQKSELPEIPASEKGLTDLVESNYPFAIDPMPNLYF<br>TRDPFATIGTGVSLNHMESETRNRETLYG**K**YIFTHHPIYGGGKVPM<br>VYDRNETTRIEGGDELVLSKDVLAVGISQRTDAASIEKLLVNIFKQ<br>NLGFKKVLAFEFANNRKFMHLDTVFTMVDYDKFTIHPEIEGDLRVY<br>SVTYDNEELHIVEE**K**GDLAELLAANLGVEKVDLIRCGGDNLVAAGR<br>EQWNDGSNTLTIAPGVVVVYNRNTITNAILESKGLKLIKIHGSELV<br>RGRGGPRCMSMPFEREDI | 13 |
| ADI [full length] D277A w/ leader | *MHHHHHHGSGENLYFQG*TAQTPIHVYSEIG**K**LKKVLLHRPG<br>KEIENLMPDYLERLLEDDIPFLEDAQKEHDAFAQALRDEGIEVLYL<br>ETLAAESLVTPEIREAFIDEYLSEANIRGRATKKAIRELLMAIEDN<br>QELIEKTMAGVQKSELPEIPASEKGLTDLVESNYPFAIDPMPNLYF<br>TRDPFATIGTGVSLNHMESETRNRETLYG**K**YIFTHHPIYGGGKVPM<br>VYDRNETTRIEGGDELVLSKDVLAVGISQRTDAASIEKLLVNIFKQ<br>NLGFKKVLAFEFANNRKFMHL**A**TVFTMVDYDKFTIHPEIEGDLRVY<br>SVTYDNEELHIVEE**K**GDLAELLAANLGVEKVDLIRCGGDNLVAAGR<br>EQWNDGSNTLTIAPGVVVVYNRNTITNAILESKGLKLIKIHGSELV<br>RGRGGPRCMSMPFEREDI | 15 |
| SpyAD [33-849 fragment] WT w/ leader | *MHHHHHHGSGENLYFQG*QVKADDRASGETKASNTHDDSLPK<br>PETIQEA**K**ATIDAVEKTLSQQKAELTELATALTKTTAEINHLKEQQ<br>DNEQKALTSAQEIYTNTLASSEETLLAQGAEHQRELTATETELHNA<br>QADQHSKETALSEQKASISAETTRAQDLVEQVKTSEQNIAKLNAMI<br>SNPDAITKAAQTANDNTKALSSELEKAKADLENQKAKVKKQLTEEL<br>AAQKAALAEKEAELSRLKSSAPSTQDSIVGNNTMKAPQGYPLEELK<br>**K**LEASGYIGSASYNNYYKEHADQIIAKASPGNQLNQYQDIPADRNR<br>FVDPDNLTPEVQNELAQFAAHMINSVRRQLGLPPVTVTAGSQEFAR<br>LLSTSYK**K**THGNTRPSFVYGQPGVSGHYGVGPHDKTIIEDSAGASG<br>LIRNDDNMYENIGAFNDVHTVNGIKRGIYDSIKYMLFTDHLHGNTY<br>GHAINFLRVDKHNPNAPVYLGFSTSNVGSLNEHFVMFPESNIANHQ<br>RENKTPIKAVGSTKDYAQRVGTVSDTIAAIKGKVSSLENRLSAIHQ<br>EADIMAAQAKVSQLQGKLASTLKQSDSLNLQVRQLNDTKGSLRTEL<br>LAAKAKQAQLEATRDQSLAKLASLKAALHQTEALAEQAAARVTALV<br>AK**K**AHLQYLRDFKLNPNRLQVIRERIDNTKQDLAKTTSSLLNAQEA<br>LAALQAKQSSLEATIATTEHQLTLLKTLANEKEYRHLDEDIATVPD<br>LQVAPPLTGVKPLSYSKIDTTPLVQEMVKETKQLLEASARLAAENT<br>SLVAEALVGQTSEMVASNAIVSKITSSITQPSSKTSYGSGSSTTSN<br>LISDVDESTQR | 9 |

TABLE 4-continued

| Exemplary Carrier Proteins | | |
|---|---|---|
| Protein | Amino Acid Sequence | SEQ ID: |
| hFL [full length] WT w/ leader | *MHHHHHHGSG*SSQIRQNYSTDVEAAVNSLVNLYLQASYTYL<br>SLGFYFDRDDVALEGVSHFFRELAEEKREGYERLLKMQNQRGGRAL<br>FQDIKKPAEDEWGKTPDAMKAAMALEKKLNQALLDLHALGSARTDP<br>HLCDFLETHFLDEEVKLIKKMGDHLTNLHRLGGPEAGLGEYLFERL<br>TLKHD | 21 |
| eCRM-pAMF6 mutant | MGADDVVDSSKSFVMENFSSYHGTKPGYVDSIQXGIQKPKS<br>GTQGNYDDDWKEFYSTDNKYDAAGYSVDNENPLSGKAGGVVKVTYP<br>GLTKVLALKVDNAETIKKELGLSLTEPLMEQVGTEEFIKRFGDGAS<br>RVVLSLPFAEGSSSVEYINNWEQAKALSVELEINFETRGKRGQDAM<br>YEYMAQACAGNRVRNSVGSSLSCINLDWDVIRDXTKTKIESLKEHG<br>PIKNKMSESPNKTVSEEKAXQYLEEFHQTALEHPELSELXTVTGTN<br>PVFAGANYAAWAVNVAQVIDSETADNLEKTTAALSILPGIGSVMGI<br>ADGAVHHNTEEIVAQSIALSSLMVAQAIPLVGELVDIGFAAYNEVE<br>SIINLFQVVHNSYNRPAYSPGHXTQPFLHDGYAVSWNTVEDSIIRT<br>GFQGESGHDIKITAENTPLPIAGVLLPTIPGKLDVNKSKTHISVNG<br>RKIRMRCRAIDGDVTFCRPKSPVYVGNGVHANLHVAFHRSSSEKIH<br>SNEISSDSIGVLGYQKTVDHTKVNSXLSLFFEIKS | 25 |

In some embodiments, the conjugate polypeptide is SpyAD and comprises four nnAAs substituted at positions K64, K287, K396, and K657 of SEQ ID NO: 9. In some embodiments, the conjugate polypeptide is SpyAD and comprises four nnAAs substituted at positions K64, K287, K396, and K657 of SEQ ID NO: 33. In some embodiments, the four nnAAs are each pAMF. In some embodiments, the conjugate polypeptide is SpyAD and comprises or consists of an amino acid sequence that is at least 95%, 96%, 97%, 98%, or 99% identical to SEQ ID NO: 11 or SEQ ID NO: 12. In some embodiments, the four nnAAs are each pAMF. In some embodiments, the conjugate polypeptide is SpyAD and comprises or consists an amino acid sequence that is at least 95%, 96%, 97%, 98%, or 99% identical to SEQ ID NO: 34. In some embodiments, the conjugate polypeptide is SpyAD and comprises or consists of the amino acid sequence of SEQ ID NO: 11 or SEQ ID NO: 12. In some embodiments, the conjugate polypeptide is Spy AD and comprises or consists of the amino acid sequence of SEQ ID NO: 34.

In some embodiments, the conjugate polypeptide is ADI and comprises three nnAAs substituted at positions K15, K193, and K316 of SEQ ID NO: 13. In some embodiments, the conjugate polypeptide is ADI and comprises three nnAAs substituted at positions K15, K193, and K316 of SEQ ID NO: 35. In some embodiments, the three nnAAs are each pAMF. In some embodiments, the conjugate polypeptide is ADI and comprises or consists of an amino acid sequence that is at least 95%, 96%, 97%, 98%, or 99% identical to any one of SEQ ID NOs: 17, 18, 19, or 20. In some embodiments, the three nnAAs are each pAMF. In some embodiments, the conjugate polypeptide is SpyAD and comprises or consists of an amino acid sequence that is at least 95%, 96%, 97%, 98%, or 99% identical to any one of SEQ ID NOs: 26, 27, 37, or 38. In some embodiments, the conjugate polypeptide is ADI and comprises or consists of the amino acid sequence of any one of SEQ ID NOs: 17, 18, 19, or 20. In some embodiments, the conjugate polypeptide is ADI and comprises or consists of the amino acid sequence of any one of SEQ ID NOs: 26, 27, 37, 38.

In some embodiments, the conjugate polypeptide is a SLO polypeptide. In some embodiments, the conjugate polypeptide is SLO(ΔC101) and comprises three or four nnAAs substituted at positions selected from selected from K98, K112, R151, K189, K272, K323, K357, K375, K407, and K464 of SEQ ID NO: 53. In some embodiments, the conjugate polypeptide is SLO(ΔC101) and comprises or consists of nnAAs substituted at positions K98, R151, K272, and K357; positions K112, K189, K323, and K375; positions R151, K272, K357, and K407; positions R151, K272, K375, and K464; positions K112, K272, K357, and K464; positions K98, K189, and K357; positions K112, K189, and K323; positions K98, R151, and K272; positions K112, K272, and K375; or positions K112, K323, and K407. In some embodiments, the three or four nnAAs are each pAMF. In some embodiments, the conjugate polypeptide is a SLO polypeptide and comprises or consists of an amino acid sequence that is at least 95%, 96%, 97%, 98%, or 99% identical to any one of SEQ ID NOs: 55, 56, 57, 58, 59, 60, 61, 62, 63, or 64. In some embodiments, the conjugate polypeptide is a SLO polypeptide and comprises or consists of the amino acid sequence of any one of SEQ ID NOs: 55, 56, 57, 58, 59, 60, 61, 62, 63, or 64.

In some embodiments, the conjugate polypeptide is a SLO polypeptide. In some embodiments, the conjugate polypeptide is SLO(ΔC101) and comprises five, six, seven, or eight nnAAs substituted at positions selected from selected from K98, K112, R151, K189, K272, K323, K357, K375, K407, and K464 of SEQ ID NO: 53. In some embodiments, the conjugate polypeptide is SLO(ΔC101) and comprises or consists of nnAAs substituted at positions K98, R151, K272, K357, and K407; positions K112, K189, K323, K375, and K464; positions K112, R151, K272, K357, and K407; positions K98, R151, K272, K357, K407, and K464; positions K112, R151, K189, K323, K375, and K464; positions K98, K112, K189, K323, K375, and K464; positions K112, R151, K189, K272, K357, K407, and K464; positions K98, R151, K189, K323, K375, K407, and K464; positions K112, K189, K272, K357, K375, K407, and K464; positions K98, K112, R151, K189, K272, K323, K357, and K375; positions K98, R151, K189, K272, K323, K357, K407, and K464; or positions K112, K189, K272, K323, K357, K375, K407, and K464. In some embodiments, the five, six, seven, or eight nnAAs are each pAMF. In some embodiments, the conjugate polypeptide is a SLO polypeptide and comprises or consists of an amino acid sequence that is at least 95%, 96%, 97%, 98%, or 99% identical to any one of SEQ ID NOs: 65, 66, 67, 68, 69, 70, 71, 72, 73, 74, 75, or 76. In some embodiments, the conjugate polypeptide is a SLO polypeptide and comprises or consists of the amino acid sequence of any one of SEQ ID NOs: 65, 66, 67, 68, 69, 70, 71, 72, 73, 74, 75, or 76.

In some embodiments, the conjugate polypeptide is ferritin and comprises one nnAA substituted at position 15 of SEQ ID NO: 21. In some embodiments, the nnAA is pAMF. In some embodiments, the conjugate polypeptide is ferritin and comprises or consists of an amino acid sequence that is at least 95%, 96%, 97%, 98%, or 99% identical to SEQ ID NO: 23 or SEQ ID NO: 24. In some embodiments, the conjugate polypeptide is ADI and comprises or consists of SEQ ID NO: 23 or SEQ ID NO: 24.

Polysaccharides

In some embodiments, the conjugate polysaccharide is a GAS polysaccharide, such as the group A carbohydrate (GAC). The GAC is composed of a polyrhamnose backbone with an immunodominant GlcNAc side chain and is present on the surface of strains of all GAS serotypes irrespective of M type and has been examined as a GAS vaccine candidate. The conjugate polysaccharide may be defined as the polysaccharide component of a conjugate. Affinity-purified anti-GAC antibodies successfully opsonized three tested GAS serotypes (Salvadori et al., 1995. J. Infect. Dis. 171:593-600.), and mice immunized with GAC were protected against both intraperitoneal and intranasal GAS challenge (Sabharwal et al., 2006. J. Infect. Dis. 193:129-135). However, immunological cross-reactivity between anti-GAC antibodies and host heart valve proteins (Goldstein et al., 1967. Nature 213:44-47) and cytoskeletal proteins, such as actin, keratin, myosin, and vimentin, raises important potential safety concerns regarding the use of GAC as a GAS vaccine constituent.

In some embodiments, a *Streptococcus pyogenes* bacterial cell may be engineered to produce a polysaccharide or a variant thereof that lacks an immunodominant N-acetyl Glucosamine (GLcNAc) side chain. Therefore, in some embodiments, the conjugate polysaccharide is a variant of the GAC that lacks the immunodominant GlcNAc side chain (See e.g., International PCT Publication No. WO 2013/020090 U.S. Pat. No. 10,780,155, and Gao, N. J. et al., Dec. 29, 2020. Infectious Microbes and Diseases, doi: 10.1097/IM9.0000000000000044). In some embodiments, the conjugate polysaccharide is a GAC comprising a polyrhamanose core. In some embodiments, the conjugate polysaccharide has an average molecular weight of about 3 kDa to about 10 kDa, about 5 kDa to about 10 kDa, about 9 kDa to about 10 kDa, about 9 kDa to about 10 kDa, about 3 kDa to about 9 kDa, about 3 kDa to about 7 kDa, about 3 kDa to about 5 kDa, about 5 kDa to about 9 kDa, or about 5 kDa to about 7 kDa. In some embodiments, the conjugate polysaccharide has an average molecular weight of about 3 kDa, 4 kDa, 5 kDa, 6 kDa, 7 kDa, 8 kDa, 9 kDa, or about 10 kDa. In some embodiments, the conjugate polysaccharide is a tetramer, a pentamer, a hexamer, a septamer, an octamer, a nonomer, or a decamer polysaccharide.

In some embodiments, the conjugate polysaccharide has an average molecular weight of between about 10 kDa to about 45 kDa. In some embodiments, the conjugate polysaccharide has an average molecular weight of about 10 kDa to about 15 kDa, about 15 kDa to about 20 kDa, about 20 kDa to about 25 kDa, about 25 kDa to about 30 kDa, about 30 kDa to about 35 kDa, or about about 35 kDa to about 40 kDa. In some embodiments, the conjugate polysaccharide has an average molecular weight of about 15 kDa to about 40 kDa, about 15 kDa to about 35 kDa, about 15 kDa to about 30 kDa, about 15 kDa to about 25 kDa, or about 15 kDa to about 45 kDa. In some embodiments, the conjugate polysaccharide has an average molecular weight of about 20 kDa to about 40 kDa, about 20 kDa to about 35 kDa, about 20 kDa to about 30 kDa, or about 20 kDa to about 45 kDa. In some embodiments, the conjugate polysaccharide has an average molecular weight of about 10 kDa, 15 kDa, 20 kDa, 25 kDa, 30 kDa, 35 kDa, 40 kD or about 45 kDa. In some embodiments, the conjugate polysaccharide has an average molecular weight of at least about 10 kDa, 15 kDa, 20 kDa, 25 kDa, 30 kDa, or about 35 kDa.

In some embodiments, the conjugate polysaccharide is purified from GAS bacterial cultures or bacterial stocks. Methods of such purification are known in the art, see e.g., WO 2010/049806, International PCT Publication No. WO 2013/020090, and van Sorge, et al., *Cell Host Microbe.,* 2014, 15 (6), 729-740. See also Example 1. In some embodiments, the conjugate polysaccharide is a synthesized polysaccharide. Methods of polysaccharide synthesis are known in the art, see e.g., Zhao, et al., *Org. Chem. Front.,* 2019, 6, 3589-3596. See also Example 3. In some embodiments, the conjugate polysaccharides are modified with a click chemistry reactive group to facilitate conjugation to the conjugate protein. Examples of click chemistry reactive groups can be found, for instance, in International PCT Publication No. WO 2018/126229, incorporated by reference herein by reference in its entirety. For example, in some embodiments, the conjugate polysaccharides are modified with DBCO or DBCO-PEG (e.g., DBCO-PEG-$NH_2$). In some embodiments, the conjugate polysaccharides are modified with DBCO-$(PEG)_4$-$NH_2$.

In some embodiments, the polypeptide-polysaccharide conjugate has an average molecular mass of about 10 kDa to about 5000 kDa. In some embodiments, the polypeptide-polysaccharide conjugate has an average molecular mass of about 10 kDa to about 50 kDa. In some embodiments, the polypeptide-polysaccharide conjugate has an average molecular mass of about 10 kDa to about 100 kDa. In some embodiments, the polypeptide-polysaccharide conjugate has an average molecular mass of about 10 kDa to about 200 kDa. In some embodiments, the polypeptide-polysaccharide conjugate has an average molecular mass of about 10 kDa to about 500 kDa. In some embodiments, the polypeptide-polysaccharide conjugate has an average molecular mass of about 10 kDa to about 1000 kDa. In some embodiments, the polypeptide-polysaccharide conjugate has an average molecular mass of about 100 kDa to about 200 kDa. In some embodiments, the polypeptide-polysaccharide conjugate has an average molecular mass of about 100 kDa to about 300 kDa. In some embodiments, the polypeptide-polysaccharide conjugate has an average molecular mass of about 100 kDa to about 400 kDa. In some embodiments, the polypeptide-polysaccharide conjugate has an average molecular mass of about 100 kDa to about 500 kDa. In some embodiments, the polypeptide-polysaccharide conjugate has an average molecular mass of about 100 kDa to about 5000 kDa. In some embodiments, the polypeptide-polysaccharide conjugate has an average molecular mass of about 500 kDa to about 5000 kDa. In some embodiments, the polypeptide-polysaccharide conjugate has an average molecular mass of about 1000 kDa to about 5000 kDa. In some embodiments, the polypeptide-polysaccharide conjugate has an average molecular mass of about 2000 kDa to about 5000 kDa. In some embodiments, the polypeptide-polysaccharide conjugate has an average molecular mass of about 3000 kDa to about 5000 kDa. In some embodiments, the polypeptide-polysaccharide conjugate has an average molecular mass of about 4000 kDa to about 5000 kDa. In some embodiments, the polypeptide-polysaccharide conjugate has an average molecular mass of about 1000 kDa to about 3000 kDa. In some embodiments, the polypeptide-polysaccharide conjugate has an average molecular mass of about 1000 kDa to about 2000 kDa. In some embodiments, the polypeptide-polysaccharide conjugate has an average molecular mass of about 2000 kDa to about 3000 kDa. In some embodiments, the polypeptide-polysaccharide conjugate has an average molecular mass of about 5000 kDa or greater.

Exemplary Combination Vaccines

In some embodiments, the present disclosure provides an immunogenic composition comprising a GAS C5a peptidase polypeptide antigen; a GAS streptolysin O (SLO) polypeptide antigen; and a polypeptide-polysaccharide conjugate comprising a SpyAD conjugate polypeptide and a GAS conjugate polysaccharide or a variant thereof that lacks an immunodominant GlcNAc side chain. In some embodiments, the SpyAD protein comprises or consists of an amino acid sequence that is at least 95% identical to SEQ ID NO: 9 or SEQ ID NO: 10 and comprises a pAMF substitution at positions K64, K287, K386, and K657. In some embodiments, the SpyAD protein comprises the amino acid sequence of SEQ ID NO: 11 or SEQ ID NO: 12. In some embodiments, the SpyAD protein comprises or consists of an amino acid sequence that is at least 95% identical to SEQ ID NO: 33 and comprises a pAMF substitution at positions K64, K287, K386, and K657. In some embodiments, the SpyAD protein comprises the amino acid sequence of SEQ ID NO: 34. In some embodiments, the SpyAD protein comprises or consists of the amino acid sequence of SEQ ID NO: 11 or SEQ ID NO: 12. In some embodiments, the SpyAD protein comprises or consists of the amino acid sequence of SEQ ID NO: 34.

In some embodiments, the present disclosure provides an immunogenic composition comprising a GAS C5a peptidase polypeptide antigen; a GAS streptolysin O (SLO) polypeptide antigen; and a polypeptide-polysaccharide conjugate comprising a SpyAD conjugate polypeptide and a GAS conjugate polysaccharide or a variant thereof that lacks an immunodominant GlcNAc side chain. In some embodiments, the SLO polypeptide antigen comprises or consists of an amino acid sequence that is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53. In some embodiments, the SLO polypeptide antigen comprises or consists of an amino acid sequence that is at least 95% identical to SEQ ID NO: 31. In some embodiments, the SLO polypeptide antigen comprises an amino acid sequence that is at least 95% identical to SEQ ID NO: 32. In some embodiments, the SLO polypeptide antigen comprises or consists of an amino acid sequence that is at least 95% identical to SEQ ID NO: 44. In some embodiments, the SLO polypeptide antigen comprises an amino acid sequence that is at least 95% identical to SEQ ID NO: 45. In some embodiments, the SLO polypeptide antigen comprises or consists of an amino acid sequence that is at least 95% identical to SEQ ID NO: 46. In some embodiments, the SLO polypeptide antigen comprises or consists of an amino acid sequence that is at least 95% identical to SEQ ID NO: 47. In some embodiments, the SLO polypeptide antigen comprises or consists of an amino acid sequence that is at least 95% identical to SEQ ID NO: 48. In some embodiments, the SLO polypeptide antigen comprises or consists of an amino acid sequence that is at least 95% identical to SEQ ID NO: 49. In some embodiments, the SLO polypeptide antigen comprises or consists of an amino acid sequence that is at least 95% identical to SEQ ID NO: 50. In some embodiments, the SLO polypeptide antigen comprises or consists of an amino acid sequence that is at least 95% identical to SEQ ID NO: 51. In some embodiments, the SLO polypeptide antigen comprises or consists of an amino acid sequence that is at least 95% identical to SEQ ID NO: 52. In some embodiments, the SLO polypeptide antigen comprises or consists of an amino acid sequence that is at least 95% identical to SEQ ID NO: 53. In some embodiments, the SLO polypeptide antigen comprises or consists of the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some embodiments, the present disclosure provides an immunogenic composition comprising a GAS C5a peptidase polypeptide antigen; a GAS streptolysin O (SLO) polypeptide antigen; and a polypeptide-polysaccharide conjugate comprising a SpyAD conjugate polypeptide and a GAS conjugate polysaccharide or a variant thereof that lacks an immunodominant GlcNAc side chain. In some embodiments, the C5a peptidase polypeptide antigen comprises or consists of an amino acid sequence that is at least 95% identical to SEQ ID NO: 29 or SEQ ID NO: 30; the SLO polypeptide antigen comprises or consists of an amino acid sequence that is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53; and the SpyAD conjugate protein comprises or consists of an amino acid sequence that is at least 95% identical to SEQ ID NO: 33 and comprises a pAMF substitution at positions K64, K287, K386, and K657. In some embodiments, the SpyAD protein comprises or consists of the amino acid sequence of SEQ ID NO: 34. In some embodiments, the C5a peptidase polypeptide antigen comprises or consists of the amino acid sequence of SEQ ID NO: 29 or SEQ ID NO: 30; the SLO polypeptide antigen comprises or consists of an amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53; and the SpyAD conjugate protein comprises or consists of an amino acid sequence of SEQ ID NO: 33 and comprises a pAMF substitution at positions K64, K287, K386, and K657. In some embodiments, the SpyAD protein comprises or consists of the amino acid sequence of SEQ ID NO: 34.

In some embodiments, the present disclosure provides an immunogenic composition comprising a C5a peptidase polypeptide antigen of SEQ ID NO: 30; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide. In some embodiments, the present disclosure provides an immunogenic composition comprising a C5a peptidase polypeptide antigen of SEQ ID NO: 30; a SLO polypeptide antigen of SEQ ID NO: 52; and a polypeptide-polysaccharide conjugate comprising a Spy AD conjugate polypeptide of SEQ ID NO: 34 and a GAS conjugate polysaccharide. In some embodiments, the present disclosure provides an immunogenic composition comprising a C5a peptidase polypeptide antigen of SEQ ID NO: 30; a SLO polypeptide antigen of SEQ ID NO: 32; and a polypeptide-polysaccharide conjugate comprising a SpyAD conjugate polypeptide of SEQ ID NO: 34 and a GAS conjugate polysaccharide. In some embodiments, the present disclosure provides an immunogenic composition comprising a C5a peptidase polypeptide antigen of SEQ ID NO: 29; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide. In some embodiments, the present disclosure provides an immunogenic composition comprising a C5a peptidase polypeptide antigen comprising or consisting of the amino acid sequence of SEQ ID NO: 30; a SLO polypeptide antigen comprising or consisting of the amino acid sequence of SEQ ID NO: 53; and a polypeptide-polysaccharide conjugate comprising a SpyAD conjugate polypeptide comprising or consisting of the amino acid sequence of SEQ ID NO: 34 and a GAS conjugate polysaccharide. In some embodiments, the present disclosure provides an immunogenic composition comprising a C5a peptidase polypeptide antigen comprising or consisting of the amino acid sequence of SEQ ID NO: 30; a SLO polypeptide antigen comprising or consisting of the amino acid sequence of SEQ ID NO: 52; and a polypeptide-polysaccharide conjugate comprising a SpyAD conjugate polypeptide comprising or consisting of the amino acid sequence of SEQ ID NO: 34 and a GAS conjugate polysaccharide. In some embodiments, the present disclosure provides an immunogenic composition comprising a C5a peptidase polypeptide antigen comprising or consisting of the amino acid sequence of SEQ ID NO: 30; a SLO polypeptide antigen comprising or consisting of the amino acid sequence of SEQ ID NO: 32; and a polypeptide-polysaccharide conjugate comprising a Spy AD conjugate polypeptide comprising or consisting of the amino acid sequence of SEQ ID NO: 34 and a GAS conjugate polysaccharide. In some embodiments, the present disclosure provides an immunogenic composition comprising a C5a peptidase polypeptide antigen comprising or consisting of the amino acid sequence of SEQ ID NO: 29; a SLO polypeptide antigen comprising or consisting of the amino acid sequence of SEQ ID NO: 53; and a polypeptide-polysaccharide conjugate comprising a SpyAD conjugate polypeptide comprising or consisting of the amino acid sequence of SEQ ID NO: 34 and a GAS conjugate polysaccharide.

In some embodiments, the present disclosure provides an immunogenic composition comprising a C5a peptidase polypeptide antigen; a GAS SLO polypeptide antigen; and a polypeptide-polysaccharide conjugate comprising an ADI conjugate polypeptide and a GAS conjugate polysaccharide or a variant thereof that lacks an immunodominant GlcNAc side chain. In some embodiments, the ADI polypeptide comprises or consists of an amino acid sequence that is at least 95% identical to any one of SEQ ID NOs: 13-16 and comprises a pAMF substitution at positions K15, K193, and K316. In some embodiments, the ADI polypeptide comprises the amino acid sequence of any one of SEQ ID NOs: 17-20. In some embodiments, the ADI polypeptide comprises or consists of an amino acid sequence that is at least 95% identical to any one of SEQ ID NOs: 35-36 and comprises a pAMF substitution at positions K15, K193, and K316. In some embodiments, the ADI polypeptide comprises or consists of the amino acid sequence of any one of SEQ ID NOs: 37-38. In some embodiments, the ADI polypeptide comprises or consists of the amino acid sequence of any one of SEQ ID NOs: 17-20. In some embodiments, the ADI polypeptide comprises or consists of an amino acid sequence that is at least 95% identical to any one of SEQ ID NOs: 35-36 and comprises a pAMF substitution at positions K15, K193, and K316. In some embodiments, the ADI polypeptide comprises or consists of the amino acid sequence of any one of SEQ ID NOs: 37-38.

In some embodiments, the present disclosure provides an immunogenic composition comprising a C5a peptidase polypeptide antigen; a GAS SLO polypeptide antigen; and a polypeptide-polysaccharide conjugate comprising a ferritin polypeptide and a GAS conjugate polysaccharide or a variant thereof that lacks an immunodominant GlcNAc side chain. In some embodiments, the ferritin polypeptide comprises or consists of an amino acid sequence that is at least 95% identical to SEQ ID NO: 21 or SEQ ID NO: 22 and comprises a pAMF substitution at position 15. In some embodiments, the ferritin polypeptide comprises the amino acid sequence of SEQ ID NO: 23 or SEQ ID NO: 24. In some embodiments, the ferritin polypeptide comprises or consists of the amino acid sequence of SEQ ID NO: 23 or SEQ ID NO: 24.

Therapeutic Methods

In some embodiments, the present disclosure provides a method of inducing a protective immune response against a GAS bacterium in a subject comprising administering an immunogenic composition described herein to the subject. In certain embodiments are provided the use of the immunogenic compositions described herein for inducing a protective immune response against a GAS bacterium in a subject. In some embodiments, provided herein are the use of the immunogenic compositions described herein in the manufacture of a medicament for inducing a protective immune response against a GAS bacterium in a subject.

Herein, the term "subject" refers to a mammal. In some embodiments, the subject is a mouse, a rat, a dog, a guinea pig, a sheep, a non-human primate, or a human. In some embodiments, the subject is a human. In some embodiments, the human subjects are 18 years of age or older. In some embodiments, the human subjects are less than 18 years of age.

In some embodiments, the human subjects are between 6 months of age and 17 years of age. In some embodiments, the human subjects are between 6 months of age and 9 years of age, between 6 months of age and 8 years of age, between 6 months of age and 7 years of age, between 6 months of age and 6 years of age, between 6 months of age and 5 years of age, between 6 months of age and 4 years of age, between 6 months of age and 3 years of age, between 6 months of age and 2 years of age, or between 6 months of age and 1 year of age. In some embodiments, the human subjects are between 5 years of age and 17 years of age, between 7 years of age and 17 years of age, between 9 years of age and 17 years of age, between 11 years of age and 17 years of age, between 13 years of age and 17 years of age, or between 15 years of age and 17 years of age. In some embodiments, the human subjects are 6 months, 1 year, 2 years, 3 years, 4 years, 5 years, 6 years, 7 years, 8 years, 9 years, 10 years, 11 years, 12 years, 13 years, 14 years, 15 years, 16 years, 17 years, or 18 years of age.

Herein, the term "protective immune response" encompasses eliciting an anti-GAS antibody response in the subject. Antibody titers generated after administration of the immunogenic compositions described herein can be determined by means known in the art, for example by ELISA assays of serum samples derived from immunized subjects (See Example 6). In some embodiments, the immunogenic compositions described herein elicit antibody responses in treated subjects, wherein the antibodies generated bind to multiple (i.e., two or more) GAS serotypes. In some embodiments, the immunogenic compositions described herein elicit antibody responses in treated subjects, wherein the antibodies generated bind to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more GAS serotypes. In some embodiments, the immunogenic compositions described herein do not elicit antibody responses against human proteins or tissue.

In some embodiments, the immunogenic compositions described herein elicit antibody responses in treated subjects, wherein the antibodies generated bind to at least one GAS serotype selected from M1, M2, M3, M4, M5, M6, M9, M11, M12, M13, M18, M22, M25, M28, M62, M71, M72, M74, M75, M77, M80, M81, M83, M87, M89, and M92. In some embodiments, the immunogenic compositions described herein elicit antibody responses in treated subjects, wherein the antibodies generated bind to two or more GAS serotypes selected from M1, M2, M3, M4, M5, M6, M9, M11, M12, M13, M18, M22, M25, M28, M62, M71, M72, M74, M75, M77, M80, M81, M83, M87, M89, and M92.

In some embodiments, the immunogenic compositions described herein elicit antibody responses in treated subjects, wherein the antibodies generated bind to at least one GAS serotype selected from M1, M2, M3, M4, M6, M11, M12, M22, M28, M75, and M89. In some embodiments, the immunogenic compositions described herein elicit antibody responses in treated subjects, wherein the antibodies generated bind to two or more GAS serotypes selected from M1, M2, M3, M4, M6, M11, M12, M22, M28, M75, and M89.

In some embodiments, the immunogenic compositions described herein elicit antibody responses in treated subjects, wherein the antibodies generated bind to at least one GAS serotype selected from M1, M3, M5, M9, M12, M18, M22, M25, M28, M71, M72, and M74. In some embodiments, the immunogenic compositions described herein elicit antibody responses in treated subjects, wherein the antibodies generated bind to two or more GAS serotypes selected from M1, M3, M5, M9, M12, M18, M22, M25, M28, M71, M72, and M74.

In some embodiments, the immunogenic compositions described herein elicit antibody responses in treated subjects, wherein the antibodies generated bind to at least one GAS serotype selected from M1, M4, M6, M11, M12, M22, M44, M75, M77, M77, and M81. In some embodiments, the immunogenic compositions described herein elicit antibody responses in treated subjects, wherein the antibodies generated bind to two or more GAS serotypes selected from M1, M4, M6, M11, M12, M22, M44, M75, M77, M77, and M81.

In some embodiments, the immunogenic compositions described herein elicit antibody responses in treated subjects, wherein the antibodies generated bind to at least one GAS serotype selected from M1, M2, M3, M4, M6, M9, M12, M18, M22, M75, M77, M89, and M92. In some embodiments, the immunogenic compositions described herein elicit antibody responses in treated subjects, wherein the antibodies generated bind to two or more GAS serotypes selected from M1, M2, M3, M4, M6, M9, M12, M18, M22, M75, M77, M89, and M92.

In some embodiments, the immunogenic compositions described herein elicit antibody responses in treated subjects, wherein the antibodies generated bind to at least one GAS serotype selected from M1, M2, M3, M4, M5, M6, M9, M11, M12, M13, M28, M62, and M89. In some embodiments, the immunogenic compositions described herein elicit antibody responses in treated subjects, wherein the antibodies generated bind to two or more GAS serotypes selected from M1, M2, M3, M4, M5, M6, M9, M11, M12, M13, M28, M62, and M89.

In some embodiments, the immunogenic compositions described herein elicit antibody responses in treated subjects, wherein the antibodies generated bind to at least one GAS serotype selected from M1, M2, M3, M4, M6, M12, M22, M28, M49, M53, M68, M77, M80, M83, M87, M89, and M92. In some embodiments, the immunogenic compositions described herein elicit antibody responses in treated subjects, wherein the antibodies generated bind to two or more GAS serotypes selected from M1, M2, M3, M4, M6, M12, M22, M28, M49, M53, M68, M77, M80, M83, M87, M89, and M92.

In some embodiments, the immunogenic compositions described herein elicit antibody responses in treated subjects that bind to one or more *Shigella* serotypes. In some embodiments, the immunogenic compositions described herein elicit antibody responses in treated subjects that bind to one or more GAS serotypes and also bind to one or more *Shigella* serotypes. In some embodiments, the *Shigella* serotypes comprise a polysaccharide comprising a polyrhamanose backbone. Exemplary *Shigella* serotypes comprising such polysaccharides include *S. flexneri* such as *S. flexneri* 2A and 3A and *S. flexneri* 6.

FURTHER NUMBERED EMBODIMENTS

Further embodiments of the instant disclosure are provided in the numbered embodiments below:

Embodiment 1: An immunogenic composition comprising a first Group A *Streptococcus* (GAS) polypeptide antigen; a second GAS polypeptide antigen; and at least one polypeptide-polysaccharide conjugate, wherein the conjugate polypeptide is a third GAS polypeptide antigen or a non-GAS carrier polypeptide and comprises at least one non-natural amino acid, and wherein the conjugate polysaccharide is a GAS polysaccharide or a variant thereof that lacks an immunodominant N-acetyl Glucosamine (GlcNAc) side chain.

Embodiment 2: The immunogenic composition of Embodiment 1, wherein at least one of the GAS polypeptide antigens is a full length GAS antigen.

Embodiment 3: The immunogenic composition of Embodiment 1, wherein at least one of the GAS polypeptide antigens is a peptide fragment of a full length GAS antigen.

Embodiment 4: The immunogenic composition of any one of Embodiments 1-3, wherein the first and second GAS polypeptide antigens are independently selected from C5a peptidase, streptolysin O (SLO), Sib35, and Sfb1.

Embodiment 5: The immunogenic composition of any one of Embodiments 1-3, wherein the first and second GAS polypeptide antigens are C5a peptidase and SLO.

Embodiment 6: The immunogenic composition of Embodiment 5, wherein the C5a peptidase polypeptide antigen comprises an amino acid sequence that is at least 95% identical to SEQ ID NO: 1 or SEQ ID NO: 3.

Embodiment 7: The immunogenic composition of Embodiment 5, wherein the C5a peptidase polypeptide antigen comprises the amino acid sequence of SEQ ID NO: 1 or SEQ ID NO: 3.

Embodiment 8: The immunogenic composition of Embodiment 5, wherein the SLO polypeptide antigen comprises an amino acid sequence that is at least 95% identical to SEQ ID NO: 5 or SEQ ID NO: 7.

Embodiment 9: The immunogenic composition of Embodiment 5, wherein the SLO polypeptide antigen comprises the amino acid sequence of SEQ ID NO: 5 or SEQ ID NO: 7.

Embodiment 10: The immunogenic composition of any one of Embodiments 1-9, wherein the non-GAS carrier polypeptide is ferritin.

Embodiment 11: The immunogenic composition of any one of Embodiments 1-10, wherein the third GAS polypeptide antigen is selected from *Streptococcus pyogenes* Adhesion and Division (SpyAD) polypeptide, arginine deiminase (ADI), eCRM, and Protein D.

Embodiment 12: The immunogenic composition of any one of Embodiments 1-11, wherein the at least one nnAA is substituted for a lysine, a leucine, or an isoleucine in the conjugate polypeptide.

Embodiment 13: The immunogenic composition of any one of Embodiments 1-11, wherein the nnAA comprises a click chemistry reactive group.

Embodiment 14: The immunogenic composition of Embodiment 13, wherein the nnAA is selected from 2-amino-3-(4-azidophenyl)propanoic acid (4-azidophenyl) propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl) propanoic acid, 2-amino-3-(6-(azidomethyl)pyridin-3-yl)propanoic acid, and 2-amino-5-azidopentanoic acid.

Embodiment 15: The immunogenic composition of Embodiment 13, wherein the nnAA is pAMF.

Embodiment 16: The immunogenic composition of any one of Embodiments 12-15, wherein the conjugate polypeptide is a third GAS protein, which is a SpyAD polypeptide and comprises an amino acid sequence that is at least 95% identical to SEQ ID NO: 9.

Embodiment 17: The immunogenic composition of Embodiment 16, wherein the SpyAD polypeptide comprises a pAMF substitution at positions K64, K287, K386, and K657 of SEQ ID NO: 9.

Embodiment 18: The immunogenic composition of Embodiment 17, wherein the SpyAD polypeptide comprises the amino acid sequence of SEQ ID NO: 9 or SEQ ID NO: 11.

Embodiment 19: The immunogenic composition of any one of Embodiments 12-15, wherein the conjugate polypeptide is a third GAS polypeptide, which is an ADI polypeptide and comprises an amino acid sequence that is at least 95% identical to SEQ ID NO: 13 or SEQ ID NO: 15.

Embodiment 20: The immunogenic composition of Embodiment 19, wherein the ADI polypeptide comprises a pAMF substitution at positions K15, K193, and K316 of SEQ ID NO: 13 or SEQ ID NO: 15.

Embodiment 21: The immunogenic composition of Embodiment 20, wherein the ADI polypeptide comprises the amino acid sequence of SEQ ID NO: 17 or SEQ ID NO: 19.

Embodiment 22: The immunogenic composition of any one of Embodiments 12-15, wherein the conjugate polypeptide is a ferritin polypeptide and comprises an amino acid sequence that is at least 95% identical to SEQ ID NO: 21.

Embodiment 23: The immunogenic composition of Embodiment 22, wherein the ferritin polypeptide comprises a pAMF substitution at position 15 of SEQ ID NO: 21.

Embodiment 24: The immunogenic composition of Embodiment 23, wherein the ferritin polypeptide comprises the amino acid sequence of SEQ ID NO: 23.

Embodiment 25: The immunogenic composition of any one of Embodiments 1-23, wherein the conjugate polysaccharide comprises a polyrhamnose core.

Embodiment 26: The immunogenic composition of any one of Embodiments 1-23, wherein the conjugate polysaccharide has an average molecular weight of about 5 KDa to about 7 KDa.

Embodiment 27: The immunogenic composition of any one of Embodiments 1-26, wherein the conjugate polysaccharide is a tetramer, a hexamer, an octamer, or a decamer polysaccharide.

Embodiment 28: An immunogenic composition comprising a Group A *Streptococcus* (GAS) C5a peptidase polypeptide antigen; a GAS streptolysin O (SLO) polypeptide antigen; and a polypeptide-polysaccharide conjugate comprising a *Streptococcus pyogenes* Adhesion and Division (SpyAD) conjugate polypeptide and a GAS conjugate polysaccharide or a variant thereof that lacks an immunodominant N-acetyl Glucosamine (GlcNAc) side chain.

Embodiment 29: The immunogenic composition of Embodiment 28, wherein the Spy AD protein comprises an amino acid sequence that is at least 95% identical to SEQ ID NO: 9 and comprises a pAMF substitution at positions K64, K287, K386, and K657.

Embodiment 30: The immunogenic composition of Embodiment 28, wherein the Spy AD protein comprises the amino acid sequence of SEQ ID NO: 9 or SEQ ID NO: 11.

Embodiment 31: An immunogenic composition comprising a Group A *Streptococcus* (GAS) C5a peptidase polypeptide antigen; a GAS streptolysin O (SLO) polypeptide antigen; and a polypeptide-polysaccharide conjugate comprising an arginine deiminase (ADI) conjugate polypeptide and a GAS conjugate polysaccharide or a variant thereof that lacks an immunodominant N-acetyl Glucosamine (GlcNAc) side chain.

Embodiment 32: The immunogenic composition of Embodiment 31, wherein the ADI polypeptide comprises an amino acid sequence that is at least 95% identical to SEQ ID NO: 13 or SEQ ID NO: 15 and comprises a pAMF substitution at positions K15, K193, and K316.

Embodiment 33: The immunogenic composition of Embodiment 31, wherein the ADI polypeptide comprises the amino acid sequence of SEQ ID NO: 17 or SEQ ID NO: 19.

Embodiment 34: An immunogenic composition comprising a Group A *Streptococcus* (GAS) C5a peptidase polypeptide antigen; a GAS streptolysin O (SLO) polypeptide antigen; and a polypeptide-polysaccharide conjugate comprising a ferritin polypeptide and a GAS conjugate polysaccharide or a variant thereof that lacks an immunodominant N-acetyl Glucosamine (GlcNAc) side chain.

Embodiment 35: The immunogenic composition of Embodiment 34, wherein the ferritin protein comprises an amino acid sequence that is at least 95% identical to SEQ ID NO: 21 and comprises a pAMF substitution at position 15.

Embodiment 35A: The immunogenic composition Embodiment 34, wherein the ferritin protein comprises the amino acid sequence of SEQ ID NO: 23.

Embodiment 36: The immunogenic composition of any one of Embodiments 1-35, wherein the composition comprises about 10% to about 50% of the first GAS antigen, about 10% to about 50% of the second GAS antigen, and about 10% to about 50% of the polypeptide-polysaccharide conjugate.

Embodiment 37: The immunogenic composition of any one of Embodiments 1-36, further comprising one or more adjuvants selected from alum, saponin, monophosphoryl lipid A (MPL), or combinations thereof.

Embodiment 38: A method of inducing a protective immune response against a Group A *Streptococcus* (GAS)

bacterium in a subject comprising administering the immunogenic composition of any one of Embodiments 1-37 to the subject.

Embodiment 38A: Use of the immunogenic composition of any one of Embodiments 1-37 for inducing a protective immune response against a Group A *Streptococcus* (GAS) bacterium in a subject.

Embodiment 38B: Use of the immunogenic composition of any one of Embodiments 1-37 in the manufacture of a medicament for inducing a protective immune response against a Group A *Streptococcus* (GAS) bacterium in a subject.

Embodiment 39: The method of any one of Embodiments 38-38B, wherein the subject is 18 years or older.

Embodiment 40: The method of any one of Embodiments 38-38B, wherein the subject is less than 18 years old.

Embodiment 41: The method of any one of Embodiments 38-38B, wherein the subject is between 5 years and 17 years old, between 6 months and 9 years old, or between 5 years and 9 years old.

Embodiment 42: The method of any one of Embodiments 38-41, wherein the GAS bacterium is of a serotype selected from M1, M2, M3, M4, M6, M11, M12, M22, M28, M75, and M89.

Embodiment 43: The method of any one of Embodiments 38-41, wherein the GAS bacterium is a serotype selected from M1, M3, M5, M9, M12, M18, M22, M25, M28, M71, M72, and M74.

Embodiment 44: The method of any one of Embodiments 38-41, wherein the GAS bacterium is a serotype selected from M1, M4, M6, M11, M12, M22, M44, M75, M77, M77, and M81.

Embodiment 45: The method of any one of Embodiments 38-41, wherein the GAS bacterium is a serotype selected from M1, M2, M3, M4, M6, M9, M12, M18, M22, M75, M77, M89, and M92.

Embodiment 46: The method of any one of Embodiments 38-41, wherein the GAS bacterium is a serotype selected from M1, M2, M3, M4, M5, M6, M9, M11, M12, M13, M28, M62, and M89.

Embodiment 47: The method of any one of Embodiments 38-41, wherein the GAS bacterium is a serotype selected from M1, M2, M3, M4, M6, M12, M22, M28, M49, M53, M68, M77, M80, M83, M87, M89, and M92.

Embodiment 48: The method of any one of Embodiments 38-47, wherein the immunogenic composition induces an antibody response in the subject against the Group A *Streptococcus* (GAS) bacterium and does not induce an antibody response in the subject against human tissue.

Embodiment 49: The method of any one of Embodiments 38-48, wherein the immunogenic composition induces a protective immune response against a *Shigella* bacterium in the subject, wherein the *Shigella* bacterium comprises a polysaccharide with a polyrhmanose backbone.

Embodiment 50: A method of inducing a protective immune response against a *Shigella* bacterium in a subject comprising administering the immunogenic composition of any one of Embodiments 1-37 to the subject.

Embodiment 51: Use of the immunogenic composition of any one of Embodiments 1-37 for inducing a protective immune response against a *Shigella* bacterium in a subject.

Embodiment 52: Use of the immunogenic composition of any one of Embodiments 1-37 in the manufacture of a medicament for inducing a protective immune response against a *Shigella* bacterium in a subject.

Embodiment 53: The method or use of any one of Embodiments 50-52, wherein the subject is 18 years or older.

Embodiment 54: The method or use of Embodiment 53, wherein the subject is less than 18 years old.

Embodiment 55: The method or use of Embodiment 54, wherein the subject is between 5 years and 17 years old, between 6 months and 9 years old, or between 5 years and 9 years old.

Embodiment II-1. An immunogenic composition comprising a. a first Group A *Streptococcus* (GAS) polypeptide antigen;

b. a second GAS polypeptide antigen; and c. at least one polypeptide-polysaccharide conjugate, wherein the conjugate polypeptide is a third GAS polypeptide antigen or a non-GAS carrier polypeptide and comprises at least one non-natural amino acid, and wherein the conjugate polysaccharide is a GAS polysaccharide or a variant thereof that lacks an immunodominant N-acetyl Glucosamine (GlcNAc) side chain.

Embodiment II-2. The immunogenic composition of embodiment II-1, wherein at least one of the GAS polypeptide antigens is a full length GAS antigen.

Embodiment II-3. The immunogenic composition of embodiment II-1, wherein at least one of the GAS polypeptide antigens is a peptide fragment of a full length GAS antigen.

Embodiment II-4. The immunogenic composition of any one of embodiments II-1 to II-3, wherein the first and second GAS polypeptide antigens are independently selected from C5a peptidase, streptolysin O (SLO), Sib35, and Sfb1.

Embodiment II-5. The immunogenic composition of any one of embodiments II-1 to II-3, wherein the first and second GAS polypeptide antigens are C5a peptidase and SLO.

Embodiment II-6. The immunogenic composition of embodiment II-5, wherein the C5a peptidase polypeptide antigen comprises an amino acid sequence that is at least 95% identical to SEQ ID NO: 1 or SEQ ID NO: 3.

Embodiment II-7. The immunogenic composition of embodiment II-5, wherein the C5a peptidase polypeptide antigen comprises the amino acid sequence of SEQ ID NO: 1 or SEQ ID NO: 3.

Embodiment II-8. The immunogenic composition of any one of embodiments II-1 to II-6 wherein the first and second GAS polypeptide antigens are C5a peptidase and SLO, and the C5a peptidase polypeptide antigen comprises the amino acid sequence of SEQ ID NO: 29 or SEQ ID NO: 30.

Embodiment II-9. The immunogenic composition of embodiment II-5, wherein the SLO polypeptide antigen comprises an amino acid sequence that is at least 95% identical to SEQ ID NO: 5 or SEQ ID NO: 7.

Embodiment II-10. The immunogenic composition of any one of embodiments II-1 to II-6 or II-9, wherein the first and second GAS polypeptide antigens are C5a peptidase and SLO, and the SLO polypeptide antigen comprises an amino acid sequence that is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment II-11. The immunogenic composition of embodiment II-5, wherein the SLO polypeptide antigen comprises the amino acid sequence of SEQ ID NO: 5 or SEQ ID NO: 7.

Embodiment II-12. The immunogenic composition of any one of embodiments II-1 to II-6, wherein the first and second GAS polypeptide antigens are C5a peptidase and SLO, and the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment II-13. The immunogenic composition of any one of embodiments II-1 to II-12, wherein the non-GAS carrier polypeptide is ferritin.

Embodiment II-14. The immunogenic composition of any one of embodiments II-1 to II-13, wherein the third GAS polypeptide antigen is selected from *Streptococcus pyogenes* Adhesion and Division (SpyAD) polypeptide, arginine deiminase (ADI), eCRM, and Protein D.

Embodiment II-15. The immunogenic composition of any one of embodiments II-1 to II-14, wherein the at least one nnAA is substituted for a lysine, a leucine, or an isoleucine in the conjugate polypeptide.

Embodiment II-16. The immunogenic composition of any one of embodiments II-1 to II-14, wherein the nnAA comprises a click chemistry reactive group.

Embodiment II-17. The immunogenic composition of embodiment II-16, wherein the nnAA is selected from 2-amino-3-(4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl) propanoic acid, 2-amino-3-(4-(azidomethyl)pyridin-2-yl)propanoic acid, 2-amino-3-(6-(azidomethyl)pyridin-3-yl)propanoic acid, and 2-amino-5-azidopentanoic acid.

Embodiment II-18. The immunogenic composition of embodiment II-16, wherein the nnAA is pAMF.

Embodiment II-19. The immunogenic composition of any one of embodiments II-15 to II-18, wherein the conjugate polypeptide is a third GAS protein, which is a SpyAD polypeptide and comprises an amino acid sequence that is at least 95% identical to SEQ ID NO: 9.

Embodiment II-20. The immunogenic composition of embodiment II-19, wherein the SpyAD polypeptide comprises a pAMF substitution at positions K64, K287, K386, and K657 of SEQ ID NO: 9.

Embodiment II-21. The immunogenic composition of embodiment II-20, wherein the SpyAD polypeptide comprises the amino acid sequence of SEQ ID NO: 9 or SEQ ID NO: 11.

Embodiment II-22. The immunogenic composition of any one of embodiments II-15 to II-18, wherein the conjugate polypeptide is a third GAS protein, which is a SpyAD polypeptide and comprises an amino acid sequence that is at least 95% identical to SEQ ID NO: 33.

Embodiment II-23. The immunogenic composition of embodiment II-22, wherein the SpyAD polypeptide comprises a pAMF substitution at positions K64, K287, K386, and K657 of SEQ ID NO: 33.

Embodiment II-24. The immunogenic composition of embodiment II-23, wherein the SpyAD polypeptide comprises the amino acid sequence of SEQ ID NO: 33 or SEQ ID NO: 34.

Embodiment II-25. The immunogenic composition of any one of embodiments II-15 to II-18, wherein the conjugate polypeptide is a third GAS polypeptide, which is an ADI polypeptide and comprises an amino acid sequence that is at least 95% identical to SEQ ID NO: 13 or SEQ ID NO: 15.

Embodiment II-26. The immunogenic composition of embodiment II-25, wherein the ADI polypeptide comprises a pAMF substitution at positions K15, K193, and K316 of SEQ ID NO: 13 or SEQ ID NO: 15.

Embodiment II-27. The immunogenic composition of embodiment II-26, wherein the ADI polypeptide comprises the amino acid sequence of SEQ ID NO: 17 or SEQ ID NO: 19.

Embodiment II-28. The immunogenic composition of any one of embodiments II-15 to II-18, wherein the conjugate polypeptide is a third GAS polypeptide, which is an ADI polypeptide and comprises an amino acid sequence that is at least 95% identical to SEQ ID NO: 35 or SEQ ID NO: 36.

Embodiment II-29. The immunogenic composition of embodiment II-28, wherein the ADI polypeptide comprises a pAMF substitution at positions K15, K193, and K316 of SEQ ID NO: 35 or SEQ ID NO: 36.

Embodiment II-30. The immunogenic composition of embodiment II-29, wherein the ADI polypeptide comprises the amino acid sequence of SEQ ID NO: 26, SEQ ID NO: 27, SEQ ID NO: 37 or SEQ ID NO: 38.

Embodiment II-31. The immunogenic composition of any one of embodiments II-15 to II-18, wherein the conjugate polypeptide is a ferritin polypeptide and comprises an amino acid sequence that is at least 95% identical to SEQ ID NO: 21.

Embodiment II-32. The immunogenic composition of embodiment II-31, wherein the ferritin polypeptide comprises a pAMF substitution at position 15 of SEQ ID NO: 21.

Embodiment II-33. The immunogenic composition of embodiment II-32, wherein the ferritin polypeptide comprises the amino acid sequence of SEQ ID NO: 23.

Embodiment II-34. The immunogenic composition of any one of embodiments II-1 to II-33, wherein the conjugate polysaccharide comprises a polyrhamnose core.

Embodiment II-35. The immunogenic composition of any one of embodiments II-1 to II-33, wherein the conjugate polysaccharide has an average molecular weight of about 5 KDa to about 7 KDa.

Embodiment II-36. The immunogenic composition of any one of embodiments II-1 to II-35, wherein the conjugate polysaccharide is a tetramer, a hexamer, an octamer, or a decamer polysaccharide.

Embodiment II-37. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising a *Streptococcus pyogenes* Adhesion and Division (SpyAD) conjugate polypeptide and a GAS conjugate polysaccharide or a variant thereof that lacks an immunodominant N-acetyl Glucosamine (GlcNAc) side chain.

Embodiment II-38. The immunogenic composition of embodiment II-37, wherein the SpyAD protein comprises an amino acid sequence that is at least 95% identical to SEQ ID NO: 9 and comprises a pAMF substitution at positions K64, K287, K386, and K657.

Embodiment II-39. The immunogenic composition of embodiment II-37, wherein the Spy AD protein comprises the amino acid sequence of SEQ ID NO: 9 or SEQ ID NO: 11.

Embodiment II-40. The immunogenic composition of embodiment II-37, wherein the SpyAD protein comprises an amino acid sequence that is at least 95% identical to SEQ ID NO: 33 and comprises a pAMF substitution at positions K64, K287, K386, and K657.

Embodiment II-41. The immunogenic composition of embodiment II-37, wherein the SpyAD protein comprises the amino acid sequence of SEQ ID NO: 9 or SEQ ID NO: 34.

Embodiment II-42. The immunogenic composition of embodiment II-41, wherein the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment II-43. The immunogenic composition of embodiment II-1 or II-37, comprising a C5a peptidase polypeptide antigen of SEQ ID NO: 30; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide.

Embodiment II-44. The immunogenic composition of embodiment II-1 or II-37, comprising a C5a peptidase polypeptide antigen of SEQ ID NO: 30; a SLO polypeptide antigen of SEQ ID NO: 52; and a polypeptide-polysaccharide conjugate comprising a SpyAD conjugate polypeptide of SEQ ID NO: 34 and a GAS conjugate polysaccharide.

Embodiment II-45. The immunogenic composition of embodiment II-1 or II-37, comprising a C5a peptidase polypeptide antigen of SEQ ID NO: 30; a SLO polypeptide antigen of SEQ ID NO: 32; and a polypeptide-polysaccharide conjugate comprising a SpyAD conjugate polypeptide of SEQ ID NO: 34 and a GAS conjugate polysaccharide.

Embodiment II-46. The immunogenic composition of embodiment II-1 or II-37, comprising a C5a peptidase polypeptide antigen of SEQ ID NO: 29; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide.

Embodiment II-47. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising an arginine deiminase (ADI) conjugate polypeptide and a GAS conjugate polysaccharide or a variant thereof that lacks an immunodominant N-acetyl Glucosamine (GlcNAc) side chain.

Embodiment II-48. The immunogenic composition of embodiment II-47, wherein the ADI polypeptide comprises an amino acid sequence that is at least 95% identical to SEQ ID NO: 13 or SEQ ID NO: 15 and comprises a pAMF substitution at positions K15, K193, and K316.

Embodiment II-49. The immunogenic composition of embodiment II-47, wherein the ADI polypeptide comprises the amino acid sequence of SEQ ID NO: 17 or SEQ ID NO: 19.

Embodiment II-50. The immunogenic composition of embodiments II-47 to II-48, wherein the ADI polypeptide comprises an amino acid sequence that is at least 95% identical to SEQ ID NO: 35 or SEQ ID NO: 36 and comprises a pAMF substitution at positions K15, K193, and K316.

Embodiment II-51. The immunogenic composition of embodiments II-47 to II-48, wherein the ADI polypeptide comprises the amino acid sequence of SEQ ID NO: 37 or SEQ ID NO: 38.

Embodiment II-52. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising a ferritin polypeptide and a GAS conjugate polysaccharide or a variant thereof that lacks an immunodominant N-acetyl Glucosamine (GlcNAc) side chain.

Embodiment II-53. The immunogenic composition of embodiment II-52, wherein the ferritin protein comprises an amino acid sequence that is at least 95% identical to SEQ ID NO: 21 and comprises a pAMF substitution at position 15.

Embodiment II-54. The immunogenic composition of embodiment II-52, wherein the ferritin protein comprises the amino acid sequence of SEQ ID NO: 23.

Embodiment II-55. The immunogenic composition of any one of embodiments II-1 to II-54, wherein the composition comprises about 10% to about 50% of the first GAS antigen, about 10% to about 50% of the second GAS antigen, and about 10% to about 50% of the polypeptide-polysaccharide conjugate.

Embodiment II-56. The immunogenic composition of any one of embodiments II-1 to II-55, further comprising one or more adjuvants selected from alum, saponin, monophosphoryl lipid A (MPL), or combinations thereof.

Embodiment II-57. A method of inducing a protective immune response against a Group A *Streptococcus* (GAS) bacterium in a subject comprising administering the immunogenic composition of any one of embodiments II-1 to II-56 to the subject.

Embodiment II-58. The method of embodiment II-57, wherein the subject is 18 years or older.

Embodiment II-59. The method of embodiment II-57, wherein the subject is less than 18 years old.

Embodiment II-60. The method of embodiment II-57, wherein the subject is between 5 years and 17 years old, between 6 months and 9 years old, or between 5 years and 9 years old.

Embodiment II-61. The method of any one of embodiments II-57 to II-60, wherein the GAS bacterium is of a serotype selected from M1, M2, M3, M4, M6, M11, M12, M22, M28, M75, and M89.

Embodiment II-62. The method of any one of embodiments II-57 to II-60, wherein the GAS bacterium is a serotype selected from M1, M3, M5, M9, M12, M18, M22, M25, M28, M71, M72, and M74.

Embodiment II-63. The method of any one of embodiments II-57 to II-60, wherein the GAS bacterium is a serotype selected from M1, M4, M6, M11, M12, M22, M44, M75, M77, M77, and M81.

Embodiment II-64. The method of any one of embodiments II-57 to II-60, wherein the GAS bacterium is a serotype selected from M1, M2, M3, M4, M6, M9, M12, M18, M22, M75, M77, M89, and M92.

Embodiment II-65. The method of any one of embodiments II-57 to II-60, wherein the GAS bacterium is a serotype selected from M1, M2, M3, M4, M5, M6, M9, M11, M12, M13, M28, M62, and M89.

Embodiment II-66. The method of any one of embodiments II-57 to II-60, wherein the GAS bacterium is a serotype selected from M1, M2, M3, M4, M6, M12, M22, M28, M49, M53, M68, M77, M80, M83, M87, M89, and M92.

Embodiment II-67. The method of any one of embodiments II-57 to II-66, wherein the immunogenic composition induces an antibody response in the subject against the Group A *Streptococcus* (GAS) bacterium and does not induce an antibody response in the subject against human tissue.

Embodiment II-68. The method of any one of embodiments II-57 to II-67, wherein the immunogenic composition induces a protective immune response against a *Shigella* bacterium in the subject, wherein the *Shigella* bacterium comprises a polysaccharide with a polyrhmanose backbone.

Embodiment II-69. A method of inducing a protective immune response against a *Shigella* bacterium in a subject comprising administering the immunogenic composition of any one of embodiments II-1 to II-56 to the subject.

Embodiment II-70. Use of the immunogenic composition of any one of embodiments II-1 to II-56 for inducing a protective immune response against a *Shigella* bacterium in a subject.

Embodiment II-71. Use of the immunogenic composition of any one of embodiments II-1 to II-56 in the manufacture of a medicament for inducing a protective immune response against a *Shigella* bacterium in a subject.

Embodiment II-72. The method or use of any one of embodiments II-69 to II-71, wherein the subject is 18 years or older.

Embodiment II-73. The method or use of embodiment II-72, wherein the subject is less than 18 years old.

Embodiment II-74. The method or use of embodiment II-73, wherein the subject is between 5 years and 17 years old, between 6 months and 9 years old, or between 5 years and 9 years old.

Embodiment III-1. An immunogenic composition comprising a. a first Group A *Streptococcus* (GAS) polypeptide antigen;
b. a second GAS polypeptide antigen; and
c. at least one polypeptide-polysaccharide conjugate, wherein the conjugate polypeptide is a third GAS polypeptide antigen or a non-GAS carrier polypeptide and comprises at least one non-natural amino acid, and wherein the conjugate polysaccharide is a GAS polysaccharide or a variant thereof that lacks an immunodominant N-acetyl Glucosamine (GlcNAc) side chain.

Embodiment III-2. The immunogenic composition of embodiment III-1, wherein at least one of the GAS polypeptide antigens is a full length GAS antigen.

Embodiment III-3. The immunogenic composition of embodiment III-1, wherein at least one of the GAS polypeptide antigens is a peptide fragment of a full length GAS antigen.

Embodiment III-4. The immunogenic composition of any one of embodiments III-1 to III-3, wherein the first and second GAS polypeptide antigens are independently selected from C5a peptidase, streptolysin O (SLO), Sib35, Sfb1, and SpyAD.

Embodiment III-5. The immunogenic composition of any one of embodiments III-1 to III-3, wherein the first and second GAS polypeptide antigens are independently selected from C5a peptidase, streptolysin O (SLO), Sib35, and Sfb1.

Embodiment III-6. The immunogenic composition of any one of embodiments III-1 to III-3, wherein the first and second GAS polypeptide antigens are C5a peptidase and SLO.

Embodiment III-7. The immunogenic composition of embodiment III-6, wherein the C5a peptidase polypeptide antigen comprises an amino acid sequence that is at least 95% identical to SEQ ID NO: 1 or SEQ ID NO: 3.

Embodiment III-7A. The immunogenic composition of embodiment III-6, wherein the C5a peptidase polypeptide antigen is at least 95% identical to SEQ ID NO: 1 or SEQ ID NO: 3.

Embodiment III-8. The immunogenic composition of embodiment III-6, wherein the C5a peptidase polypeptide antigen comprises the amino acid sequence of SEQ ID NO: 1 or SEQ ID NO: 3.

Embodiment III-9. The immunogenic composition of any one of embodiments III-1 to III-6 wherein the first and second GAS polypeptide antigens are C5a peptidase and SLO, and the C5a peptidase polypeptide antigen comprises the amino acid sequence of SEQ ID NO: 29 or SEQ ID NO: 30.

Embodiment III-9A. The immunogenic composition of any one of embodiments III-1 to III-6 wherein the first and second GAS polypeptide antigens are C5a peptidase and SLO, and the C5a peptidase polypeptide antigen consisting of the amino acid sequence of SEQ ID NO: 29 or SEQ ID NO: 30.

Embodiment III-10. The immunogenic composition of embodiment III-6, wherein the SLO polypeptide antigen comprises an amino acid sequence that is at least 95% identical to SEQ ID NO: 5 or SEQ ID NO: 7.

Embodiment III-10A. The immunogenic composition of embodiment III-6, wherein the SLO polypeptide antigen is at least 95% identical to SEQ ID NO: 5 or SEQ ID NO: 7.

Embodiment III-11. The immunogenic composition of any one of embodiments III-1 to III-7 or III-10, wherein the first and second GAS polypeptide antigens are C5a peptidase and SLO, and the SLO polypeptide antigen comprises an amino acid sequence that is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment III-11A. The immunogenic composition of any one of embodiment III-17, III-10, III-7A or III-10A, wherein the first and second GAS polypeptide antigens are C5a peptidase and SLO, and the SLO polypeptide antigen is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment III-12. The immunogenic composition of embodiment III-6, wherein the SLO polypeptide antigen comprises the amino acid sequence of SEQ ID NO: 5 or SEQ ID NO: 7.

Embodiment III-12A. The immunogenic composition of embodiment III-6, wherein the SLO polypeptide antigen consisting of the amino acid sequence of SEQ ID NO: 5 or SEQ ID NO: 7.

Embodiment III-13. The immunogenic composition of any one of embodiments III-1 to III-7, wherein the first and second GAS polypeptide antigens are C5a peptidase and SLO, and the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment III-13A. The immunogenic composition of any one of embodiments III-1 to III-7 or III-7A, wherein the first and second GAS polypeptide antigens are C5a peptidase and SLO, and the SLO polypeptide antigen consisting of the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment III-14. The immunogenic composition of any one of embodiments III-1 to III-3, wherein the first and second GAS polypeptide antigens are C5a peptidase and Spy AD.

Embodiment III-15. The immunogenic composition of embodiment III-14, wherein the C5a peptidase polypeptide antigen comprises an amino acid sequence that is at least 95% identical to SEQ ID NO: 29 or SEQ ID NO: 30.

Embodiment III-15A. The immunogenic composition of embodiment III-14, wherein the C5a peptidase polypeptide antigen is at least 95% identical to SEQ ID NO: 1 or SEQ ID NO: 3.

Embodiment III-16. The immunogenic composition of embodiment III-14, wherein the C5a peptidase polypeptide antigen comprises the amino acid sequence of SEQ ID NO: 29 or SEQ ID NO: 30.

Embodiment III-16A. The immunogenic composition of embodiment III-14, wherein the C5a peptidase polypeptide antigen consisting of the amino acid sequence of SEQ ID NO: 1 or SEQ ID NO: 3.

Embodiment III-17. The immunogenic composition of any one of embodiments III-1 to III-16, wherein the non-GAS carrier polypeptide is ferritin.

Embodiment III-18. The immunogenic composition of any one of embodiments III-1 to III-16, wherein the third GAS polypeptide antigen is selected from *Streptococcus pyogenes* Adhesion and Division (SpyAD) polypeptide, arginine deiminase (ADI), eCRM, and Protein D.

Embodiment III-19. The immunogenic composition of any one of embodiments III-1 to III-16, wherein the third GAS polypeptide antigen is selected from *Streptococcus pyogenes* Adhesion and Division (SpyAD) polypeptide, arginine deiminase (ADI), eCRM, Protein D, and SLO.

Embodiment III-20. The immunogenic composition of any one of embodiments III-1 to III-19, wherein the at least one nnAA is substituted for a lysine, a leucine, or an isoleucine in the conjugate polypeptide.

Embodiment III-21. The immunogenic composition of any one of embodiments III-1 to III-19, wherein the nnAA comprises a click chemistry reactive group.

Embodiment III-22. The immunogenic composition of embodiment III-16, wherein the nnAA is selected from 2-amino-3-(4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl) propanoic acid, 2-amino-3-(4-(azidomethyl)pyridin-2-yl)propanoic acid, 2-amino-3-(6-(azidomethyl)pyridin-3-yl)propanoic acid, and 2-amino-5-azidopentanoic acid.

Embodiment III-23. The immunogenic composition of embodiment III-21, wherein the nnAA is pAMF.

Embodiment III-24. The immunogenic composition of any one of embodiments III-20 to III-23, wherein the conjugate polypeptide is a third GAS protein, which is a SpyAD polypeptide and comprises an amino acid sequence that is at least 95% identical to SEQ ID NO: 9.

Embodiment III-24A. The immunogenic composition of any one of embodiments III-20 to III-23, wherein the conjugate polypeptide is a third GAS protein, which is a SpyAD polypeptide is at least 95% identical to SEQ ID NO: 9.

Embodiment III-25. The immunogenic composition of embodiment III-24, wherein the SpyAD polypeptide comprises a pAMF substitution at positions K64, K287, K386, and K657 of SEQ ID NO: 9.

Embodiment III-26. The immunogenic composition of embodiment III-25, wherein the SpyAD polypeptide comprises the amino acid sequence of SEQ ID NO: 9 or SEQ ID NO: 11.

Embodiment III-26A. The immunogenic composition of embodiment III-25, wherein the SpyAD polypeptide comprises consisting of the amino acid sequence of SEQ ID NO: 9 or SEQ ID NO: 11.

Embodiment III-27. The immunogenic composition of any one of embodiments III-20 to III-23, wherein the conjugate polypeptide is a third GAS protein, which is a SpyAD polypeptide and comprises an amino acid sequence that is at least 95% identical to SEQ ID NO: 33.

Embodiment III-27A. The immunogenic composition of any one of embodiments III-20 to III-23, wherein the conjugate polypeptide is a third GAS protein, which is a SpyAD polypeptide and is at least 95% identical to SEQ ID NO: 33.

Embodiment III-28. The immunogenic composition of embodiment III-27, wherein the SpyAD polypeptide comprises a pAMF substitution at positions K64, K287, K386, and K657 of SEQ ID NO: 33.

Embodiment III-29. The immunogenic composition of embodiment III-28, wherein the Spy AD polypeptide comprises the amino acid sequence of SEQ ID NO: 33 or SEQ ID NO: 34.

Embodiment III-30. The immunogenic composition of any one of embodiments III-20 to III-23, wherein the conjugate polypeptide is a third GAS polypeptide, which is an ADI polypeptide and comprises an amino acid sequence that is at least 95% identical to SEQ ID NO: 13 or SEQ ID NO: 15.

Embodiment III-30A. The immunogenic composition of any one of embodiments III-20 to III-23, wherein the conjugate polypeptide is a third GAS polypeptide, which is an ADI polypeptide and is at least 95% identical to SEQ ID NO: 13 or SEQ ID NO: 15.

Embodiment III-31. The immunogenic composition of embodiment III-30, wherein the ADI polypeptide comprises a pAMF substitution at positions K15, K193, and K316 of SEQ ID NO: 13 or SEQ ID NO: 15.

Embodiment III-32. The immunogenic composition of embodiment III-31, wherein the ADI polypeptide comprises the amino acid sequence of SEQ ID NO: 17 or SEQ ID NO: 19.

Embodiment III-32A. The immunogenic composition of embodiment III-31, wherein the ADI polypeptide consisting of the amino acid sequence of SEQ ID NO: 17 or SEQ ID NO: 19.

Embodiment III-33. The immunogenic composition of any one of embodiments III-20 to III-23, wherein the conjugate polypeptide is a third GAS polypeptide, which is an ADI polypeptide and comprises an amino acid sequence that is at least 95% identical to SEQ ID NO: 35 or SEQ ID NO: 36.

Embodiment III-33A. The immunogenic composition of any one of embodiments III-20 to III-23, wherein the conjugate polypeptide is a third GAS polypeptide, which is an ADI polypeptide and is at least 95% identical to SEQ ID NO: 35 or SEQ ID NO: 36.

Embodiment III-34. The immunogenic composition of embodiment III-33, wherein the ADI polypeptide comprises a pAMF substitution at positions K15, K193, and K316 of SEQ ID NO: 35 or SEQ ID NO: 36.

Embodiment III-35. The immunogenic composition of embodiment III-34, wherein the ADI polypeptide comprises the amino acid sequence of SEQ ID NO: 26, SEQ ID NO: 27, SEQ ID NO: 37 or SEQ ID NO: 38.

Embodiment III-35A. The immunogenic composition of embodiment III-34, wherein the ADI polypeptide consisting of the amino acid sequence of SEQ ID NO: 26, SEQ ID NO: 27, SEQ ID NO: 37 or SEQ ID NO: 38.

Embodiment III-36. The immunogenic composition of any one of embodiments III-20 to III-23, wherein the conjugate polypeptide is a third GAS polypeptide, which is a SLO polypeptide and comprises an amino acid sequence that is at least 95% identical to SEQ ID NO: 31, SEQ ID NO: 32, or SEQ ID NO: 53.

Embodiment III-36A. The immunogenic composition of any one of embodiments III-20 to III-23, wherein the conjugate polypeptide is a third GAS polypeptide, which is a SLO polypeptide and is at least 95% identical to SEQ ID NO: 6, SEQ ID NO: 8, or SEQ ID NO: 53.

Embodiment III-37. The immunogenic composition of embodiment III-36, wherein the SLO polypeptide comprises 3 or 4 pAMF substitutions at positions selected from K98, K112, R151, K189, K272, K323, K357, K375, K407, or K464.

Embodiment III-38. The immunogenic composition of embodiment III-36 or III-37, wherein the SLO polypeptide comprises the amino acid sequence of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, or SEQ ID NO: 64.

Embodiment III-38A. The immunogenic composition of embodiment III-36 or III-37, wherein the SLO polypeptide consisting of the amino acid sequence of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, or SEQ ID NO: 64.

Embodiment III-39. The immunogenic composition of any one of embodiments III-20 to III-23, wherein the conjugate polypeptide is a ferritin polypeptide and comprises an amino acid sequence that is at least 95% identical to SEQ ID NO: 21.

Embodiment III-39A. The immunogenic composition of any one of embodiments III-20 to III-23, wherein the conjugate polypeptide is a ferritin polypeptide and is at least 95% identical to SEQ ID NO: 21.

Embodiment III-40. The immunogenic composition of embodiment III-39, wherein the ferritin polypeptide comprises a pAMF substitution at position 15 of SEQ ID NO: 21.

Embodiment III-41. The immunogenic composition of embodiment III-40, wherein the ferritin polypeptide comprises the amino acid sequence of SEQ ID NO: 23.

Embodiment III-41A. The immunogenic composition of embodiment III-40, wherein the ferritin polypeptide consisting of the amino acid sequence of SEQ ID NO: 23.

Embodiment III-42. The immunogenic composition of any one of embodiments III-1 to III-41, wherein the conjugate polysaccharide comprises a polyrhamnose core.

Embodiment III-43. The immunogenic composition of any one of embodiments III-1 to III-41, wherein the conjugate polysaccharide has an average molecular weight of about 5 KDa to about 7 KDa.

Embodiment III-44. The immunogenic composition of any one of embodiments III-1 to III-43, wherein the conjugate polysaccharide is a tetramer, a hexamer, an octamer, or a decamer polysaccharide.

Embodiment III-45. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising a *Streptococcus pyogenes* Adhesion and Division (SpyAD) conjugate polypeptide and a GAS conjugate polysaccharide or a variant thereof that lacks an immunodominant N-acetyl Glucosamine (GlcNAc) side chain.

Embodiment III-46. The immunogenic composition of embodiment III-45, wherein the SpyAD protein comprises an amino acid sequence that is at least 95% identical to SEQ ID NO: 9 and comprises a pAMF substitution at positions K64, K287, K386, and K657.

Embodiment III-46A. The immunogenic composition of embodiment III-45, wherein the SpyAD protein is at least 95% identical to SEQ ID NO: 9 and comprises a pAMF substitution at positions K64, K287, K386, and K657.

Embodiment III-47. The immunogenic composition of embodiment III-45, wherein the Spy AD protein comprises the amino acid sequence of SEQ ID NO: 9 or SEQ ID NO: 11.

Embodiment III-47A. The immunogenic composition of embodiment III-45, wherein the SpyAD protein consisting of the amino acid sequence of SEQ ID NO: 9 or SEQ ID NO: 11.

Embodiment III-48. The immunogenic composition of embodiment III-45, wherein the Spy AD protein comprises an amino acid sequence that is at least 95% identical to SEQ ID NO: 33 and comprises a pAMF substitution at positions K64, K287, K386, and K657.

Embodiment III-48A. The immunogenic composition of embodiment III-45, wherein the SpyAD protein is at least 95% identical to SEQ ID NO: 33 and comprises a pAMF substitution at positions K64, K287, K386, and K657.

Embodiment III-49. The immunogenic composition of embodiment III-45, wherein the SpyAD protein comprises the amino acid sequence of SEQ ID NO: 9 or SEQ ID NO: 34.

Embodiment III-49A. The immunogenic composition of embodiment III-45, wherein the SpyAD protein consisting of the amino acid sequence of SEQ ID NO: 9 or SEQ ID NO: 34.

Embodiment III-50. The immunogenic composition of embodiment III-49, wherein the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment III-50A. The immunogenic composition of embodiment III-49 or III-49A, wherein the SLO polypeptide antigen consisting of the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment III-51. The immunogenic composition of embodiment III-1 or III-45, comprising a C5a peptidase polypeptide antigen of SEQ ID NO: 30; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide.

Embodiment III-52. The immunogenic composition of embodiment III-1 or III-45, comprising a C5a peptidase polypeptide antigen of SEQ ID NO: 30; a SLO polypeptide antigen of SEQ ID NO: 52; and a polypeptide-polysaccharide conjugate comprising a SpyAD conjugate polypeptide of SEQ ID NO: 34 and a GAS conjugate polysaccharide.

Embodiment III-53. The immunogenic composition of embodiment III-1 or III-45, comprising a C5a peptidase polypeptide antigen of SEQ ID NO: 30; a SLO polypeptide antigen of SEQ ID NO: 32; and a polypeptide-polysaccharide conjugate comprising a SpyAD conjugate polypeptide of SEQ ID NO: 34 and a GAS conjugate polysaccharide.

Embodiment III-54. The immunogenic composition of embodiment III-1 or III-45, comprising a C5a peptidase polypeptide antigen of SEQ ID NO: 29; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide.

Embodiment III-55. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising an arginine deiminase (ADI) conjugate polypeptide and a GAS conjugate polysaccharide or a variant thereof that lacks an immunodominant N-acetyl Glucosamine (GlcNAc) side chain.

Embodiment III-56. The immunogenic composition of embodiment III-55, wherein the ADI polypeptide comprises an amino acid sequence that is at least 95% identical to SEQ ID NO: 13 or SEQ ID NO: 15 and comprises a pAMF substitution at positions K15, K193, and K316.

Embodiment III-56A. The immunogenic composition of embodiment III-55, wherein the ADI polypeptide is at least 95% identical to SEQ ID NO: 13 or SEQ ID NO: 15 and comprises a pAMF substitution at positions K15, K193, and K316.

Embodiment III-57. The immunogenic composition of embodiment III-55, wherein the ADI polypeptide comprises the amino acid sequence of SEQ ID NO: 17 or SEQ ID NO: 19.

Embodiment III-57A. The immunogenic composition of embodiment III-55, wherein the ADI polypeptide consisting of the amino acid sequence of SEQ ID NO: 17 or SEQ ID NO: 19.

Embodiment III-58. The immunogenic composition of embodiments III-55 to III-56, wherein the ADI polypeptide comprises an amino acid sequence that is at least 95% identical to SEQ ID NO: 35 or SEQ ID NO: 36 and comprises a pAMF substitution at positions K15, K193, and K316.

Embodiment III-58A. The immunogenic composition of any one of embodiments III-55 to III-56 or III-56A, wherein the ADI polypeptide is at least 95% identical to SEQ ID NO: 35 or SEQ ID NO: 36 and comprises a pAMF substitution at positions K15, K193, and K316.

Embodiment III-59. The immunogenic composition of embodiments III-55 to III-56, wherein the ADI polypeptide comprises the amino acid sequence of SEQ ID NO: 37 or SEQ ID NO: 38.

Embodiment III-59A. The immunogenic composition of any one of embodiments III-55 to III-56 or III-56A, wherein the ADI polypeptide consisting of the amino acid sequence of SEQ ID NO: 37 or SEQ ID NO: 38.

Embodiment III-60. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising a ferritin polypeptide and a GAS conjugate polysaccharide or a variant thereof that lacks an immunodominant N-acetyl Glucosamine (GlcNAc) side chain.

Embodiment III-61. The immunogenic composition of embodiment III-60, wherein the ferritin protein comprises an amino acid sequence that is at least 95% identical to SEQ ID NO: 21 and comprises a pAMF substitution at position 15.

Embodiment III-61A. The immunogenic composition of embodiment III-60, wherein the ferritin protein is at least 95% identical to SEQ ID NO: 21 and comprises a pAMF substitution at position 15.

Embodiment III-62. The immunogenic composition of embodiment III-60, wherein the ferritin protein comprises the amino acid sequence of SEQ ID NO: 23.

Embodiment III-62A. The immunogenic composition of embodiment III-60, wherein the ferritin protein consisting of the amino acid sequence of SEQ ID NO: 23.

Embodiment III-63. The immunogenic composition of any one of embodiments III-1 to III-62, wherein the composition comprises about 10% to about 50% of the first GAS antigen, about 10% to about 50% of the second GAS antigen, and about 10% to about 50% of the polypeptide-polysaccharide conjugate.

Embodiment III-64. The immunogenic composition of any one of embodiments III-1 to III-63, further comprising one or more adjuvants selected from alum, saponin, monophosphoryl lipid A (MPL), or combinations thereof.

Embodiment III-65. A method of inducing a protective immune response against a Group A *Streptococcus* (GAS) bacterium in a subject comprising administering the immunogenic composition of any one of embodiments III-1-56 to the subject.

Embodiment III-66. The method of embodiment III-65, wherein the subject is 18 years or older.

Embodiment III-67. The method of embodiment III-65, wherein the subject is less than 18 years old.

Embodiment III-68. The method of embodiment III-65, wherein the subject is between 5 years and 17 years old, between 6 months and 9 years old, or between 5 years and 9 years old.

Embodiment III-69. The method of any one of embodiments III-65 to III-68, wherein the GAS bacterium is of a serotype selected from M1, M2, M3, M4, M6, M11, M12, M22, M28, M75, and M89.

Embodiment III-70. The method of any one of embodiments III-65 to III-68, wherein the GAS bacterium is a serotype selected from M1, M3, M5, M9, M12, M18, M22, M25, M28, M71, M72, and M74.

Embodiment III-71. The method of any one of embodiments III-65 to III-68, wherein the GAS bacterium is a serotype selected from M1, M4, M6, M11, M12, M22, M44, M75, M77, M77, and M81.

Embodiment III-72. The method of any one of embodiments III-65 to III-68, wherein the GAS bacterium is a serotype selected from M1, M2, M3, M4, M6, M9, M12, M18, M22, M75, M77, M89, and M92.

Embodiment III-73. The method of any one of embodiments III-65 to III-68, wherein the GAS bacterium is a serotype selected from M1, M2, M3, M4, M5, M6, M9, M11, M12, M13, M28, M62, and M89.

Embodiment III-74. The method of any one of embodiments III-65 to III-68, wherein the GAS bacterium is a serotype selected from M1, M2, M3, M4, M6, M12, M22, M28, M49, M53, M68, M77, M80, M83, M87, M89, and M92.

Embodiment III-75. The method of any one of embodiments III-65 to III-74, wherein the immunogenic composition induces an antibody response in the subject against the Group A *Streptococcus* (GAS) bacterium and does not induce an antibody response in the subject against human tissue.

Embodiment III-76. The method of any one of embodiments III-65 to III-75, wherein the immunogenic composition induces a protective immune response against a *Shigella* bacterium in the subject, wherein the *Shigella* bacterium comprises a polysaccharide with a polyrhmanose backbone.

Embodiment III-77. A method of inducing a protective immune response against a *Shigella* bacterium in a subject comprising administering the immunogenic composition of any one of embodiments III-1-56 to the subject.

Embodiment III-78. Use of the immunogenic composition of any one of embodiments III-1 to III-54 for inducing a protective immune response against a *Shigella* bacterium in a subject.

Embodiment III-79. Use of the immunogenic composition of any one of embodiments III-1 to III-54 in the manufacture of a medicament for inducing a protective immune response against a *Shigella* bacterium in a subject.

Embodiment III-80. The method or use of any one of embodiments III-77 to III-79, wherein the subject is 18 years or older.

Embodiment III-81. The method or use of embodiment III-80, wherein the subject is less than 18 years old.

Embodiment III-82. The method or use of embodiment III-81, wherein the subject is between 5 years and 17 years old, between 6 months and 9 years old, or between 5 years and 9 years old.

Embodiment IV-1. An immunogenic composition comprising a. a first Group A *Streptococcus* (GAS) polypeptide antigen;
b. a second GAS polypeptide antigen; and
c. at least one polypeptide-polysaccharide conjugate, wherein the conjugate polypeptide is a third GAS polypeptide antigen or a non-GAS carrier polypeptide and comprises at least one non-natural amino acid, and wherein the conjugate polysaccharide is a GAS polysaccharide or a variant thereof that lacks an immunodominant N-acetyl Glucosamine (GlcNAc) side chain.

Embodiment IV-2. The immunogenic composition of embodiment IV-1, wherein at least one of the GAS polypeptide antigens is a full length GAS antigen.

Embodiment IV-3. The immunogenic composition of embodiment IV-1, wherein at least one of the GAS polypeptide antigens is a peptide fragment of a full length GAS antigen.

Embodiment IV-4. The immunogenic composition of any one of embodiments IV-1 to IV-3, wherein the first and second GAS polypeptide antigens are independently selected from C5a peptidase, streptolysin O (SLO), Sib35, Sfb1, and SpyAD.

Embodiment IV-5. The immunogenic composition of any one of embodiments IV-1 to IV-3, wherein the first and second GAS polypeptide antigens are independently selected from C5a peptidase, streptolysin O (SLO), Sib35, and Sfb1.

Embodiment IV-6. The immunogenic composition of any one of embodiments IV-1 to IV-3, wherein the first and second GAS polypeptide antigens are C5a peptidase and SLO.

Embodiment IV-7. The immunogenic composition of any one of embodiments IV-1 to IV-6, wherein the C5a peptidase polypeptide antigen comprises an amino acid sequence that is at least 95% identical to SEQ ID NO: 29 or SEQ ID NO: 30.

Embodiment IV-8. The immunogenic composition of any one of embodiments IV-1 to IV-5, wherein the C5a peptidase polypeptide antigen is at least 95% identical to SEQ ID NO: 29 or SEQ ID NO: 30.

Embodiment IV-9. The immunogenic composition of embodiment IV-6, wherein the C5a peptidase polypeptide antigen comprises the amino acid sequence of SEQ ID NO: 29 or SEQ ID NO: 30.

Embodiment IV-10. The immunogenic composition of any one of embodiments IV-1 to IV-6 wherein the first and second GAS polypeptide antigens are C5a peptidase and SLO, and the C5a peptidase polypeptide antigen comprises the amino acid sequence of SEQ ID NO: 29 or SEQ ID NO: 30.

Embodiment IV-11. The immunogenic composition of any one of embodiments IV-1 to IV-6 wherein the first and second GAS polypeptide antigens are C5a peptidase and SLO, and the C5a peptidase polypeptide antigen consists of the amino acid sequence of SEQ ID NO: 29 or SEQ ID NO: 30.

Embodiment IV-12. The immunogenic composition of any one of embodiments IV-1 to IV-11, wherein the SLO polypeptide antigen comprises an amino acid sequence that is at least 95% identical to SEQ ID NO: 31 or SEQ ID NO: 32.

Embodiment IV-13. The immunogenic composition of any one of embodiments IV-1 to IV-11, wherein the SLO polypeptide antigen is at least 95% identical to SEQ ID NO: 31 or SEQ ID NO: 32.

Embodiment IV-14. The immunogenic composition of any one of embodiments IV-1 to IV-9, wherein the first and second GAS polypeptide antigens are C5a peptidase and SLO, and the SLO polypeptide antigen comprises an amino acid sequence that is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment IV-15. The immunogenic composition of any one of embodiments IV-1 to IV-9, wherein the first and second GAS polypeptide antigens are C5a peptidase and SLO, and the SLO polypeptide antigen is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment IV-16. The immunogenic composition of any one of embodiments IV-1 to IV-11, wherein the SLO polypeptide antigen comprises the amino acid sequence of SEQ ID NO: 31 or SEQ ID NO: 32.

Embodiment IV-17. The immunogenic composition of embodiment IV-6, wherein the SLO polypeptide antigen consists of the amino acid sequence of SEQ ID NO: 31 or SEQ ID NO: 32.

Embodiment IV-18. The immunogenic composition of any one of embodiments IV-1 to IV-9, wherein the first and second GAS polypeptide antigens are C5a peptidase and SLO, and the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment IV-19. The immunogenic composition of any one of embodiments IV-1 to IV-9, wherein the first and second GAS polypeptide antigens are C5a peptidase and SLO, and the SLO polypeptide antigen consists of the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment IV-20. The immunogenic composition of any one of embodiments IV-1 to IV-4, wherein the first and second GAS polypeptide antigens are C5a peptidase and SpyAD.

Embodiment IV-21. The immunogenic composition of any one of embodiments IV-1 to IV-6, 16-17, or 20, wherein the C5a peptidase polypeptide antigen comprises an amino acid sequence that is at least 95% identical to SEQ ID NO: 29 or SEQ ID NO: 30.

Embodiment IV-22. The immunogenic composition of embodiment IV-20 or IV-21, wherein the C5a peptidase polypeptide antigen is at least 95% identical to SEQ ID NO: 29 or SEQ ID NO: 30.

Embodiment IV-23. The immunogenic composition of any one of embodiments IV-1 to IV-6, 16-17 or 20, wherein the C5a peptidase polypeptide antigen comprises the amino acid sequence of SEQ ID NO: 29 or SEQ ID NO: 30.

Embodiment IV-24. The immunogenic composition of any one of embodiments IV-1 to IV-6, 16-17, 20, or 23, wherein the C5a peptidase polypeptide antigen consists of the amino acid sequence of SEQ ID NO: 20 or SEQ ID NO: 30.

Embodiment IV-25. The immunogenic composition of any one of embodiments IV-1 to IV-24, wherein the non-GAS carrier polypeptide is ferritin.

Embodiment IV-26. The immunogenic composition of any one of embodiments IV-1 to IV-24, wherein the third GAS polypeptide antigen or non-GAS polypeptide antigen is selected from *Streptococcus pyogenes* Adhesion and Division (SpyAD) polypeptide, arginine deiminase (ADI), SEQ ID NO: 25, and Protein D.

Embodiment IV-27. The immunogenic composition of any one of embodiments IV-1 to IV-24, wherein the third GAS polypeptide antigen or non-GAS polypeptide antigen is selected from *Streptococcus pyogenes* Adhesion and Division (SpyAD) polypeptide, arginine deiminase (ADI), SEQ ID NO: 25, Protein D, and SLO.

Embodiment IV-28. The immunogenic composition of any one of embodiments IV-1 to IV-27, wherein the at least one nnAA is substituted for a lysine, a leucine, an arginine, or an isoleucine in the conjugate polypeptide.

Embodiment IV-29. The immunogenic composition of any one of embodiments IV-1 to IV-27, wherein the nnAA comprises a click chemistry reactive group.

Embodiment IV-30. The immunogenic composition of any one of embodiments IV-1 to IV-29, wherein the nnAA is selected from 2-amino-3-(4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl) propanoic acid, 2-amino-3-(6-(azidomethyl)pyridin-3-yl)propanoic acid, and 2-amino-5-azidopentanoic acid.

Embodiment IV-31. The immunogenic composition of embodiment IV-29 or IV-30, wherein the nnAA is pAMF.

Embodiment IV-32. The immunogenic composition of any one of embodiments IV-26 to IV-31, wherein the conjugate polypeptide is a third GAS protein, which is a SpyAD polypeptide and comprises an amino acid sequence that is at least 95% identical to SEQ ID NO: 33.

Embodiment IV-33. The immunogenic composition of any one of embodiments IV-28 to IV-32, wherein the conjugate polypeptide is a third GAS protein, which is a SpyAD polypeptide and is at least 95% identical to SEQ ID NO: 33.

Embodiment IV-34. The immunogenic composition of any one of embodiments IV-26 to IV-33, wherein the SpyAD polypeptide comprises a pAMF substitution at positions K64, K287, K386, and K657 of SEQ ID NO: 33.

Embodiment IV-35. The immunogenic composition of any one of embodiments IV-26 to IV-31 or 34, wherein the SpyAD polypeptide comprises the amino acid sequence of SEQ ID NO: 33 or SEQ ID NO: 34.

Embodiment IV-36. The immunogenic composition of embodiment IV-34, wherein the SpyAD polypeptide consisting of the amino acid sequence of SEQ ID NO: 33 or SEQ ID NO: 34.

Embodiment IV-37. The immunogenic composition of any one of embodiments IV-26 to IV-31, wherein the conjugate polypeptide is a third GAS polypeptide, which is an ADI polypeptide and comprises an amino acid sequence that is at least 95% identical to SEQ ID NO: 35 or SEQ ID NO: 36.

Embodiment IV-38. The immunogenic composition of any one of embodiments IV-26 to IV-31, wherein the conjugate polypeptide is a third GAS polypeptide, which is an ADI polypeptide and is at least 95% identical to SEQ ID NO: 35 or SEQ ID NO: 36.

Embodiment IV-39. The immunogenic composition of any one of embodiments IV-26 to IV-31 or 37-38, wherein the ADI polypeptide comprises a pAMF substitution at positions K15, K193, and K316 of SEQ ID NO: 35 or SEQ ID NO: 36.

Embodiment IV-40. The immunogenic composition of embodiment IV-39, wherein the ADI polypeptide comprises the amino acid sequence of SEQ ID NO: 27, SEQ ID NO: 37 or SEQ ID NO: 38.

Embodiment IV-41. The immunogenic composition of any one of embodiments IV-26 to IV-31 or 39, wherein the ADI polypeptide consist of the amino acid sequence of SEQ ID NO: 27, SEQ ID NO: 37 or SEQ ID NO: 38.

Embodiment IV-42. The immunogenic composition of any one of embodiments IV-27 to IV-31, wherein the conjugate polypeptide is a third GAS polypeptide, which is a SLO polypeptide and comprises an amino acid sequence that is at least 95% identical to SEQ ID NO: 31, SEQ ID NO: 32, or SEQ ID NO: 53.

Embodiment IV-43. The immunogenic composition of any one of embodiments IV-27 to IV-31, wherein the conjugate polypeptide is a third GAS polypeptide, which is a SLO polypeptide and is at least 95% identical to SEQ ID NO: 31, SEQ ID NO: 32, or SEQ ID NO: 53.

Embodiment IV-44. The immunogenic composition of embodiment IV-42 or IV-43, wherein the SLO polypeptide comprises 3 or 4 pAMF substitutions at positions selected from K98, K112, R151, K189, K272, K323, K357, K375, K407, or K464.

Embodiment IV-45. The immunogenic composition of embodiment IV-44, wherein the SLO polypeptide comprises the amino acid sequence of SEQ ID NO: 55, SEQ ID NO:

56, SEQ ID NO: 57, SEQ ID NO: 58, SEQ ID NO: 59, SEQ ID NO: 60, SEQ ID NO: 61, SEQ ID NO: 62, SEQ ID NO: 63, or SEQ ID NO: 64.

Embodiment IV-46. The immunogenic composition of embodiment IV-44, wherein the SLO polypeptide consists of the amino acid sequence of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, or SEQ ID NO: 64.

Embodiment IV-47. The immunogenic composition of embodiment IV-42 or IV-43, wherein the SLO polypeptide comprises 5, 6, 7, or 8 pAMF substitutions at positions selected from K98, K112, R151, K189, K272, K323, K357, K375, K407, or K464

Embodiment IV-48. The immunogenic composition of embodiment IV-47, wherein the SLO polypeptide comprises the amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, or SEQ ID NO: 76.

Embodiment IV-49. The immunogenic composition of embodiment IV-47, wherein the SLO polypeptide consists of the amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, or SEQ ID NO: 76.

Embodiment IV-50. The immunogenic composition of any one of embodiments IV-28 to IV-31, wherein the conjugate polypeptide is a ferritin polypeptide and comprises an amino acid sequence that is at least 95% identical to SEQ ID NO: 21.

Embodiment IV-51. The immunogenic composition of any one of embodiments IV-28 to IV-31, wherein the conjugate polypeptide is a ferritin polypeptide and is at least 95% identical to SEQ ID NO: 21.

Embodiment IV-52. The immunogenic composition of embodiment IV-50 or IV-51, wherein the ferritin polypeptide comprises a pAMF substitution at position 15 of SEQ ID NO: 21.

Embodiment IV-53. The immunogenic composition of embodiment IV-52, wherein the ferritin polypeptide comprises the amino acid sequence of SEQ ID NO: 23.

Embodiment IV-54. The immunogenic composition of embodiment IV-52, wherein the ferritin polypeptide consists of the amino acid sequence of SEQ ID NO: 23.

Embodiment IV-55. The immunogenic composition of any one of embodiments IV-1 to IV-54, wherein the conjugate polysaccharide lacks the immunodominant GlcNAc side chain.

Embodiment IV-56. The immunogenic composition of any one of embodiments IV-1 to IV-56, wherein the conjugate polysaccharide has an average molecular weight of about 5 kDa to about 7 kDa.

Embodiment IV-57. The immunogenic composition of any one of embodiments IV-1 to IV-56, wherein the conjugate polysaccharide has an average molecular weight of about 10 kDa to about 45 kDa.

Embodiment IV-58. The immunogenic composition of any one of embodiments IV-1 to IV-55, wherein the conjugate polysaccharide is a tetramer, a hexamer, an octamer, or a decamer polysaccharide.

Embodiment IV-59. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising a *Streptococcus pyogenes* Adhesion and Division (SpyAD) conjugate polypeptide and a GAS conjugate polysaccharide or a variant thereof that lacks an immunodominant N-acetyl Glucosamine (GlcNAc) side chain.

Embodiment IV-60. The immunogenic composition of embodiment IV-59, wherein the SpyAD protein comprises an amino acid sequence that is at least 95% identical to SEQ ID NO: 33 and comprises a pAMF substitution at positions K64, K287, K386, and K657.

Embodiment IV-61. The immunogenic composition of embodiment IV-59, wherein the SpyAD protein is at least 95% identical to SEQ ID NO: 33 and comprises a pAMF substitution at positions K64, K287, K386, and K657.

Embodiment IV-62. The immunogenic composition of embodiments IV-59 to IV-61, wherein the SpyAD protein comprises the amino acid sequence of SEQ ID NO: 34.

Embodiment IV-63. The immunogenic composition of embodiments IV-59 to IV-61, wherein the SpyAD protein consists of the amino acid sequence of SEQ ID NO: 34.

Embodiment IV-64. The immunogenic composition of any one of embodiments IV-59 to IV-63, wherein the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment IV-65. The immunogenic composition of any one of embodiments IV-59 to IV-64, wherein the SLO polypeptide antigen consists of the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

Embodiment IV-66. The immunogenic composition of embodiment IV-1 or IV-59, comprising a C5a peptidase polypeptide antigen of SEQ ID NO: 30; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide.

Embodiment IV-67. The immunogenic composition of embodiment IV-1 or IV-59, comprising a C5a peptidase polypeptide antigen of SEQ ID NO: 30; a SLO polypeptide antigen of SEQ ID NO: 52; and a polypeptide-polysaccharide conjugate comprising a SpyAD conjugate polypeptide of SEQ ID NO: 34 and a GAS conjugate polysaccharide.

Embodiment IV-68. The immunogenic composition of embodiment IV-1 or IV-59, comprising a C5a peptidase polypeptide antigen of SEQ ID NO: 30; a SLO polypeptide antigen of SEQ ID NO: 32; and a polypeptide-polysaccharide conjugate comprising a SpyAD conjugate polypeptide of SEQ ID NO: 34 and a GAS conjugate polysaccharide.

Embodiment IV-69. The immunogenic composition of embodiment IV-1 or IV-59, comprising a C5a peptidase polypeptide antigen of SEQ ID NO: 29; a SLO polypeptide antigen of SEQ ID NO: 53; and a polypeptide-polysaccharide conjugate comprising a SpyAD conjugate polypeptide of SEQ ID NO: 34 and a GAS conjugate polysaccharide.

Embodiment IV-70. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising an arginine deiminase (ADI) conjugate polypeptide and a GAS conjugate polysaccharide or a variant thereof that lacks an immunodominant N-acetyl Glucosamine (GlcNAc) side chain.

Embodiment IV-71. The immunogenic composition of embodiment IV-70, wherein the ADI polypeptide comprises an amino acid sequence that is at least 95% identical to SEQ ID NO: 35 or SEQ ID NO: 36 and comprises a pAMF substitution at positions K15, K193, and K316.

Embodiment IV-72. The immunogenic composition of embodiment IV-70, wherein the ADI polypeptide is at least 95% identical to SEQ ID NO: 35 or SEQ ID NO: 36 and comprises a pAMF substitution at positions K15, K193, and K316.

Embodiment IV-73. The immunogenic composition of embodiment IV-72, wherein the ADI polypeptide comprises the amino acid sequence of SEQ ID NO: 37 or SEQ ID NO: 38.

Embodiment IV-74. The immunogenic composition of any one of embodiment IV-72, wherein the ADI polypeptide consists of the amino acid sequence of SEQ ID NO: 37 or SEQ ID NO: 38.

Embodiment IV-75. An immunogenic composition comprising a. a Group A *Streptococcus* (GAS) C5a peptidase polypeptide antigen;
b. a GAS streptolysin O (SLO) polypeptide antigen; and
c. a polypeptide-polysaccharide conjugate comprising a ferritin polypeptide and a GAS conjugate polysaccharide or a variant thereof that lacks an immunodominant N-acetyl Glucosamine (GlcNAc) side chain.

Embodiment IV-76. The immunogenic composition of embodiment IV-75, wherein the ferritin protein comprises an amino acid sequence that is at least 95% identical to SEQ ID NO: 21 and comprises a pAMF substitution at position 15.

Embodiment IV-77. The immunogenic composition of embodiment IV-75, wherein the ferritin protein is at least 95% identical to SEQ ID NO: 21 and comprises a pAMF substitution at position 15.

Embodiment IV-78. The immunogenic composition of embodiment IV-75, wherein the ferritin protein comprises the amino acid sequence of SEQ ID NO: 23.

Embodiment IV-79. The immunogenic composition of embodiment IV-75, wherein the ferritin protein consists of the amino acid sequence of SEQ ID NO: 23.

Embodiment IV-80. The immunogenic composition of any one of embodiments IV-1 to IV-79, wherein the composition comprises about 10% to about 50% of the first GAS antigen, about 10% to about 50% of the second GAS antigen, and about 10% to about 50% of the polypeptide-polysaccharide conjugate.

Embodiment IV-81. The immunogenic composition of any one of embodiments IV-1 to IV-80, further comprising one or more adjuvants selected from alum, saponin, monophosphoryl lipid A (MPL), or combinations thereof.

Embodiment IV-82. The immunogenic composition of any one of embodiments IV-1 to IV-81, wherein the polypeptide-polysaccharide conjugate has an average molecular mass of about 10 kDa to about 5000 kDa.

Embodiment IV-83. A method of inducing a protective immune response against a Group A *Streptococcus* (GAS) bacterium in a subject comprising administering the immunogenic composition of any one of embodiments IV-1 to IV-82 to the subject.

Embodiment IV-84. The method of embodiment IV-83, wherein the subject is 18 years or older.

Embodiment IV-85. The method of embodiment IV-65, wherein the subject is less than 18 years old.

Embodiment IV-86. The method of embodiment IV-65, wherein the subject is between 5 years and 17 years old, between 6 months and 9 years old, or between 5 years and 9 years old.

Embodiment IV-87. The method of any one of embodiments IV-83 to IV-86, wherein the GAS bacterium is of a serotype selected from M1, M2, M3, M4, M6, M11, M12, M22, M28, M75, and M89.

Embodiment IV-88. The method of any one of embodiments IV-83 to IV-86, wherein the GAS bacterium is a serotype selected from M1, M3, M5, M9, M12, M18, M22, M25, M28, M71, M72, and M74.

Embodiment IV-89. The method of any one of embodiments IV-83 to IV-86, wherein the GAS bacterium is a serotype selected from M1, M4, M6, M11, M12, M22, M44, M75, M77, M77, and M81.

Embodiment IV-90. The method of any one of embodiments IV-83 to IV-86, wherein the GAS bacterium is a serotype selected from M1, M2, M3, M4, M6, M9, M12, M18, M22, M75, M77, M89, and M92.

Embodiment IV-91. The method of any one of embodiments IV-83 to IV-86, wherein the GAS bacterium is a serotype selected from M1, M2, M3, M4, M5, M6, M9, M11, M12, M13, M28, M62, and M89.

Embodiment IV-92. The method of any one of embodiments IV-83 to IV-86, wherein the GAS bacterium is a serotype selected from M1, M2, M3, M4, M6, M12, M22, M28, M49, M53, M68, M77, M80, M83, M87, M89, and M92.

Embodiment IV-93. The method of any one of embodiments IV-83 to IV-92, wherein the immunogenic composition induces an antibody response in the subject against the Group A *Streptococcus* (GAS) bacterium and does not induce an antibody response in the subject against human tissue.

Embodiment IV-94. The method of any one of embodiments IV-83 to IV-93, wherein the immunogenic composition induces a protective immune response against a *Shigella* bacterium in the subject, wherein the *Shigella* bacterium comprises a polysaccharide with a polyrhmanose backbone.

Embodiment IV-95. A method of inducing a protective immune response against a *Shigella* bacterium in a subject comprising administering the immunogenic composition of any one of embodiments IV-1 to IV-82 to the subject.

Embodiment IV-96. Use of the immunogenic composition of any one of embodiments IV-1 to IV-82 for inducing a protective immune response against a *Shigella* bacterium in a subject.

Embodiment IV-97. Use of the immunogenic composition of any one of embodiments IV-1 to IV-82 in the manufacture of a medicament for inducing a protective immune response against a *Shigella* bacterium in a subject.

Embodiment IV-98. Use of the immunogenic composition of any one of embodiments IV-1 to IV-82 in the manufacture of a medicament for inducing a protective immune response against a GAS bacterium in a subject.

Embodiment IV-99. Use of the immunogenic composition of any one of embodiments IV-1 to IV-82 for inducing a protective immune response against a GAS bacterium in a subject.

Embodiment IV-100. The method or use of any one of embodiments IV-93 to IV-99, wherein the subject is 18 years or older.

Embodiment IV-101. The method or use of embodiment IV-100, wherein the subject is less than 18 years old.

Embodiment IV-102. The method or use of embodiment IV-100, wherein the subject is between 5 years and 17 years old, between 6 months and 9 years old, or between 5 years and 9 years old.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

Example 1: Expression and Purification of GAS Polysaccharides

Experiments were performed to express and purify GAS polysaccharides from GAS bacterial cultures.

500 mL starter cultures were prepared from the appropriate recombinant GAS colony, allowing the bacteria to grow for several hours before inoculating a large 1.25 L culture for overnight growth at 37° C. without shaking. The bacteria were pelleted, washing once with PBS. 5 mL of cold, 48% aqueous hydrofluoric acid was added to the cell pellet in a 50 ml conical tube using polystyrene tips, carefully pipetting up and down using a serological pipette to disrupt the pellet. Using a small magnetic stir bar, the mixture was stirred for 48 hours at 4° C. In a fume hood, with the conical tubes on ice, 45 mL (10× volume of 48% HF) of ice cold Milli-Q® (ultrapure) water was added to the bacterial suspension in preparation for dialysis.

For dialysis, 4 L plastic beakers for dialysis were filled with deionized water. A stir bar was added to each, and the beakers were left to cool, covered, in the cold room. 1000 MWCO Regenerated Cellulose dialysis tubing was cut for each bacteria culture (~17 cm max for 4 L beakers). 3 cuts of tubing is needed for six 1.25 L cultures. Tubes were washed with DI water and rinsed with Milli-Q® (ultrapure) water before submerging in the beakers containing cold Milli-Q® (ultrapure) water. In a fume hood, the tubing was placed in the beakers before carefully being filled with the diluted bacterial suspension and sealed with a clip. The samples were dialyzed as follows: Day 1:4° C. with stirring; Day 2: water change, 4° C., with stirring; Day 3: water change, room temperature, with stirring.

The contents of the dialysis tubing were transferred to centrifuge tubes and spun at 14,000 rpm for 20 min at 4° C. 50 ml conical tubes were rinsed with Milli-Q® (ultrapure) water 3× to remove any soluble plastic residues. Up to 30 mL of the supernatant containing polysaccharide was decanted into each tube and frozen in dry ice for 1 hour. The frozen samples were then lyophilized, and the residue was resuspended in 8 mL cold water, with gentle sonication if necessary. 1 mL of 10× proteinase K buffer (500 mM Tris HCl, 10 mM $CaCl_2$)) and 12.5 mg of proteinase K per polysaccharide prep was added. The samples were incubated at 56° C. in a hybridization oven overnight, mixing occasionally. The reaction was terminated using 100 μL of 100 mM PMSF in ethanol (5 mM final) and was incubated for 1-2 hours at 37° C., mixing periodically. The mixture was then dialyzed in DI water with 0.05% sodium azide, with stirring, for 24 hours to remove salts. The resulting crude polysaccharide solution was frozen and lyophilized.

The crude polysaccharide was purified by size exclusion chromatography using a 100 cm×1.5 cm Biogel P4 column pre-equilibrated with 7% ethanol, equipped with a spiral collector set for 20.0 min per sample. The crude material was re-suspended in 500 μL of 7% ethanol and centrifuged at 4000 rpm for 5 minutes to remove any insoluble particulate matter. The sample was loaded onto the column, and the preload volume and four subsequent fractions were eluted with 500 μL of 7% ethanol. The column was eluted with 7% ethanol, collecting for about 20 hours. Fractions were analyzed using the phenol-sulfuric acid method to detect the presence of polysaccharide, and samples were read at 490 nm to quantify. Fractions that tested positive in the phenol-sulfuric acid test were pooled and lyophilized to give the final purified PS product.

Example 2: Expression and Purification of pAMF-Modified Conjugate Polypeptide Experiments were performed to express and purify pAMF-modified conjugate polypeptides from a cell free protein synthesis extract.

Conjugate polypeptides, for instance, SpyAD (SEQ ID NO: 11 or SEQ ID NO: 34), containing nnAAs (e.g., pAMF) were expressed in a cell free protein synthesis (CFPS) reaction, using an extract (XtractCF$^+$) derived from *E. coli* engineered to produce an orthogonal tRNA for insertion of a nnAA at an amber stop codon. Sample protocols used for cloning, expression, and purification of these modified conjugate polypeptides may be found, for example, in Kapoor et al., *Biochemistry,* 2018, 57 (5), 516-519.

Figure 17:
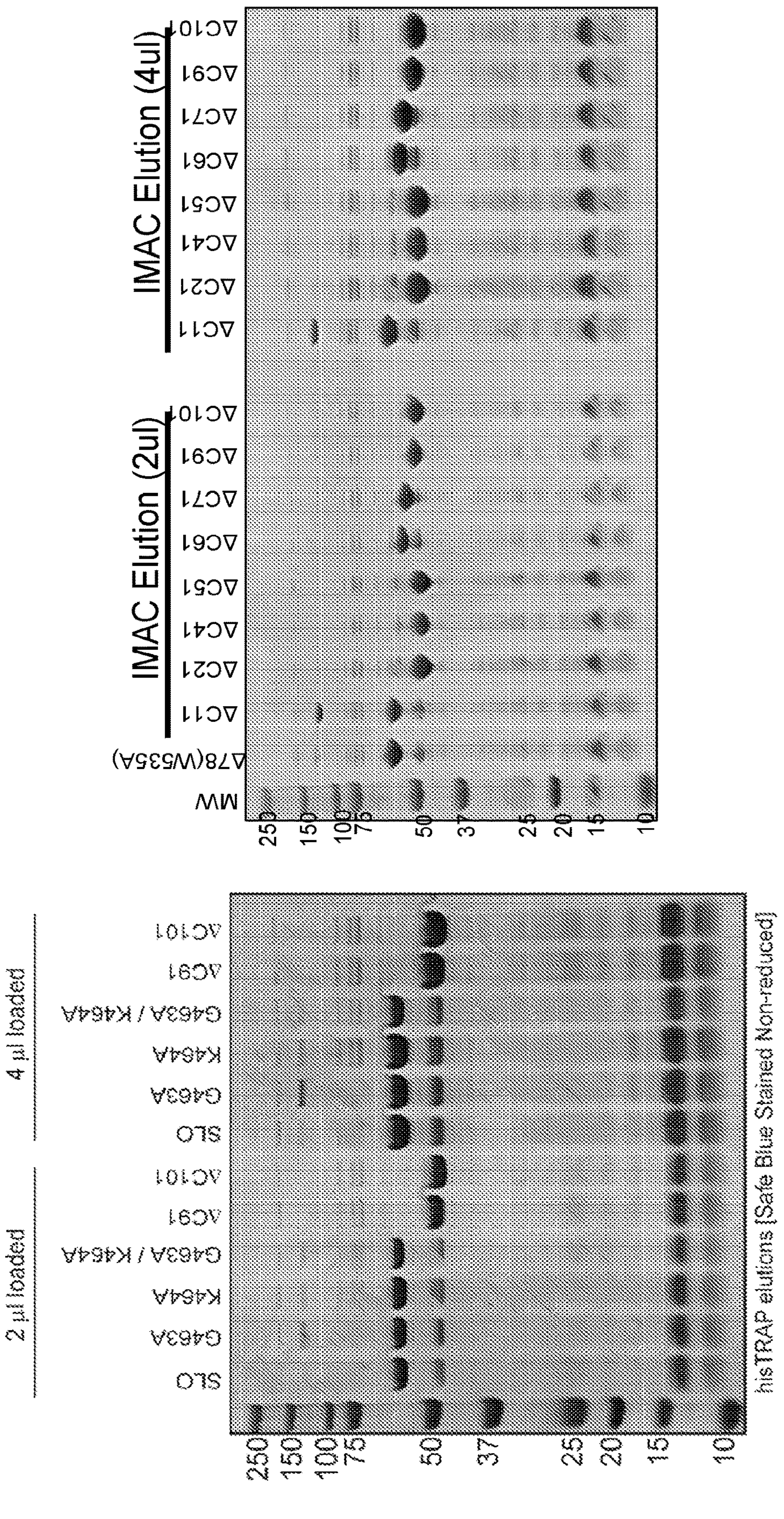
FIG. 17 shows purity of captured peptide fragments by HisTrap column chromatography.
Figure 18:
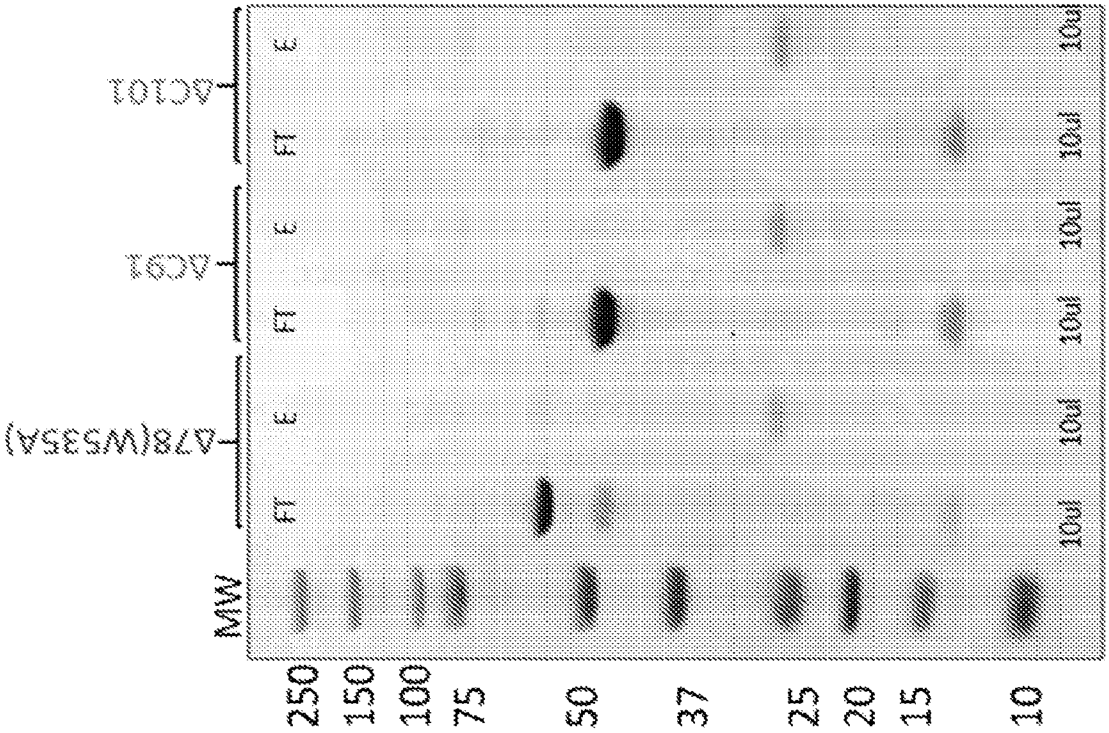
FIG. 18 shows purity of select expressed peptides after TEV cleavage and HisTrap purification.
Figure 19:
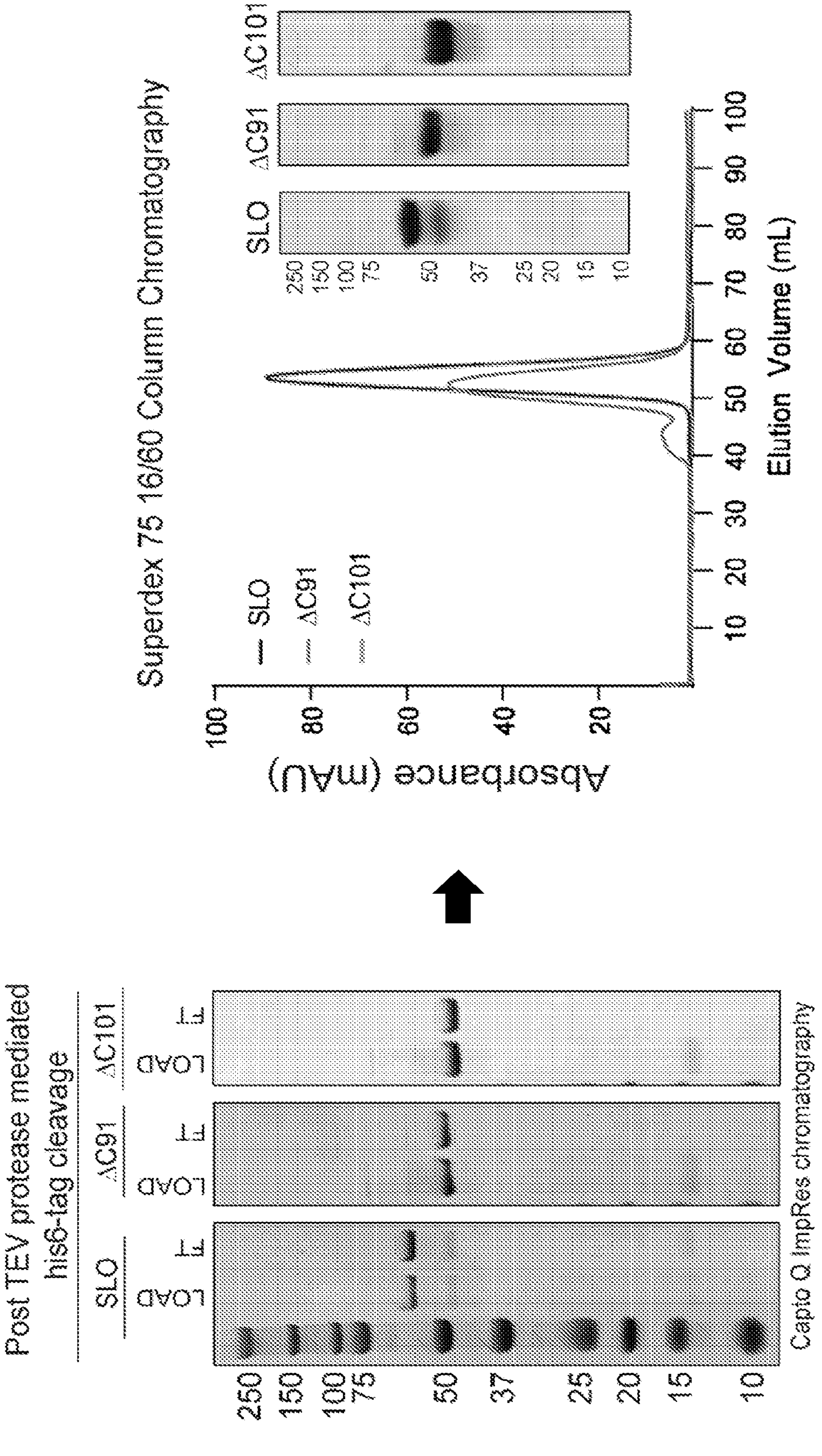
FIG. 19 shows the results of purification of expressed peptides by size exclusion chromatography.

As an example, controlled large scale antigen expression can be performed using a DASbox mini bioreactor system for 10 h at 25° C. with constant 650 rpm stirring, pH 7.2, dissolved oxygen 30%. After 10 h, reactions were harvested and spun down at 15,000×g at 4° C. for 30 min, passed through a 0.45 μm filter, filtrate loaded on a 5 ml HisTrap excel column (Cytiva) equilibrated and extensively washed with Buffer A [50 mM Tris, 150 mM M NaCl, 10 mM imidazole] until absorbance returned to baseline (FIG. 17 shows sample gels from the purification of select SLO variants). Proteins were eluted using a 50% Step gradient of Buffer B [50 mM Tris, 150 mM M NaCl, 500 mM Imidazole], and elution fractions pooled, concentrated and incubated with excess purified his6-tagged TEV protease overnight while dialyzing against Buffer A (FIG. 18 shows a sample gel following the TEV cleavage of SLO peptides). The dialyzed cleavage reaction was loaded back onto a pre-equilibrated HisTrap excel 5 ml column (Cytiva) and untagged proteins collected in the flow-through (FT) fractions. Thereafter, the FT was concentrated and loaded onto a Superdex 200 26/60 size exclusion chromatography (SEC) column pre-equilibrated with Buffer S [50 mM Tris pH 8.0, 150 mM NaCl] and purity of eluted fractions assessed by SDS-PAGE gel analysis (FIG. 19 shows the purity of select SLO variants following size exclusion chromatography). Purified Spy AD[4pAMF] was with incubated excess Dibenzocyclooctyne-PEG4-tetramethylrhodamine (DBCO-TAMRA) dye for 1 h at room temperature to confirm pAMF sites by SDS-PAGE gel and fluorescence readout was recorded using a Syngene G-box gel imager.

Figure 12:
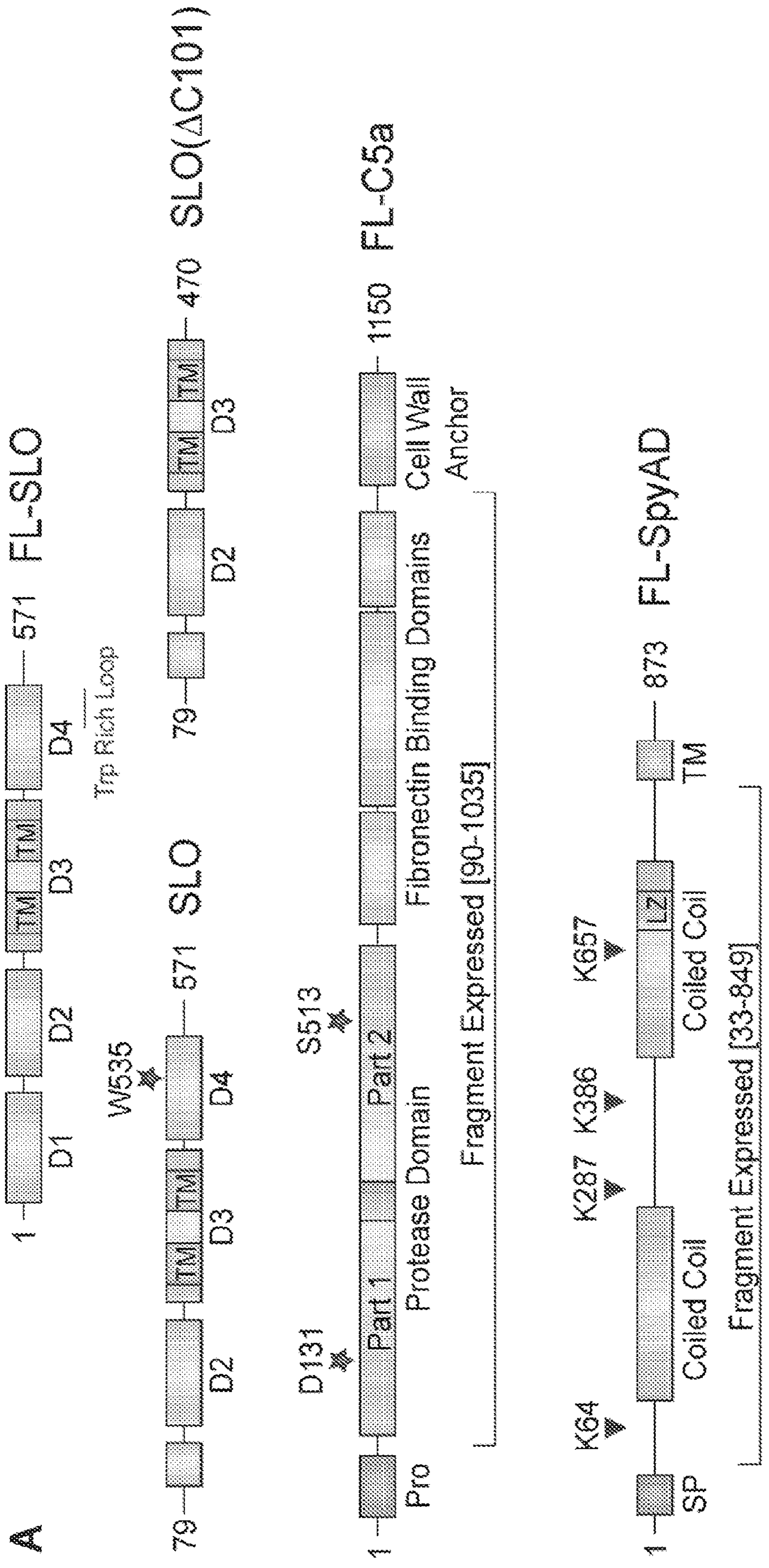
FIG. 12 is a graphical representation of fragment sequences for select antigens.

Polypeptides unmodified by nnAA were prepared using CFPS according to methods similar to the ones described above. FIG. 12 shows the modular architecture of GAS protein antigens and select immunogenic core fragments expressed in CFPS.

Figure 1B:
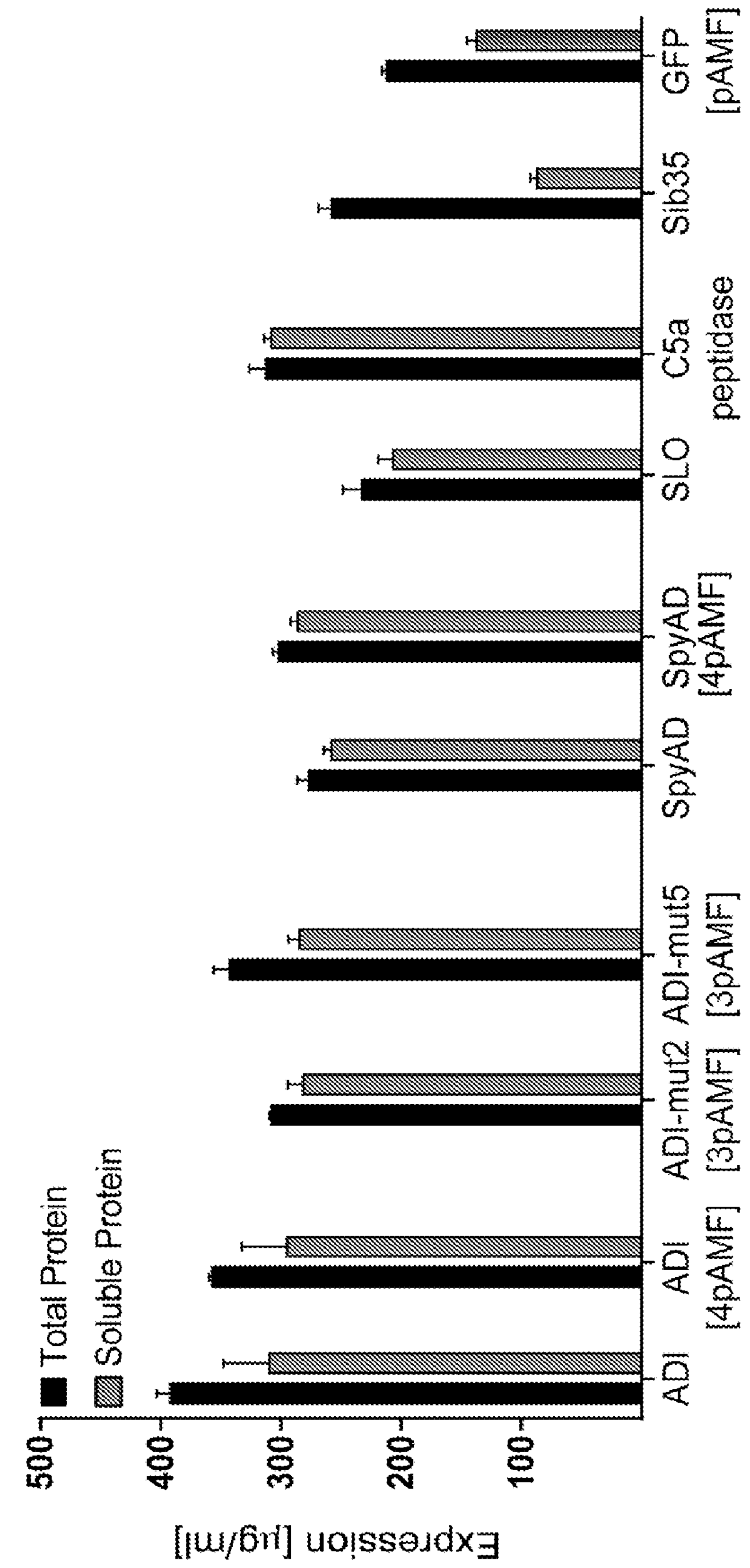
Figure 13:
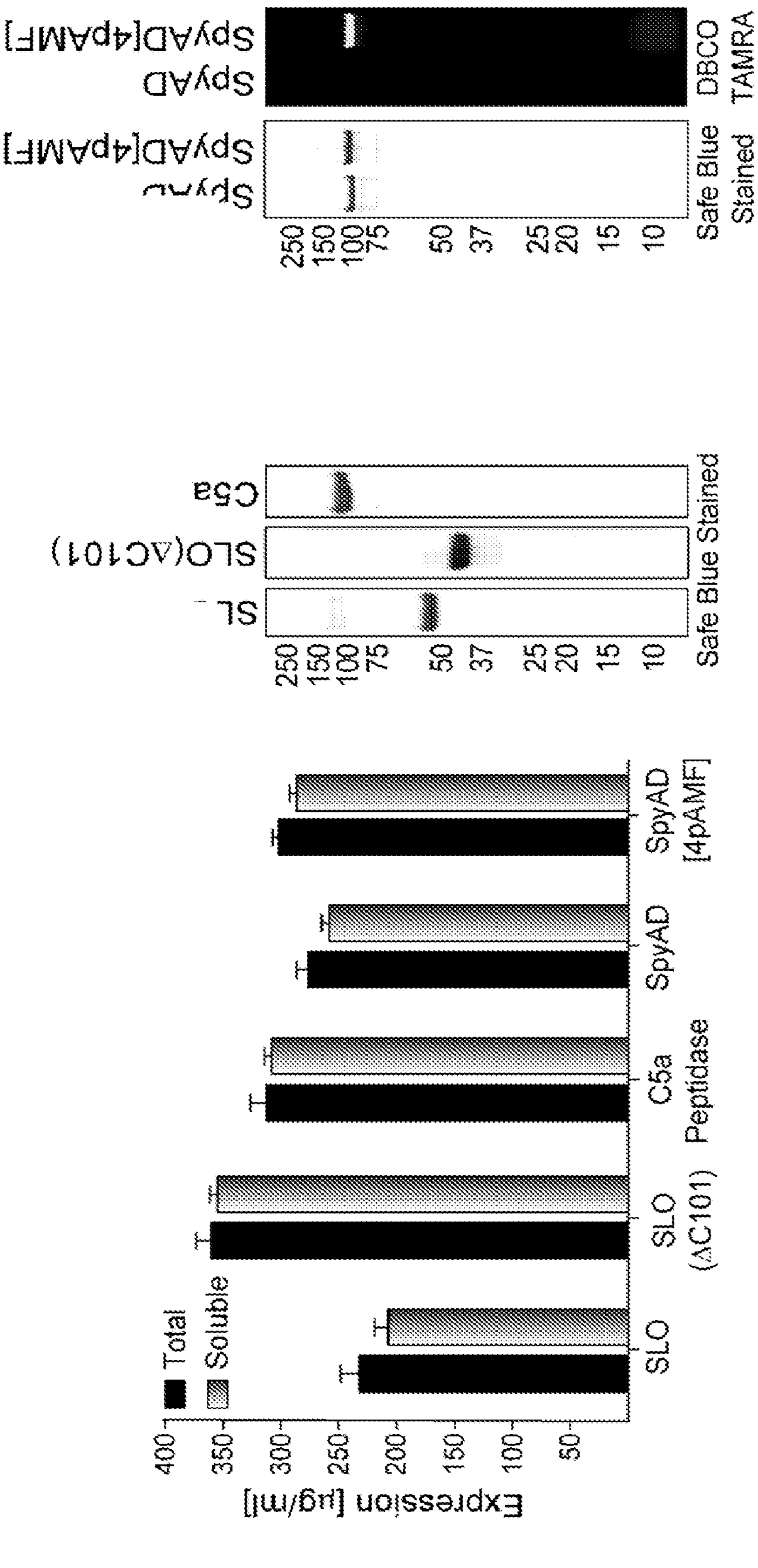
FIG. 13 shows comparative expression data of select antigens.
Figure 14:
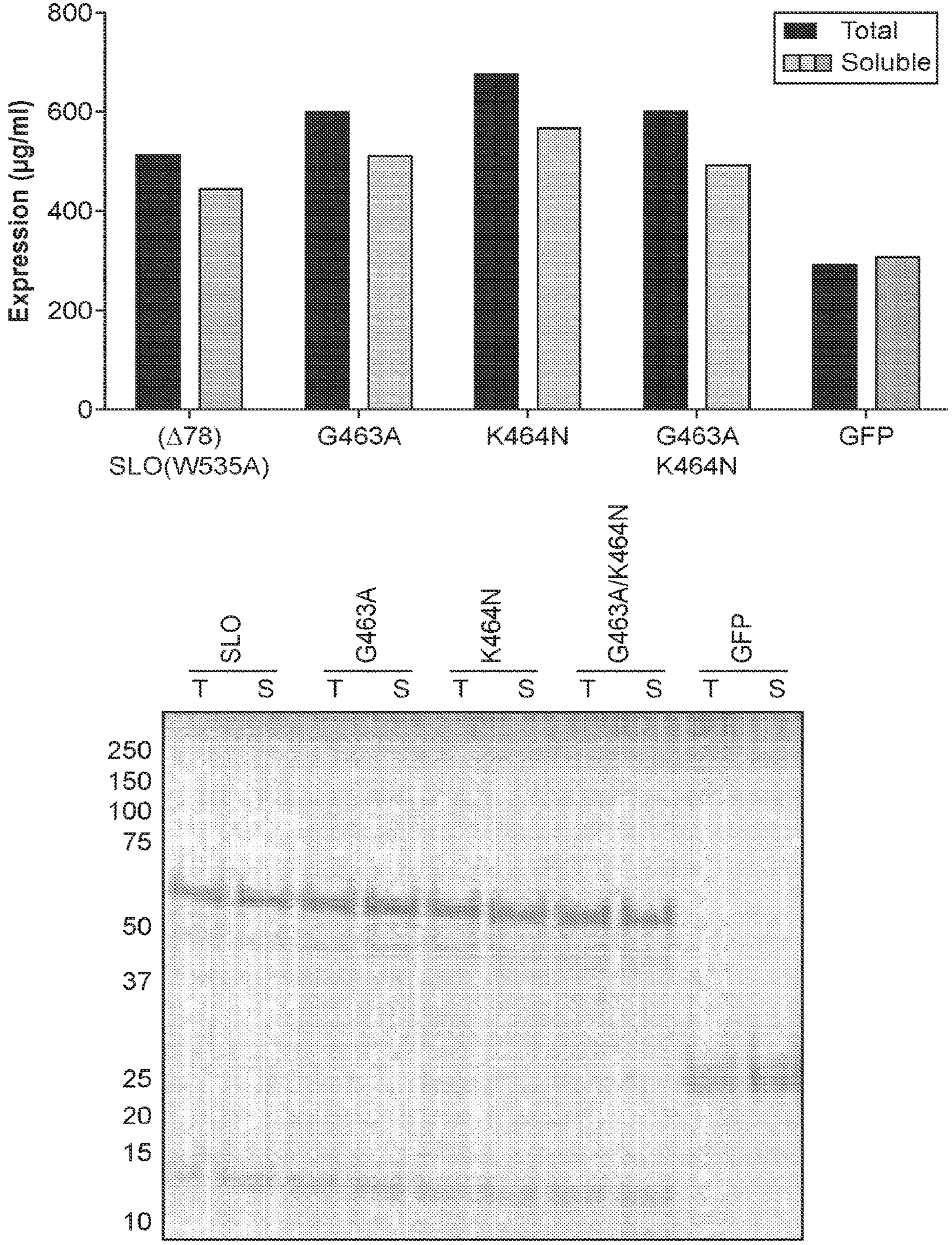
FIG. 14 shows expression data of select single and double SLO mutants compared to GFP.

Single site mutagenesis studies were conducted on SpyAD (SEQ ID NO: 9), to understand how replacement of single amino acid residues with pAMF affected expression, as measured in both total protein and soluble protein. FIG. 1A shows the expression levels resulting from a lysine-scanning mutagenesis study. As shown, introduction of pAMF residues at single points in the SpyAD protein had variable effects on the total and soluble protein expression. FIG. 1B shows expression levels for antigens and antigen conjugates containing nnAAs. FIG. 13 shows greater than 95% purity of SLO variants, C5a peptidase, and SpyAD as measured by Safe Blue staining, and further shows incorporation of pAMF into SpyAD variant Spy AD[4pAMF] as confirmed by DBCO-TAMRA labeling.

Example 3: Synthesis and Purification of Rhamnose Polysaccharides Modified with Click Chemistry Reactive Groups DBCO-modified polysaccharides were synthesized using a stepwise approach, allowing for tuning of oligomer length.

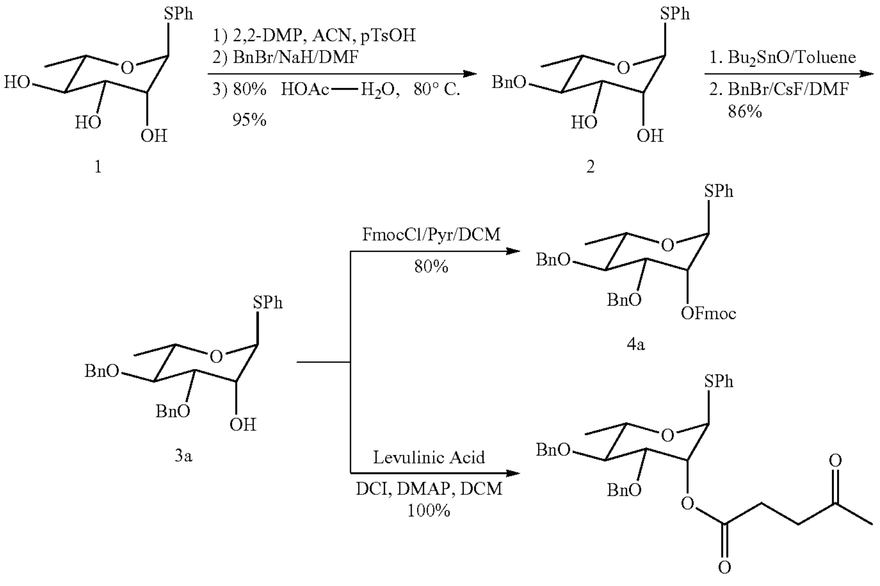

1

2

3a

4a

4b

Synthesis of Monosaccharide Intermediates 4a and 4b: Monomer 1 was mono-benzylated to furnish 2, which was further benzyl-protected to give intermediate 3a. Treatment of 3a with levulinic acid under esterification conditions provides levulinic (Lev)-ester monomer 4a. Alternatively, Fmoc-protection of 3a furnished monomer 4b.

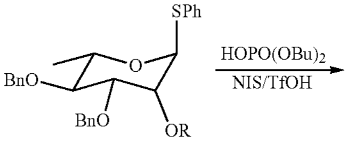

4a R = Fmoc
4b R = Lev

-continued

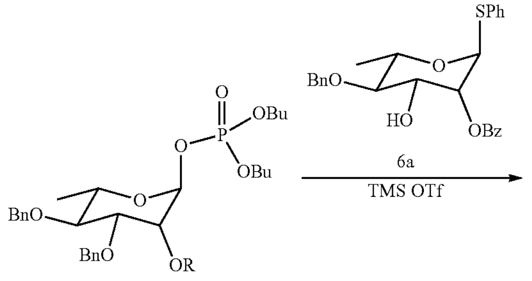

5a R = Fmoc
5b R = Lev

-continued

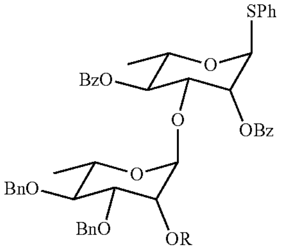

7a R = Fmoc
7b R = Lev

Synthesis of Disaccharide Donors 7a and 7b: Monosaccharide intermediates 4a/b were converted to phosphate esters 5a/b, which were subsequently treated with TMSOTf and 6a to furnish disaccharide donors 7a/b.

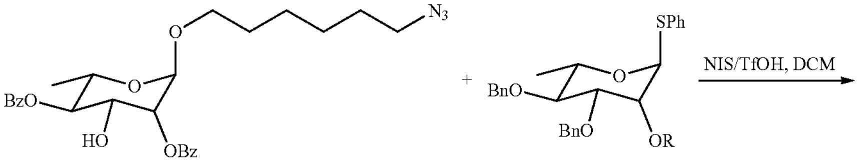
8
4b R = Lev
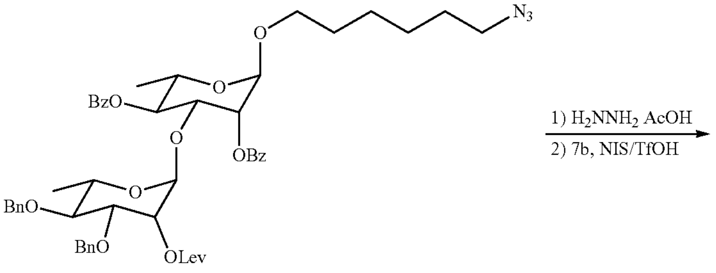
9b
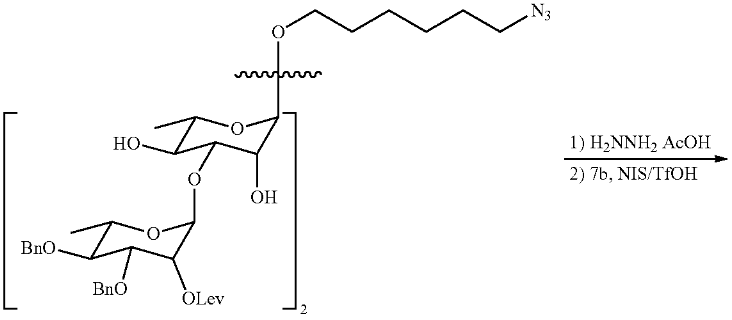
10b
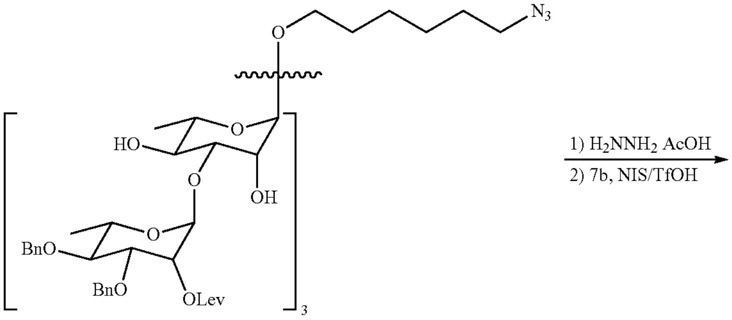
11b
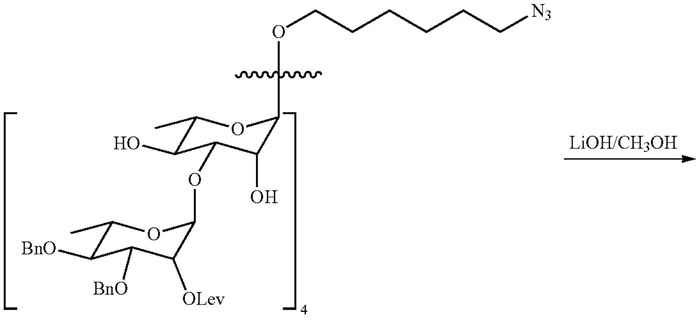
12b -continued

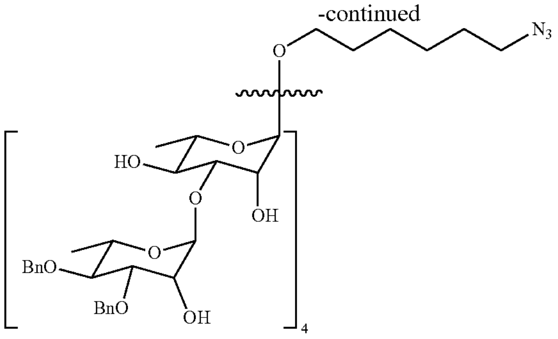

13

$H_2NNH_2/Pd(OH)_2$

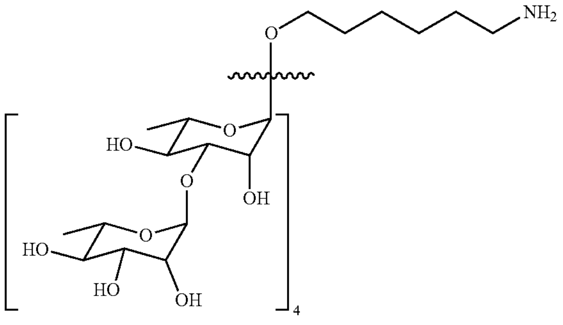

14

DBCO-NHS
DMF

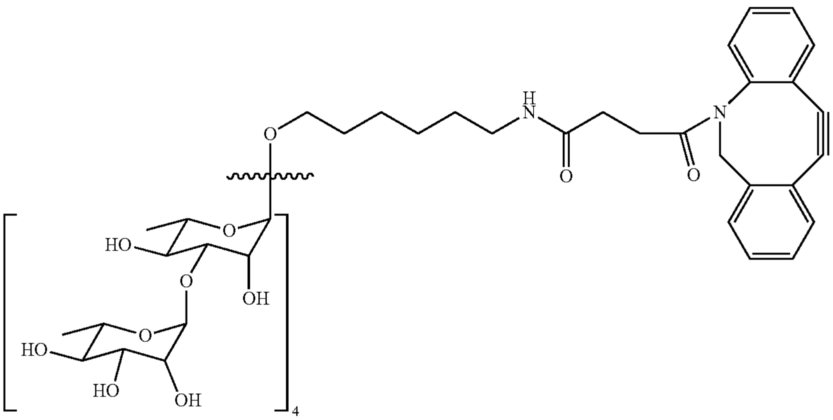

15

Synthesis of Rhamnose Octasaccharide with a Click Chemistry Reactive Group: Azide intermediate 8 was coupled to monosaccharide intermediate 4b in the presence of NIS/TfOH to give dimer 9b, which was then subjected to three sequential deprotection/coupling reaction sequences with disaccharide donor 7b to give partially protected octamer intermediate 12b. Treatment of 12b with LiOH/methanol hydrolyzed the levulinic ester to give 13, and further treatment with $H_2NNH_2/Pd(OH)_2$ concomitantly reduced the pendent azide and reductively cleaved the remaining benzyl ethers to furnish 14. Coupling of 14 with DBCO-NHS gave the final octasaccharide 15.

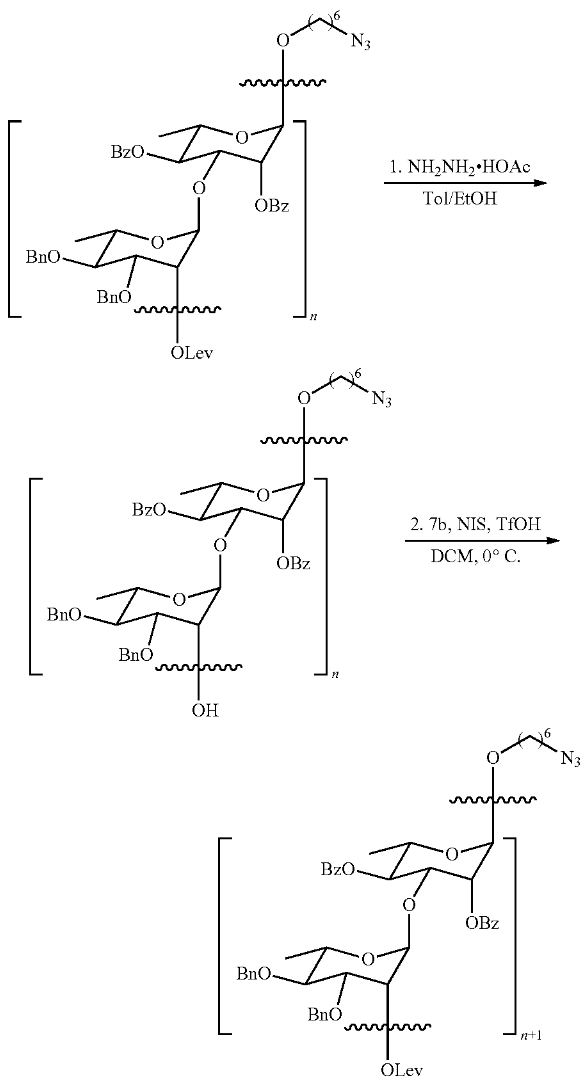

Polysaccharides of varying lengths, for instance the dodecasaccharide and hexasaccharide, can be prepared by altering the number of deprotection/coupling sequences with donor 7b as shown in the generic reaction scheme above.

Polysaccharides of the present disclosure can also be synthesized through solid-phase synthesis using the Fmoc-protected derivatives of the above intermediates, originating with monomer 4a.

Example 4: Linkage of Purified PS to DBCO-PEG Linker

Purified polysaccharides, for instance those produced by the methods of Example 1, can be functionalized with a DBCO-PEG linker.

Generally, to a solution of polysaccharide in water (5.5 mM final concentration after all reagents are added), borate buffer (1M, pH 8.5) was added such that the final concentration of borate is 100 mM in the final volume. Water was then added to fill any extra reaction volume. 2.5 equivalents (with respect to the polysaccharide repeating unit) of 1-cyano-4-dimethylaminopyridinium tetra fluoroborate (CDAP; from 100 mg/mL solution in acetonitrile) was added with vigorous stirring. CDAP is stored at −20° C. and solution must be prepared immediately before use. Five minutes after the addition of CDAP (this timing is critical-any longer than 5 min results in reduced DBCO-PEG-Amine incorporation), 0.5 molar equivalents of dibenzocyclooctyne-amine linker (from DMSO stock solution, final concentration of DMSO is 5% v/v) was added. DBCO-PEG4-Amine linker is stored at −20° C. and must be prepared immediately before use. After one hour of further reaction, glycine (2M, pH 8.35) was added 1:10 by volume to give a final concentration of 200 mM glycine to quench any unreacted cyanate esters. After 1 h of quenching, the derivatized polysaccharide was then purified via Zeba spin column. 2-3 mL of solution was added to each 10 mL Zeba column. The purified polysaccharide was analyzed on Bound/Free DBCO HPLC method to determine if residual DBCO-PEG4-Amine linker and DMAP were completely removed by column purification. The material can be further purified if necessary. The polysaccharide concentration was measured using an anthrone assay, and dibenzocyclooctyne concentration was measured using absorbance at 309 nm. These two values axcyte: were combined to give an estimate of the percentage of polysaccharide derivatized with a dibenzocyclooctyne functional group. Percent DBCO should be between 5-10% for CDAP reactions.

DBCO-PEG4 Derivatization of GAC: To a 6 mM solution of GAC in 100 mM Borate Buffer pH 8.5, three equivalents (to the polysaccharide repeating unit) of 1-cyano-4-dimethylaminopyridinium tetrafluoroborate (CDAP; from 100 mg/mL solution in acetonitrile) were added with vigorous stirring to facilitate cyanylation at reactive hydroxyl groups. 5 minutes after addition of CDAP, 2 molar equivalents of dibenzocyclooctyne-amine linker stock in DMSO was added such that the final DMSO concentration was 5% (v/v). After DBCO-derivatization, 200 mM glycine was added to the reaction to quench unreacted cyanate esters. The DBCO-derivatized polysaccharide was purified via zeba spin desalting column and the purity of the recovered material was assessed by reverse phase. A single peak in HPLC when absorbance was monitored at 309 nm confirmed complete removal of excess DBCO linker and other reaction byproducts. Finally, the polysaccharide concentration was measured using anthrone assay (see below) and dibenzocyclooctyne concentration was measured using absorbance at 309 nm. These two values were combined to give an estimate of the percentage of polysaccharide derivatized with a dibenzocyclooctyne functional group. For conjugation, % DBCO derivatization of the GAC was kept between 5-10%.

Anthrone assay for total polysaccharide concentration: A stock of 2 mg/ml of the anthrone reagent (Sigma-Aldrich, CAS #90-44-8) was prepared in cold sulfuric acid while a 1 mM stock of polysaccharide repeating unit (PSRU) comprising 2× rhamnose was prepared in water as a standard. In triplicate wells, 100 µl of PSRU stock (serially diluted into reference standards) or the unknown samples (diluted 1:3) were plated (96-well plate) followed by addition of 200 µl/well of the anthrone reagent stock. All reactions were thoroughly mixed and sealed with a plate cover for incubation at 95° C. for 10 min. The plate was briefly placed on ice to cool to ambient temperature before absorbance is measured at 620 nm using a UV/VIS plate reader. To determine concentration of unknown samples, PSRU standard concentrations and absorbances were used to generate a least-square fit regression.

Example 5: Conjugation of Carrier Protein to DBCO-Derivatized Polysaccharides

Generally, carrier proteins ferritin (SEQ ID NO: 23), SpyAD (SEQ ID NO: 34), ADI (SEQ ID NO: 27 and SEQ ID NO: 38), SEQ ID NO: 25, and Protein D containing nnAAs (e.g., pAMF) were conjugated to the purified DBCO-derivatized polysaccharides of Example 3 and Example 4 by reacting the cyclooctyne moiety of the DBCO group with the azide moiety of the nnAA side-chain incorporated into the carrier protein. Sample protocols for the conjugation reaction between the DBCO and azide groups may be found, for example, in Zimmerman et al., *Bioconjugate Chemistry,* 2014, 25 (2), 351-361 and Kapoor et al., *Biochemistry,* 2018, 57 (5), 516-519.

Figure 9:
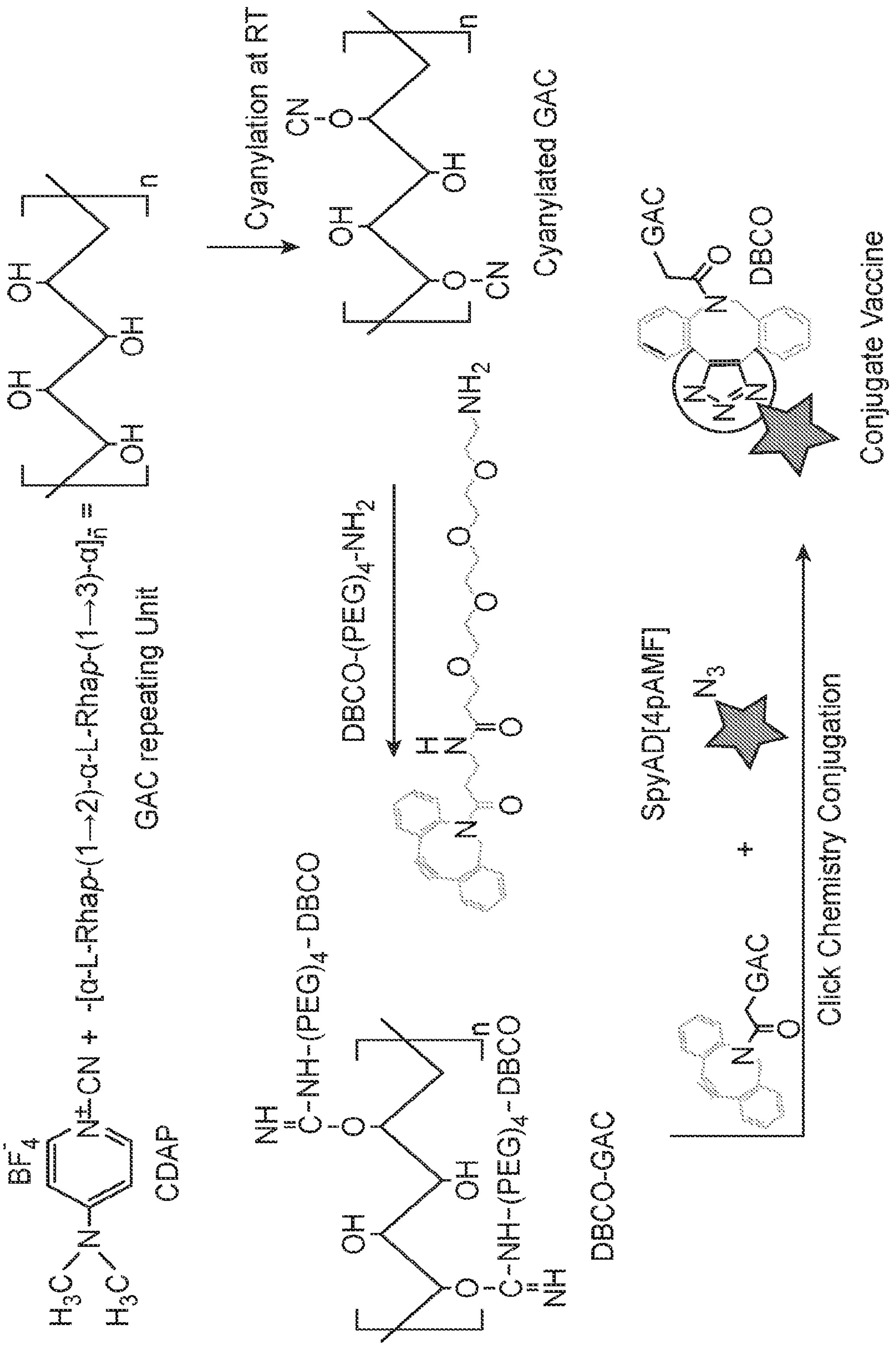
FIG. 9 shows the general reaction scheme for derivatization of GAC with DBCO-$PEG_4$-$NH_2$ and subsequent conjugation to pAMF-modified SpyAD.
Figure 10:
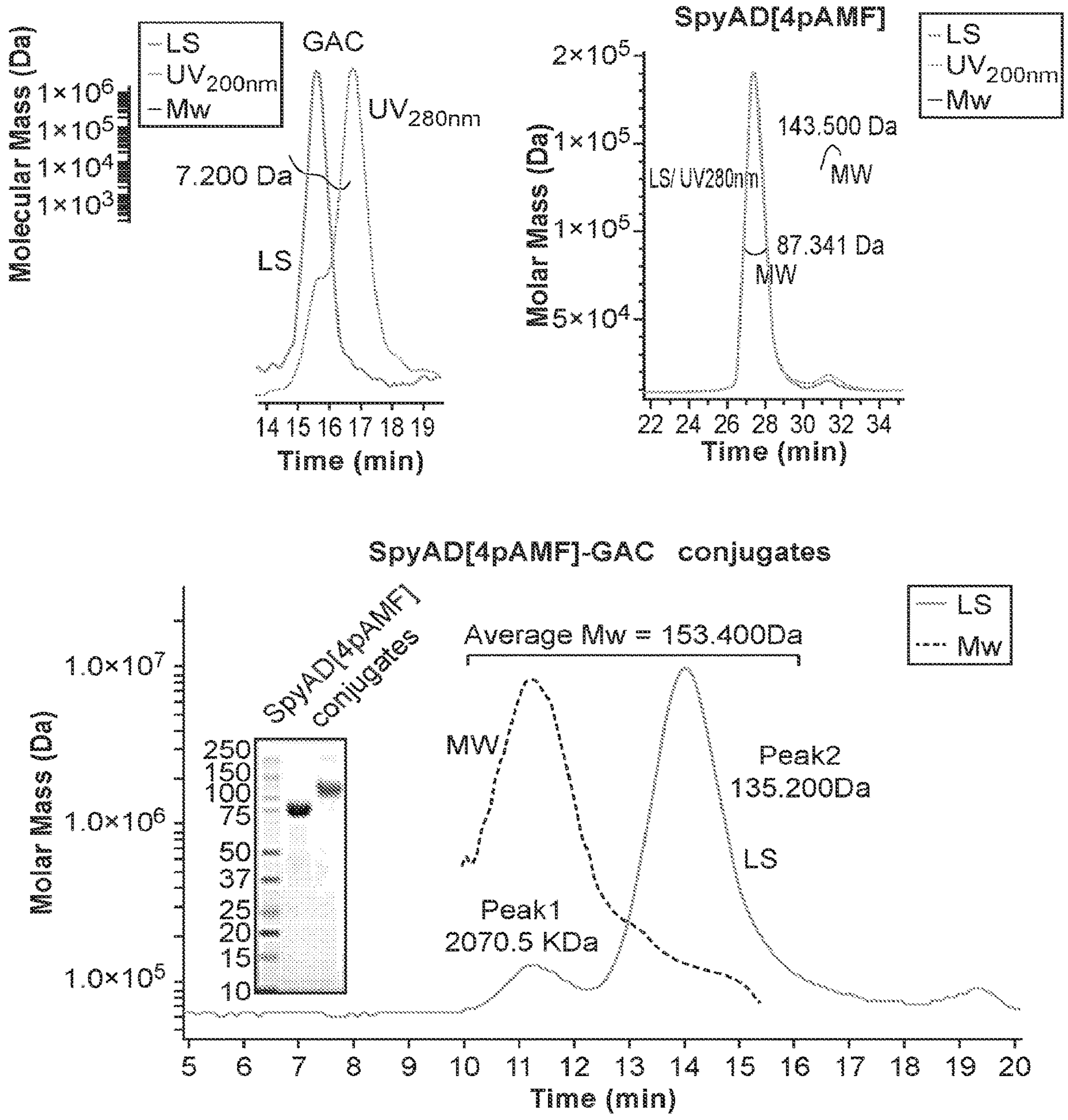
FIG. 10 shows SEC MALS analysis of purified native GAC, purified native SpyAD[4pAMF], and purified polypeptide-polysaccharide conjugates thereof.

Conjugation of pAMF-derivatized GAC to SpyAD): SpyAD[4pAMF] (SEQ ID NO: 34) was mixed with DBCO-derivatized GAC at a 1:1 ratio [0.5 mg/ml each] to facilitate conjugation via click chemistry. Post-conjugation, the reaction mixture was dialyzed against a 50 kDa cutoff membrane to remove excess unreacted free polysaccharide. The recovered conjugates were analyzed by SEC (multi-angle light scattering) MALS and the concentration was estimated using an anthrone assay. FIG. 9 is a scheme outlining the derivatization of GAC with DBCO-$(PEG)_4$-$NH_2$ and subsequent conjugation to pAMF-derivatized SpyAD. FIG. 10 shows SEC MALS analysis of purified native GAC, purified native SpyAD[4pAMF], and purified conjugates. SEC-MALS analysis of purified native GAC estimates an average molecular mass of 7.2 kDa. SEC-MALS analysis of purified native SpyAD[4pAMF] estimates an average molecular mass of 87.3 kDa. Post click chemistry SEC-MALS analysis of purified conjugates estimates an average combined molecular mass of 153.4 kDa. Inset shows the safe blue stained SDS-PAGE analysis of SpyAD[4pAMF] pre- and post-conjugation, with no unreacted protein left after conjugation.

SEC MALS-UV-RI was performed with an Agilent HPLC 1100 degasser, temperature-controlled auto-sampler (4° C.), column compartment (25° C.) and UV-VIS diode array detector (Agilent, Santa Clara, CA) in line with a DAWN-HELEOS multi-angle laser light scattering detector and Optilab T-rEX differential refractive interferometer (Wyatt Technology, Santa Barbara, CA) coupled to three TOSOH columns in series: TSKgel Guard PWXL 6.0 mm ID×4.0 cm long, 12 μm particle; TOSOH TSKgel 6000 PWXL 7.8 mm ID×30 cm long, 13 μm particle; and a TSKgel 3000 PWXL 7.8 mm ID×30 cm long, 7 μm particle. A mobile phase consisting of 0.2 μm filtered 1×PBS with 5% (v/v) acetonitrile was used at a 0.5 mL/min flow rate and 50-100 μg sample was injected for analysis. Agilent Open Lab software was used to control the HPLC, and Wyatt Astra 7 software was used for data collection and molecular weight analysis.

Example 6: Antibody Responses Induced by GAS Antigens and Antigen-Polysaccharide Conjugates Experiments were performed to assess the antibody responses produced purified GAS antigens and conjugates thereof. Briefly, rabbits were immunized intramuscularly with 50 μg of each indicated antigen or conjugate or vehicle control on days 0, 14, and 28. Animals were bled prior to immunization (pre-bleed), and on Days 7, 21, and 35 (terminal bleed) after immunizations. Serum was harvested from each blood sample and antibody titers against the immunizing antigens were assessed by ELISA.

For ELISA analysis of antibody titers, the indicated recombinant protein antigen was plated in sterile PBS at a concentration of 3 μg/well. High-binding, flat bottom 96-well plates were coated with 100 μL of prepared antigen, incubating overnight at room temperature without agitation. The plates were washed 3 times with 100 μL PBS+0.05% Tween 20 using an Aquamax Microplate Washer, then blotted dry onto paper towels. Wells were blocked with 100 μL of Reagent Diluent 2 for 2 hours. 100 μL of PBS with 1% BSA can also be used. Plates covered with a lid and sealed can be stored in block solution at 4° C. for 3 days. Plates were then washed 3 times with 100 μL PBS+0.05% Tween 20 as before.

Sera samples are prepared by diluting the sample into 1× Reagent Diluent 2 (typical dilution is 1:400 to $1:10^6$). 100 μL of the prepared sera was then added to the plates, followed by 2 hours of incubation. Pooled pre-immunization rabbit serum was used as a negative control, and wells with no rabbit serum were used as a background control. Plates were washed 3 times with 100 μL PBS=0.05% Tween 20 as before. Plates were then incubated with 100 μL of HRP-conjugated goat-anti rabbit IgG (H+L) secondary antibody (diluted 1:4000 into 1× Reagent Diluent 2) for 2 hours. Plates were then washed 3 times with 100 μL of PBS+0.05% Tween 20 as before. TMB substrate was prepared following the manufacturer's instructions, and equal volumes of reagent A and reagent B were added at room temperature. 100 μL of prepared TMB substrate was added per well, and the plates were incubated protected from light for no more than 30 minutes. 50 μL of 2N sulfuric acid was added per well to stop the reaction. ELISA plates are read at 450 nm and 540 nm, subtracting the values at 540 nm from the values at 450 nm to correct for background. Titers were determined based on cut off: absorbance value of background controls+3* standard deviation of background controls.

Figure 2:
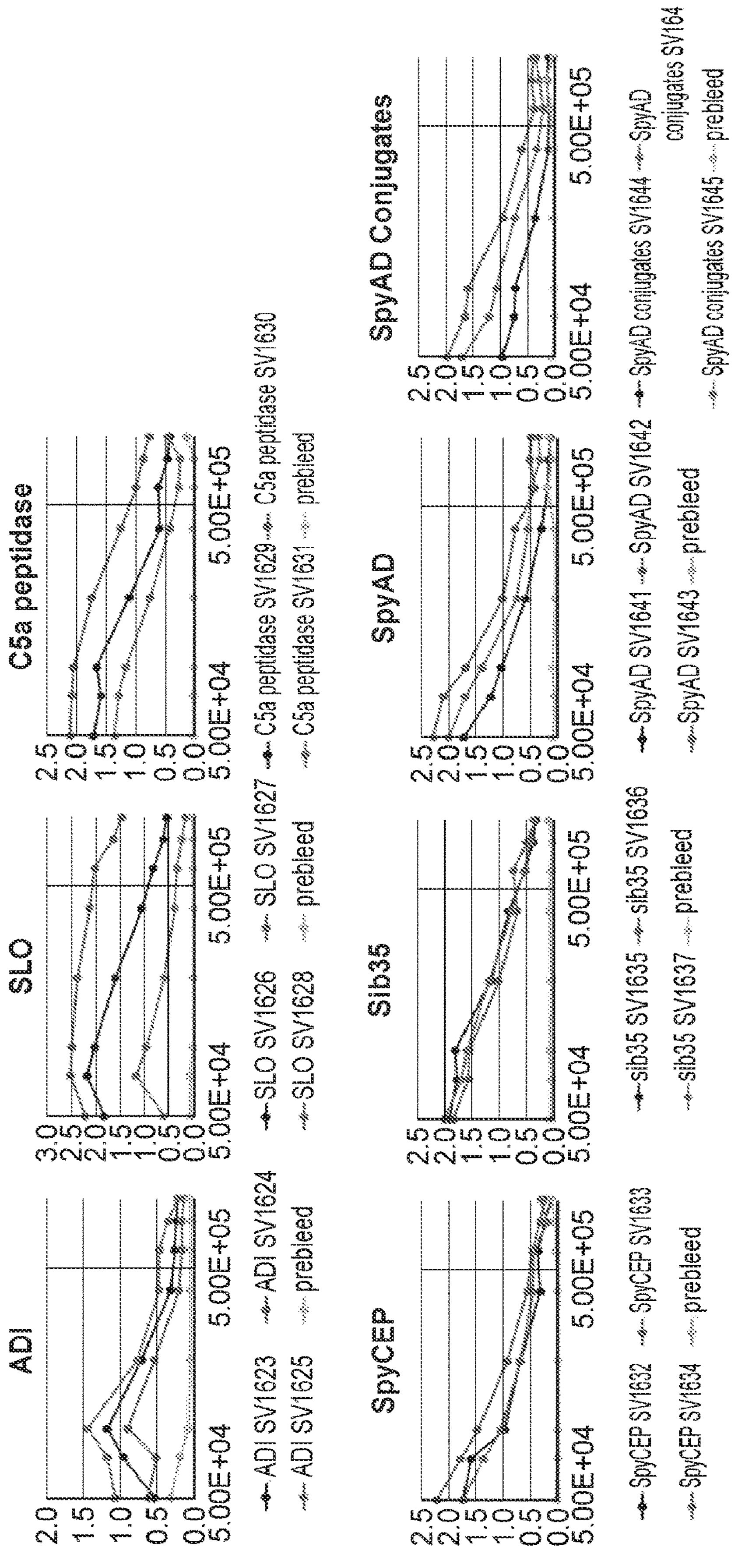
FIG. 2 shows polypeptide antigen- and polypeptide-polysaccharide conjugate-immunized sera titers compared to a pre-bleed control.

As shown in FIG. 2, immunization with ADI (SEQ ID NO: 38), SLO (SEQ ID NO: 32), C5a (SEQ ID NO: 30), SpyCEP, Sib35, SpyAD (SEQ ID NO: 33), and SpyAD-PS conjugates (conjugates of pAMF-substituted SEQ ID NO: 34) elicited a robust antibody response as compared to pre-bleed controls. Sfb1 was also tested but generated weak antibody titers. Each individual antigen identifier in the different panels represents a different rabbit in the experiment.

Example 7: GAS-Antigen Elicited Antibody Binding to GAS Serotypes

Experiments were performed to assess the ability of GAS-antigen induced antibody responses to bind various GAS serotypes. Briefly, rabbits were immunized with 20 μg of Spy AD-PS conjugate or 50 μg of C5a peptidase on days 0, 14, and 28. Animals were bled prior to immunization (pre-immune serum), and on Days 7, 21, and 35 after immunization (immune serum). Serum was harvested from each blood sample.

All serum samples were heat inactivated at 55° C. for 30 minutes. GAS of various serotypes were grown to OD600-0.4, washed and frozen at $2\times10^8$ cfu/mL. Frozen GAS stock was thawed, 10% goat serum was added, and the mixture was incubated at room temperature for 1 hour. For the binding assay, 100 μL blocked GAS (together with goat serum) was added to 1.5 mL micro centrifuge tubes. 2 μL pre-immune or immune serum was added to each tube. The samples were mixed well and incubated at room temperature for 1 hour. The samples were spun down at 3500 G for 5 minutes washed 1 time with 500 μL PBS. Samples were then incubated with a fluorescent secondary anti-rabbit secondary antibody for. The samples were then transferred to FACS tubes in 500 μL PBS. Fluorescent signal intensity was measured by flow cytometry and calculated using FlowJo software, comparing the signal intensity of immune and pre-immune serum.

Figure 3A:
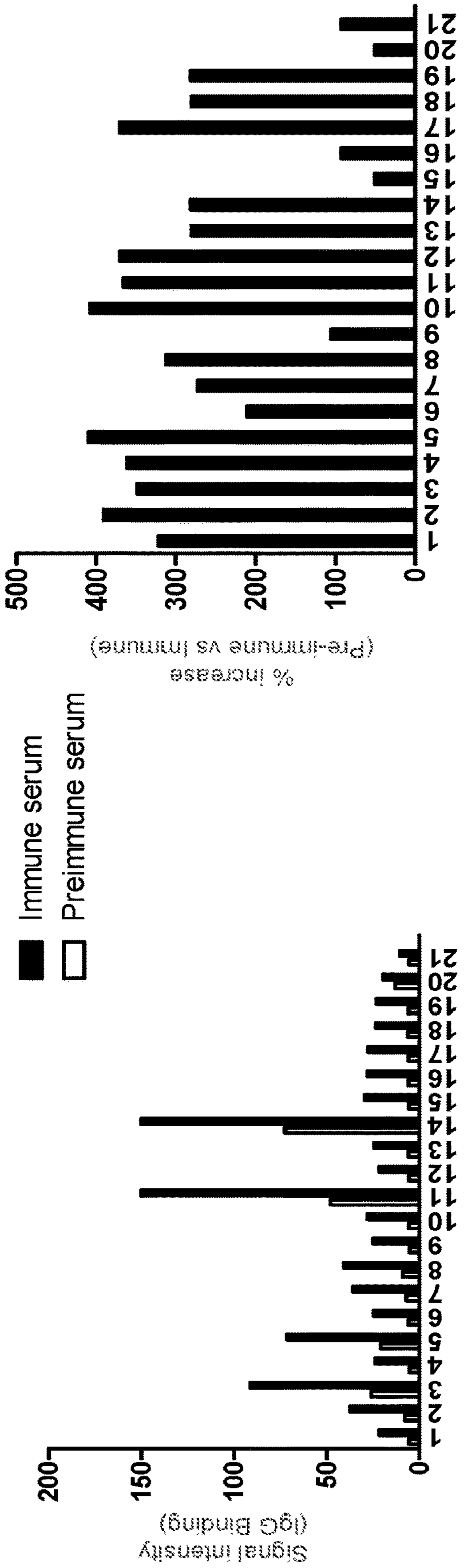
FIG. 3A, FIG. 3B, FIG. 3C, FIG. 3D, and FIG. 3E show antibody titers and the IgG binding change of immune serum compared to a pre-immune serum control.
Figure 3B:
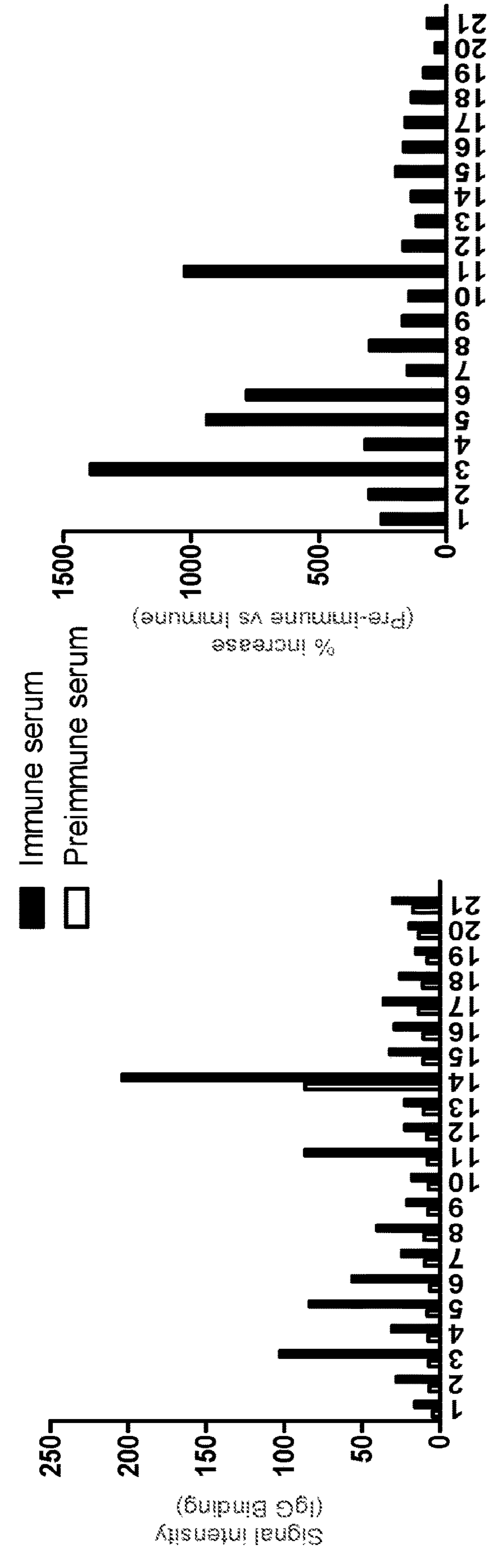
Figure 3C:
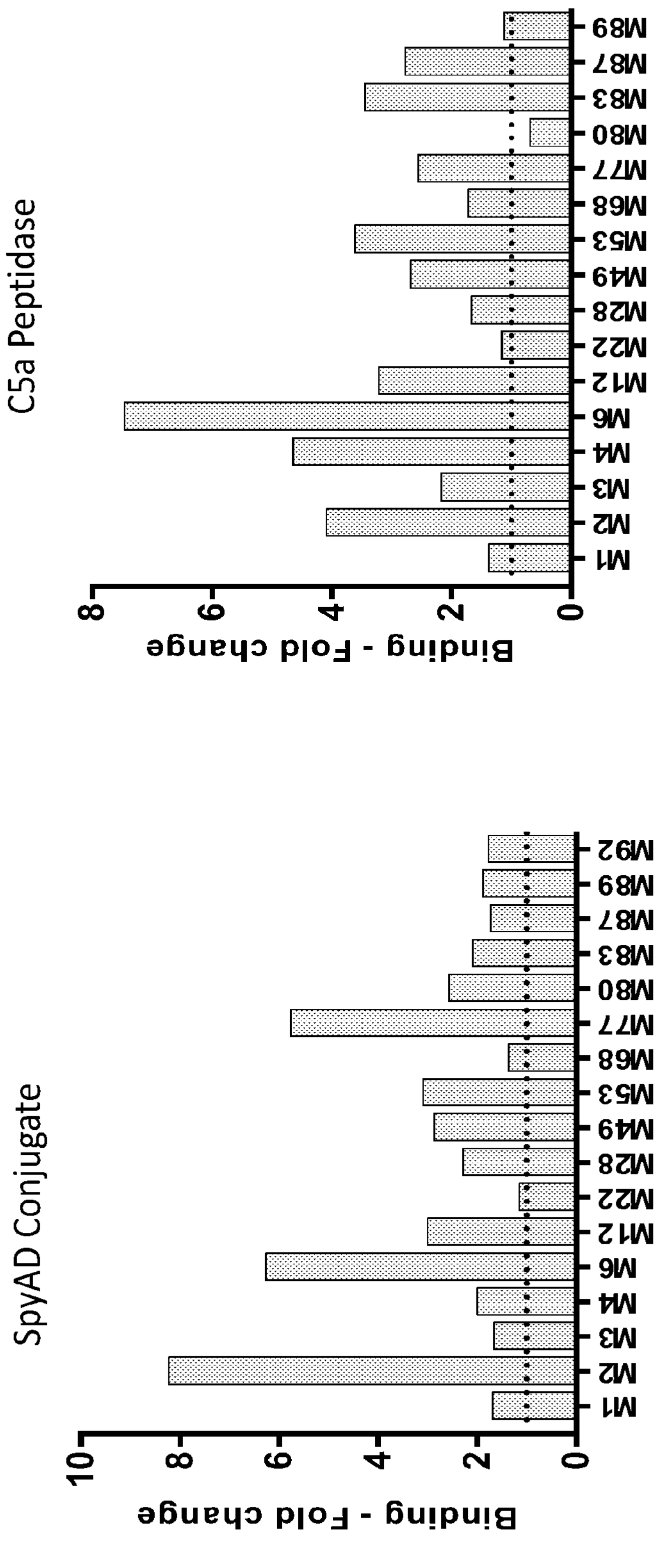

FIG. 3A shows the IgG-binding of sera post-immunization with SpyAD-conjugate (conjugate of SEQ ID NO: 34) vs. that of pre-immune sera to strains of M1 (1-21). FIG. 3B shows the IgG-binding of sera post-immunization with C5a Peptidase (SEQ ID NO: 30) vs. that of pre-immune sera to various M1 strains (1-21). The extent of IgG to SpyAD Conjugate and C5a Peptidase binding to all clinically relevant GAS strains is shown in FIG. 3C, with both showing strong binding to >95% of clinically relevant GAS.

Figure 3D:
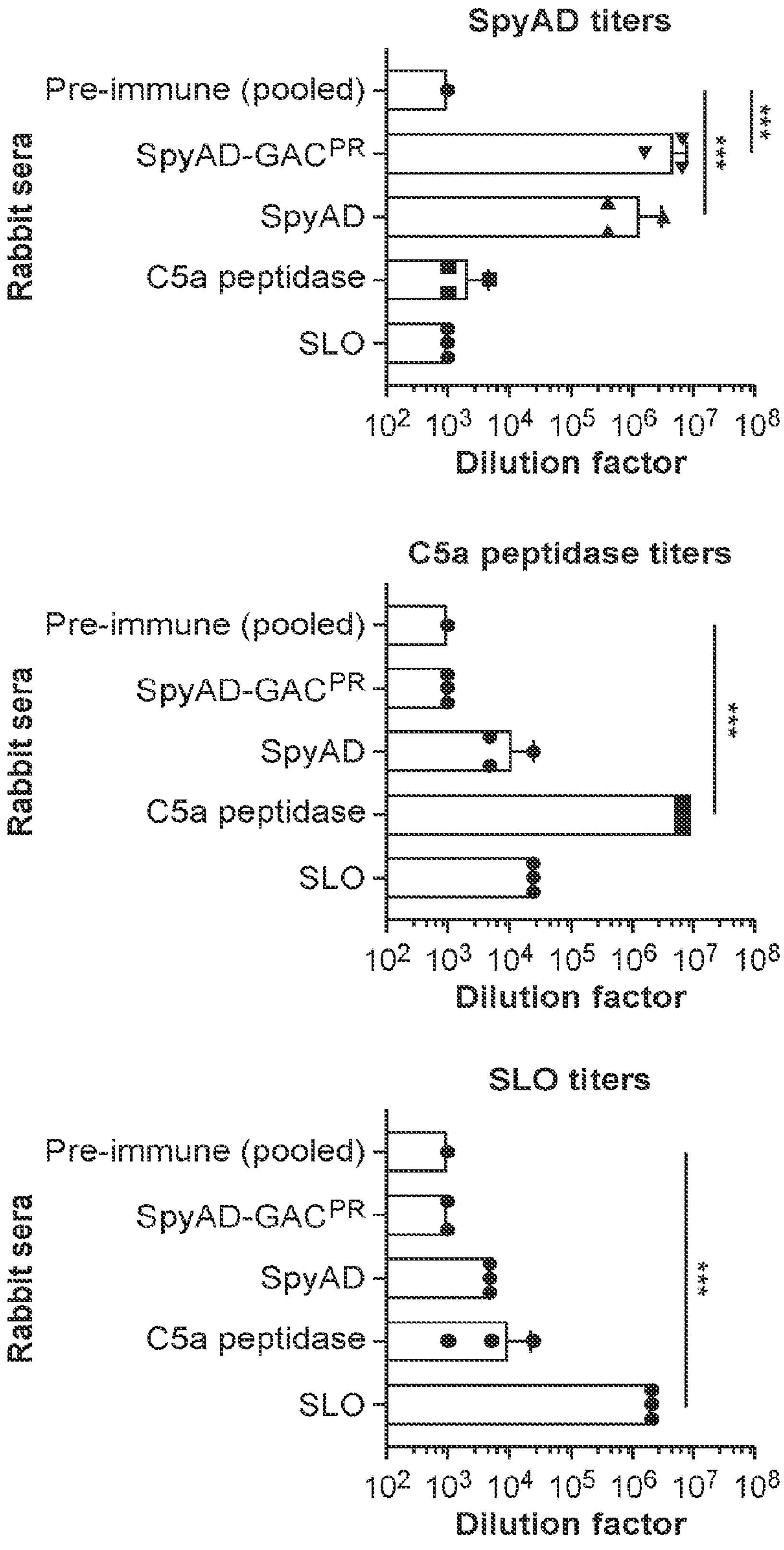
Figure 3E:
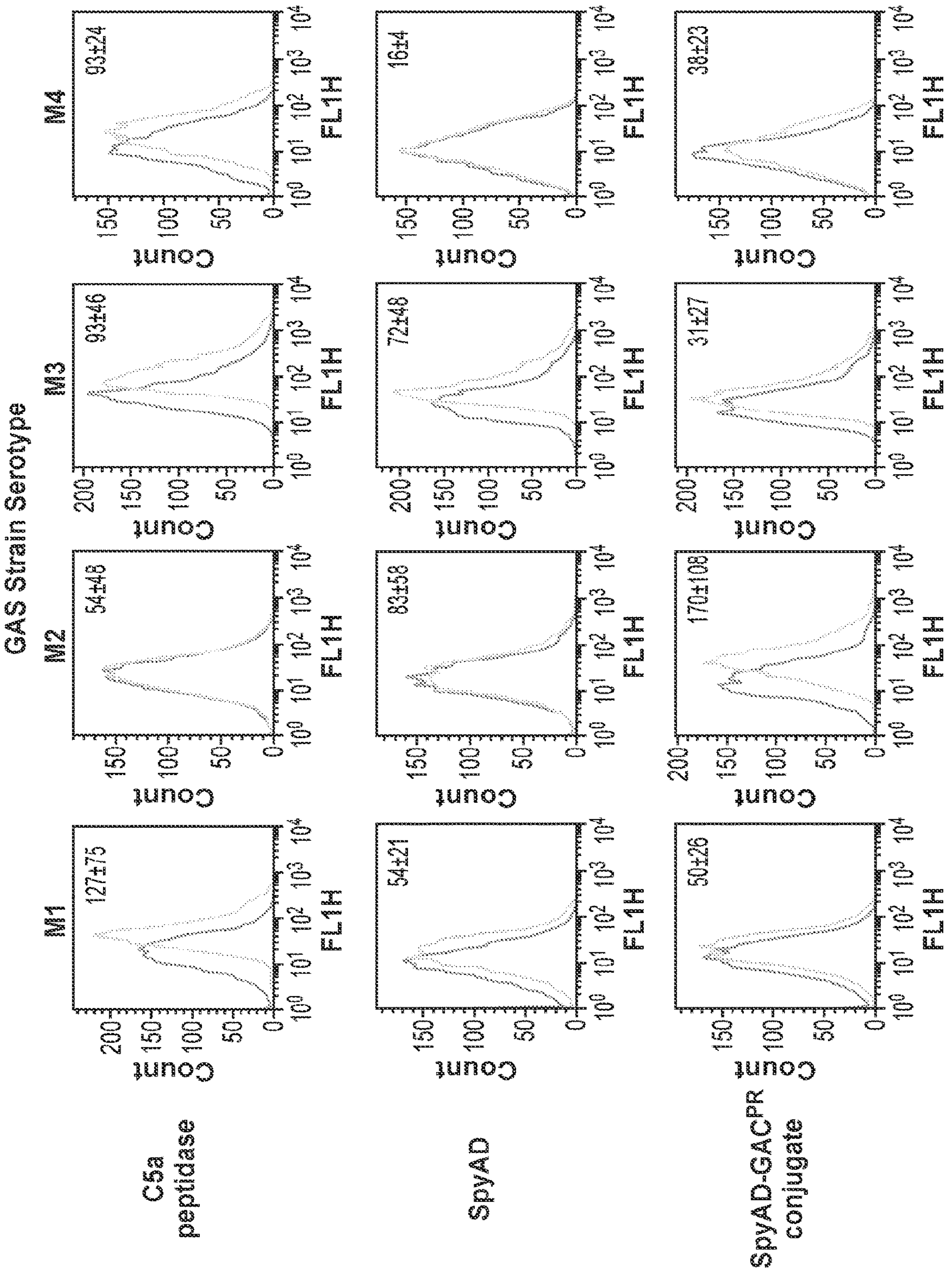
Figure 3E:
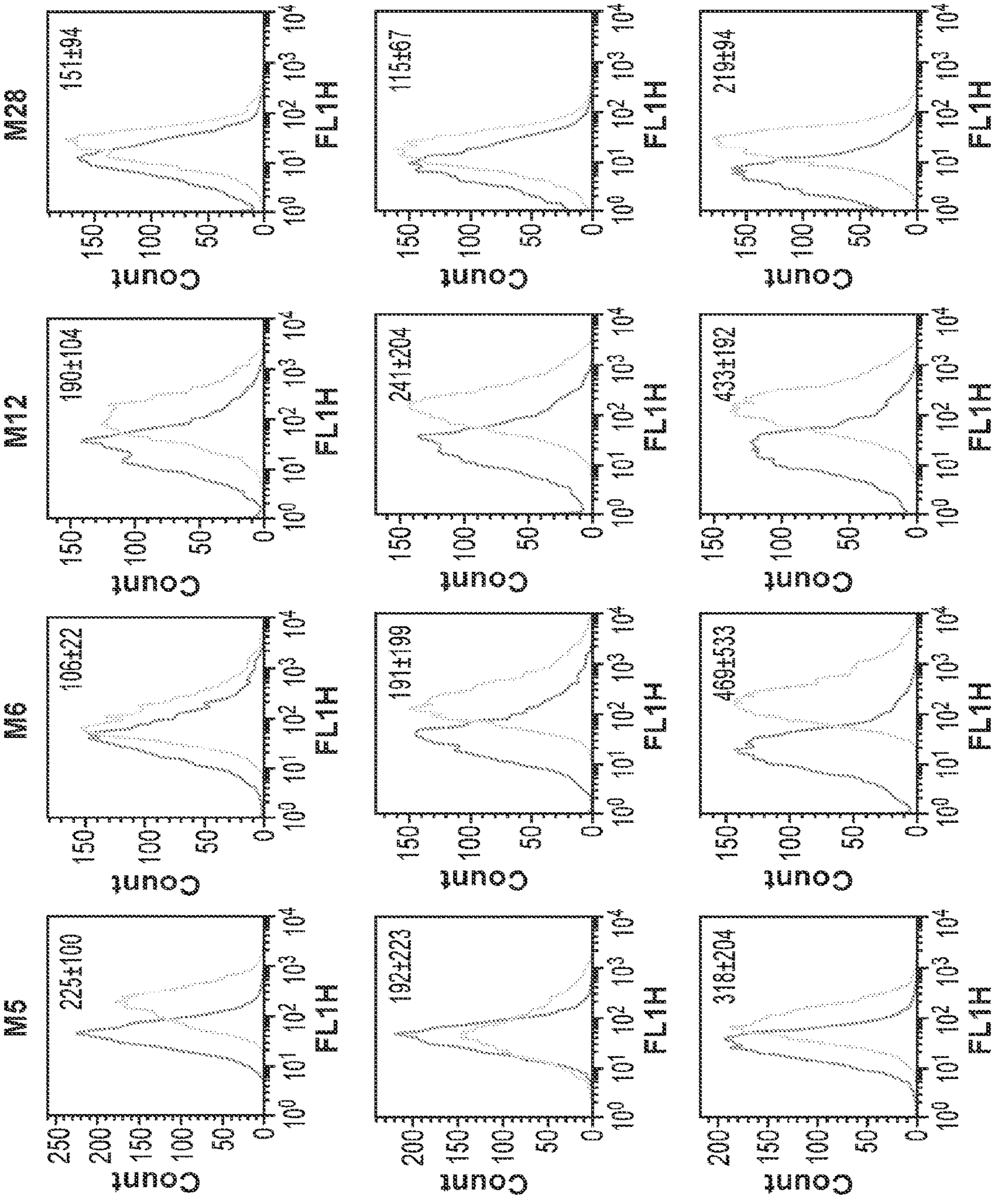
Figure 3F:
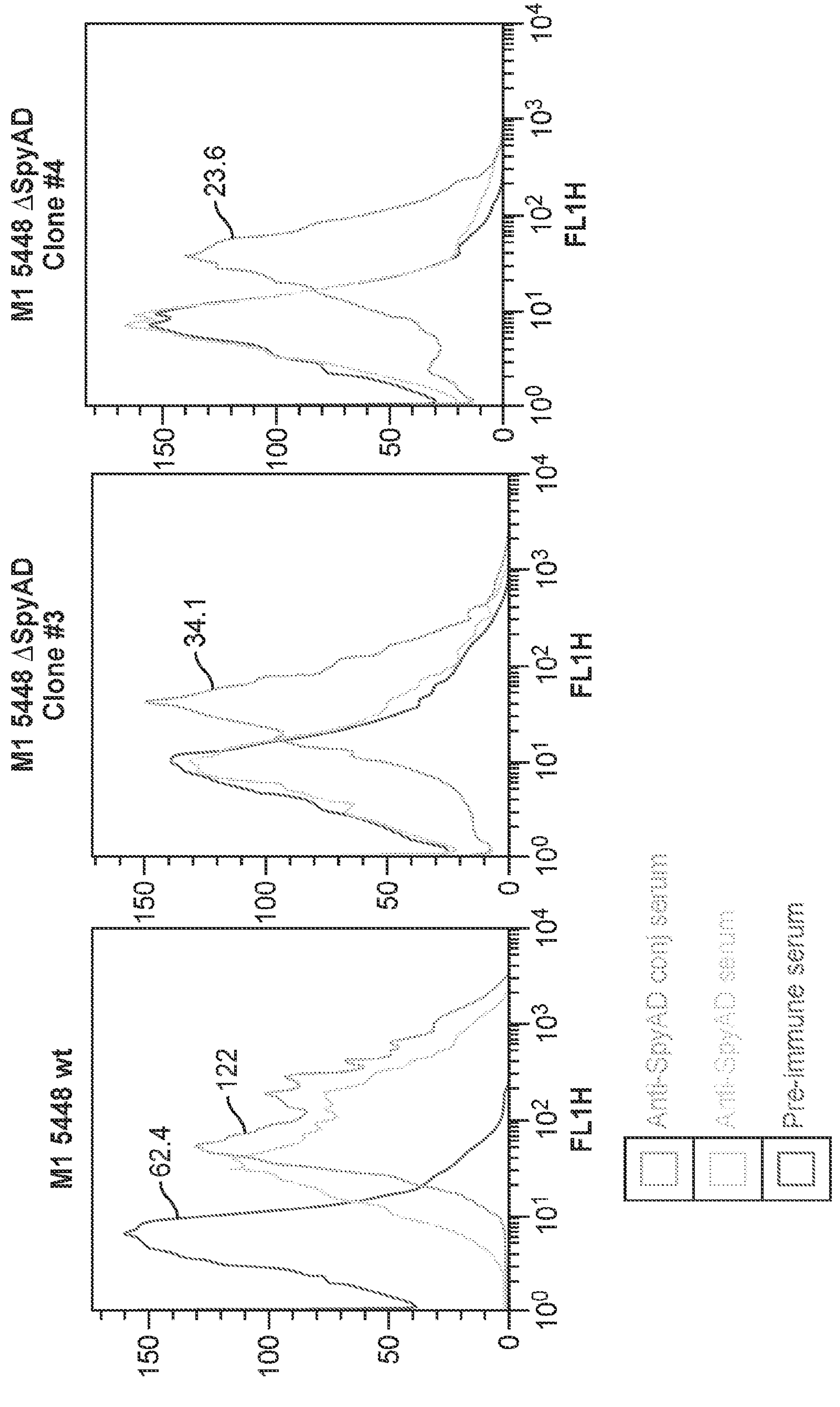
FIG. 3F shows rabbit IgG binding to SpyAD knockout GAS, confirming binding to native GAC.

Additional Evaluation of GAS Vaccine Antigens for Immunogenicity: According to the protocols above, animals were immunized with 5 μg of either SLO, C5a peptidase, or SpyAD-GAC conjugate in 240 μL total volume succinate bugger adjuvanted with Adju-phos (Invivogen). The determine immunoglobulin g (IgG) titers elicited by vaccination, terminal bleed (day 35) rabbit antisera were evaluated by ELISA. For all three protein antigens (Spy AD, C5a peptidase, and SLO), the group of rabbits immunized with the recombinant protein showed significantly increased (3- to 4-$\log_{10}$ fold) antibody titers against the target antigen compared to either pooled serum from the rabbits before immunization ("pre-immune (pooled)") or the other immunized rabbit groups (FIG. 3D, each point represents serum derived from one animal, run with 2-3 animals per group), confirming specificity of the response to each respective antigen. The anti-Spy AD protein titer generated by the Spy AD-GAC conjugate was not inferior to that of the SpyAD recombinant protein alone, suggesting that key B cell epitopes were not impacted by pAMF sites. Flow cytometry was used to evaluate the binding affinity of rabbit-derived IgG to the surface of eight live wild-type GAS strains of different M protein serotypes (m1-6, M12, M28). For the great preponderance of strains, the respective immunized serum yielded an increase in binding of 1000-400% over the baseline IgG binding of the pre-immune serum (FIG. 3E, numbers in the top right corner of each histogram show the mean percentage of increased signal of immunized rabbit serum over pre-immunized serum signal). For six of the eight strains, the GAS surface binding of the antisera raised against the SpyAD-GAC conjugate roughly doubled the level of IgG binding seen with antisera raised against SpyAD alone. FIG. 3F shows rabbit IgG binding to SpyAD knockout GAS, confirming binding to native GAC.

Example 8: Neutrophil Killing Assay

Experiments were performed to determine the ability of immune sera from antigen and conjugate-immunized rabbits to elicit neutrophil killing of M1, M3, and M3 strains of GAS. Rabbits were immunized with the indicated antigens according to the protocol described in Example 7. For single antigens, rabbits were immunized with 50 μg of antigen. For conjugate antigens, rabbits were immunized with 20 μg of conjugate.

Neutrophil isolation: 25 mL blood was drawn from healthy volunteers, using 21 G butterfly needles, into vacutainer heparin tubes. Neutrophils were isolated from fresh blood using Polymorphprep following the manufacturer's protocol. All serum, including pre-immune serum, immune serum, and FBS, were heated at 65° C. for 30 minutes with occasional mixing before being used in the assay.

Neutrophil Killing Assay Protocol: Overnight cultures of GAS strains were inoculated in Todd Hewitt Broth (THB) at a ratio of 1:10. When the culture reaches OD600=0.4, the culture was centrifuged and re-suspended in HBSS with 10% pre-immune or immune serum to $5\times10^5$ colony forming units (CFU)/mL. GAS strains were kept in RPMI+serum for 30 minutes at room temperature. Prepped neutrophils were re-suspended in HBSS+4% FBS+4% Baby Rabbit complement (BRC) in a concentration of $5\times10^6$ cells/mL. 100 μL neutrophils ($5\times10^5$ cells) were seeded in a 96-well flat bottom plate, with each condition run in triplicate. 100 μL of prepared bacteria ($5\times10^4$ cfu/well) were added to each well of neutrophils. The inoculated bacteria were plated on blood agar plate in serial dilutions to later count inoculum cfu. The 96 well plate was centrifuged at 500 G for 5 minutes and then incubated at 37° C.+5% $CO_2$ for 30 minutes. Following 30 minutes of incubation, the samples were mixed well, plated on blood agar plates in serial dilutions, and incubated at 37° C. overnight. GAS colonies were counted and the % ratio of inoculum CFU versus recovered CFU is calculated as % survival. Increase in % kill compared to the pre-immune serum group was calculated by first calculating % killing (100-% survival) in both pre-immune and immune serum groups. Then, the % increase in the killing of the immune serum group was calculated compared to the % killing of the pre-immune serum group.

Figure 4:
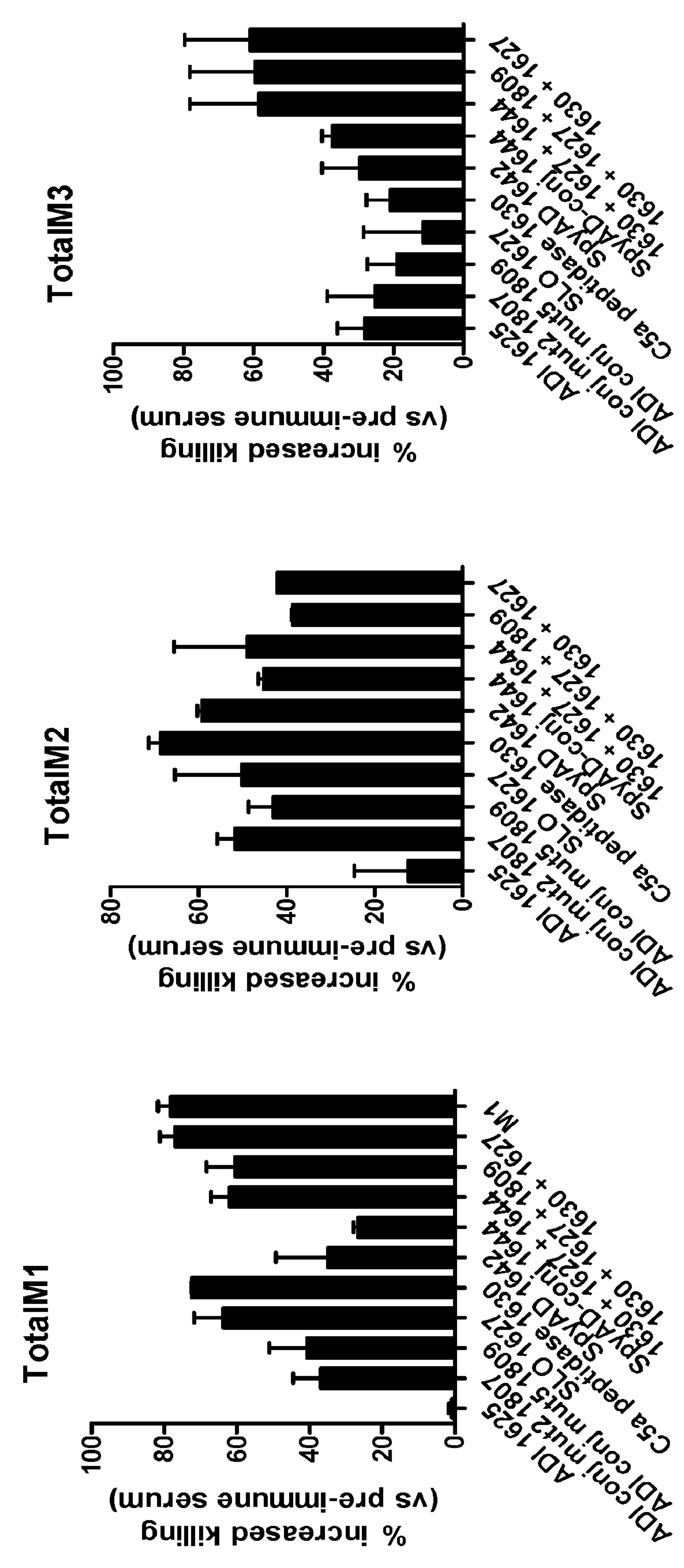
FIG. 4 shows the increased killing capacity of immune serum vs. a pre-immune serum control.

FIG. 4 shows the ability of serum resulting from immunization by antigens ADI 1625 (SEQ ID NO: 36), ADI conjugate mutant 1807 (conjugate of pAMF-substituted SEQ ID NO: 38), ADI conjugant mutant 1809 (conjugate of SEQ ID NO: 38), SLO 1627 (SEQ ID NO: 32), C5a peptidase 1630 (SEQ ID NO: 30), SpyAD 1642 (SEQ ID NO: 33), SpyAD-conjugate 1644, 1630+1627+1644, 1630+1627+1809, 1630+1627, and M1 to increase killing of GAS serotypes M1, M2, and M3 over pre-immune serum. The pAMF-substituted SpyAD conjugates were made using the peptide of SEQ ID NO: 12, and the ADI conjugates were made using the peptide of SEQ ID NO: 20.

Example 9: GAS Antigens and Conjugates Elicit Active Immune Responses that Increase Survival after GAS Challenge Mice were actively immunized prior to being challenged by subdermal and IP injection.

TABLE 5

Active Immunization Experiment Timeline - Subdermal and IP Challenges

| Subdermal Challenge - Steps | IP Challenge - Steps |
|---|---|
| Day 1: $1^{st}$ immunization | Day 1: $1^{st}$ immunization |
| Day 14: $2^{nd}$ immunization | Day 14: $2^{nd}$ immunization |
| Day 28: $3^{rd}$ immunization | Day 28: $3^{rd}$ immunization |
| Day 42: infection challenge | Day 41: shave mice |
| Day 49: terminate experiment | Day 42: infection challenge |
| | Day 45: euthanize mice and collect lesions |

$1^{st}$, $2^{nd}$, and $3^{rd}$ Immunizations—Subdermal and IP Challenges: Antigen/adjuvant mixtures were prepared by combining 50 μL alum (Alhydrogel) with 10 μg antigen(s) or 5 μg of conjugate and mixing rigorously to allow antigens to adsorb onto the alum. Each antigen/adjuvant mixture was drawn into 1 mL syringes fitted with 26½ gauge needles. Each mouse was anesthetized with inhaled isoflurane and injected with 100 μL of the prepared vaccine into the hind leg muscle.

Preparation of Mice for Challenge-Subdermal Challenge: Mice were anesthetized with isoflurane. The backs of the mice were shaved with an electric razor, with care taken not to nick the skin. Hair depilation cream was applied to the shaved backs and was allowed to sit for a few minutes before thoroughly wiping them clean with damp paper towels. The mice were patted dry and allowed to recover from isoflurane treatment.

Preparation of Materials for Challenge Subdermal and IP Challenges: M1 89155 strain GAS was grown to mid-logarithmic phase. The cell concentration was adjusted with sterile phosphate buffered saline, serially diluting and plating bacteria onto agar to confirm bacterial dose. For Subdermal Challenge, the targeted CFU per 10 μL per mouse was $1\times10^6$, and the bacteria was drawn into 500 μL Hamilton syringes fitted with 26½ gauge needles. For IP Challenge on day 35, the targeted CFU per 100 μL per mouse is $1\times10^7$, and the bacteria was drawn into 1 mL syringes fitted with 26½ gauge needles. The mice were anesthetized with inhaled isoflurane and then injected with 200 μL of M1 89155 bacteria into the peritoneal cavity. The mice were allowed to recover from the anesthetic in normal air. Survival of the mice was tracked over the course of 1 week, checking multiple times per day.

Subdermal Challenge and Lesion Collection: For subdermal challenges on day 35, the mice were anesthetized with inhaled isoflurane and then injected with 10 μL of M1 89155 bacteria into the shaved backs using a repeat dispenser for the Hamilton syringe. Lesion sizes were tracked daily over the course of 3 days by photographing isoflurane-anesthetized mice alongside a ruler. Prior to lesion collection on day 3, sterile 2 mL screw cap tubes with 1.0 mm silica beads and 1 mL PBS for each skin lesion were prepared. The weights of each tube were recorded. On day 3, when lesions were fully developed, the mice were euthanized with $CO_2$ and cervical dislocation. Using clean surgical instruments, each skin lesion was cut out and placed into the pre-weighed tubes. Tube weights are recorded for tissue mass calculations. The tubes were placed into a MagnaLyser bead beater, and the tubes were beat at 6000 rpm for 60 s. The tubes were then placed onto ice to cool for 60 s before repeating the beating cycle. Samples were serially diluted, and the lysate is placed onto agar to quantify bacterial burden.

Figure 5A:
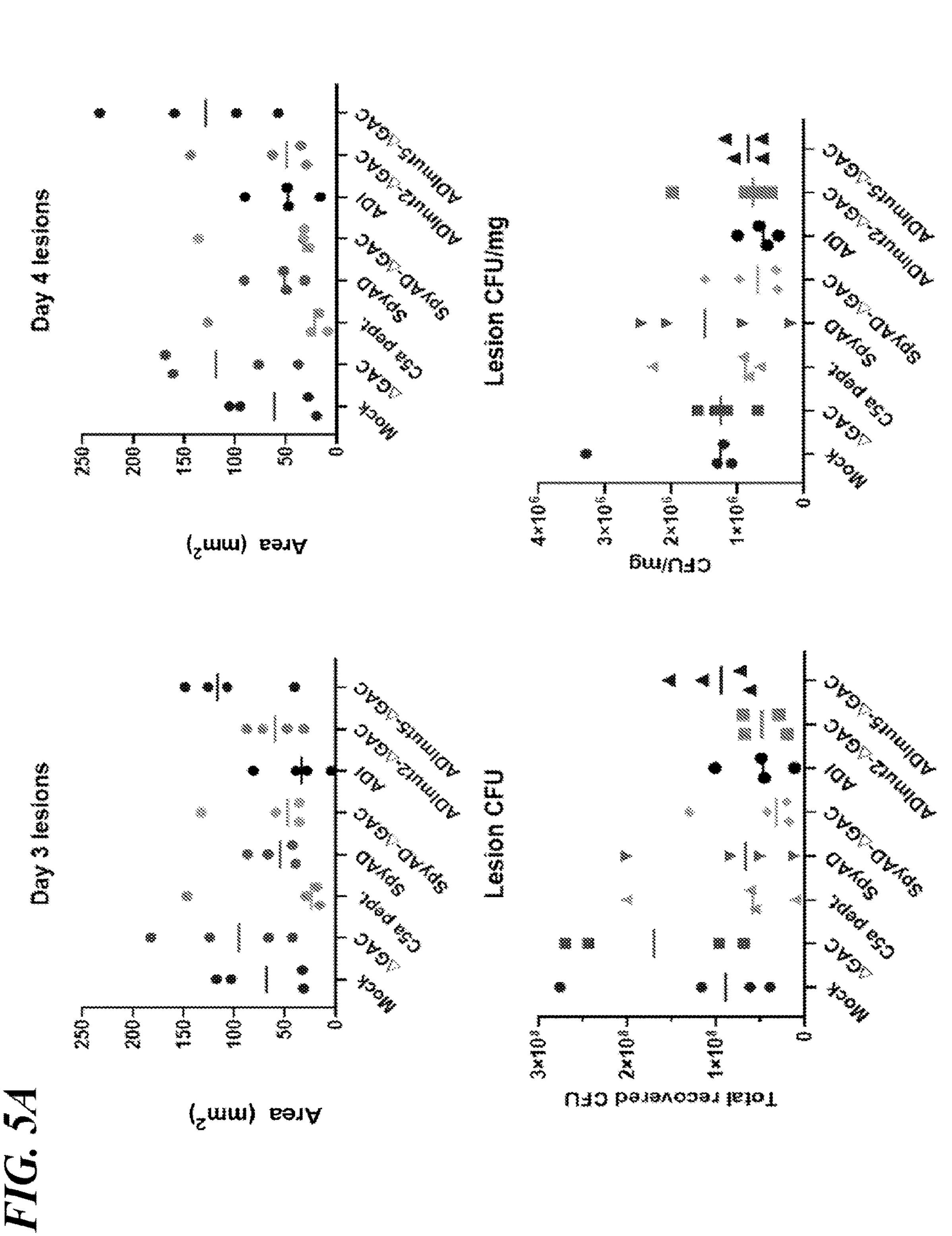
FIG. 5A, FIG. 5B, FIG. 5C, FIG. 5D, FIG. 5E, and FIG. 5F show the results of active immunization experiments, including antibody titers, lesion size, and bacterial burden, and percent survival.
Figure 5B:
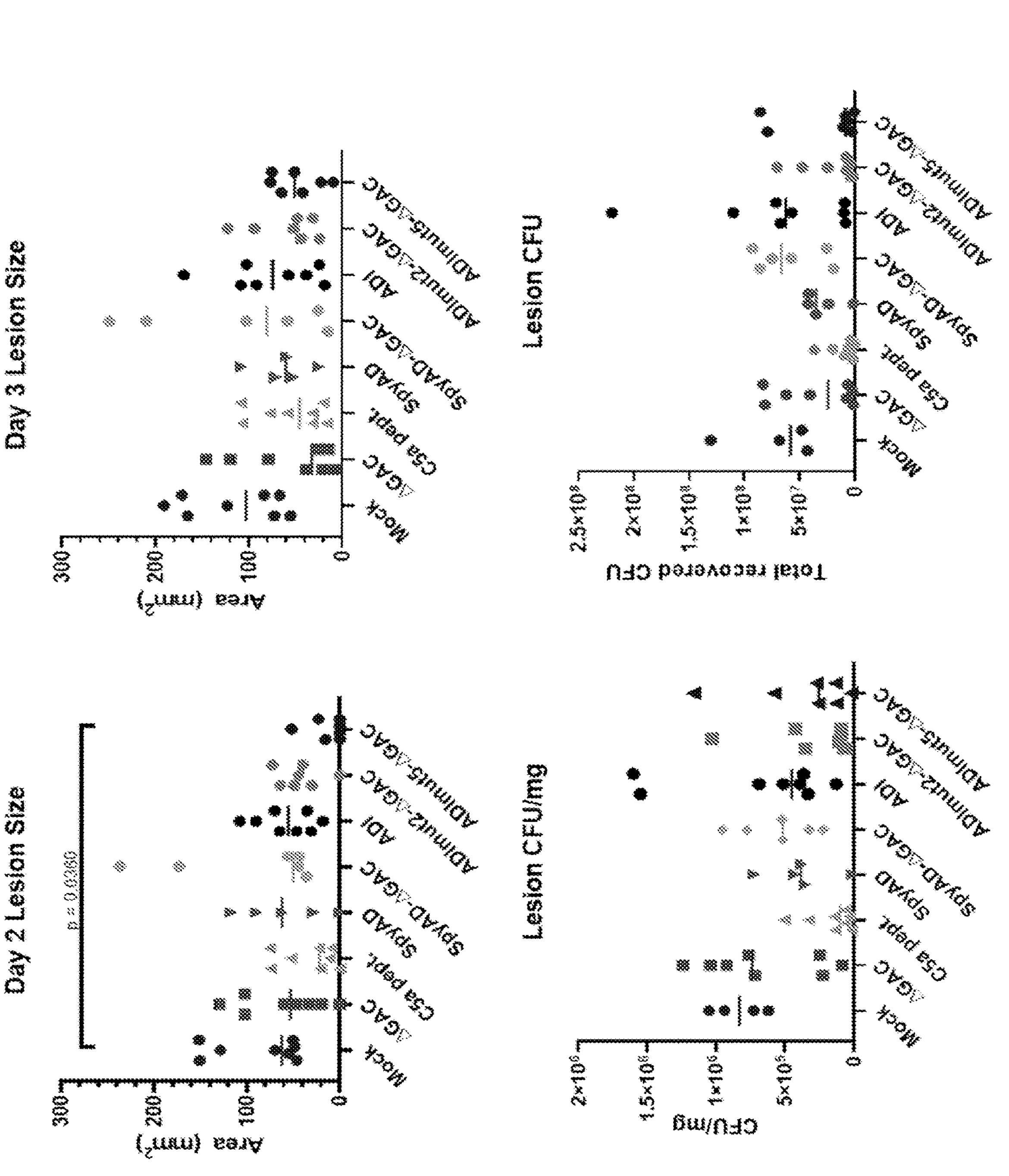
Figure 5C:
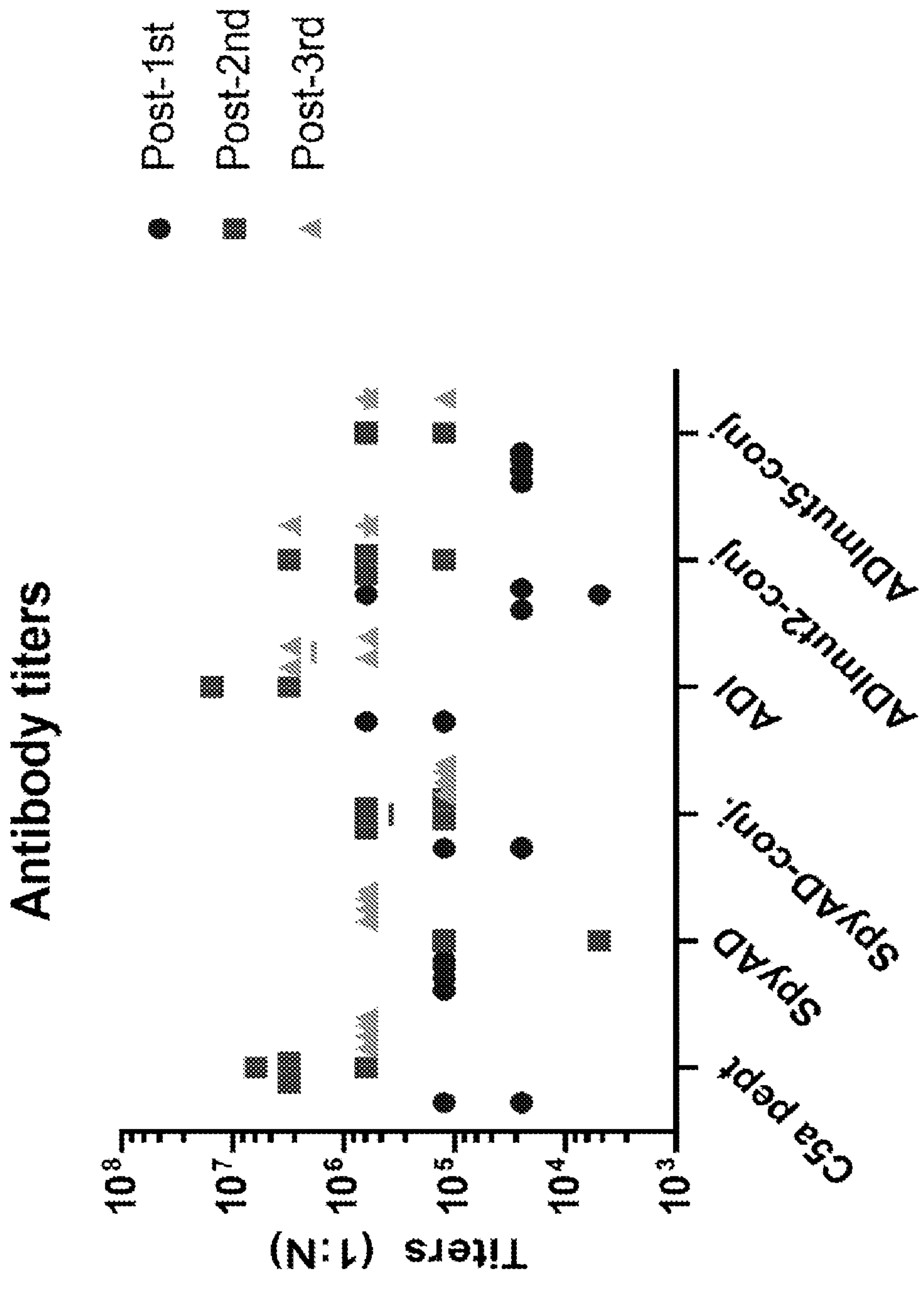
Figure 5D:
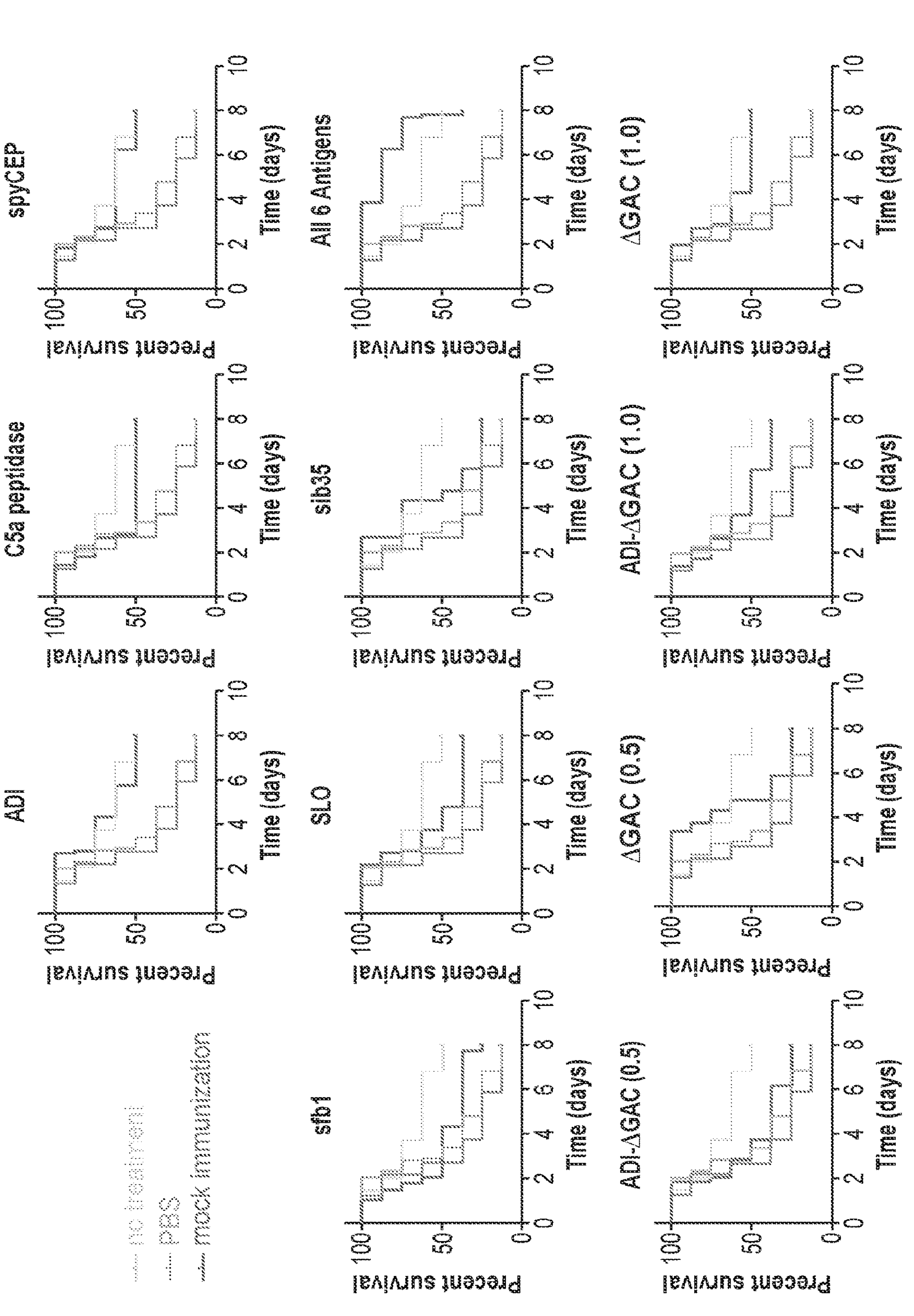

Two parallel experiments were performed in which in one set of animals were bled throughout the experiment in order to test for antigen-specific antibody titers post-vaccination. In the other arm, the mice were not bled during the course of the experiment. Both set of animals were challenged similarly in the end to perform the lesion size & CFU/mg analysis. FIG. 5A shows the results of bled-arm active immunization experiments as measured by lesion size and lesion CFU/mg, demonstrating that the conjugates of the present disclosure perform better than polysaccharides alone. Similarly, FIG. 5B show the results of the no-bleed-arm active immunization experiments as measured by lesion size and lesion CFU/mg, wherein the GAC conjugates of SpyAD (conjugates of pAMF-substituted SEQ ID NO: 34) and ADI (ADImut2 conjugates use pAMF-substituted SEQ ID NO: 27, and ADImut5 conjugates use pAMF-substituted SEQ ID NO: 38) conveyed better protection than the corresponding protein alone. The best protection was conferred by C5a peptidase (SEQ ID NO: 4). FIG. 5C shows the first, second, and third antibody titers after each immunization. FIG. 5D shows survival data for mice that have undergone active immunization and were subsequently subjected to IP challenge. The only group to show some protection was the group administered a 6-antigen combination with 30 μg total protein.

Active Immunization with Antigen or Antigen Conjugate Combinations: As above, mice were actively immunized with one or more antigen or antigen conjugate prior to being challenged by IP injection.

TABLE 6

| Active Immunization Experiment Timeline - Subdermal and IP Challenges IP Challenge - Steps |
|---|
| Day 1: $1^{st}$ immunization |
| Day 14: $2^{nd}$ immunization |
| Day 28: $3^{rd}$ immunization |
| Day 42: IP challenge |

Mice (n=10 per group) were immunized with one of 8 treatments: mock immunization (PBS+alum); 5 μg of SpyAD-GAC conjugate (conjugate of pAMF-substituted SEQ ID NO: 34); 5 μg of ADImut5-GAC conjugate (conjugate of pAMF-substituted SEQ ID NO: 38); 10 μg of C5a peptidase (SEQ ID NO: 30); 10 μg streptolysin O (SEQ ID NO: 32); a combination of 10 μg of C5a peptidase (SEQ ID NO: 30) and 10 μg streptolysin O (SEQ ID NO: 32); a combination of 10 μg of C5a peptidase (SEQ ID NO: 30), 10 μg streptolysin O (SEQ ID NO: 32), and 5 μg of SpyAD-GAC conjugate (conjugate of pAMF-substituted SEQ ID NO: 34); or a combination of 10 μg of C5a peptidase (SEQ ID NO: 30), 10 μg streptolysin O (SEQ ID NO: 32), and 5 μg of ADImut5-GAC conjugate (conjugate of pAMF-substituted SEQ ID NO: 38). The SpyAD conjugates were made using the peptide of SEQ ID NO: 12, and the ADImut5 conjugates were made using the peptide of SEQ ID NO: 20.

Figure 5E:
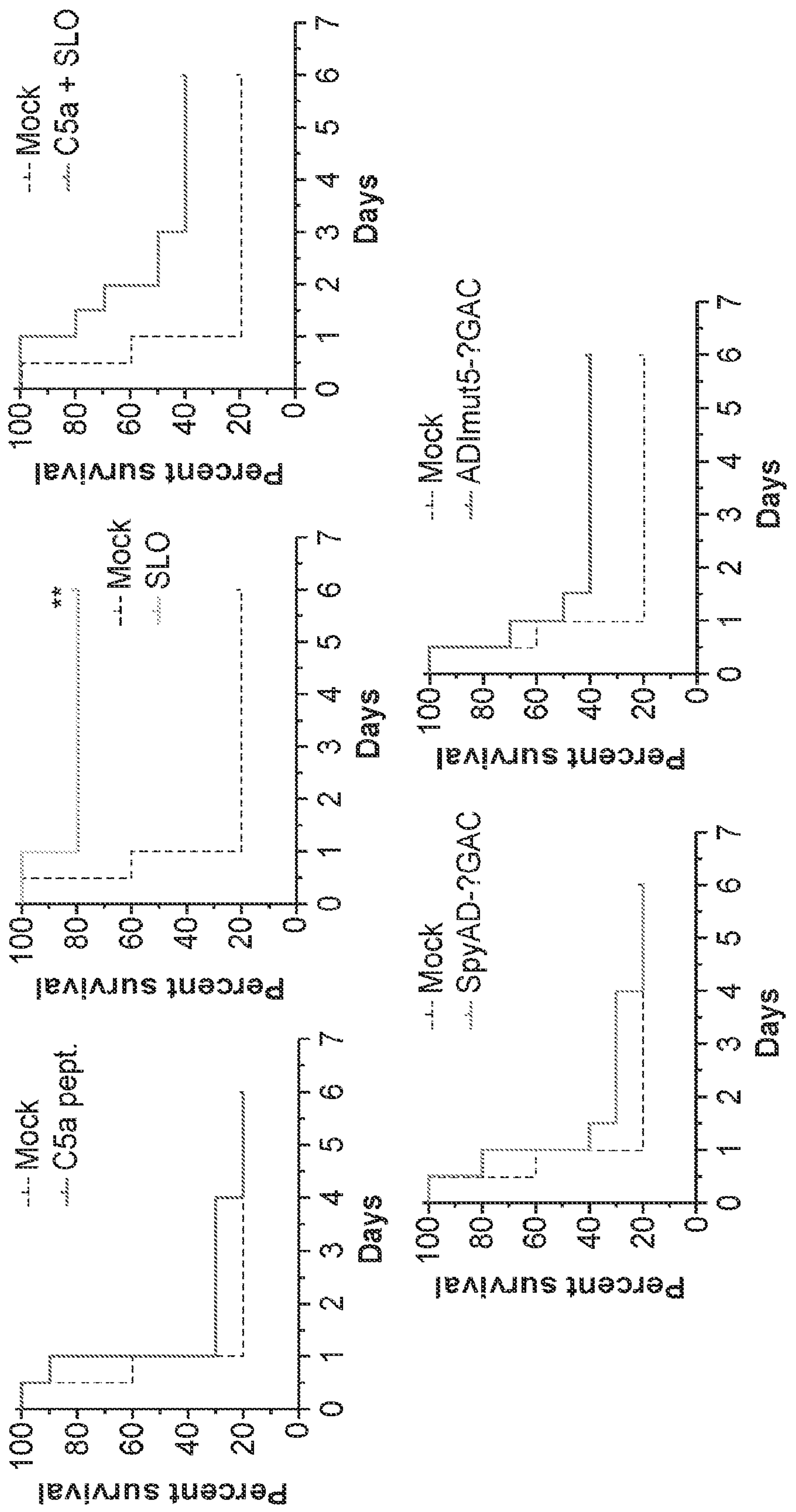
Figure 5F:
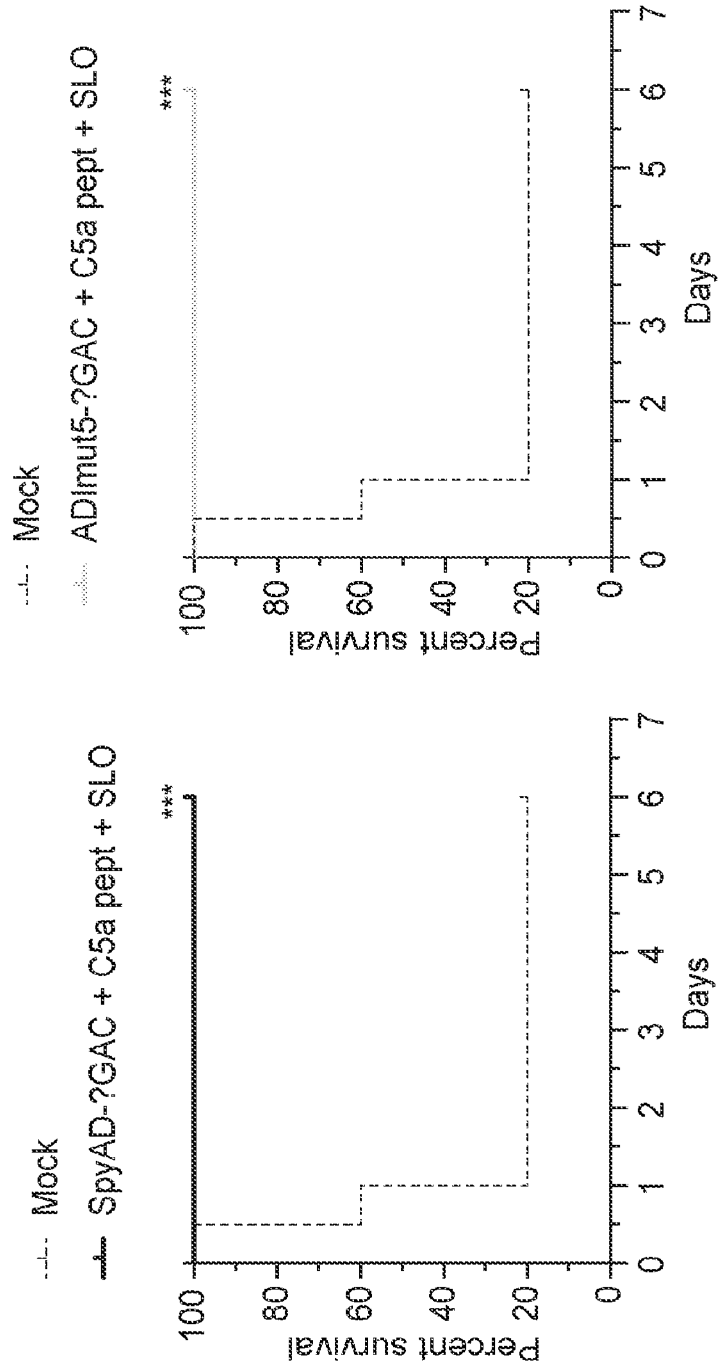

FIG. 5E shows the survival of mice actively immunized with single antigens/antigen conjugates or two antigens/antigen conjugates (combination) after IP challenge. Mice immunized with SLO along had the greatest survival, but no individual or dual antigen combination provided 100% protection six days after challenge. Notably, when mice were actively immunized with the triple combinations prior to IP challenge, 100 percent survival was observed after 6 days. These data are shown in FIG. 5F.

Example 10: GAS Antigens and Conjugates Elicit Passive Immune Responses that Increase Survival after GAS Challenge Mice were passively immunized prior to being challenged by IP injection.

Experiments were performed to assess the protection conferred by anti-sera isolated from GAS antigen and GAS conjugate-immunized mice when transferred to mice that were subsequently challenged with GAS. Briefly, rabbits were vaccinated with 5 μg of ADI antigen (SEQ ID NO: 36), C5a antigen (SEQ ID NO: 30), Sfb1 antigen (SEQ ID NO: 28), SpyAD antigen (SEQ ID NO: 33), ADI: GAC conjugates (conjugates of pAMF-substituted SEQ ID NO: 38), or SpyAD: GAC conjugates (conjugates of pAMF-substituted SEQ ID NO: 34) at weeks 0, 3 and 6. Serum was collected from each animal on week 8.

Passive Immunization-IP Challenge: Thawed rabbit serum (approximately 200 μL per mouse), transferred on ice, was drawn into a 1 mL syringes fitted with 30 gauge needles. M1 89155 strain GAS, grown to mid-logarithmic phase, was diluted with sterile phosphate buffered saline to adjust cell concentration. The targeted CFU per 100 μL per mouse was $1\times10^7$, and the bacteria was drawn into 1 mL syringes fitted with 26½ gauge needles. The rabbit serum was warmed in syringes to room temperature, and the mice were anesthetized with inhaled isoflurane. 200 μL of the rabbit serum was retro-orbitally transferred into each anesthetized mouse. Five minutes after serum transfer, 200 μL of the M1 81955 bacteria was injected into the peritoneal cavity, and the mice were allowed to recover from the isoflurane in normal air. Survival of the mice was tracked over the course of 1 week, checking multiple times per day.

Figure 6A:
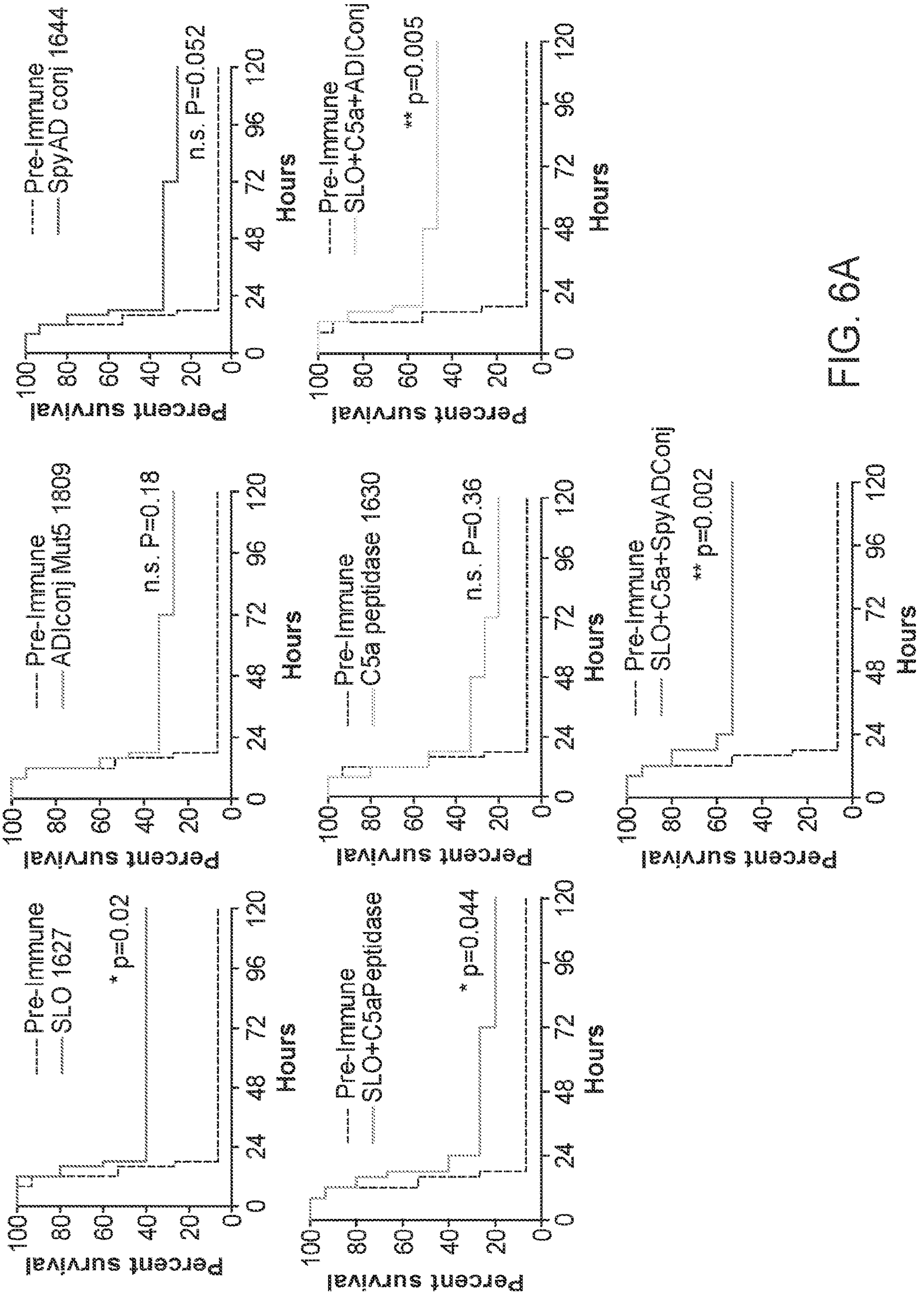
FIG. 6A and FIG. 6B show percent survival data following passive immunization of mice subjected to an IP challenge.
Figure 6B:
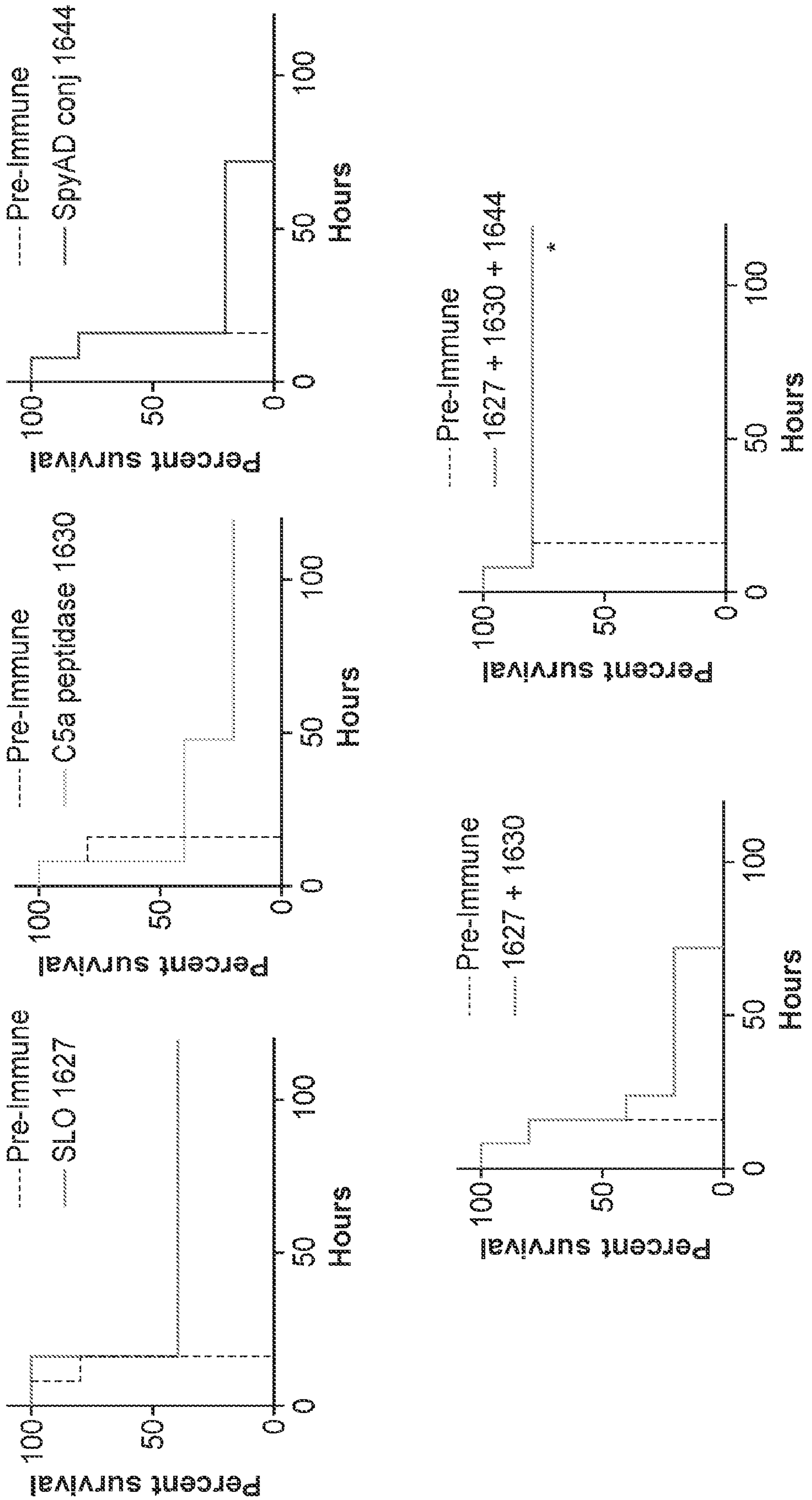

Survival of mice that have undergone passive immunization and were subjected to subsequent GAS challenge are shown in FIG. 6A and FIG. 6B. All groups treated with antigens and antigen conjugates (pAMF conjugates) of SLO 1627, ADI-conjugate Mut5 1809, SpyAD conjugate 1644, C5a peptidase 1630, SLO+C5a peptidase, SLO+C5a+ADI-conjugate, and SLO+C5a+SpyAD-conjugate showed improved survival over the pre-immune immunized cohort.

Example 11: GAS Antigens and Conjugates Elicit Passive Immune Responses that Increase Survival after GAS Challenge Mice were passively immunized prior to being challenged by subdermal injection.

TABLE 7

| Passive Immunization Experiment Timeline - Subdermal Challenge<br>Subdermal Challenge - Steps |
|---|
| Day −1: prepare mice<br>Day 0: prepare materials, serum transfer, and challenge<br>Day 3: lesion collection |

Preparation of Mice for Challenge-Subdermal Challenge: Mice were anesthetized with isoflurane. The backs of the mice were shaved with an electric razor, with care taken not to nick the skin. Hair depilation cream was applied to the shaved backs and is allowed to sit for a few minutes before thoroughly wiping them clean with damp paper towels. The mice were patted dry and allowed to recover from isoflurane treatment.

Preparation of Materials, Serum Transfer, and Challenge-Subdermal Challenge: M1 89155 strain GAS was grown to mid-logarithmic phase. The cell concentration was adjusted with sterile phosphate buffered saline, serially diluting and plating bacteria onto agar to confirm bacterial dose. For Subdermal Challenge, the targeted CFU per 10 μL per mouse was $1\times10^6$, and the bacteria was drawn into 500 μL Hamilton syringes fitted with 26½ gauge needles. Rabbit serum was thawed and transferred on ice before being drawn into 1 mL syringes fitted with 30 gauge needles. The rabbit serum was warmed in syringes to room temperature, and the mice were anesthetized with inhaled isoflurane. 200 μL of the rabbit serum is retro-orbitally transferred into each anesthetized mouse. Five minutes after serum transfer, 10 μL of the M1 81955 bacteria was injected into the shaved backs of the mice using a repeat dispenser, and the mice were allowed to recover from the isoflurane in normal air. Lesion sizes were tracked daily over the course of 3 days by photographing isoflurane-anesthetized mice alongside a ruler.

Lesion Collection for bacterial burden analyses: Prior to lesion collection on day 3, sterile 2 mL screw cap tubes with 1.0 mm silica beads and 1 mL PBS for each skin lesion were prepared. The weights of each tube were recorded. On day 3, when lesions are fully developed, the mice were euthanized with $CO_2$ and cervical dislocation. Using clean surgical instruments, each skin lesion was cut out and placed into the pre-weighed tubes. Tube weights were recorded for tissue mass calculations. The tubes were placed into a MagnaLyser bead beater, and the tubes were beat at 6000 rpm for 60 s. The tubes were then placed onto ice to cool for 60 s before repeating the beating cycle. Samples are serially diluted, and the lysate was placed onto agar to quantify bacterial burden.

Figure 7:
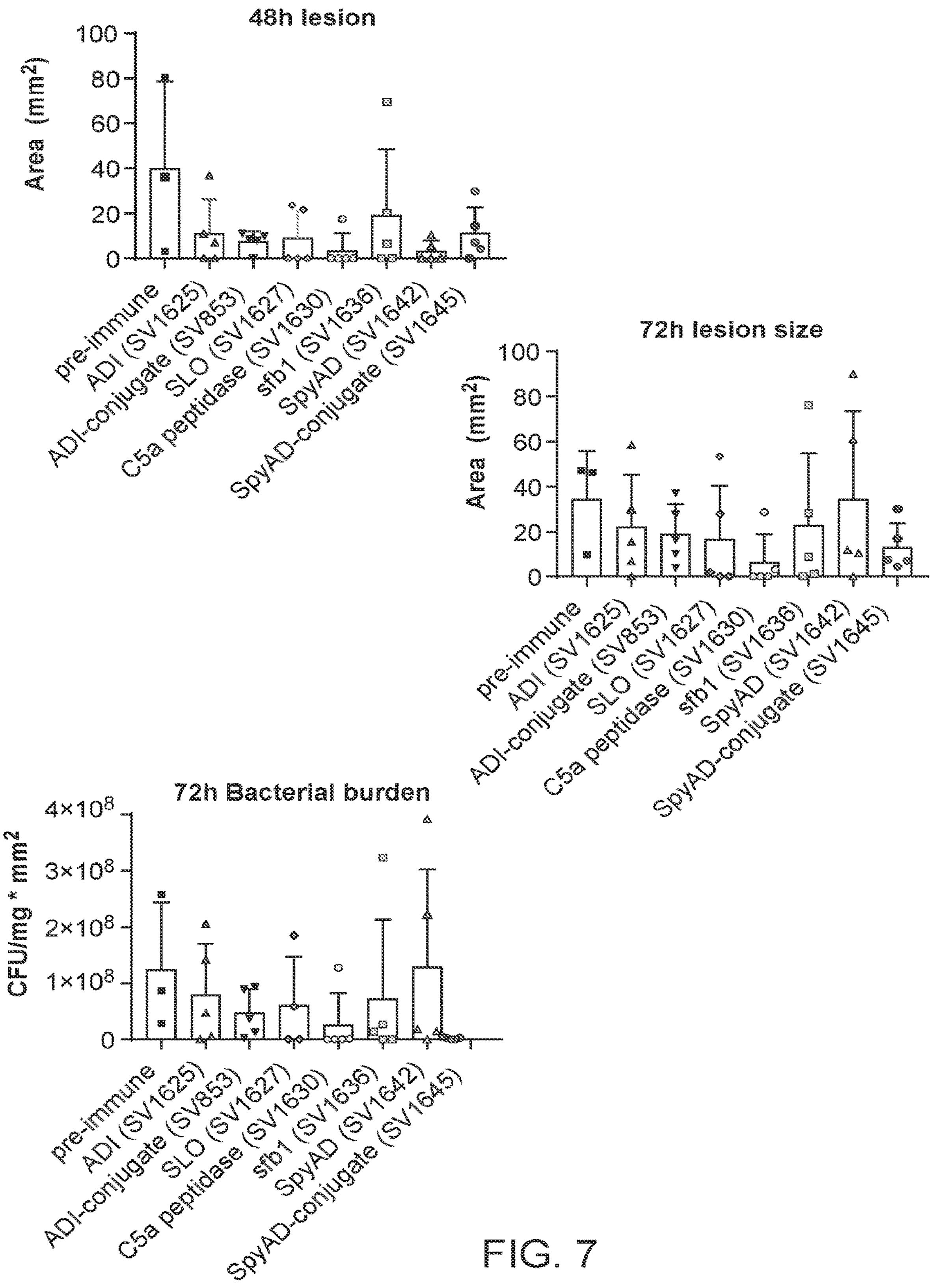
FIG. 7 shows lesion size and bacterial burden data following passive immunization of mice subjected to a subdermal challenge.

Lesion size and bacterial burden data of mice that have undergone passive immunization and were subjected to subdermal challenge with GAS are shown in FIG. 7. Mice (n=10 treated with antigens and antigen conjugates ADI (SEQ ID NO: 36), ADI-conjugate (SEQ ID NO: 38), SLO (SEQ ID NO: 32), C5a peptidase (SEQ ID NO: 30), sfb1 (SEQ ID NO: 28), SpyAD (SEQ ID NO: 33), SpyAD-conjugate (conjugate of pAMF-substituted SEQ ID NO: 34) exhibited reduced lesion size after 48 h compared to the pre-immune cohort, and bacterial burden in most arms was significantly lower after 72 hours, with the Spy AD conjugate performing the best at reducing bacterial burden.

Example 12: Human Phase I and Phase IIA Clinical Trial Design

Initial Phase I clinical studies will be a randomized, placebo-controlled, ascending dose study in healthy adults 18-29 years of age (N=96) (Table 3). Objectives of this initial clinical study will be safety, dose response, and immunogenicity (IgG antibody). Since many individuals at this age range will have pre-existing exposure and immunity to GAS, baseline immunity will be fully evaluated to understand the impact of pre-existing immunity on vaccine responses. IgG response to each vaccine component and OPK antibody titer against a diverse panel of contemporary GAS isolates of different M serotypes will be evaluated.

TABLE 8

Phase I Clinical Trial Groups
Phase I Clinical Trial Design

| Group | N | Treatment | Dose | Schedule |
|---|---|---|---|---|
| 1A | 24 | GAS vaccine | Low | Day 0, 28 |
| 1B | 8 | Placebo | | Day 0, 28 |
| 2A | 24 | GAS vaccine | Mid | Day 0, 28 |
| 2B | 8 | Placebo | | Day 0, 28 |
| 3A | 24 | GAS vaccine | High | Day 0, 28 |
| 3B | 8 | Placebo | | Day 0, 28 |

The Phase 2A clinical study will be a randomized, placebo controlled, multi-center study to evaluate the vaccine in successive cohorts of individuals from 10 to 17 years of age, followed by children 5 to 9 years old (N=96) (Table 4). The objectives of this study will be safety, immunogenicity (IgG antibody responses and opsonophagocytic activity of serum), and an evaluation of preliminary efficacy (incidence of GAS pharyngitis). Each patient will be monitored for 12 months to determine the incidence of strep pharyngitis in the treatment groups.

TABLE 9

| Phase IIA Clinical Trial Groups<br>Phase IIA Clinical Trial Design | | | | |
|---|---|---|---|---|
| N | Age (yr) | Treatment | Dose | Schedule |
| 36 | 10-17 | GAS vaccine | Determined by PI | Day 0, 28 |
| 12 | 10-17 | Placebo | | Day 0, 28 |
| 36 | 5-9 | GAS vaccine | Mid | Day 0, 28 |
| 12 | 5-9 | Placebo | | Day 0, 28 |

Example 13: GAS Conjugates Induce Generation of Anti-Sera that Binds to *S. flexneri* 2a OPS in a Cross-Reactivity Experiment Experiments were performed to assess the binding of anti-sera produced by purified GAS conjugates to *S. flexneri* 2a O-antigen polysaccharide (OPS).

OPS Purification: OPS was harvested directly from lipopolysaccharide (LPS) in *Shigella* cell biomass transformed with pSEC10-wzzB plasmid to overexpress wzzB, resulting in increased OPS chain length and conditioned growth media of fermentation (supplemented with amino acids), or shake flask (STm D65) cultures, by reducing the culture pH to 3.5-3.7 with glacial acetic acid, and incubating at 100° C. for 4 h in glass bottles submerged in a boiling water bath. Post-hydrolysis supernatants were separated from insoluble material by centrifugation at 10 k×g at 4° C. for 30 minutes using a GS3 Rotor in a Sorvall RC5 refrigerated centrifuge. The supernatant fraction was brought to 1 M NaCl and filtered by tangential flow microfiltration through a 0.2 μm hollow-fiber filter at 4.5 psi transmembrane pressure (TMP), passing the full volume through, followed by flushing with an equivalent volume of 1 M NaCl. The 0.2 μm-cleared 1 M NaCl permeate was then concentrated 10-fold on a 30 kDa Hydrosart TFF membrane at 14 psi TMP and diafiltered against 35 diavolumes of 1 M NaCl, followed by 10 diavolumes of 50 mM Tris pH 7.

The retentate fraction in 20 mM Tris pH 7, 50 mM NaCl was then passed through 3×3 mL Sartobind NanoQ anion exchange membranes, linked in series, using an AKTA Purifier at 10 mL/min in 20 mM Tris pH 7, 50 mM NaCl. The flow-through fraction was brought to 25% (v/v) ammonium sulfate and incubated overnight at 4° C. Precipitated material was removed by centrifugation at 10 k×g/4° C. for 30 min using a GS3 rotor in a Sorvall RC5 refrigerated centrifuge followed by filtration through a 0.45 μm Stericup vacuum filter unit (Millipore, MA). Filtrates were then concentrated 10-fold by TFF with a Slice 200 TFF device using a 10 kDa Hydrosart membrane at 7.5 psi TMP, and diafiltered against 10 diavolumes of de-ionized water. TFF retentates were lyophilized and stored at −20° C. until use.

Immunization: Briefly, rabbits were immunized intramuscularly with ADI-mut2, ADI-mut5, and SpyAD conjugates according to the protocols of Example 6.

Serum IgG ELISA: Serum was harvested from each terminal blood draw, and serum IgG antibody titers against *S. flexneri* 2a OPS were assessed by ELISA. A working solution for the 2a OPS antigen was prepared as follows: 5.0 μg/ml of purified 2a OPS was diluted in carbonate coating buffer pH 9.6. Subsequently, Immulon 2HB "U" bottom microtiter plates (Thermo Labsystems #3655) were coated by adding 100 μl of the working solution to each well of a plate. Plates were then incubated at 37° C. for 3 h. Following this incubation, plates were washed six times with PBS-Tween (0.05%) with a two-minute soaking period between washes. Then the plates were blocked overnight at 4° C. with 1×PBS containing 10% non-fat dry milk (NFDM) at 250 μl/well. After blocking, the plates were washed again as stated above.

The test samples (rabbit sera) and pre-bleed controls were diluted in PBS-Tween 10% NFDM and were added to the plates. The specimens and controls were tested in duplicate in a series of dilutions performed on each plate. Plates were incubated for 1 h at 37° C. and then washed with PBS-Tween as described above. Next, Horseradish Peroxidase (HRP)-labeled anti-Rabbit IgG (Invitrogen #65-6120) was diluted to 1:2000 in PBS-Tween 10% non-fat dry milk (NFDM). All wells received 100 μl of the appropriate antibody solution and plates were incubated for 1 h at 37° C. Plates were again washed and 100 μl of TMB Microwell Peroxidase Substrate (SeraCare #5120-0047) was added to each well. Plates were incubated at room temperature for 15 minutes in darkness with agitation. The colorimetric reaction was stopped by adding 100 μl of 1M phosphoric acid to all wells. Absorbance values at 450 nm were immediately measured using a Multiskan FC™ Microplate Reader.

Figure 8:
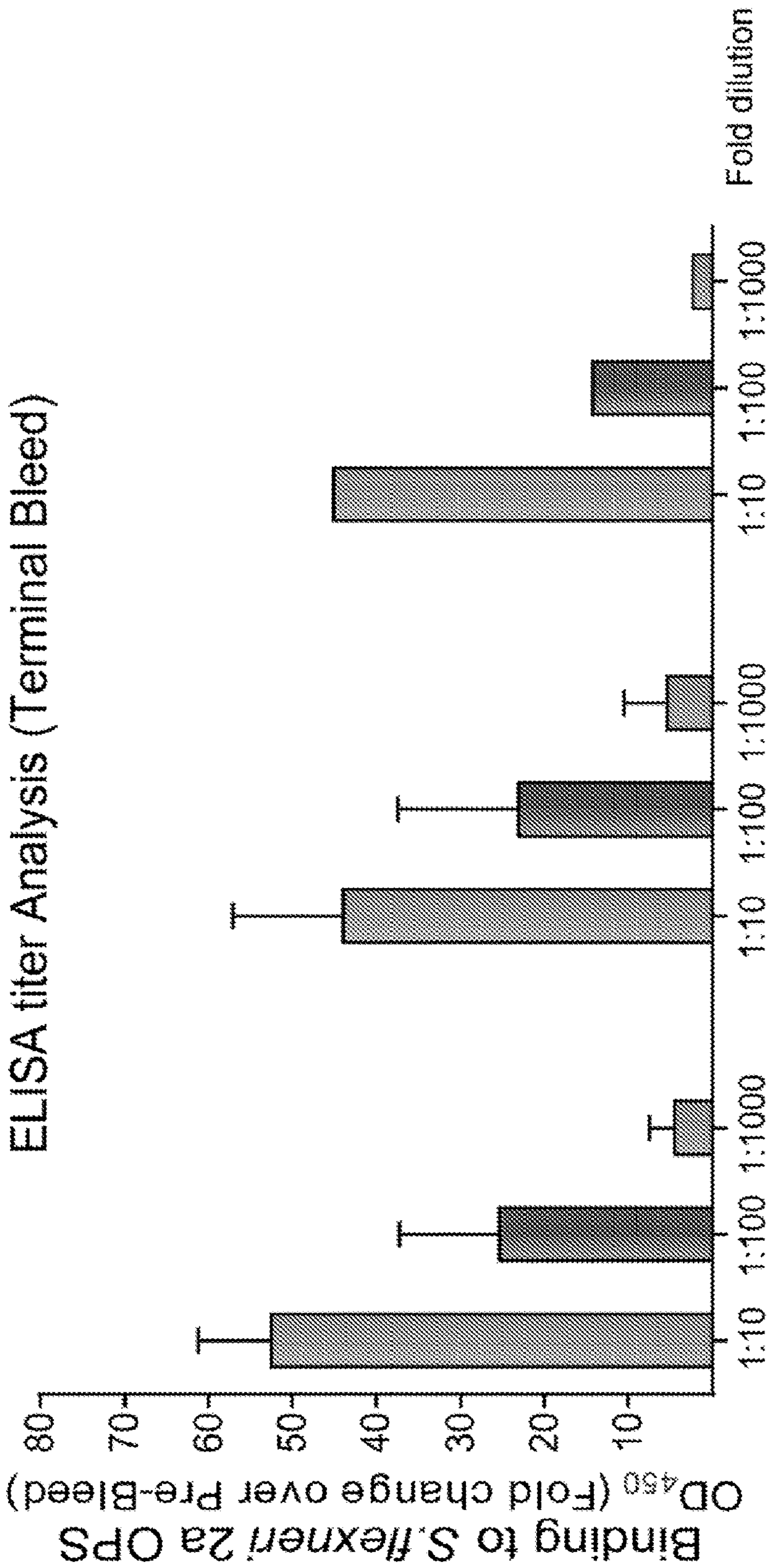
FIG. 8 shows an ELISA titer analysis of immune serum against *S. flexneri* 2a OPS.

FIG. 8 shows the result of the titer analysis. Notably, sera derived from all three GAS conjugates, ADI-mut2 (conjugates of pAMF-substituted SEQ ID NO: 27), ADI-mut5 (conjugates of pAMF-substituted SEQ ID NO: 38), and SpyAD (conjugates of pAMF-substituted SEQ ID NO: 34), exhibited up to approximately 60-fold increase in binding to *S. flexneri* 2a OPS at a 1:10 dilution versus pre-bleed control.

Example 14: GAS Conjugates Demonstrate Bactericidal Activity Against *S. flexneri* Strains in a Serum Bactericidal Assay (SBA)

Experiments were performed, to determine the ability of immune sera from GAS conjugate-immunized rabbits to elicit neutrophil killing of *S. flexneri* strains. Rabbits were immunized with the indicated conjugates according to the protocol described in Example 7 prior to performing the bactericidal assay. Briefly, the serum bactericidal assay (SBA) and digital image analysis of colonies was performed according to methods previously described (Nahm, et al. mSphere, 2018, 2018 Jun. 13; 3 (3), pii: e00146-18, and SBA Protocol linked to therein).

Table 9 shows the bactericidal ability of sera resulting from immunization by SpyAD conjugate 1645 (conjugate of pAMF-substituted SEQ ID NO: 34) and ADI conjugant mutants 1807, 1808, 1809, and 1810 (conjugates of pAMF-substituted SEQ ID NO: 38) against *S. flexneri* 2a, 3a, and 6. Values shown are SBA (serum bactericidal activity) titers, and all five conjugates demonstrated bactericidal activity versus pre-immune control. No killing was observed for *S. sonnei*, and titers in this arm are therefore reported as half of the lowest dilution tested. PnQC19, a human control serum, was used to normalize *Shigella* SBA titers as previously described (Nahm, et al. mSphere, 2018, 2018 Jun. 13; 3 (3), pii: e00146-18). Titers shown for *S. flexneri* 6 are the average of raw titers (2 experiments). There is no assigned PnQC19 value for *S. flexneri* 6.

TABLE 10

Serum Bactericidal Activity of Rabbit GAS antibodies

| Conjugate | *S. flexneri* 2a | *S. flexneri* 3a | *S. flexneri* 6 | *S. sonnei* |
|---|---|---|---|---|
| pre-immune serum | nd | nd | 233 | nd |
| 1645 | 1301 | 1333 | 980 | 30 |
| 1807 | 384 | 2496 | 553 | 30 |
| 1808 | 671 | 703 | 394 | 30 |
| 1809 | 487 | 1325 | 1401 | 30 |
| 1810 | 1654 | 652 | 532 | 30 |
| PnQC19 | 28000 | 19000 | 6915 | 1100 |

Example 15: Immunization with SpyAD-GAC does not Incite Detectable Levels of Antibodies Cross-Reactive to Human Heart Epitopes Varying amounts of normal adult human heart tissue lysate (Novus Biologicals cat #NB820-59217) with SDS-containing denaturing loading dye were separated by SDS-PAGE using 4-12% Bis-Tris gels before transfer onto a PVDF membrane using the manufacturer's protocol on iBlot (Thermo Fisher). Finally, the blot was blocked at ambient temperature for 1 h, followed by probing with rabbit antisera generated against each of the GAS antigens (diluted 1:1000). After three 30 min washes, HRP conjugated anti-rabbit (Jackson ImmunoResearch Laboratories, Inc., Cat #211-035-109) secondary antibody (diluted 1:10,000) was added and chemiluminescence recorded on an Syngene G-Box F3 image scanner after incubation of the blot with the pico substrate (Thermo Fisher Scientific Cat #34580). All blot blocking, washes, and antibody/serum dilutions were done in TBS+5% BSA.

Figure 11:
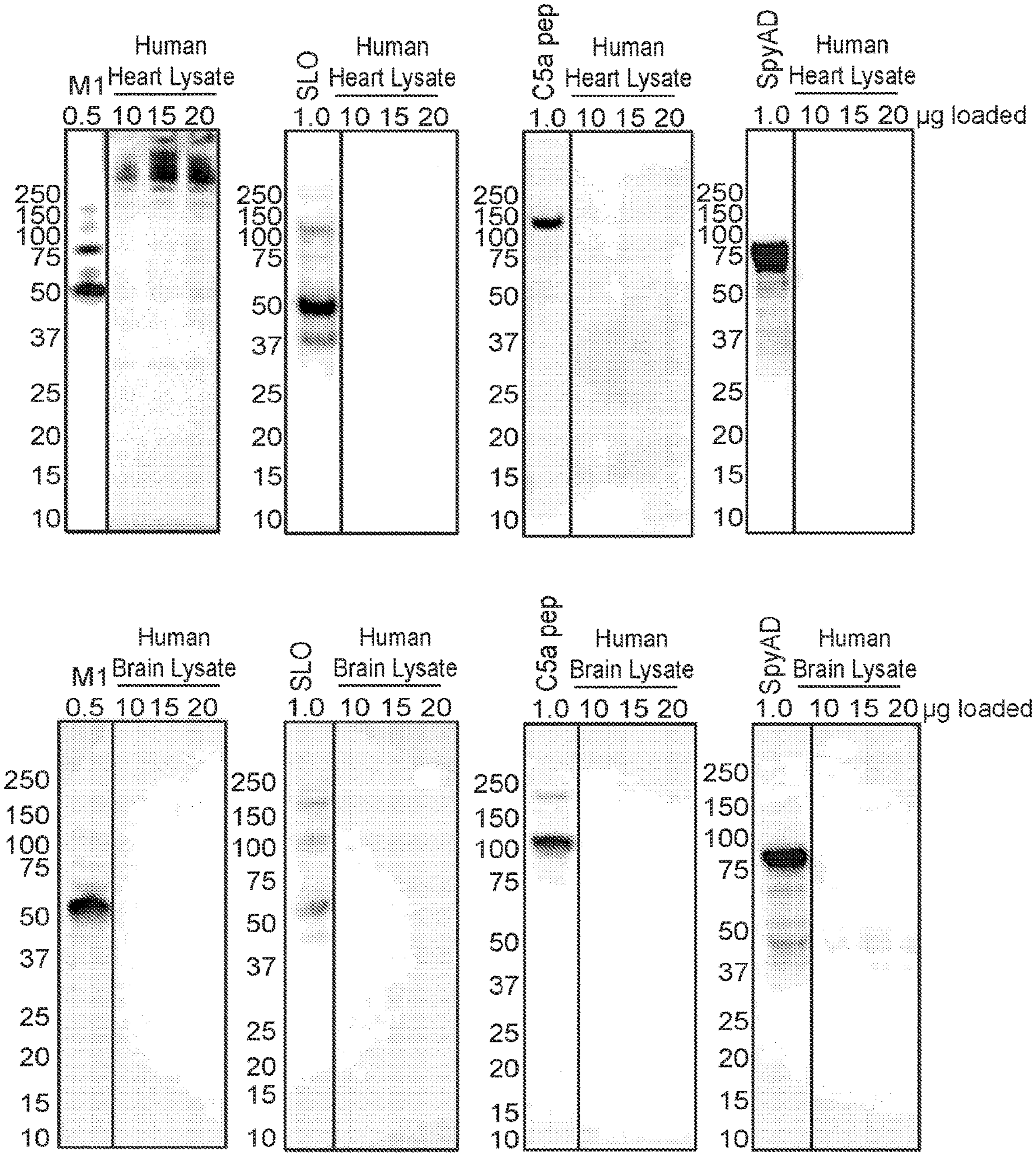
FIG. 11 shows a Western blot analysis assessing antigen-specific antisera for cross-reactivity to human heart lysate.

Western blot analysis of the SLO, C5a peptidase and SpyAD-GAC rabbit immune sera on normal human heart lysates separated by polyacrylamide gel electrophoresis was performed. Antisera raised against the intact GAS M1 protein using the same rabbit immunization protocol served as a control. As shown in FIG. 11, while anti-M1 antisera reacted to very high molecular weight components of the lysate, no cross-reactivity to the human heart tissue was seen for the SLO (SEQ ID NO: 8), C5a peptidase (SEQ ID NO: 4) and SpyAD-GAC (conjugate of pAMF-substituted SEQ ID NO: 12) antisera, although they recognized the respective cognate GAS protein (or protein carrier in the case of SpyAD-GAC). This analysis is consistent with (a) the lack of sequence homology of SLO, C5a peptidase or SpyAD to human proteins, and (b) knowledge that GAC is comprised solely of repeating rhamnose, a sugar absent in humans, following the genetic deletion of its GlcNAc side chain, which represented a common mammalian sugar epitope.

Figure 15:
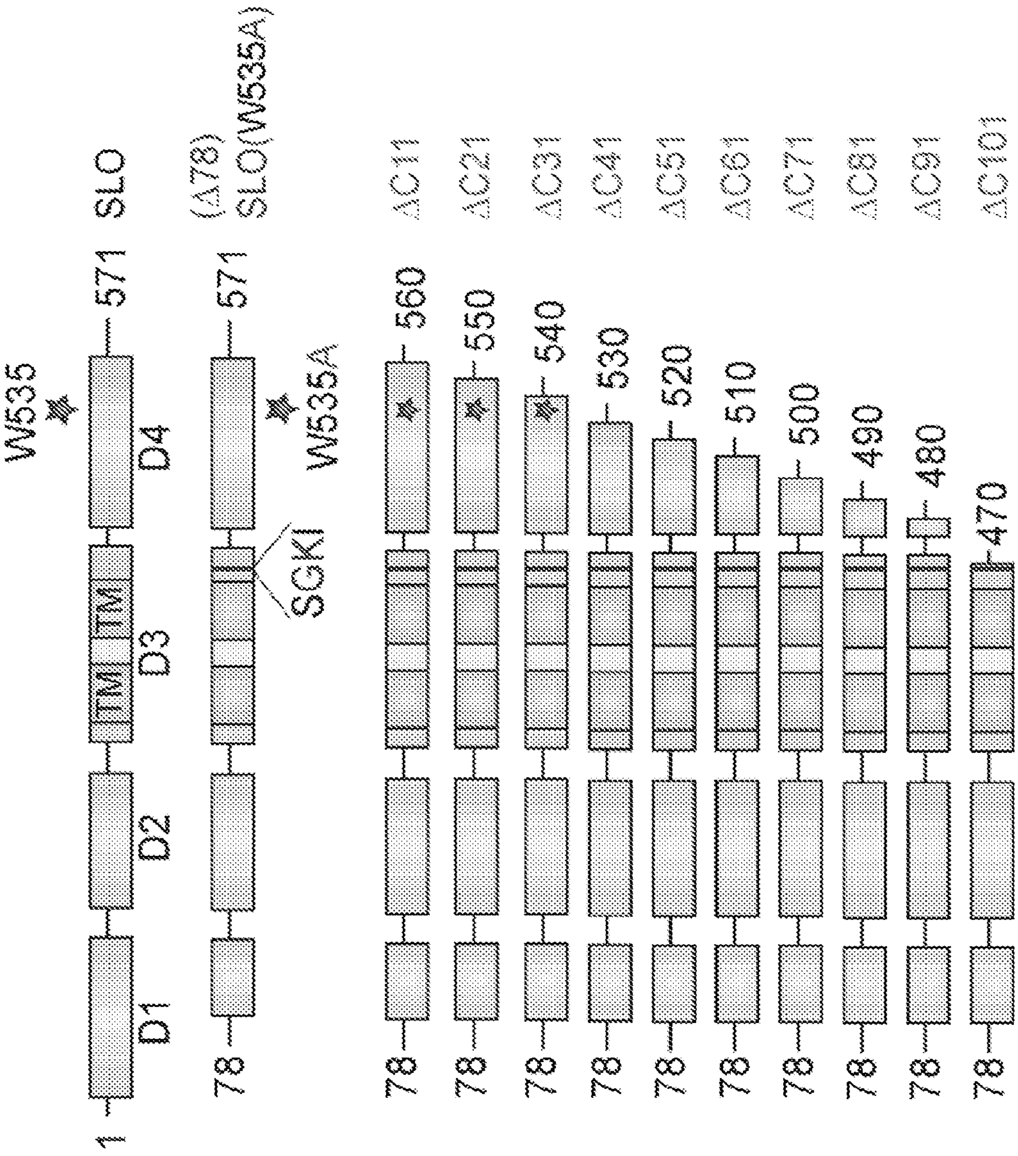
FIG. 15 is a graphical representation of truncated SLO sequences compared to the non-truncated SLO sequence.
Figure 16:
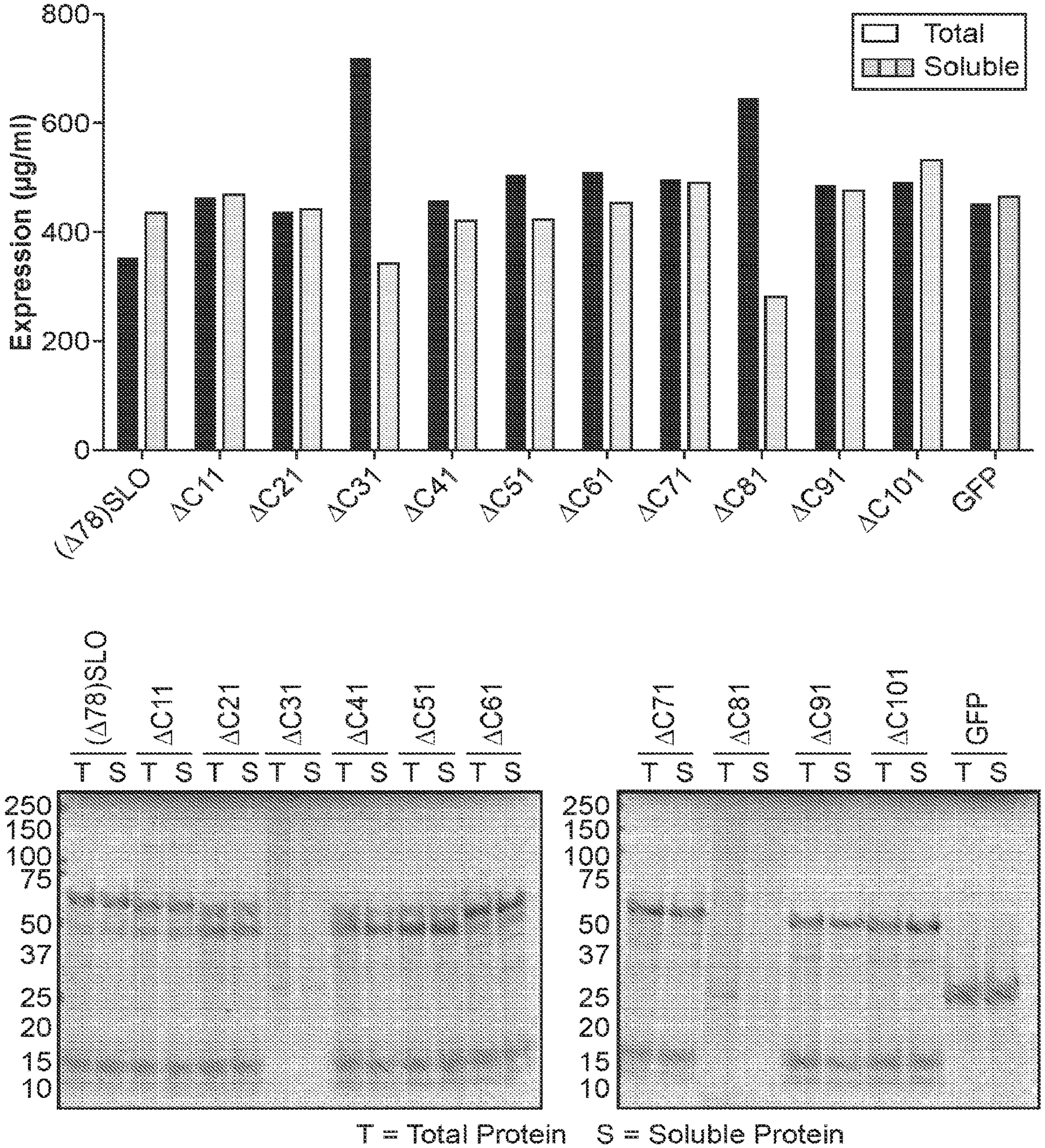
FIG. 16 shows expression levels (total and soluble) for truncated SLO variants.

Example 16: Truncated SLO Peptides were Expressed and Assessed for their Immunogenicity in Both Rabbit and Murine Models Truncated SLO variants were expressed, for instance, according to the above methods. FIG. 15 shows a graphical representation of 10 such variant sequences (ΔC11, ΔC21, ΔC31, ΔC41, ΔC51, ΔC61, ΔC71, ΔC81, ΔC91, and ΔC101), corresponding to SEQ ID NO: 44 to SEQ ID NO: 53 (post-TEV cleavage). FIG. 16 shows the expression of these variants, in both total and soluble protein concentration with their corresponding gels. It is worth noting the differential truncation patterns observed for each variant. Some variants, like ΔC41 and ΔC51 has several closely eluting bands around 50 kDa, whereas variants like ΔC31 or ΔC81 don't show any discernible bands corresponding to their molecular masses.

FIG. 17 compares expression of several peptides, including truncated SLO variants after initial purification by HisTrap chromatography. Variants ΔC91 and ΔC101 expressed as single distinct bands corresponding to the correct molecular mass of the protein, along with some smaller truncation fragments. FIG. 18 and FIG. 19 compare SLO, and variants ΔC91 and ΔC101, during the steps of TEV cleavage and additional purification by HisTrap (FIG. 18) and size exclusion chromatography (FIG. 19).

Figure 20:
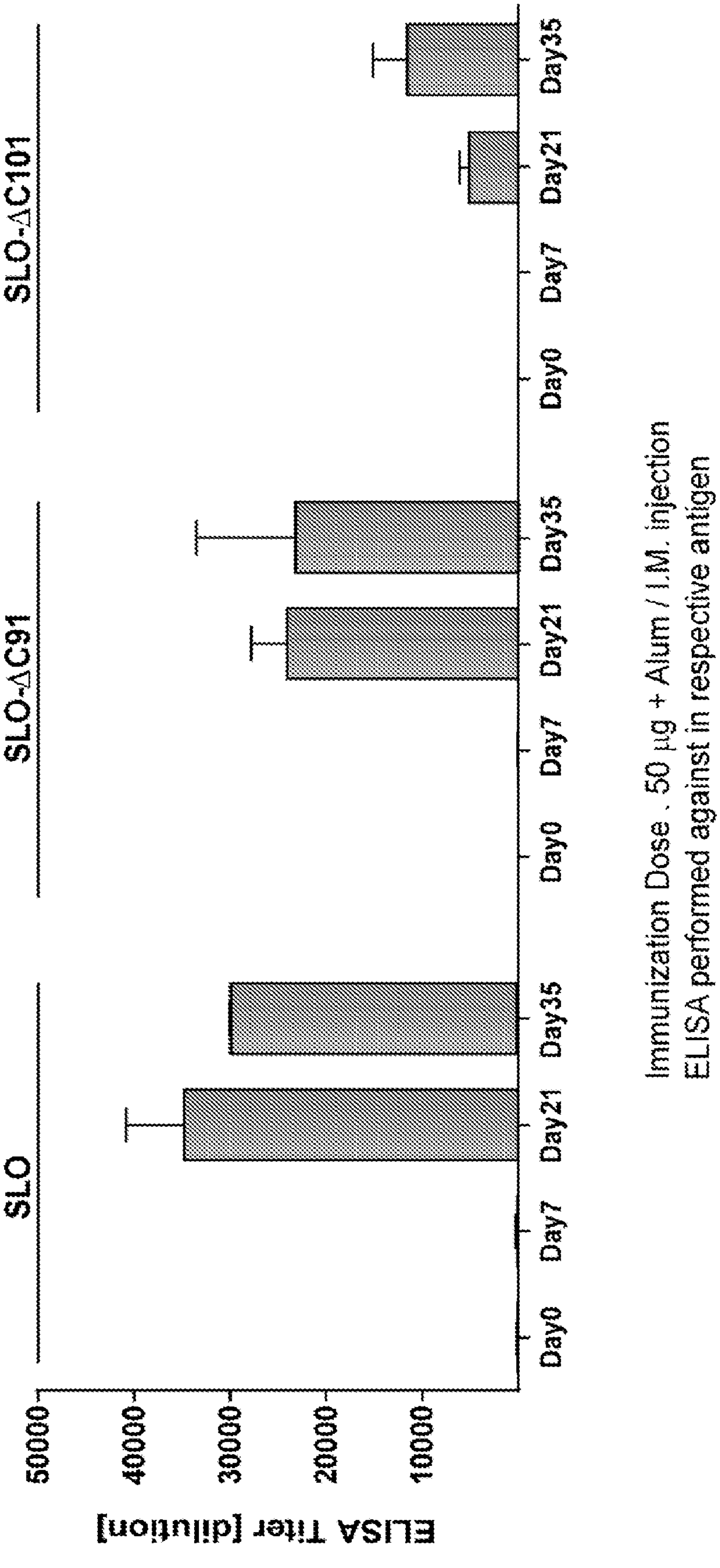
FIG. 20 shows the in vivo assessment of immunogenicity of select SLO fragments in rabbits.

Generation of immunized rabbit serum: Rabbits were intramuscularly immunized with alum+50 μg of SLO, SLO ΔC91, or SLO ΔC101 through protocols similar to those described above. Animals were bled, and an ELISA titer against each respective antigen was performed for sera on days 0, 7, 21, and 35. FIG. 20 shows the ELISA titer for each of the three SLO variants.

Figure 21:
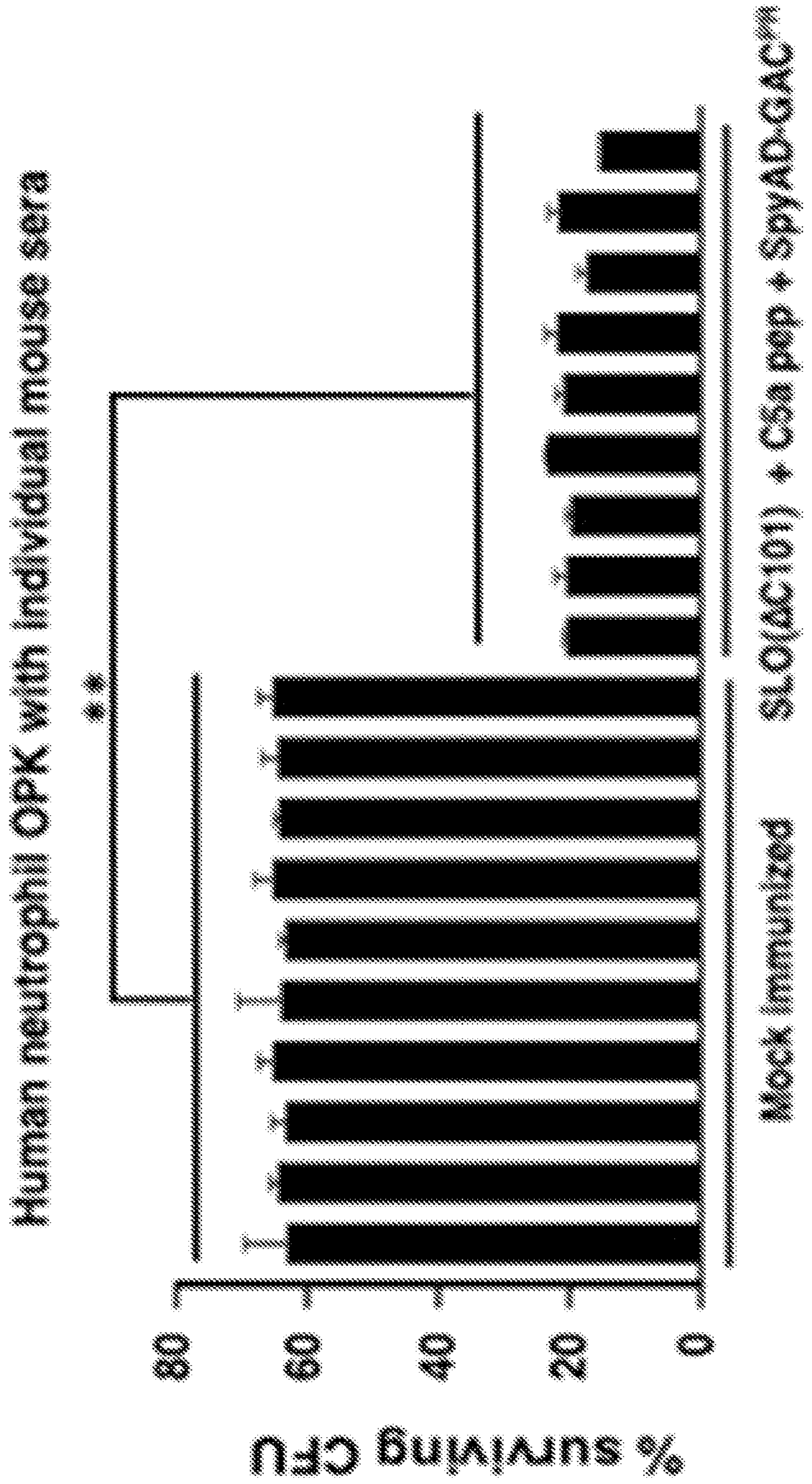
FIG. 21 shows the use of serum from mock and peptide combination-immunized mice to opsonize GAS in an OPK assay.
Figure 22A:
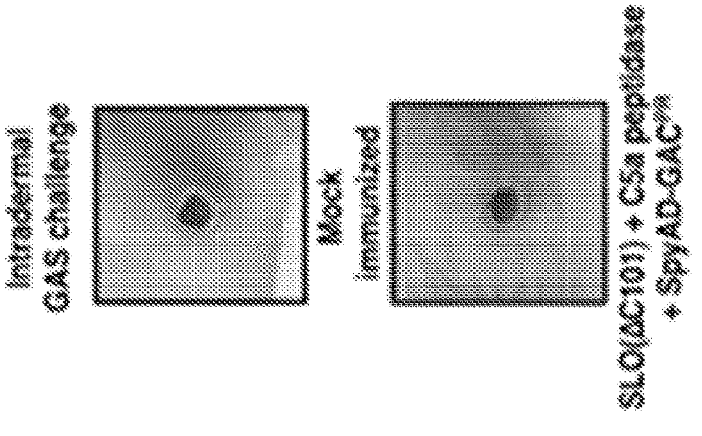
FIG. 22A, FIG. 22B, and FIG. 22C show the results of an intradermal challenge (with M1 89155 GAS) of wild-type CD-1 mice immunized with mock or a peptide combination, including lesion size and GAS burden data.
Figure 22B:
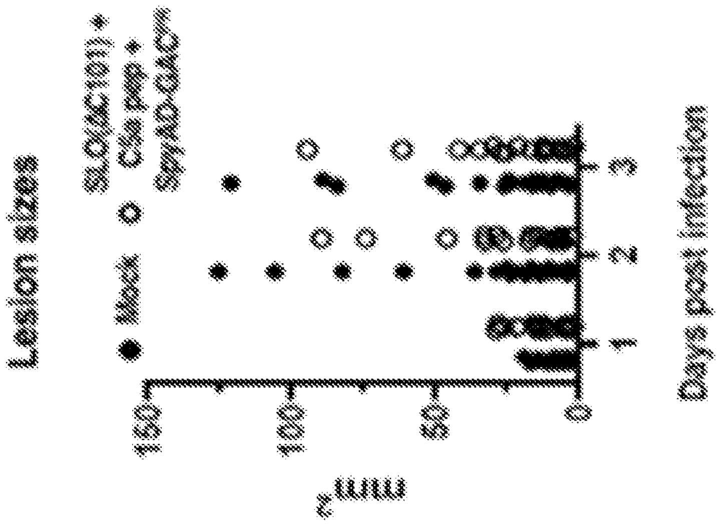
Figure 22C:
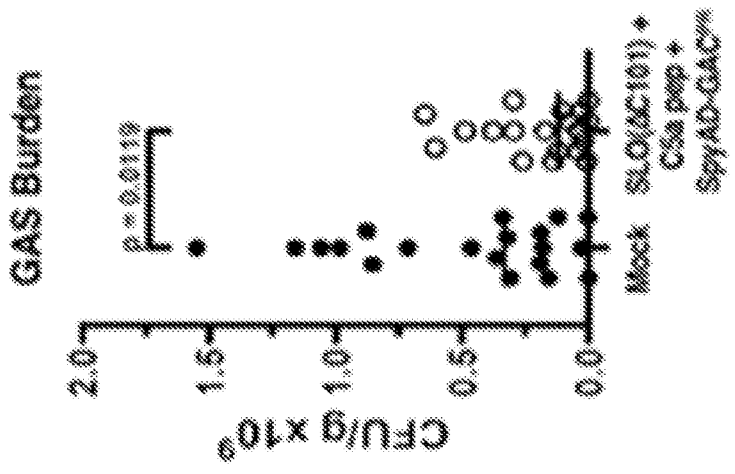

Immunization with a multivalent glycoconjugate vaccine provides significant protection against systemic and intradermal GAS challenge: CD-1 mice were actively immunized with intramuscular injections of antigens at days 0, 14, and 28 to examine the contribution of enhanced bacterial clearance to the strong protective efficacy of a 3 component/4 GAS antigen formulation of SpyAD-GAC+SLO(ΔC101)+C5a peptidase. Mouse sera were collected from 9 immunized (and 10 mock immunized) animals at day 42 following the challenge, and the efficacy of these antisera tested for promoting ex vivo OPK killing of M1 GAS by freshly isolated human neutrophils (FIG. 21). When GAS were opsonized with post-immune SpyAD-GACPR290+SLO (ΔC101)+C5a peptidase mouse antisera, ~20% of the original inoculum of M1 GAS was recovered following neutrophil exposure, compared to ~60% CFU recovery in control studies in 292 which GAS were opsonized with mock immune mouse sera (FIG. 21, $P<0.01$). Also, mice immunized with SpyAD-GACPR+SLO(ΔC101)+C5a peptidase or mock (PBS and adjuvant alone) control were challenged using intradermal M1 GAS infection. The size of necrotic lesions generated by the resulting acute inflammatory response did not differ significantly between the two groups (FIGS. 22A and 22B), but the recovered bacterial CFU/gm was reduced more than two-fold in the debrided tissue at the site of infection in the SpyAD-GACPR+SLO(ΔC101)+C5a peptidase immunized group (FIG. 22C, $P=0.0012$).

Figure 23:
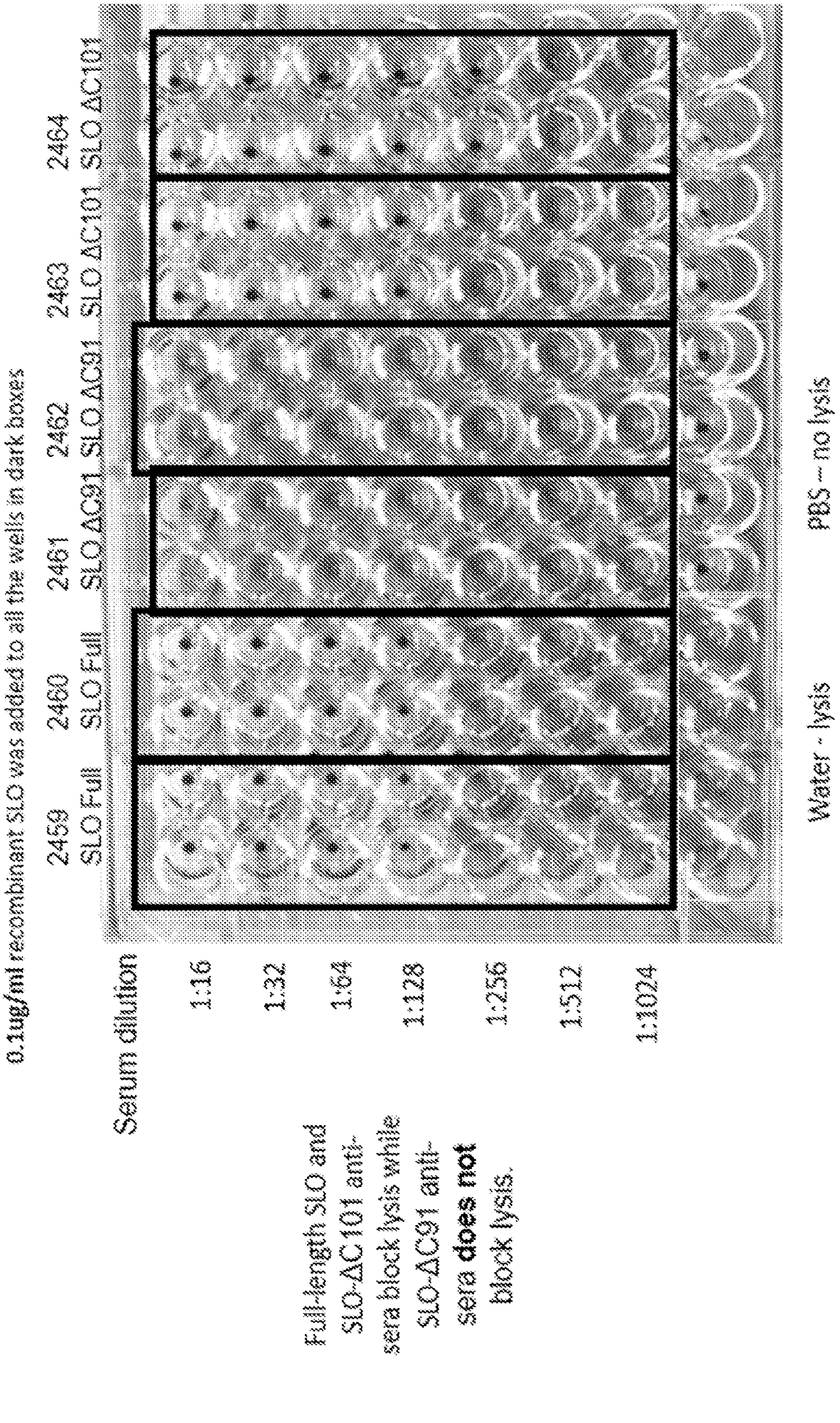
FIG. 23 shows the results of a red blood cell hemolysis assay to assess the presence of functional antibody against SLO variants.

Red blood cell hemolysis assay to assess the presence of functional antibodies against SLO variants: Antisera against SLO truncated variants were tested for their ability to block hemolytic activity of the corresponding SLO when added to red blood cells. FIG. 23 shows the results when 0.1 μg/mL of recombinant SLO was added to wells with red blood cells and antisera. Full-length SLO and SLO(ΔC101) anti-sera block cell lysis, while SLO (ΔC91) anti-sera does not block lysis.

Figure 24A:
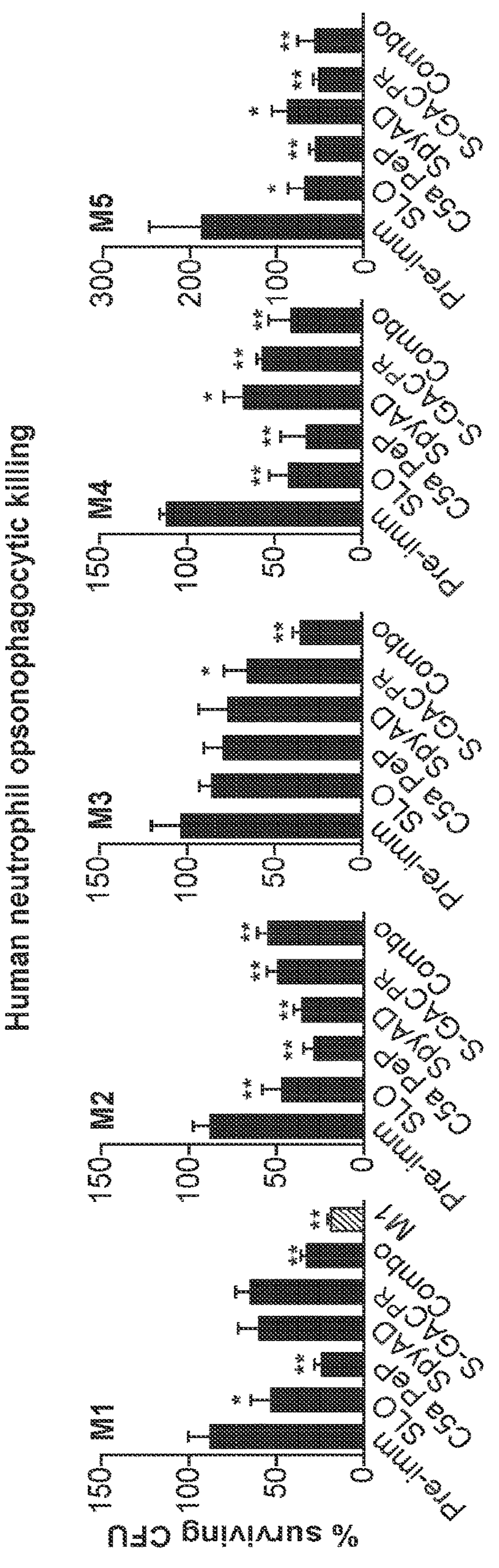
FIG. 24A, FIG. 24B, and FIG. 24C show the opsonophagocytic killing of GAS of different human neutrophil serotypes in the presence of immune serum from immunized rabbits, the blocking of lysis by antisera, and the oxidative burst capacity of human neutrophils exposed to GAS supernatants containing SLO.
Figure 24B:
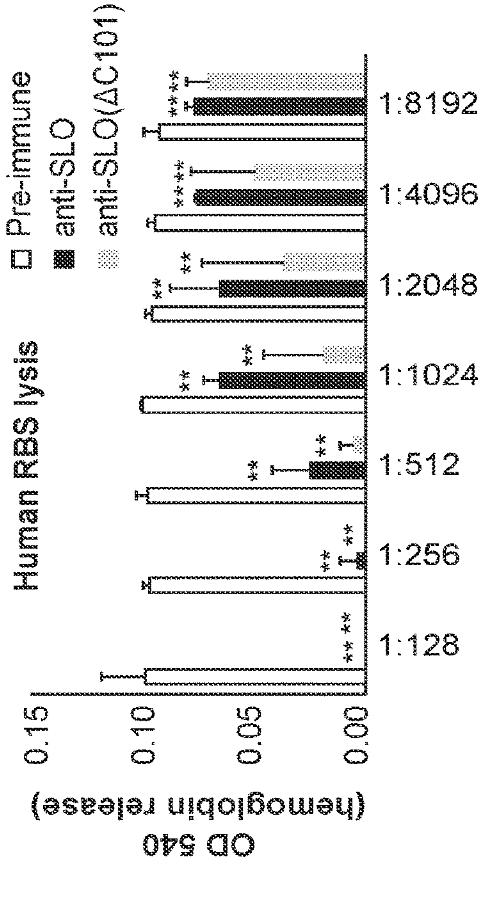
Figure 24C:
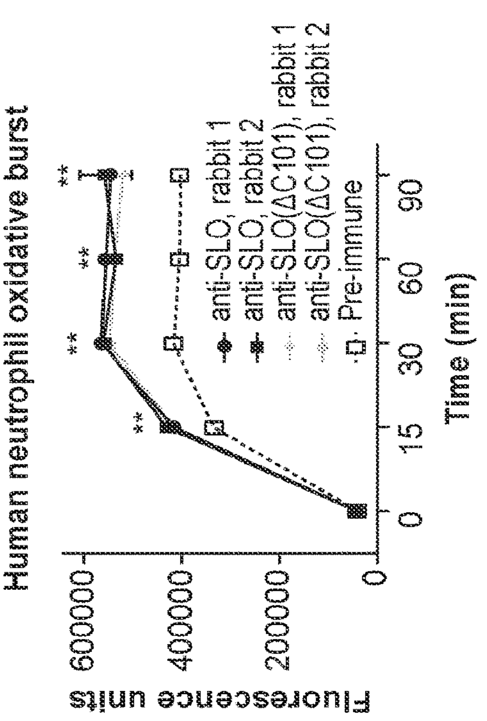

Evaluation of vaccine antisera in GAS opsonophagocytic killing and blocking SLO activity: The ability of the rabbit antisera raised against the GAS vaccine antigens (SLO, C5a peptidase, SpyAD and SpyAD-GAC) to promote human neutrophil opsonophagocytic killing (OPK) was evaluated using GAS strains of five different M protein serotypes (M1-M5). This assay was performed with 30 min pre-opsonization with the respective heat-inactivated antisera or pre-immune sera control, then 30 min exposure to freshly isolated human neutrophils at multiplicity of infection (MOI)=0.1 bacteria per neutrophil in the presence of 2% baby rabbit complement. All antisera induced a statistically significant increase in short-term OPK of GAS (FIG. 24A,). The assay uses a 100 to 1,000-fold greater GAS inoculum than published OPK assays employing the human promyelocytic leukemia HL-60 cell line at MOI=0.00140 or MOI=0.000141, to more accurately recapitulate the immunization target of supporting primary human innate immune cell function. Antisera raised against the SpyAD protein and SpyAD-GAC performed similarly. Moreover, a combination antiserum, composed of one-third of each antiserum raised against SLO, C5a peptidase, and SpyAD-GAC to maintain a consistent total serum concentration, performed similarly or better than the individual components, indicating no cross-253 interference in their OPK functions. As SLO is a secreted cytotoxin not anchored to the GAS surface, its contribution to enhanced neutrophil killing is accrued not from increased phagocytic uptake, but rather reducing SLO-mediated membrane damage and impairment of neutrophil antimicrobial functions. The anti-SLO rabbit immune serum, whether elicited by the SLO or SLO(ΔC101) antigens, significantly inhibited hemolytic activity of purified SLO against human red blood cells up to a dilution of 1:2,048 (FIG. 24B). Furthermore, anti-SLO or anti-SLO (ΔC101) immune serum equally preserved neutrophil oxidative burst function (superoxide generation) against GAS supernatant (SLO)-mediated suppression (FIG. 24C).

Figure 25A:
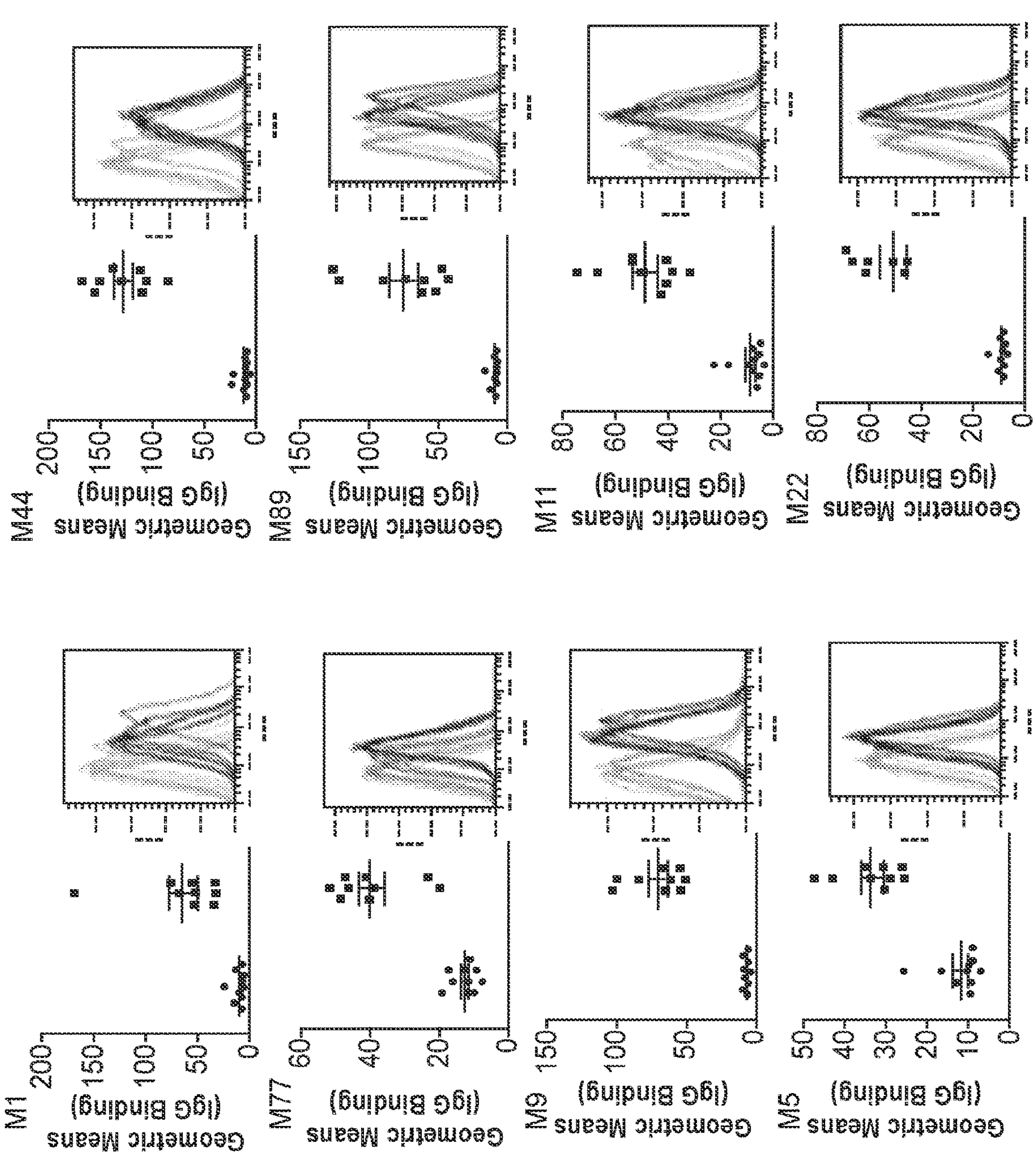
FIG. 25A and FIG. 25B shows differential IgG binding of immune sera to additional GAS serotype surface antigens.
Figure 25B:
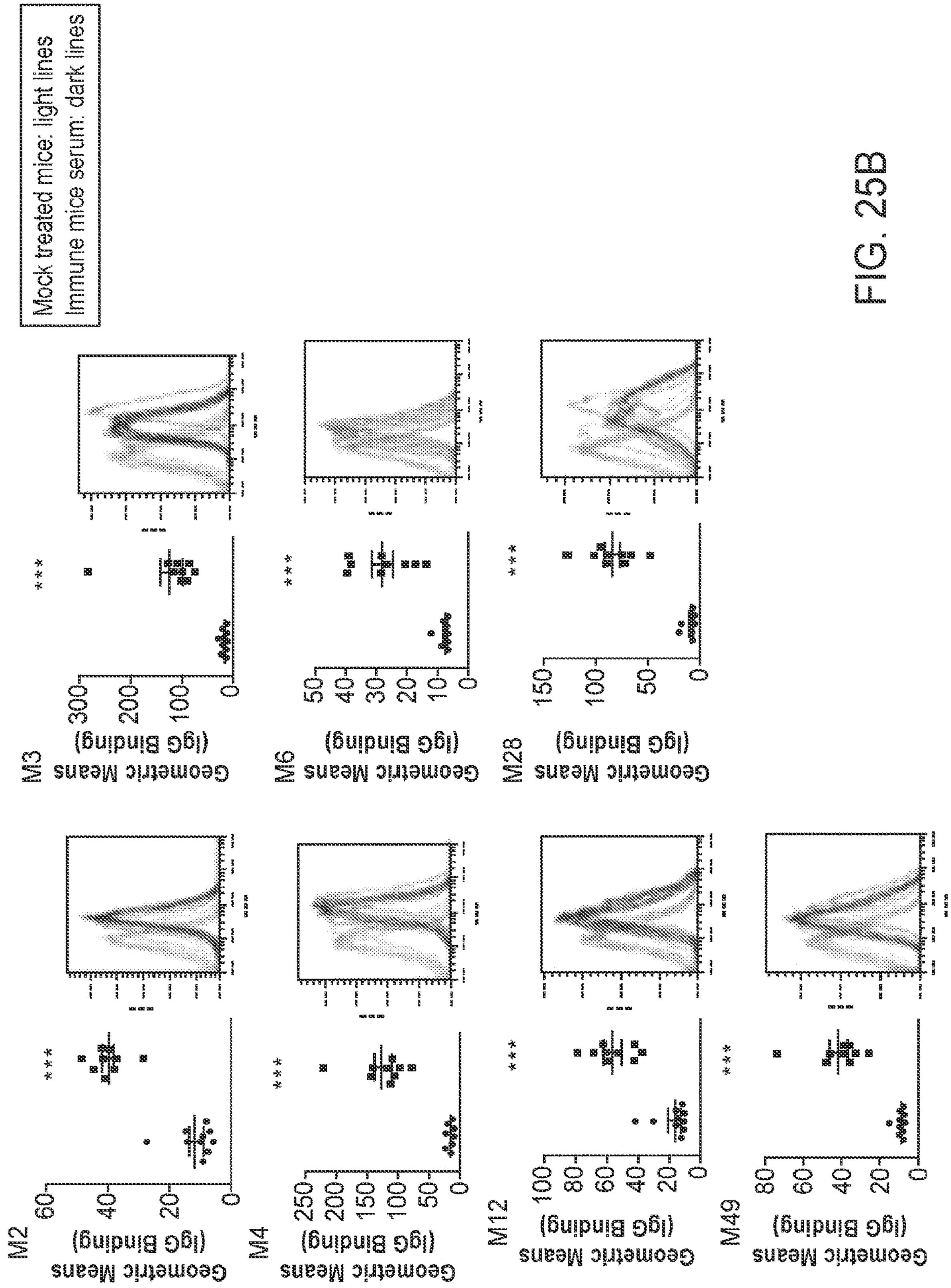

Additional serotypes were tested in an IgG binding assay run similarly to those methods described above. Mouse sera were collected from 9 immunized (and 10 mock immunized) animals on day 42 following the three dose immunization (intramuscular injections of antigens on days 0, 14 and 28), and the efficacy of these antisera tested for IgG binding to live GAS strains via flow cytometry. Serum was collected from female CD-1 mice that were immunized with 3 doses of either mock or combination SpyAD-GACP R+SLO (ΔC101)+C5a peptidase. FIGS. 25A and 25B show the fluorescent intensities of murine IgG from mock antisera (light histograms) or multivalent combination antisera (dark histograms) bound to GAS surface antigens of multiple serotypes as quantified via flow cytometry. Mean fluorescence intensities are summarized in column scatter plots, with each point representing individual mouse serum (circles are mock treatment mice, and square are treatment group mice). Methicillin-resistant *Staphylococcus aureus* USA300 was added as a control to show GAS-specificity of IgG binding.

Figure 26:
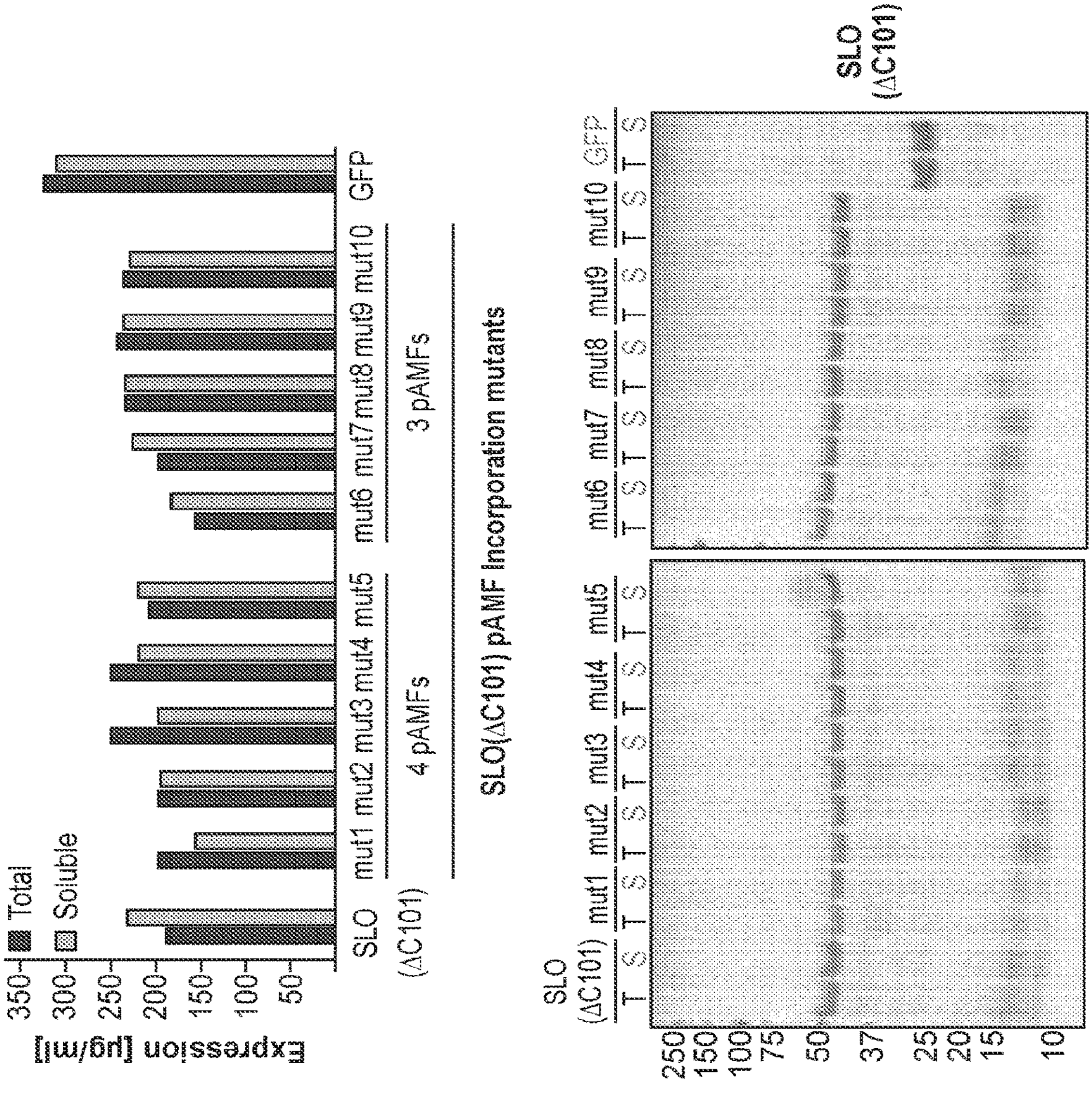
FIG. 26 shows expression of 10 pAMF-containing SLO polypeptide variants.
Figure 27A:
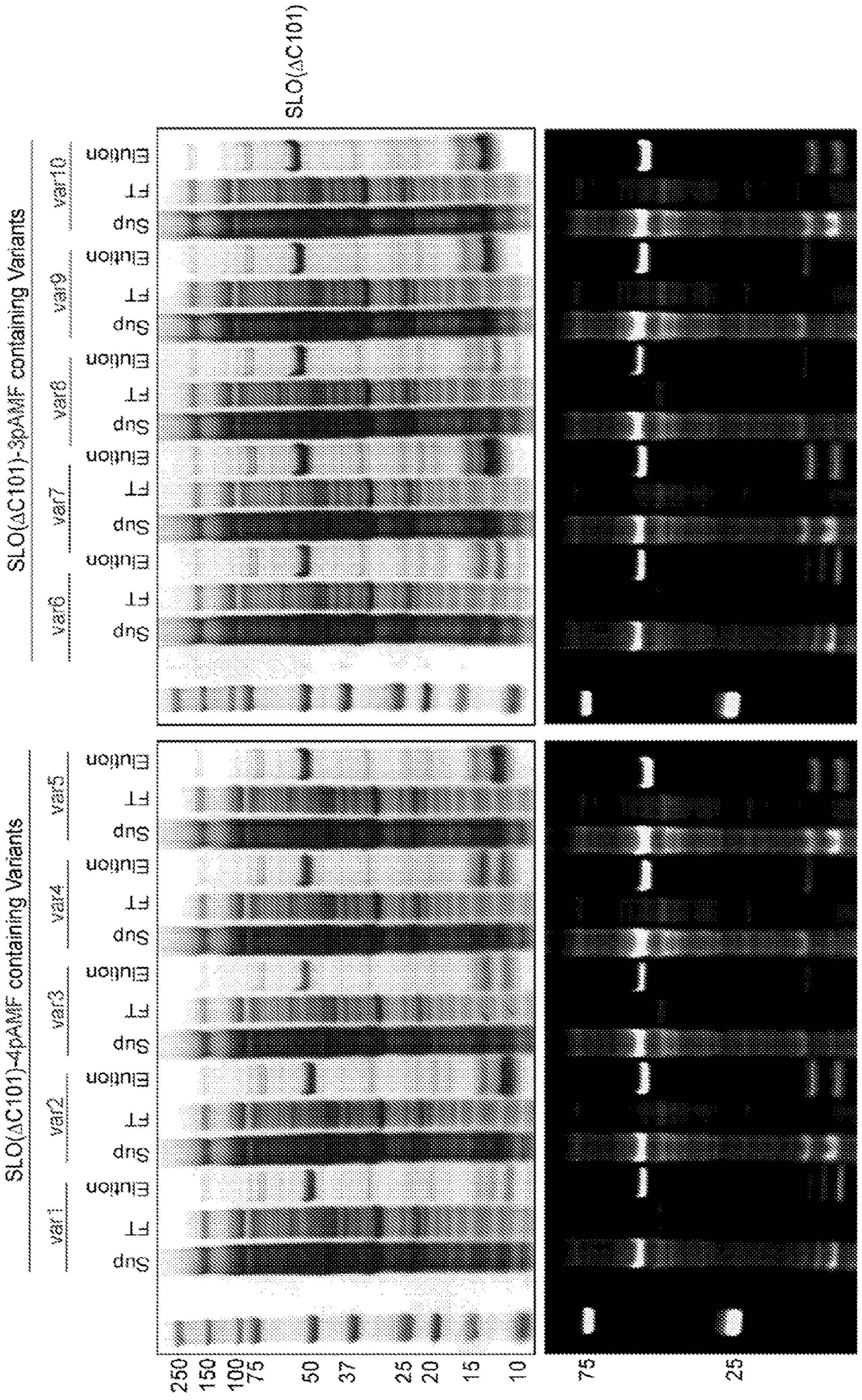
FIGS. 27A and 27B shows SDS-PAGE analysis for SLO variants during two steps of purification.
Figure 27B:
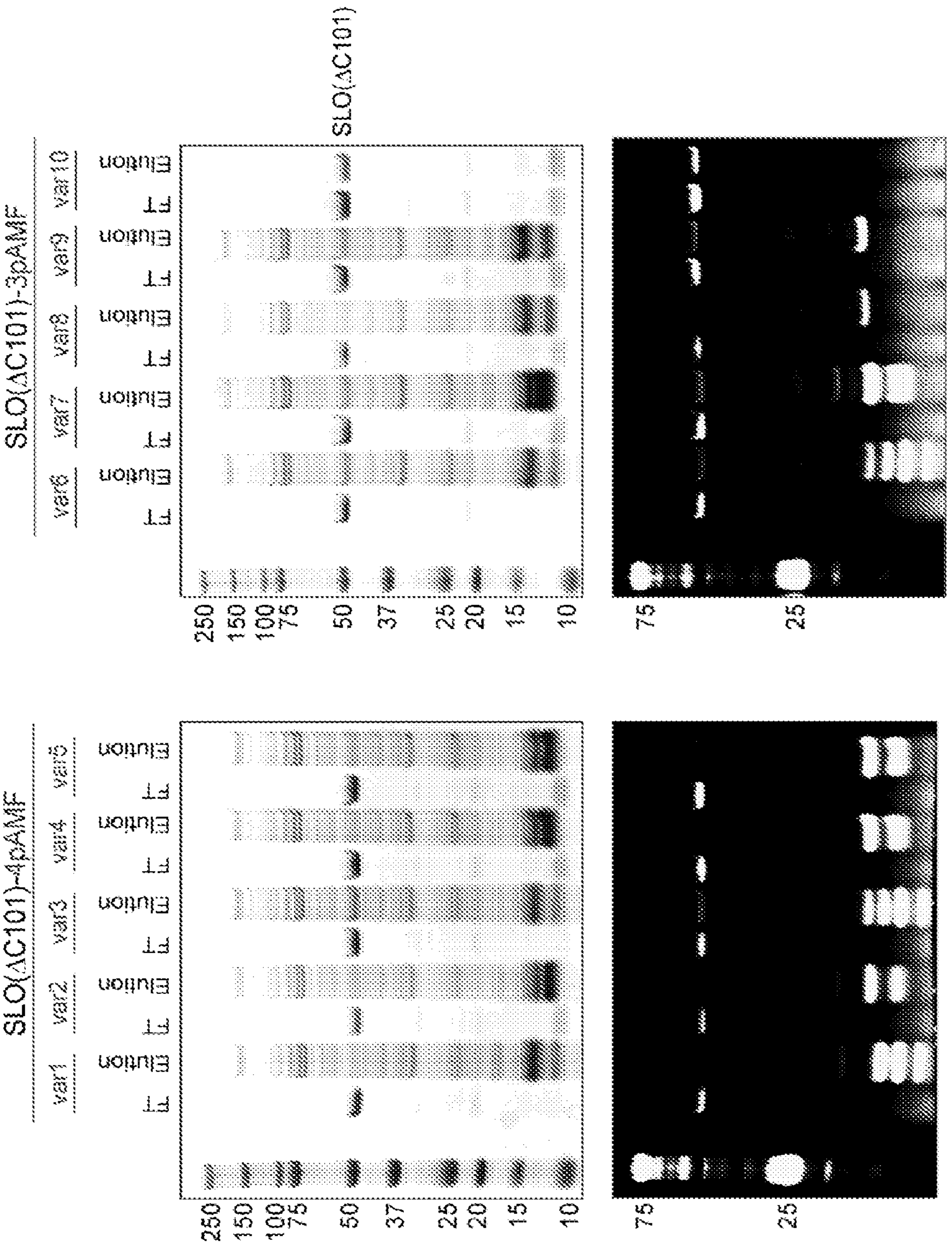

Example 17: Truncated SLO(ΔC101) Polypeptides with 3 or 4 nnAAs were Expressed and Conjugated Truncated SLO(ΔC101) variants containing nnAAs were expressed, for instance, according to the above methods. The variants contain 3 or 4 pAMF residues, corresponding to SEQ ID NO: 55 to SEQ ID NO: 64. SEQ ID NO: 54 contains all of the nnAA-containing residues. FIG. 26 shows the expression levels of these 10 variants, in both total and soluble protein concentration, with their corresponding gels. Purification proceeded as described previously. In short, The CFPS was harvested, spun down and filtered before loading onto a pre-equilibrated hisTRAP excel 1 ml column at 0.75 ml/min and eluted in a single step of 250 mM imidazole in a 6 ml final volume. 5 ul of each step fraction was analyzed using SDS-PAGE. FIG. 27A shows the gels of the variants after initial purification by hisTRAP. The hisTRAP elution fractions were then diluted 3× in 50 mM Tris pH8 for bring the final salt concentration to 50 mM NaCl before loading onto an AEX column. Both FT and elution fractions were analyzed using the SDS-PAGE analysis to detect presence of each of the variants. FIG. 27B shows gels of the variants after the second purification step. Table 11 shows the final concentration of the expressed variants after recovery from 2-2.5 mL of solution.

TABLE 11

Final variant concentrations after purification

| Protein name | Concentration (mg/ml) |
|---|---|
| SLO(ΔC101)-var1 | 0.8 |
| SLO(ΔC101)-var2 | 1.0 |
| SLO(ΔC101)-var3 | 0.6 |
| SLO(ΔC101)-var4 | 1.0 |
| SLO(ΔC101)-var5 | 1.2 |
| SLO(ΔC101)-var6 | 2.7 |
| SLO(ΔC101)-var7 | 2.3 |
| SLO(ΔC101)-var8 | 1.0 |
| SLO(ΔC101)-var9 | 2.2 |
| SLO(ΔC101)-var10 | 1.6 |

Figure 29:
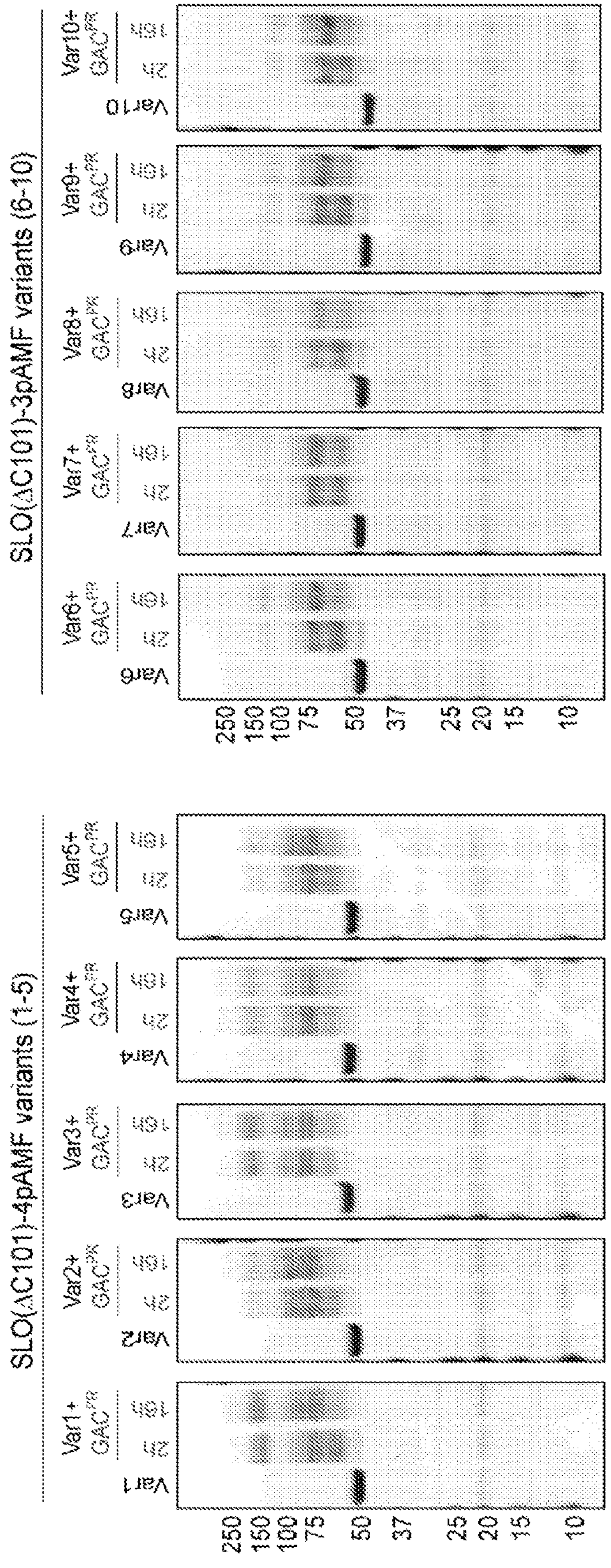
FIG. 29 shows SDS-PAGE analysis of 3- and 4-pAMF variant SLO variant conjugates.
Figure 30:
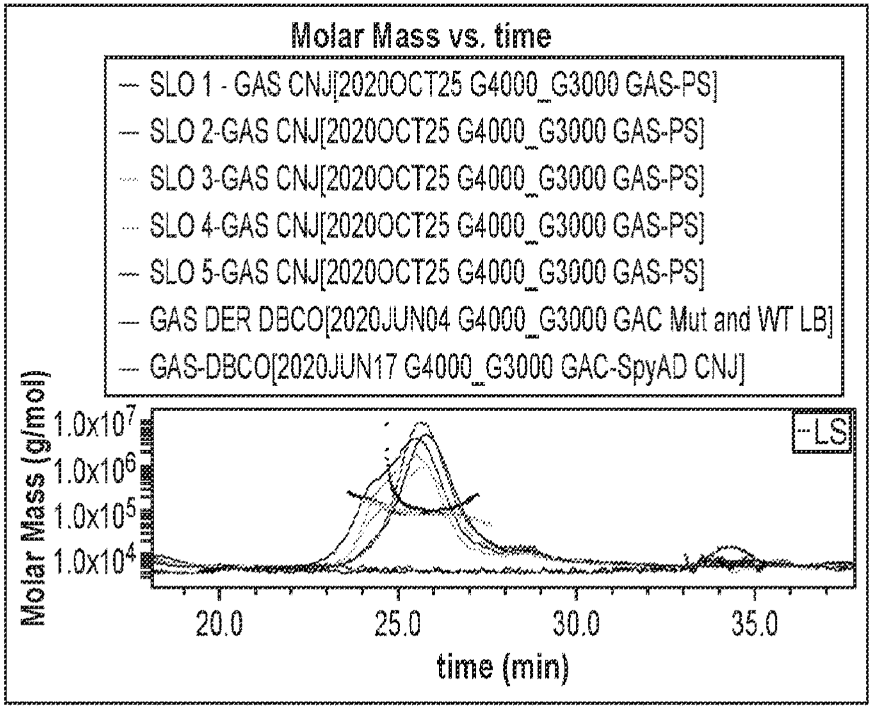
FIG. 30 shows SEC-MALS data for 3- and 4-pAMF variant SLO variant conjugates.
Figure 30:
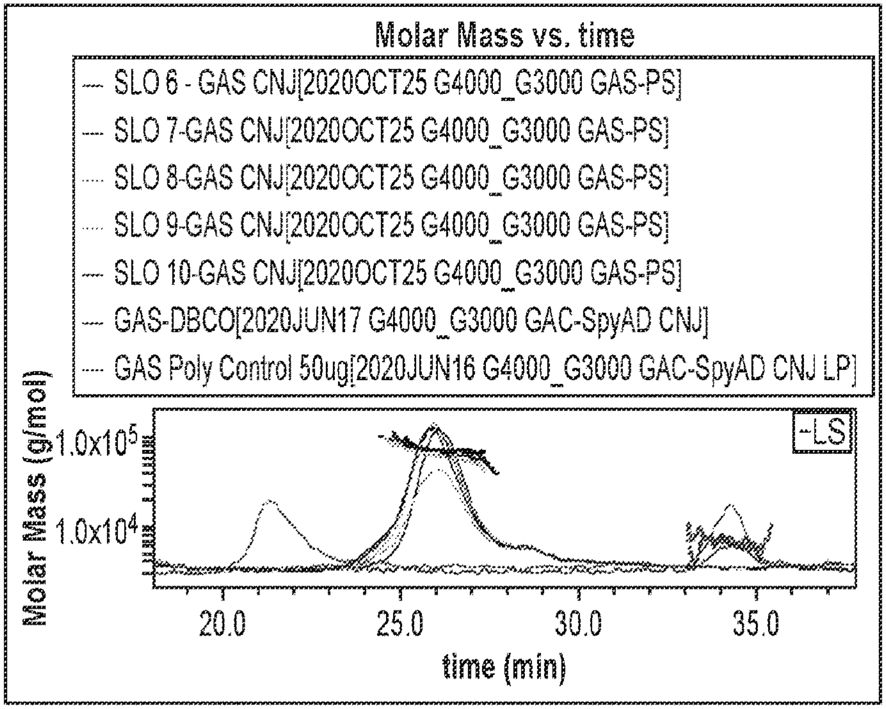

The SLO(ΔC101) variants were conjugated to DBCO-derivatized GAC as described above. FIG. 28 shows specific conjugation conditions for each variant. The conjugation reactions were analyzed by SDS page, as shown in FIG. 29. The first lane of each gel shows protein pre-conjugation. The final conjugate sizes were determined by SEC-MALS, the results of which are shown in FIG. 30.

Example 18: Truncated SLO(ΔC101) Polypeptides with 3 or 4 nnAAs were Assessed for their Immunogenicity in Murine Models and for their Hemolytic Titer The 3- and 4-pAMF SLO(ΔC101) variants, and their polysaccharide conjugates, of Example 17 are assessed in murine models by methods as described above in Example 9. Mice are immunized on days 0, 7, and 14, followed by a terminal bleed on day 21 post-sacrifice.

Figure 31A:
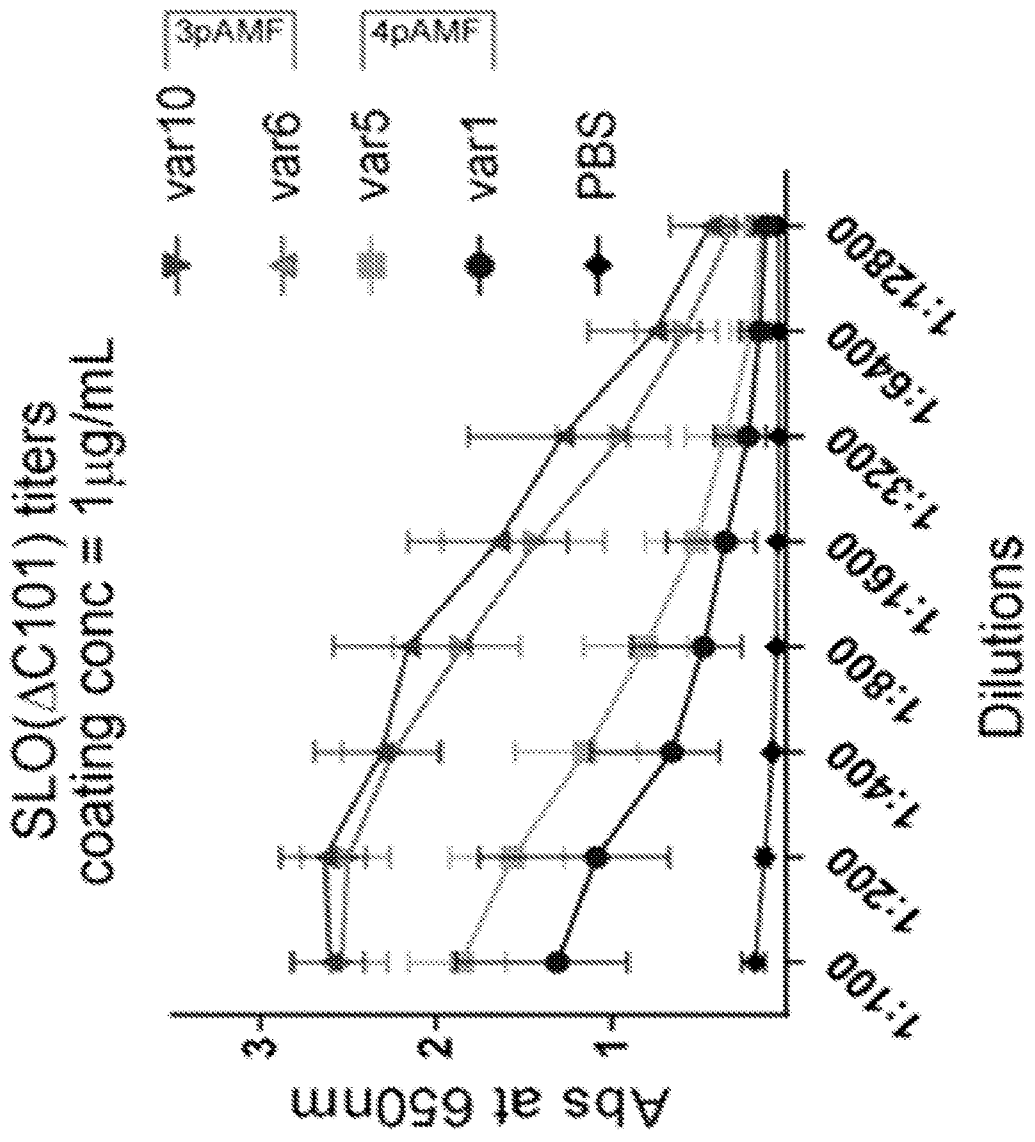
FIG. 31A and FIG. 31B show the antibody titers of mice post-immunization using conjugates made with select SLO (ΔC101) variants as carrier proteins, and the results of a hemolysis assay using anti-sera generated from mice vaccinated with conjugates made with those same variants.
Figure 31B:
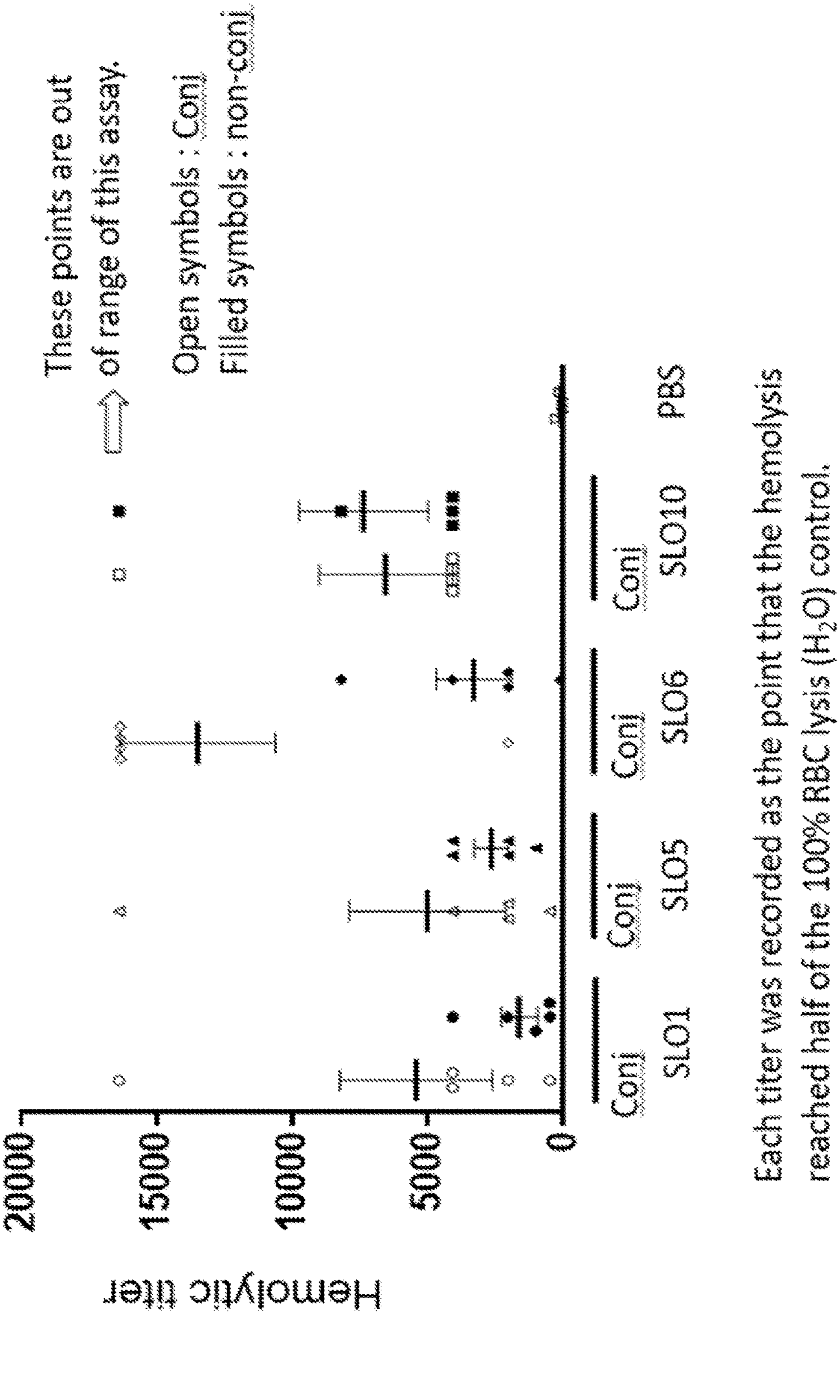
Figure 31C:
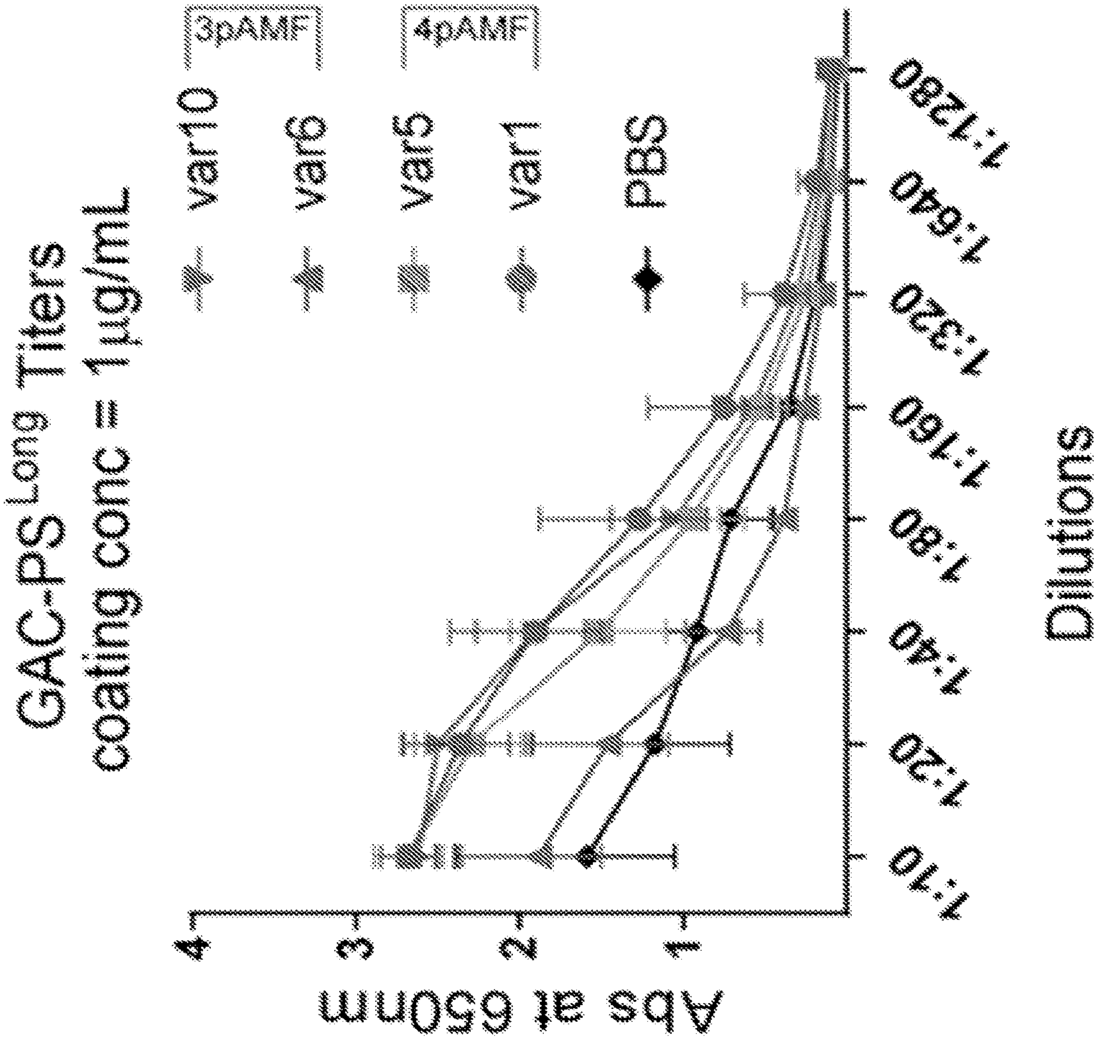
FIG. 31C shows the antibody titers of mice post-immunization using conjugates made with select SLO(ΔC101) variants, and using long polysaccharide as the coating antigen in the ELISA.

5 μg each of the polysaccharide conjugates of pAMF-substituted SLO(ΔC101)-var1, SLO(ΔC101)-var5, SLO (ΔC101)-var6, and SLO(ΔC101)-var10 of Example 17 (corresponding to SEQ ID NO: 55, 59, 60, and 64) were used to immunize mice. The antibody titers against SLO(ΔC101) measured after the terminal bleed are shown in FIG. 31A. The same variants and their GAC conjugates were also evaluated in a hemolysis assay according to the protocols of Example 16. The results are shown in FIG. 31B. FIG. 31C also shows antibody titers measured after the terminal bleed, however this ELISA utilized a long polysaccharide (produced by the methods of Example 19) as the coating antigen, rather than SLO(ΔC101). Together, these data show that the conjugates of pAMF-substituted variants SLO(ΔC101)-var1, SLO(ΔC101)-var5, SLO(ΔC101)-var6, and SLO (ΔC101)-var10 produce antibodies against both the PS and peptide components, individually.

Example 19: Expression, Purification, and Conjugation of Higher Molecular Weight (Long) Polysaccharides Experiments were performed to extract and purify GAS polysaccharides from GAS bacterial cultures.

Base Hydrolysis: A prepared GAS cell pellet was re-suspended in 50 mM NaCl solution. Using a serological pipette, 50 mL NaCl was added and vortexed until re-suspended. 10N sodium hydroxide & 1M sodium borohydride were added to reach a final concentration of 4N NaOH and 25 mM NaBH4. The re-suspended pellet was split between centrifuge bottles with a final target volume of 160 mL per 1 L fermentation volume. When splitting the solution, constant swirling was used to ensure homogeneity. Bottles were placed on a shaker in the pre-heated incubator at 65° C. for 2 hours. After incubation, the hydrolysis solution was centrifuged for 30 min at 14,000×g at 25° C. to pellet any cell debris, making sure to let the hydrolysis sample cool down to room temperature prior to centrifugation. The supernatant was collected once centrifugation stopped, in order not to disturb the pellet, and the supernatant was neutralized to pH 6.5±0.3. When neutralizing, the bottle was placed on a 4° C. ice bath, using 37% HCl to adjust pH, with 1M NaOH used for further adjustment if necessary. The sample is then incubated at 4° C. overnight.

Filtration: After incubation, a white precipitate forms. The solution was centrifuged for 30 min at 10,000×g. A bulky white pellet is formed, containing host cell proteins (HCPs). The clear supernatant was collected. The pH was adjusted to 3.0 using 37% HCl, and the solution was incubated for 1 hour at RT. Using a Clarisolve Filter μPod-40 MS, the sample was filtered. For example: at a pump flow rate of 23 mL/min, water was flushed through the filter until primed, and the valve was then opened and flushed with 120 mL volume, and equilibrated using 15 mM NaCl for a volume of 120 mL. The extract was run through the filter at the same pump flow rate of 23 mL/min, and the clear permeate coming from the filter was collected. The filter was washed with 60 mL of 15 mM NaCl, and flushed out the tubes and filter content. The filter was discarded. The sample pH was readjusted to 6.5±0.3. Tangential flow filtration (TFF-10 k) was then conducted to remove salts, concentrated (ultrafiltered), then buffer exchanged (diafiltered) in 10 mM NaCl.

Mutanolysin Treatment: The solution was prepared for mutanolysin treatment by adding 1M $MgCl_2$ to reach a final conc. of 1 mM $MgCl_2$, and 200 mM sodium phosphate (10×) to reach a final concentration of 20 mM sodium phosphate at pH 6.8. Mutanolysin solution (5000 IU/mL) to reach 120 IU/mL. The sample was incubated at 37° C. overnight with shaking.

Proteinase-K Treatment: The sample was then treated with Proteinase-K by adding Proteinase-K solution to achieve a final concentration of 40 IU/mL (Proteinase-K at 45 u/mg). The mixture was incubated at 50° C. overnight while mixing gently.

Precipitation and Filtration: To precipitate enzymes, nucleic acids and HCPs in the sample, CTAB in 20 mM sodium phosphate buffer at pH 6.8 was added, shaking for 1 hour at 30° C. The solutions used were all pre-warmed: the PS sample, 5% CTAB stock solution and 200 mM Na Phosphate pH 6.8. The PS solution was mixed (magnetic stir bar) while being heated, and the heated stir plate was set up with an internal thermometer in order to monitor temperature in the solution at all times. 200 mM sodium phosphate (pH 6.8) solution was added to the PS solution, to reach a final concentration of 20 mM sodium phosphate. 5% CTAB was added to the PS solution to reach a 1% CTAB concentration. The solution was allowed to mix for 1 hour. Using a 40 MS filter, a depth filtration is conducted over the precipitating solution. For example, the system was flushed with 200 mL MilliQ H20 at a pump flow rate of 23 mL/min, and once water started to come out from the vent, it was closed so the solution is forced to come out from the outlet (priming). The system was then flushed with 75 mL of a solution of 20 mM sodium phosophate (pH 6.8) and 15 mM NaCl. The sample was filtered at 23 mL/min, and flushed with 60 mL of 20 mM sodium phosphate (pH 6.8) and 15 mM NaCl solution at 20 mL/min. The permeate was collected until air bubbles eluted. The filter was discarded.

The PS solution and 274 mM KI was warmed to 30° C. Enough 274 mM KI was added to the mixing PS solution to achieve a final concentration of 27.4 mM KI. The mixture was incubated at 30° C. with mixing for 1 hour. The solution was centrifuged post incubation at 30° C., 10,000×g for 30 minutes. The supernatant was collected and the pellet was discarded, be cautious as the pellet breaks up easily. The supernatant was then vacuum filtered through a 0.45 μm filter.

The sample was first concentrated by TFF-10 k, followed by diafiltration with 9DVs of 350 mM NaCl and finally 2 DVs with MilliQ water. For example, the TFF system volume is around 35 mL, with pump flow set at 200 mL/min, and the diafiltration is conducted with 9 DV (50 mL) of buffer TMP: 7-8 psi The polysaccharide solution was then purified by hydrophobic interaction chromatography using HiPrep™ Butyl Fast Flow 16/10 pre-equilibrated with 3M sodium chloride and 50 mM sodium phosphate pH 6.8. Sodium chloride and phosphate buffer were added to the polysaccharide solution in order to reach 3M sodium chloride and 50 mM potassium phosphate (pH 6.8). The polysaccharide solution was passed over HIC resin and was operated in flow through mode. The resin is washed with the same equilibration buffer and both the flow-through and wash were collected for further processing.

A final TFF 10 kDa/3 kDa was conducted in order to remove high NaCl content in the PS sample by diafiltration against 9DV of 15 mM NaCl or WFI. The purified PS solution was then 0.22 μm filtered.

Figure 36A:
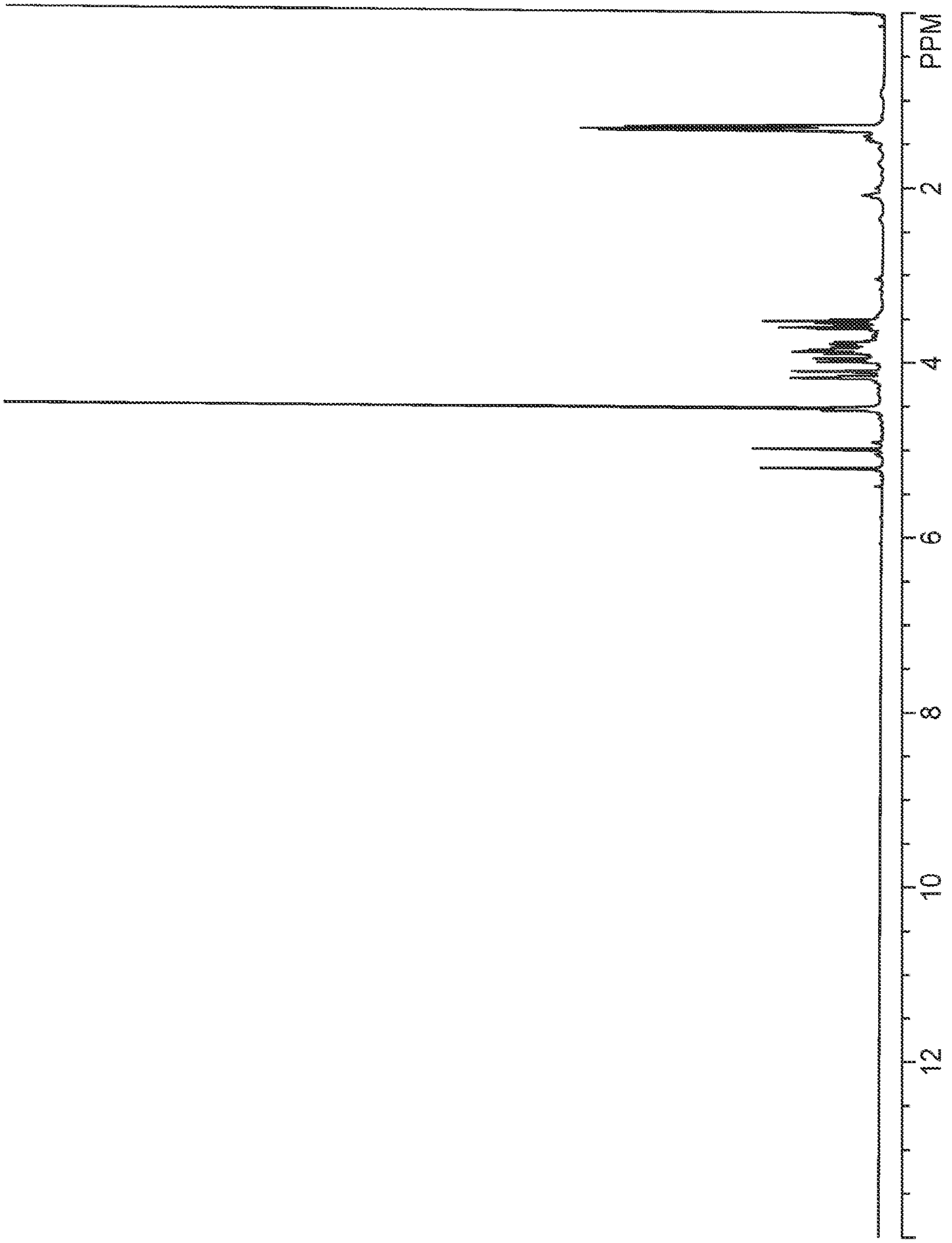
FIG. 36A, FIG. 36B, and FIG. 36C show NMR analysis of purified polysaccharide originating from a GAS bacterial strain expressing PS lacking GlcNAc.
Figure 36B:
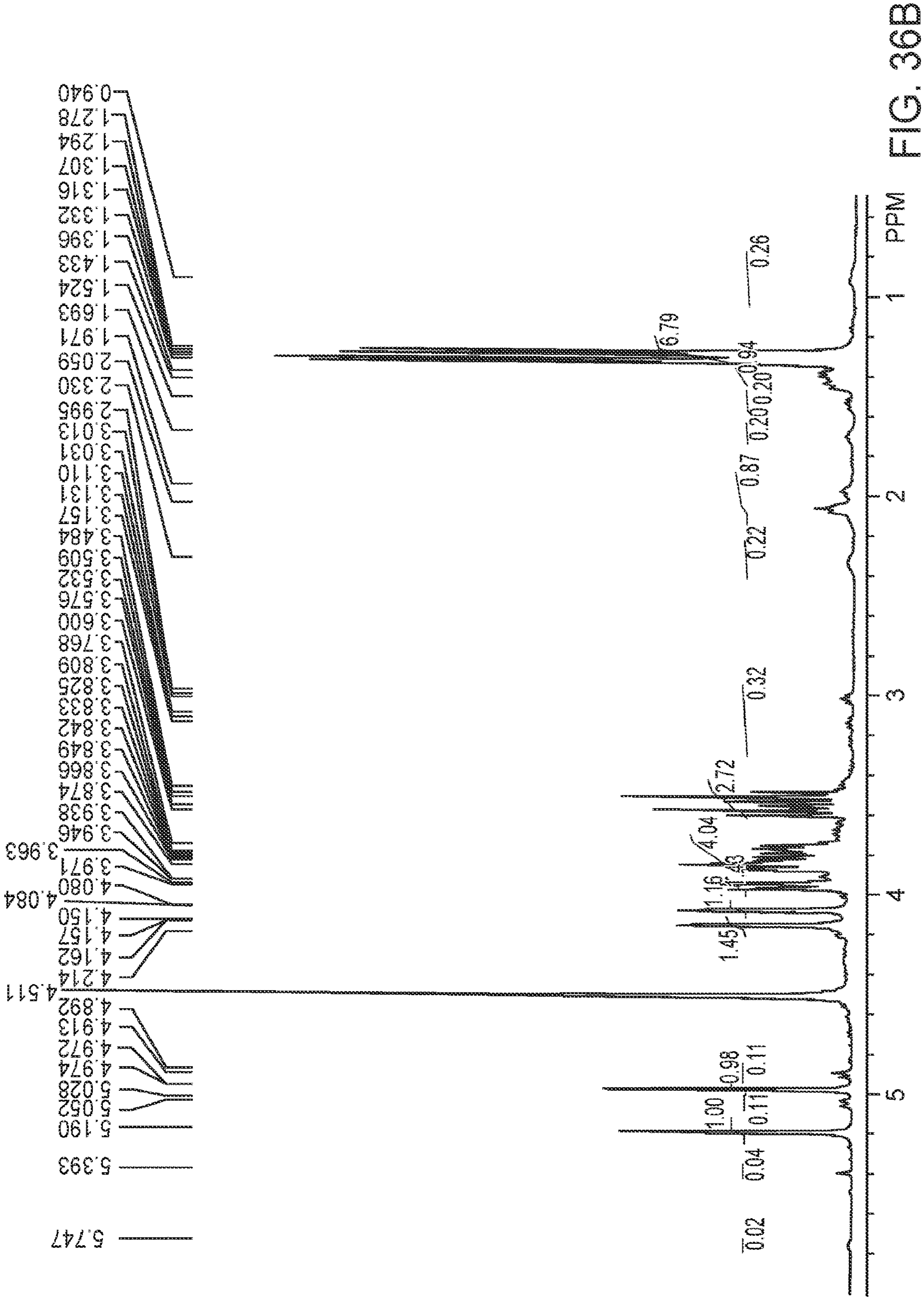
Figure 36C:
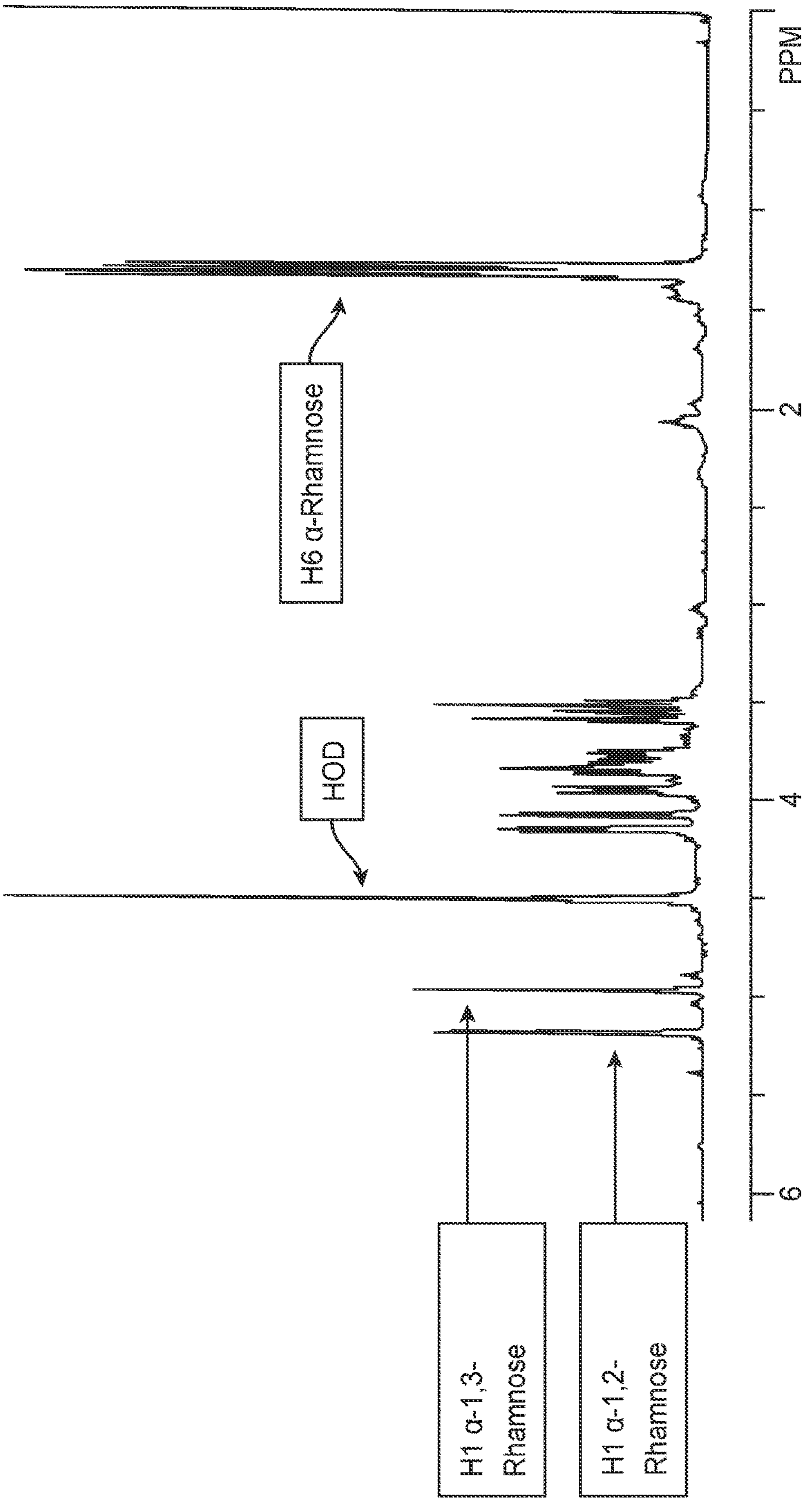
Figure 37:
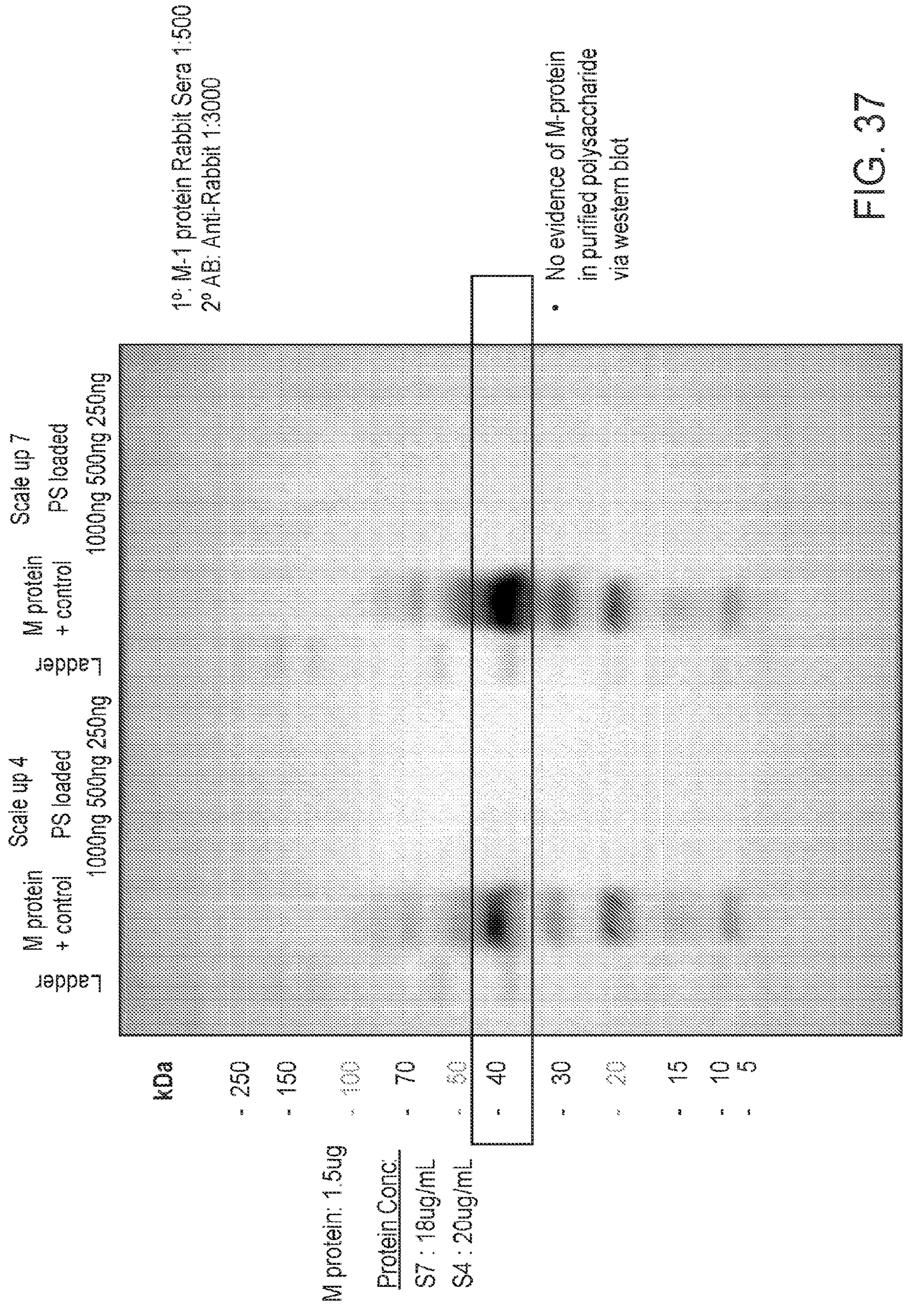
FIG. 37 shows a western blot demonstrating M-protein is removed from polysaccharide when purified as described in Example 19.

FIG. 36A, FIG. 36B, and FIG. 36C show NMR analysis of purified polysaccharide produced by Synthetic Example 1, originating from a GAS bacterial strain expressing PS lacking GlcNAc (see PCT/US2012/049604). The NMR confirms the presence of polyrhamnose and the absence of GlcNAc. For sample preparation, the purified polysaccharide solution was lyophilized and exchanged into D20 with TSP added as an internal standard. A proton NMR spectrum was obtained at 50° C. on a 400 MHz instrument, with signal averaging over 40 scans. 0.2 Hz of line broadening was applied. The purification protocol was also able to produce purified polysaccharide free of M-protein, as evidenced by the western blot of FIG. 37.

Figure 32:
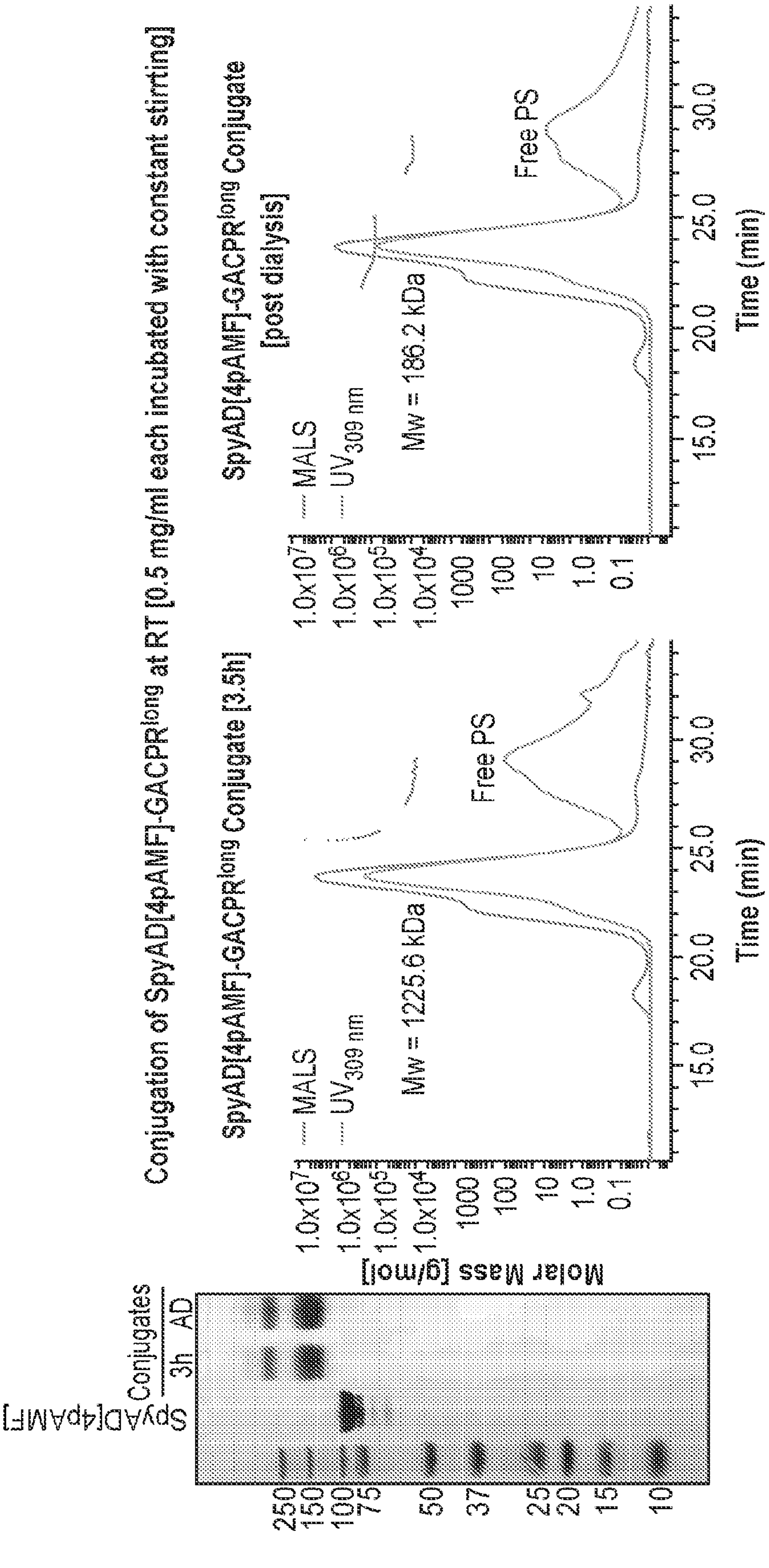
FIG. 32 shows SEC-MALS data for a conjugate of SpyAD[4pAMF] and long polysaccharide.

Derivitization and Conjugation of Long Polysaccharides: The higher-molecular weight (long) polysaccharides are derivatized with DBCO-PEG as previously described in the above methods (Example 4). The DBCO-derivatized PS is then conjugated to the carrier proteins described herein according to the methods of Example 4. For instance, SpyAD[4pAMF] (SEQ ID NO: 34) was conjugated to the long polysaccharide and analyzed after 3.5 hours and post-dialysis. The SEC-MALS analysis of these conjugates is shown in FIG. 32. After 3.5 hours, conjugates greater than 1 MDa were observed. Post-dialysis, the isolated conjugate size distribution showed a peak at approximately 186 kDa.

Figure 33A:
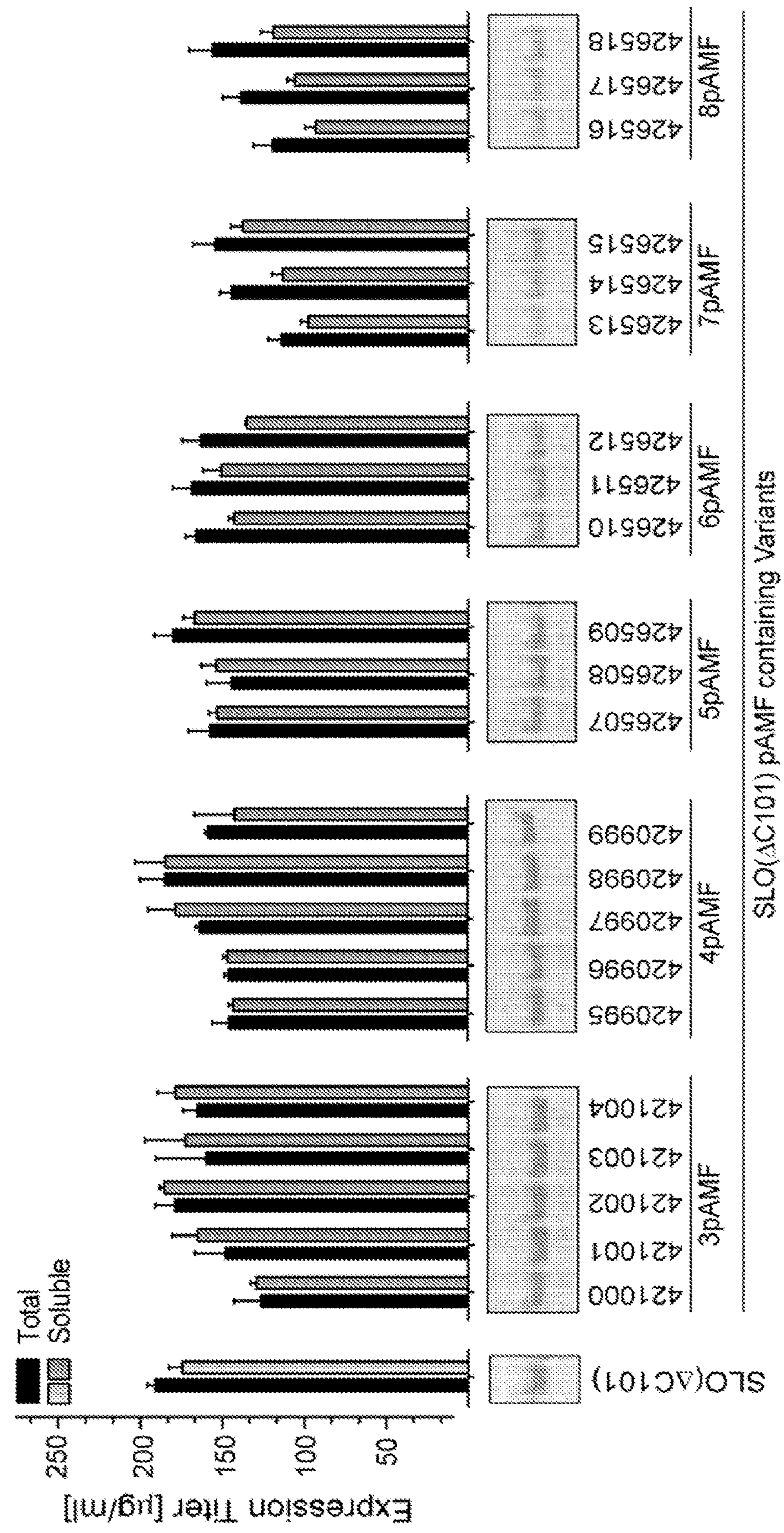
FIG. 33A and FIG. 33B show the expression levels of 22 SLO variants with 3-8 pAMF, and the corresponding gels for purified 5-8 pAMF containing variants.
Figure 33B:
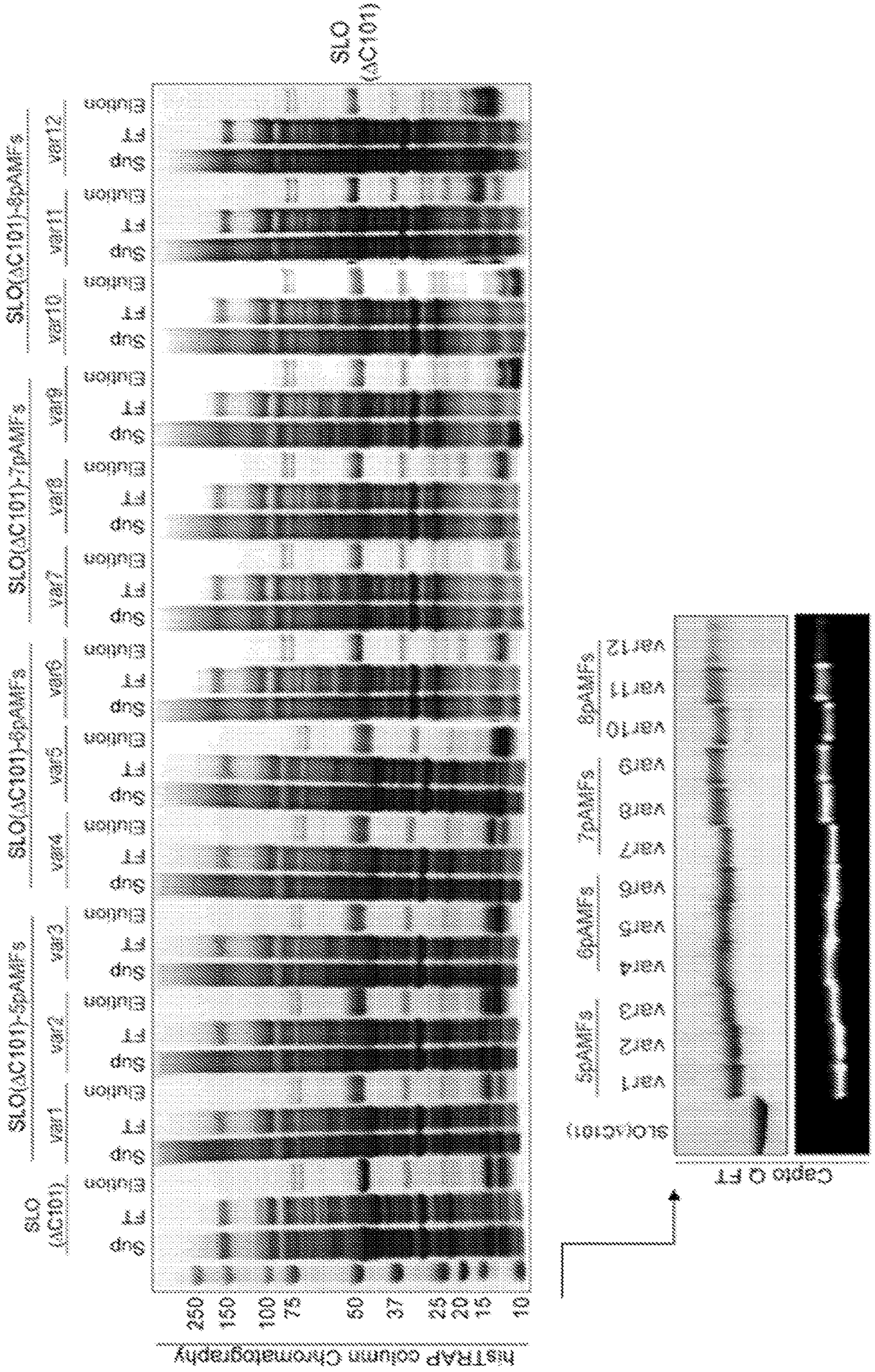

Example 20: Truncated SLO(ΔC101) Polypeptides with 5, 6, 7, or 8 nnAAs were Expressed, Purified, and Conjugated Truncated SLO(ΔC101) variants containing nnAAs are expressed, for instance, according to the above methods. The variants contain 5, 6, 7, or 8 pAMF residues, corresponding to SEQ ID NO: 65, SEQ ID NO: 66, SEQ ID NO: 67, SEQ ID NO: 68, SEQ ID NO: 69, SEQ ID NO: 70, SEQ ID NO:

71, SEQ ID NO: 72, SEQ ID NO: 73, SEQ ID NO: 74, SEQ ID NO: 75, and SEQ ID NO: 76. FIG. 33A shows the expression levels of these 12 pAMF variants (5pAMF-8pAMF), as well as for the variants of example 17, in both total and soluble protein concentration. FIG. 33B shows the corresponding gels for the expression (SEQ ID NOs: 65-76 correspond to var1-var12). Purification proceeded as described previously. In short, The CFPS was harvested, spun down and filtered before loading onto a pre-equilibrated hisTRAP excel 1 ml column at 0.75 ml/min and eluted in a single step of 250 mM imidazole in a 6 ml final volume. 5 μl of each step fraction was analyzed using SDS-PAGE safe blue staining. Thereafter, the elutions were 3× diluted and loaded onto the CaptoQ column for final purification and analyzed using Safe Blue staining and DBCO TAMRA labeling. The FT fractions were concentrated and stored at −80C in 200 μl aliquots.

Figure 34:
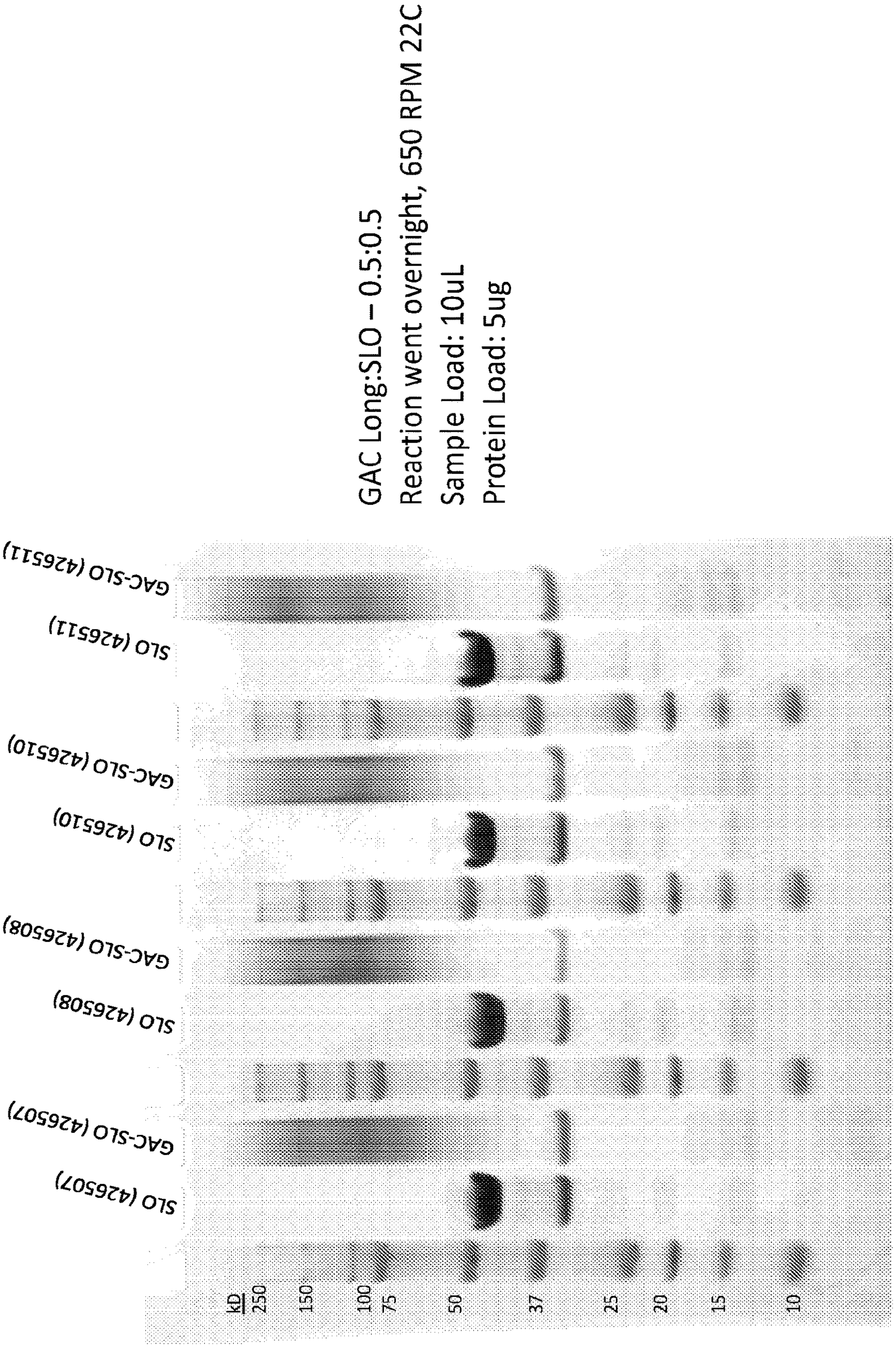
FIG. 34 shows SDS-PAGE analysis of 5- and 6-pAMF variant SLO conjugates with long GAC.

Conjugation of SLO (40101) polypeptides with 5, 6, 7, or 8 nnAAs: The polypeptides containing 5, 6, 7, or 8 nnAAs are conjugated to GAS polysaccharides using the methods described above, including in Example 4. In this way, the pAMF-containing SLO(ΔC101) variants of SEQ ID NO: 65, SEQ ID NO: 66, SEQ ID NO: 68, and SEQ ID NO: 69 were conjugated to long DBCO-derivatized GAC. The conjugation reactions were analyzed by SDS page, as shown in FIG. 34. The first lane for each variant shows the protein pre-conjugation.

Figure 35:
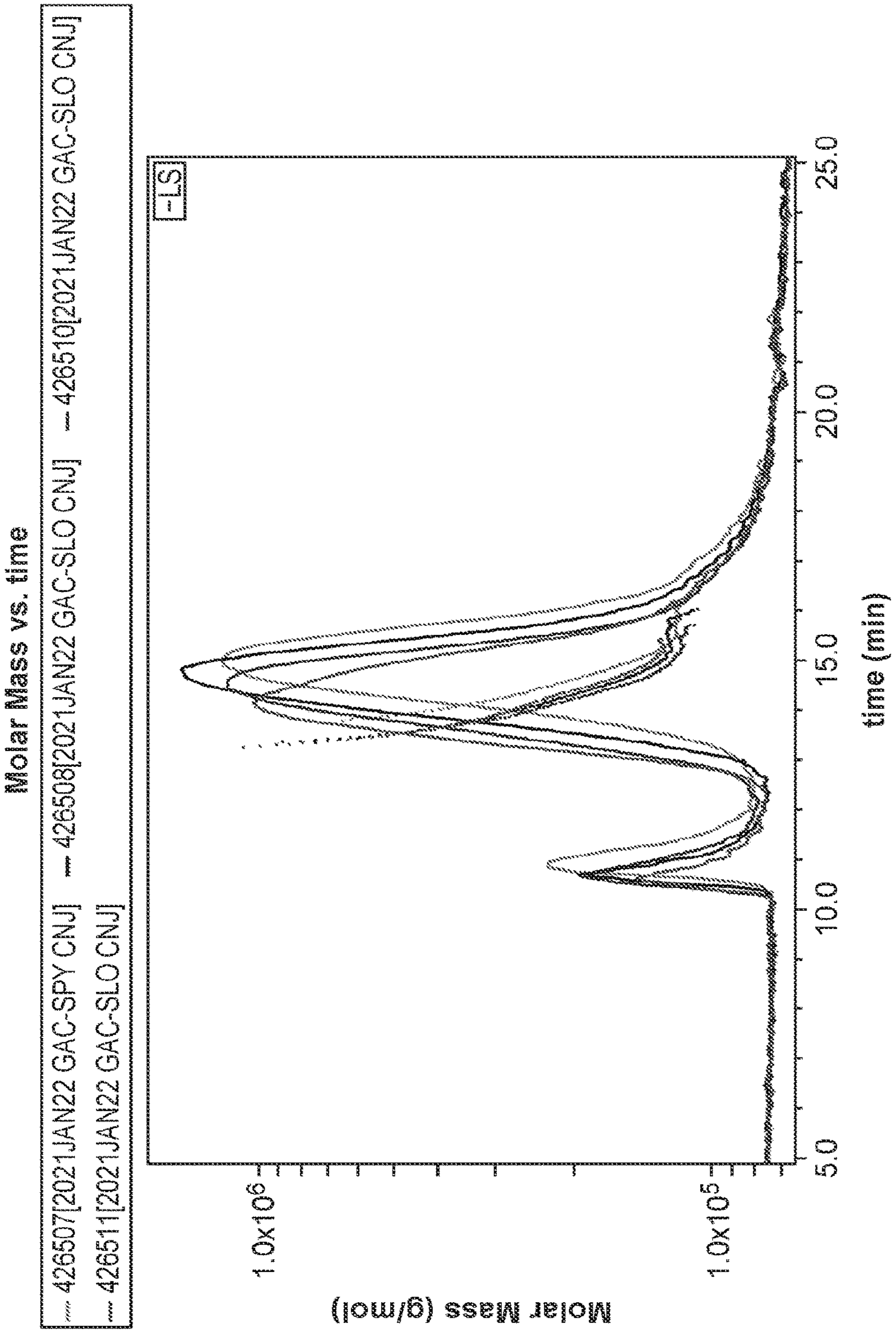
FIG. 35 shows SEC-MALS data for 5- and 6-pAMF variant SLO conjugates with long GAC.

The final conjugate sizes were determined by SEC-MALS, the results of which are shown in FIG. 35.

Sequence identifier descriptions

| Seq ID | Name/description | Amino acid sequence |
|---|---|---|
| 1 | C5a [90-1035 fragment] WT w/ leader | MHHHHHHGSGENLYFQGKTADTPVTSKATIRDLNDPSQVKTLQE<br>KAGKGAGTVVAVIDAGFDKNHEAWRLTDKTKARYQSKEDLEKAK<br>KEHGITYGEWVNDKVAYYHDYSKDGKTAVDQEHGTHVSGILSGN<br>APSETKEPYRLEGAMPEAQLLLMRVEIVNGLADYARNYAQAIRD<br>AVNLGAKVINMSFGNAALAYANLPDETKKAFDYAKSKGVSIVTS<br>AGNDSSFGGKTRLPLADHPDYGVVGTPAAADSTLTVASYSPDKQ<br>LTETATVKTADKQDKEMPVLSTNRFEPNKAYDYAYANRGMKEDD<br>FKDVKGKIALIERGDIDFKDKIANAKKAGAVGVLIYDNQDKGFP<br>IELPNVDQMPAAFISRKDGLLLKDNPKKTITFNATPKVLPTASG<br>TKLSRFSSWGLTADGNIKPDIAAPGQDILSSVANNKYAKLSGTS<br>MSAPLVAGIMGLLQKQYETQYPDMTPSERLDLAKKVLMSSATAL<br>YDEDEKAYFSPRQQGAGAVDAKKASAATMYVTDKDNTSSKVHLN<br>NVSDTFEVTVTVHNKSDKPQELYYQATVQTDKVDGKHFALAPKA<br>LYETSWQKITIPANSSKQVTVPIDASRFSKDLLAQMKNGYFLEG<br>FVRFKQDPTKEELMSIPYIGERGDFGNLSALEKPIYDSKDGSSY<br>YHEANSDAKDQLDGDGLQFYALKNNFTALTTESNPWTIIKAVKE<br>GVENIEDIESSEITETIFAGTFAKQDDDSHYYIHRHANGKPYAA<br>ISPNGDGNRDYVQFQGTFLRNAKNLVAEVLDKEGNVVWTSEVTE<br>QVVKNYNNDLASTLGSTRFEKTRWDGKDKDGKVVANGTYTYRVR<br>YTPISSGAKEQHTDFDVIVDNTTPEVATSATESTEDRRLTLASK<br>PKTSQPVYRERIAYTYMDEDLPTTEYISPNEDGTFTLPEEAETM<br>EGATVPLKMSDFTYVVEDMAGNITYTPVTKLLEGHSNK |
| 2 | C5a [90-1035 fragment] WT w/o leader | KTADTPVTSKATIRDLNDPSQVKTLQEKAGKGAGTVVAVIDAGF<br>DKNHEAWRLTDKTKARYQSKEDLEKAKKEHGITYGEWVNDKVAY<br>YHDYSKDGKTAVDQEHGTHVSGILSGNAPSETKEPYRLEGAMPE<br>AQLLLMRVEIVNGLADYARNYAQAIRDAVNLGAKVINMSFGNAA<br>LAYANLPDETKKAFDYAKSKGVSIVTSAGNDSSFGGKTRLPLAD<br>HPDYGVVGTPAAADSTLTVASYSPDKQLTETATVKTADKQDKEM<br>PVLSTNRFEPNKAYDYAYANRGMKEDDFKDVKGKIALIERGDID<br>FKDKIANAKKAGAVGVLIYDNQDKGFPIELPNVDQMPAAFISRK<br>DGLLLKDNPKKTITFNATPKVLPTASGTKLSRESSWGLTADGNI<br>KPDIAAPGQDILSSVANNKYAKLSGTSMSAPLVAGIMGLLQKQY<br>ETQYPDMTPSERLDLAKKVLMSSATALYDEDEKAYESPRQQGAG<br>AVDAKKASAATMYVTDKDNTSSKVHLNNVSDTFEVTVTVHNKSD<br>KPQELYYQATVQTDKVDGKHFALAPKALYETSWQKITIPANSSK<br>QVTVPIDASRFSKDLLAQMKNGYFLEGFVRFKQDPTKEELMSIP<br>YIGFRGDFGNLSALEKPIYDSKDGSSYYHEANSDAKDQLDGDGL<br>QFYALKNNFTALTTESNPWTIIKAVKEGVENIEDIESSEITETI<br>FAGTFAKQDDDSHYYIHRHANGKPYAAISPNGDGNRDYVQFQGT<br>FLRNAKNLVAEVLDKEGNVVWTSEVTEQVVKNYNNDLASTLGST<br>RFEKTRWDGKDKDGKVVANGTYTYRVRYTPISSGAKEQHTDFDV<br>IVDNTTPEVATSATESTEDRRLTLASKPKTSQPVYRERIAYTYM<br>DEDLPTTEYISPNEDGTFTLPEEAETMEGATVPLKMSDFTYVVE<br>DMAGNITYTPVTKLLEGHSNK |
| 3 | C5a [90-1035 fragment] D131A/S513A w/ leader | MHHHHHHGSGENLYFQGKTADTPVTSKATIRDLNDPSQVKTLQE<br>KAGKGAGTVVAVIAAGFDKNHEAWRLTDKTKARYQSKEDLEKAK<br>KEHGITYGEWVNDKVAYYHDYSKDGKTAVDQEHGTHVSGILSGN<br>APSETKEPYRLEGAMPEAQLLLMRVEIVNGLADYARNYAQAIRD<br>AVNLGAKVINMSFGNAALAYANLPDETKKAFDYAKSKGVSIVTS<br>AGNDSSFGGKTRLPLADHPDYGVVGTPAAADSTLTVASYSPDKQ<br>LTETATVKTADKQDKEMPVLSTNRFEPNKAYDYAYANRGMKEDD<br>FKDVKGKIALIERGDIDFKDKIANAKKAGAVGVLIYDNQDKGFP<br>IELPNVDQMPAAFISRKDGLLLKDNPKKTITFNATPKVLPTASG<br>TKLSRFSSWGLTADGNIKPDIAAPGQDILSSVANNKYAKLSGTA<br>MSAPLVAGIMGLLQKQYETQYPDMTPSERLDLAKKVLMSSATAL |

-continued

Sequence identifier descriptions

| Seq ID | Name/description | Amino acid sequence |
| --- | --- | --- |
| | | YDEDEKAYFSPRQQGAGAVDAKKASAATMYVTDKDNTSSKVHLN<br>NVSDTFEVTVTVHNKSDKPQELYYQATVQTDKVDGKHFALAPKA<br>LYETSWQKITIPANSSKQVTVPIDASRFSKDLLAQMKNGYFLEG<br>FVRFKQDPTKEELMSIPYIGERGDFGNLSALEKPIYDSKDGSSY<br>YHEANSDAKDQLDGDGLQFYALKNNFTALTTESNPWTIIKAVKE<br>GVENIEDIESSEITETIFAGTFAKQDDDSHYYIHRHANGKPYAA<br>ISPNGDGNRDYVQFQGTFLRNAKNLVAEVLDKEGNVVWTSEVTE<br>QVVKNYNNDLASTLGSTRFEKTRWDGKDKDGKVVANGTYTYRVR<br>YTPISSGAKEQHTDEDVIVDNTTPEVATSATESTEDRRLTLASK<br>PKTSQPVYRERIAYTYMDEDLPTTEYISPNEDGTFTLPEEAETM<br>EGATVPLKMSDFTYVVEDMAGNITYTPVTKLLEGHSNK |
| 4 | C5a [90-1035 fragment] D131A/S513A w/o leader | KTADTPVTSKATIRDLNDPSQVKTLQEKAGKGAGTVVAVIAAGF<br>DKNHEAWRLTDKTKARYQSKEDLEKAKKEHGITYGEWVNDKVAY<br>YHDYSKDGKTAVDQEHGTHVSGILSGNAPSETKEPYRLEGAMPE<br>AQLLLMRVEIVNGLADYARNYAQAIRDAVNLGAKVINMSFGNAA<br>LAYANLPDETKKAFDYAKSKGVSIVTSAGNDSSFGGKTRLPLAD<br>HPDYGVVGTPAAADSTLTVASYSPDKQLTETATVKTADKQDKEM<br>PVLSTNRFEPNKAYDYAYANRGMKEDDFKDVKGKIALIERGDID<br>FKDKIANAKKAGAVGVLIYDNQDKGFPIELPNVDQMPAAFISRK<br>DGLLLKDNPKKTITFNATPKVLPTASGTKLSRFSSWGLTADGNI<br>KPDIAAPGQDILSSVANNKYAKLSGTAMSAPLVAGIMGLLQKQY<br>ETQYPDMTPSERLDLAKKVLMSSATALYDEDEKAYFSPRQQGAG<br>AVDAKKASAATMYVTDKDNTSSKVHLNNVSDTFEVTVTVHNKSD<br>KPQELYYQATVQTDKVDGKHFALAPKALYETSWQKITIPANSSK<br>QVTVPIDASRFSKDLLAQMKNGYFLEGFVRFKQDPTKEELMSIP<br>YIGFRGDFGNLSALEKPIYDSKDGSSYYHEANSDAKDQLDGDGL<br>QFYALKNNFTALTTESNPWTIIKAVKEGVENIEDIESSEITETI<br>FAGTFAKQDDDSHYYIHRHANGKPYAAISPNGDGNRDYVQFQGT<br>FLRNAKNLVAEVLDKEGNVVWTSEVTEQVVKNYNNDLASTLGST<br>RFEKTRWDGKDKDGKVVANGTYTYRVRYTPISSGAKEQHTDFDV<br>IVDNTTPEVATSATFSTEDRRLTLASKPKTSQPVYRERIAYTYM<br>DEDLPTTEYISPNEDGTFTLPEEAETMEGATVPLKMSDFTYVVE<br>DMAGNITYTPVTKLLEGHSNK |
| 5 | SLO [79-571 fragment] WT w/ His tag and TEV sequence | MHHHHHHGSGENLYFQGAPKEMPLESAEKEEKKSEDKKKSEEDH<br>TEEINDKIYSLNYNELEVLAKNGETIENFVPKEGVKKADKFIVI<br>ERKKKNINTTPVDISIIDSVTDRTYPAALQLANKGFTENKPDAV<br>VTKRNPQKIHIDLPGMGDKATVEVNDPTYANVSTAIDNLVNQWH<br>DNYSGGNTLPARTQYTESMVYSKSQIEAALNVNSKILDGTLGID<br>FKSISKGEKKVMIAAYKQIFYTVSANLPNNPADVEDKSVTFKEL<br>QRKGVSNEAPPLEVSNVAYGRTVFVKLETSSKSNDVEAAFSAAL<br>KGTDVKINGKYSDILENSSFTAVVLGGDAAEHNKVVTKDEDVIR<br>NVIKDNATFSRKNPAYPISYTSVFLKNNKIAGVNNRTEYVETTS<br>TEYTSGKINLSHQGAYVAQYEILWDEINYDDKGKEVITKRRWDN<br>NWYSKTSPFSTVIPLGANSRNIRIMARECTGLAWEWWRKVIDER<br>DVKLSKEINVNISGSTLSPYGSITYK |
| 6 | SLO [79-571 fragment] WT w/o leader | APKEMPLESAEKEEKKSEDKKKSEEDHTEEINDKIYSLNYNELE<br>VLAKNGETIENFVPKEGVKKADKFIVIERKKKNINTTPVDISII<br>DSVTDRTYPAALQLANKGFTENKPDAVVTKRNPQKIHIDLPGMG<br>DKATVEVNDPTYANVSTAIDNLVNQWHDNYSGGNTLPARTQYTE<br>SMVYSKSQIEAALNVNSKILDGTLGIDFKSISKGEKKVMIAAYK<br>QIFYTVSANLPNNPADVEDKSVTFKELQRKGVSNEAPPLFVSNV<br>AYGRTVFVKLETSSKSNDVEAAFSAALKGTDVKINGKYSDILEN<br>SSFTAVVLGGDAAEHNKVVTKDEDVIRNVIKDNATFSRKNPAYP<br>ISYTSVFLKNNKIAGVNNRTEYVETTSTEYTSGKINLSHQGAYV<br>AQYEILWDEINYDDKGKEVITKRRWDNNWYSKTSPFSTVIPLGA<br>NSRNIRIMARECTGLAWEWWRKVIDERDVKLSKEINVNISGSTL<br>SPYGSITYK |
| 7 | SLO [79-571 fragment] W535A w/ leader | MHHHHHHGSGENLYFQGAPKEMPLESAEKEEKKSEDKKKSEEDH<br>TEEINDKIYSLNYNELEVLAKNGETIENFVPKEGVKKADKFIVI<br>ERKKKNINTTPVDISIIDSVTDRTYPAALQLANKGFTENKPDAV<br>VTKRNPQKIHIDLPGMGDKATVEVNDPTYANVSTAIDNLVNQWH<br>DNYSGGNTLPARTQYTESMVYSKSQIEAALNVNSKILDGTLGID<br>FKSISKGEKKVMIAAYKQIFYTVSANLPNNPADVEDKSVTFKEL<br>QRKGVSNEAPPLFVSNVAYGRTVFVKLETSSKSNDVEAAFSAAL<br>KGTDVKINGKYSDILENSSFTAVVLGGDAAEHNKVVTKDEDVIR<br>NVIKDNATFSRKNPAYPISYTSVFLKNNKIAGVNNRTEYVETTS<br>TEYTSGKINLSHQGAYVAQYEILWDEINYDDKGKEVITKRRWDN<br>NWYSKTSPFSTVIPLGANSRNIRIMARECTGLAAEWWRKVIDER<br>DVKLSKEINVNISGSTLSPYGSITYK |

-continued

Sequence identifier descriptions

| Seq ID | Name/description | Amino acid sequence |
|---|---|---|
| 8 | SLO [79-571 fragment] W535A w/o leader | APKEMPLESAEKEEKKSEDKKKSEEDHTEEINDKIYSLNYNELE<br>VLAKNGETIENFVPKEGVKKADKFIVIERKKKNINTTPVDISII<br>DSVTDRTYPAALQLANKGFTENKPDAVVTKRNPQKIHIDLPGMG<br>DKATVEVNDPTYANVSTAIDNLVNQWHDNYSGGNTLPARTQYTE<br>SMVYSKSQIEAALNVNSKILDGTLGIDFKSISKGEKKVMIAAYK<br>QIFYTVSANLPNNPADVEDKSVTFKELQRKGVSNEAPPLFVSNV<br>AYGRTVFVKLETSSKSNDVEAAFSAALKGTDVKINGKYSDILEN<br>SSFTAVVLGGDAAEHNKVVTKDEDVIRNVIKDNATFSRKNPAYP<br>ISYTSVFLKNNKIAGVNNRTEYVETTSTEYTSGKINLSHQGAYV<br>AQYEILWDEINYDDKGKEVITKRRWDNNWYSKTSPFSTVIPLGA<br>NSRNIRIMARECTGLAAEWWRKVIDERDVKLSKEINVNISGSTL<br>SPYGSITYK |
| 9 | SpyAD [33-849 fragment] WT w/ leader | MHHHHHHGSGENLYFQGQVKADDRASGETKASNTHDDSLPKPET<br>IQEAKATIDAVEKTLSQQKAELTELATALTKTTAEINHLKEQQD<br>NEQKALTSAQEIYTNTLASSEETLLAQGAEHQRELTATETELHN<br>AQADQHSKETALSEQKASISAETTRAQDLVEQVKTSEQNIAKLN<br>AMISNPDAITKAAQTANDNTKALSSELEKAKADLENQKAKVKKQ<br>LTEELAAQKAALAEKEAELSRLKSSAPSTQDSIVGNNTMKAPQG<br>YPLEELKKLEASGYIGSASYNNYYKEHADQIIAKASPGNQLNQY<br>QDIPADRNRFVDPDNLTPEVQNELAQFAAHMINSVRRQLGLPPV<br>TVTAGSQEFARLLSTSYKKTHGNTRPSFVYGQPGVSGHYGVGPH<br>DKTIIEDSAGASGLIRNDDNMYENIGAFNDVHTVNGIKRGIYDS<br>IKYMLFTDHLHGNTYGHAINFLRVDKHNPNAPVYLGFSTSNVGS<br>LNEHFVMFPESNIANHQRENKTPIKAVGSTKDYAQRVGTVSDTI<br>AAIKGKVSSLENRLSAIHQEADIMAAQAKVSQLQGKLASTLKQS<br>DSLNLQVRQLNDTKGSLRTELLAAKAKQAQLEATRDQSLAKLAS<br>LKAALHQTEALAEQAAARVTALVAKKAHLQYLRDFKLNPNRLQV<br>IRERIDNTKQDLAKTTSSLLNAQEALAALQAKQSSLEATIATTE<br>HQLTLLKTLANEKEYRHLDEDIATVPDLQVAPPLTGVKPLSYSK<br>IDTTPLVQEMVKETKQLLEASARLAAENTSLVAEALVGQTSEMV<br>ASNAIVSKITSSITQPSSKTSYGSGSSTTSNLISDVDESTQR |
| 10 | SpyAD [33-849 fragment] WT w/o leader | QVKADDRASGETKASNTHDDSLPKPETIQEAKATIDAVEKTLSQ<br>QKAELTELATALTKTTAEINHLKEQQDNEQKALTSAQEIYTNTL<br>ASSEETLLAQGAEHQRELTATETELHNAQADQHSKETALSEQKA<br>SISAETTRAQDLVEQVKTSEQNIAKLNAMISNPDAITKAAQTAN<br>DNTKALSSELEKAKADLENQKAKVKKQLTEELAAQKAALAEKEA<br>ELSRLKSSAPSTQDSIVGNNTMKAPQGYPLEELKKLEASGYIGS<br>ASYNNYYKEHADQIIAKASPGNQLNQYQDIPADRNRFVDPDNLT<br>PEVQNELAQFAAHMINSVRRQLGLPPVTVTAGSQEFARLLSTSY<br>KKTHGNTRPSFVYGQPGVSGHYGVGPHDKTIIEDSAGASGLIRN<br>DDNMYENIGAFNDVHTVNGIKRGIYDSIKYMLFTDHLHGNTYGH<br>AINFLRVDKHNPNAPVYLGFSTSNVGSLNEHFVMFPESNIANHQ<br>RFNKTPIKAVGSTKDYAQRVGTVSDTIAAIKGKVSSLENRLSAI<br>HQEADIMAAQAKVSQLQGKLASTLKQSDSLNLQVRQLNDTKGSL<br>RTELLAAKAKQAQLEATRDQSLAKLASLKAALHQTEALAEQAAA<br>RVTALVAKKAHLQYLRDFKLNPNRLQVIRERIDNTKQDLAKTTS<br>SLLNAQEALAALQAKQSSLEATIATTEHQLTLLKTLANEKEYRH<br>LDEDIATVPDLQVAPPLTGVKPLSYSKIDTTPLVQEMVKETKQL<br>LEASARLAAENTSLVAEALVGQTSEMVASNAIVSKITSSITQPS<br>SKTSYGSGSSTTSNLISDVDESTQR |
| 11 | SpyAD [33-849 fragment] nnAA (e.g., pAMF)mutant w/ leader<br>X = nnAA (e.g., pAMF) positions K64/K287/K386/K 657 - numbered according to full length sequence | MHHHHHHGSGENLYFQGQVKADDRASGETKASNTHDDSLPKPET<br>IQEAXATIDAVEKTLSQQKAELTELATALTKTTAEINHLKEQQD<br>NEQKALTSAQEIYTNTLASSEETLLAQGAEHQRELTATETELHN<br>AQADQHSKETALSEQKASISAETTRAQDLVEQVKTSEQNIAKLN<br>AMISNPDAITKAAQTANDNTKALSSELEKAKADLENQKAKVKKQ<br>LTEELAAQKAALAEKEAELSRLKSSAPSTQDSIVGNNTMKAPQG<br>YPLEELKXLEASGYIGSASYNNYYKEHADQIIAKASPGNQLNQY<br>QDIPADRNRFVDPDNLTPEVQNELAQFAAHMINSVRRQLGLPPV<br>TVTAGSQEFARLLSTSYKXTHGNTRPSFVYGQPGVSGHYGVGPH<br>DKTIIEDSAGASGLIRNDDNMYENIGAFNDVHTVNGIKRGIYDS<br>IKYMLFTDHLHGNTYGHAINFLRVDKHNPNAPVYLGESTSNVGS<br>LNEHFVMFPESNIANHQRENKTPIKAVGSTKDYAQRVGTVSDTI<br>AAIKGKVSSLENRLSAIHQEADIMAAQAKVSQLQGKLASTLKQS<br>DSLNLQVRQLNDTKGSLRTELLAAKAKQAQLEATRDQSLAKLAS<br>LKAALHQTEALAEQAAARVTALVAKXAHLQYLRDFKLNPNRLQV<br>IRERIDNTKQDLAKTTSSLLNAQEALAALQAKQSSLEATIATTE<br>HQLTLLKTLANEKEYRHLDEDIATVPDLQVAPPLTGVKPLSYSK<br>IDTTPLVQEMVKETKQLLEASARLAAENTSLVAEALVGQTSEMV<br>ASNAIVSKITSSITQPSSKTSYGSGSSTTSNLISDVDESTQR |

-continued

Sequence identifier descriptions

| Seq ID | Name/description | Amino acid sequence |
|---|---|---|
| 12 | SpyAD [33-849 fragment] nnAA (e.g., pAMF) mutant w/o leader X = nnAA (e.g., pAMF) K64/K287/K386/K 657 - numbered according to full-length sequence | QVKADDRASGETKASNTHDDSLPKPETIQEAXATIDAVEKTLSQ<br>QKAELTELATALTKTTAEINHLKEQQDNEQKALTSAQEIYTNTL<br>ASSEETLLAQGAEHQRELTATETELHNAQADQHSKETALSEQKA<br>SISAETTRAQDLVEQVKTSEQNIAKLNAMISNPDAITKAAQTAN<br>DNTKALSSELEKAKADLENQKAKVKKQLTEELAAQKAALAEKEA<br>ELSRLKSSAPSTQDSIVGNNTMKAPQGYPLEELKXLEASGYIGS<br>ASYNNYYKEHADQIIAKASPGNQLNQYQDIPADRNRFVDPDNLT<br>PEVQNELAQFAAHMINSVRRQLGLPPVTVTAGSQEFARLLSTSY<br>KXTHGNTRPSFVYGQPGVSGHYGVGPHDKTIIEDSAGASGLIRN<br>DDNMYENIGAFNDVHTVNGIKRGIYDSIKYMLFTDHLHGNTYGH<br>AINFLRVDKHNPNAPVYLGFSTSNVGSLNEHFVMFPESNIANHQ<br>RFNKTPIKAVGSTKDYAQRVGTVSDTIAAIKGKVSSLENRLSAI<br>HQEADIMAAQAKVSQLQGKLASTLKQSDSLNLQVRQLNDTKGSL<br>RTELLAAKAKQAQLEATRDQSLAKLASLKAALHQTEALAEQAAA<br>RVTALVAKXAHLQYLRDFKLNPNRLQVIRERIDNTKQDLAKTTS<br>SLLNAQEALAALQAKQSSLEATIATTEHQLTLLKTLANEKEYRH<br>LDEDIATVPDLQVAPPLTGVKPLSYSKIDTTPLVQEMVKETKQL<br>LEASARLAAENTSLVAEALVGQTSEMVASNAIVSKITSSITQPS<br>SKTSYGSGSSTTSNLISDVDESTQR |
| 13 | ADI [full length] WT w/ leader | MHHHHHHGSGENLYFQGTAQTPIHVYSEIGKLKKVLLHRPGKEI<br>ENLMPDYLERLLEDDIPFLEDAQKEHDAFAQALRDEGIEVLYLE<br>TLAAESLVTPEIREAFIDEYLSEANIRGRATKKAIRELLMAIED<br>NQELIEKTMAGVQKSELPEIPASEKGLTDLVESNYPFAIDPMPN<br>LYFTRDPFATIGTGVSLNHMFSETRNRETLYGKYIFTHHPIYGG<br>GKVPMVYDRNETTRIEGGDELVLSKDVLAVGISQRTDAASIEKL<br>LVNIFKQNLGFKKVLAFEFANNRKFMHLDTVFTMVDYDKFTIHP<br>EIEGDLRVYSVTYDNEELHIVEEKGDLAELLAANLGVEKVDLIR<br>CGGDNLVAAGREQWNDGSNTLTIAPGVVVVYNRNTITNAILESK<br>GLKLIKIHGSELVRGRGGPRCMSMPFEREDI |
| 14 | ADI [full length] WT w/o leader | TAQTPIHVYSEIGKLKKVLLHRPGKEIENLMPDYLERLLEDDIP<br>FLEDAQKEHDAFAQALRDEGIEVLYLETLAAESLVTPEIREAFI<br>DEYLSEANIRGRATKKAIRELLMAIEDNQELIEKTMAGVQKSEL<br>PEIPASEKGLTDLVESNYPFAIDPMPNLYFTRDPFATIGTGVSL<br>NHMFSETRNRETLYGKYIFTHHPIYGGGKVPMVYDRNETTRIEG<br>GDELVLSKDVLAVGISQRTDAASIEKLLVNIFKQNLGFKKVLAF<br>EFANNRKFMHLDTVFTMVDYDKFTIHPEIEGDLRVYSVTYDNEE<br>LHIVEEKGDLAELLAANLGVEKVDLIRCGGDNLVAAGREQWNDG<br>SNTLTIAPGVVVVYNRNTITNAILESKGLKLIKIHGSELVRGRG<br>GPRCMSMPFEREDI |
| 15 | ADI [full length] D277A w/ leader | MHHHHHHGSGENLYFQGTAQTPIHVYSEIGKLKKVLLHRPGKEI<br>ENLMPDYLERLLFDDIPFLEDAQKEHDAFAQALRDEGIEVLYLE<br>TLAAESLVTPEIREAFIDEYLSEANIRGRATKKAIRELLMAIED<br>NQELIEKTMAGVQKSELPEIPASEKGLTDLVESNYPFAIDPMPN<br>LYFTRDPFATIGTGVSLNHMFSETRNRETLYGKYIFTHHPIYGG<br>GKVPMVYDRNETTRIEGGDELVLSKDVLAVGISQRTDAASIEKL<br>LVNIFKQNLGFKKVLAFEFANNRKFMHLATVFTMVDYDKFTIHP<br>EIEGDLRVYSVTYDNEELHIVEEKGDLAELLAANLGVEKVDLIR<br>CGGDNLVAAGREQWNDGSNTLTIAPGVVVVYNRNTITNAILESK<br>GLKLIKIHGSELVRGRGGPRCMSMPFEREDI |
| 16 | ADI [full length] D277A w/o leader | TAQTPIHVYSEIGKLKKVLLHRPGKEIENLMPDYLERLLEDDIP<br>FLEDAQKEHDAFAQALRDEGIEVLYLETLAAESLVTPEIREAFI<br>DEYLSEANIRGRATKKAIRELLMAIEDNQELIEKTMAGVQKSEL<br>PEIPASEKGLTDLVESNYPFAIDPMPNLYFTRDPFATIGTGVSL<br>NHMFSETRNRETLYGKYIFTHHPIYGGGKVPMVYDRNETTRIEG<br>GDELVLSKDVLAVGISQRTDAASIEKLLVNIFKQNLGFKKVLAF<br>EFANNRKFMHLATVFTMVDYDKFTIHPEIEGDLRVYSVTYDNEE<br>LHIVEEKGDLAELLAANLGVEKVDLIRCGGDNLVAAGREQWNDG<br>SNTLTIAPGVVVVYNRNTITNAILESKGLKLIKIHGSELVRGRG<br>GPRCMSMPFEREDI |
| 17 | ADI [full length] nnAA (e.g., pAMF) w/ leader X = nnAA (e.g., pAMF) positions - K15, K193, K316 | MHHHHHHGSGENLYFQGTAQTPIHVYSEIGXLKKVLLHRPGKEI<br>ENLMPDYLERLLEDDIPFLEDAQKEHDAFAQALRDEGIEVLYLE<br>TLAAESLVTPEIREAFIDEYLSEANIRGRATKKAIRELLMAIED<br>NQELIEKTMAGVQKSELPEIPASEKGLTDLVESNYPFAIDPMPN<br>LYFTRDPFATIGTGVSLNHMFSETRNRETLYGXYIFTHHPIYGG<br>GKVPMVYDRNETTRIEGGDELVLSKDVLAVGISQRTDAASIEKL<br>LVNIFKQNLGFKKVLAFEFANNRKFMHLDTVFTMVDYDKFTIHP |

-continued

Sequence identifier descriptions

| Seq ID | Name/description | Amino acid sequence |
|---|---|---|
| | | EIEGDLRVYSVTYDNEELHIVEEXGDLAELLAANLGVEKVDLIR CGGDNLVAAGREQWNDGSNTLTIAPGVVVVYNRNTITNAILESK GLKLIKIHGSELVRGRGGPRCMSMPFEREDI |
| 18 | ADI [full length] nnAA (e.g., pAMF) mutant w/o leader X = nnAA (e.g., pAMF) positions - K15, K193, K316 | TAQTPIHVYSEIGXLKKVLLHRPGKEIENLMPDYLERLLEDDIP FLEDAQKEHDAFAQALRDEGIEVLYLETLAAESLVTPEIREAFI DEYLSEANIRGRATKKAIRELLMAIEDNQELIEKTMAGVQKSEL PEIPASEKGLTDLVESNYPFAIDPMPNLYFTRDPFATIGTGVSL NHMFSETRNRETLYGXYIFTHHPIYGGGKVPMVYDRNETTRIEG GDELVLSKDVLAVGISQRTDAASIEKLLVNIFKQNLGFKKVLAF EFANNRKFMHLDTVFTMVDYDKFTIHPEIEGDLRVYSVTYDNEE LHIVEEXGDLAELLAANLGVEKVDLIRCGGDNLVAAGREQWNDG SNTLTIAPGVVVVYNRNTITNAILESKGLKLIKIHGSELVRGRG GPRCMSMPFEREDI |
| 19 | ADI (mut5) [full length] D277A nnAA (e.g., pAMF) w/ leader X = nnAA (e.g., pAMF) positions - K15, K193, K316 | MHHHHHHGSGENLYFQGTAQTPIHVYSEIGXLKKVLLHRPGKEI ENLMPDYLERLLEDDIPFLEDAQKEHDAFAQALRDEGIEVLYLE TLAAESLVTPEIREAFIDEYLSEANIRGRATKKAIRELLMAIED NQELIEKTMAGVQKSELPEIPASEKGLTDLVESNYPFAIDPMPN LYFTRDPFATIGTGVSLNHMFSETRNRETLYGXYIFTHHPIYGG GKVPMVYDRNETTRIEGGDELVLSKDVLAVGISQRTDAASIEKL LVNIFKQNLGFKKVLAFEFANNRKFMHLATVFTMVDYDKFTIHP EIEGDLRVYSVTYDNEELHIVEEXGDLAELLAANLGVEKVDLIR CGGDNLVAAGREQWNDGSNTLTIAPGVVVVYNRNTITNAILESK GLKLIKIHGSELVRGRGGPRCMSMPFEREDI |
| 20 | ADI (mut5) [full length] D277A nnAA (e.g., pAMF) w/o leader X = nnAA (e.g., pAMF) positions - K15, K193, K316 | TAQTPIHVYSEIGXLKKVLLHRPGKEIENLMPDYLERLLEDDIP FLEDAQKEHDAFAQALRDEGIEVLYLETLAAESLVTPEIREAFI DEYLSEANIRGRATKKAIRELLMAIEDNQELIEKTMAGVQKSEL PEIPASEKGLTDLVESNYPFAIDPMPNLYFTRDPFATIGTGVSL NHMFSETRNRETLYGXYIFTHHPIYGGGKVPMVYDRNETTRIEG GDELVLSKDVLAVGISQRTDAASIEKLLVNIFKQNLGFKKVLAF EFANNRKFMHLATVFTMVDYDKFTIHPEIEGDLRVYSVTYDNEE LHIVEEXGDLAELLAANLGVEKVDLIRCGGDNLVAAGREQWNDG SNTLTIAPGVVVVYNRNTITNAILESKGLKLIKIHGSELVRGRG GPRCMSMPFEREDI |
| 21 | hFL [full length] WT w/ leader | MHHHHHHGSGSSQIRQNYSTDVEAAVNSLVNLYLQASYTYLSLG FYFDRDDVALEGVSHFFRELAEEKREGYERLLKMQNQRGGRALF QDIKKPAEDEWGKTPDAMKAAMALEKKLNQALLDLHALGSARTD PHLCDFLETHFLDEEVKLIKKMGDHLTNLHRLGGPEAGLGEYLF ERLTLKHD |
| 22 | hFL [full length] WT w/o leader | SSQIRQNYSTDVEAAVNSLVNLYLQASYTYLSLGFYFDRDDVAL EGVSHFFRELAEEKREGYERLLKMQNQRGGRALFQDIKKPAEDE WGKTPDAMKAAMALEKKLNQALLDLHALGSARTDPHLCDFLETH FLDEEVKLIKKMGDHLTNLHRLGGPEAGLGEYLFERLTLKHD |
| 23 | hFL [full length] nnAA (e.g., pAMF) w/ leader X = nnAA (e.g., pAMF) position - 15 | MHHHHHHGSGSSQXRQNYSTDVEAAVNSLVNLYLQASYTYLSLG FYFDRDDVALEGVSHFFRELAEEKREGYERLLKMQNQRGGRALF QDIKKPAEDEWGKTPDAMKAAMALEKKLNQALLDLHALGSARTD PHLCDFLETHFLDEEVKLIKKMGDHLTNLHRLGGPEAGLGEYLF ERLTLKHD |
| 24 | hFL [full length] nnAA (e.g., pAMF) w/o leader X = nnAA (e.g., pAMF) position - I5 | SSQXRQNYSTDVEAAVNSLVNLYLQASYTYLSLGFYFDRDDVAL EGVSHFFRELAEEKREGYERLLKMQNQRGGRALFQDIKKPAEDE WGKTPDAMKAAMALEKKLNQALLDLHALGSARTDPHLCDFLETH FLDEEVKLIKKMGDHLTNLHRLGGPEAGLGEYLFERLTLKHD |
| 25 | eCRM-pAMF6 mutant | MGADDVVDSSKSFVMENFSSYHGTKPGYVDSIQXGIQKPKSGTQ GNYDDDWKEFYSTDNKYDAAGYSVDNENPLSGKAGGVVKVTYPG LTKVLALKVDNAETIKKELGLSLTEPLMEQVGTEEFIKREGDGA SRVVLSLPFAEGSSSVEYINNWEQAKALSVELEINFETRGKRGQ DAMYEYMAQACAGNRVRNSVGSSLSCINLDWDVIRDXTKTKIES LKEHGPIKNKMSESPNKTVSEEKAXQYLEEFHQTALEHPELSEL XTVTGTNPVFAGANYAAWAVNVAQVIDSETADNLEKTTAALSIL PGIGSVMGIADGAVHHNTEEIVAQSIALSSLMVAQAIPLVGELV |

-continued

Sequence identifier descriptions

| Seq ID | Name/description | Amino acid sequence |
|---|---|---|
| | | DIGFAAYNFVESIINLFQVVHNSYNRPAYSPGHXTQPFLHDGYA VSWNTVEDSIIRTGFQGESGHDIKITAENTPLPIAGVLLPTIPG KLDVNKSKTHISVNGRKIRMRCRAIDGDVTFCRPKSPVYVGNGV HANLHVAFHRSSSEKIHSNEISSDSIGVLGYQKTVDHTKVNSXL SLFFEIKS |
| 26 | ADI (mut2) [full length] D277A nnAA (e.g., pAMF) w/ leader X = nnAA (e.g., pAMF) positions - K123, K247, K316 | MHHHHHHGSGENLYFQGTAQTPIHVYSEIGKLKKVLLHRPGKEI ENLMPDYLERLLEDDIPFLEDAQKEHDAFAQALRDEGIEVLYLE TLAAESLVTPEIREAFIDEYLSEANIRGRATKKAIRELLMAIED NQELIEXTMAGVQKSELPEIPASEKGLTDLVESNYPFAIDPMPN LYFTRDPFATIGTGVSLNHMFSETRNRETLYGKYIFTHHPIYGG GKVPMVYDRNETTRIEGGDELVLSKDVLAVGISQRTDAASIEXL LVNIFKQNLGFKKVLAFEFANNRKFMHLATVFTMVDYDKFTIHP EIEGDLRVYSVTYDNEELHIVEEXGDLAELLAANLGVEKVDLIR CGGDNLVAAGREQWNDGSNTLTIAPGVVVVYNRNTITNAILESK GLKLIKIHGSELVRGRGGPRCMSMPFEREDI |
| 27 | ADI (mut2) [full length] D277A nnAA (e.g., pAMF) w/o leader, with G overhang from cleavage X = nnAA (e.g., pAMF) positions - K123, K247, K316 | GTAQTPIHVYSEIGKLKKVLLHRPGKEIENLMPDYLERLLEDDI PFLEDAQKEHDAFAQALRDEGIEVLYLETLAAESLVTPEIREAF IDEYLSEANIRGRATKKAIRELLMAIEDNQELIEXTMAGVQKSE LPEIPASEKGLTDLVESNYPFAIDPMPNLYFTRDPFATIGTGVS LNHMFSETRNRETLYGKYIFTHHPIYGGGKVPMVYDRNETTRIE GGDELVLSKDVLAVGISQRTDAASIEXLLVNIFKQNLGFKKVLA FEFANNRKFMHLATVFTMVDYDKFTIHPEIEGDLRVYSVTYDNE ELHIVEEXGDLAELLAANLGVEKVDLIRCGGDNLVAAGREQWND GSNTLTIAPGVVVVYNRNTITNAILESKGLKLIKIHGSELVRGR GGPRCMSMPFEREDI |
| 28 | Sfb1 repeat region with leader | MHHHHHHGSGVETEDTKEPGVLMGGQSESVEFTKDTQTGMSGQT TPQVETEDTKEPGVLMGGQSESVEFTKDTQTGMSGQTASQVETE DTKEPGVLMGGQSESVEFTKDTQTGMSGQTTPQVETEDTKEPGV LMGGQSESVEFTKDTQTGMSGFSET |
| 29 | C5a [90-1035 fragment] WT w/o leader, with G overhang from cleavage | GKTADTPVTSKATIRDLNDPSQVKTLQEKAGKGAGTVVAVIDAG FDKNHEAWRLTDKTKARYQSKEDLEKAKKEHGITYGEWVNDKVA YYHDYSKDGKTAVDQEHGTHVSGILSGNAPSETKEPYRLEGAMP EAQLLLMRVEIVNGLADYARNYAQAIRDAVNLGAKVINMSFGNA ALAYANLPDETKKAFDYAKSKGVSIVTSAGNDSSFGGKTRLPLA DHPDYGVVGTPAAADSTLTVASYSPDKQLTETATVKTADKQDKE MPVLSTNRFEPNKAYDYAYANRGMKEDDFKDVKGKIALIERGDI DFKDKIANAKKAGAVGVLIYDNQDKGFPIELPNVDQMPAAFISR KDGLLLKDNPKKTITFNATPKVLPTASGTKLSRFSSWGLTADGN IKPDIAAPGQDILSSVANNKYAKLSGTSMSAPLVAGIMGLLQKQ YETQYPDMTPSERLDLAKKVLMSSATALYDEDEKAYESPRQQGA GAVDAKKASAATMYVTDKDNTSSKVHLNNVSDTFEVTVTVHNKS DKPQELYYQATVQTDKVDGKHFALAPKALYETSWQKITIPANSS KQVTVPIDASRFSKDLLAQMKNGYFLEGFVRFKQDPTKEELMSI PYIGFRGDEGNLSALEKPIYDSKDGSSYYHEANSDAKDQLDGDG LQFYALKNNFTALTTESNPWTIIKAVKEGVENIEDIESSEITET IFAGTFAKQDDDSHYYIHRHANGKPYAAISPNGDGNRDYVQFQG TFLRNAKNLVAEVLDKEGNVVWTSEVTEQVVKNYNNDLASTLGS TRFEKTRWDGKDKDGKVVANGTYTYRVRYTPISSGAKEQHTDED VIVDNTTPEVATSATFSTEDRRLTLASKPKTSQPVYRERIAYTY MDEDLPTTEYISPNEDGTFTLPEEAETMEGATVPLKMSDFTYVV EDMAGNITYTPVTKLLEGHSNK |
| 30 | C5a [90-1035 fragment] D131A/S513A w/o leader, with G overhang from cleavage | GKTADTPVTSKATIRDLNDPSQVKTLQEKAGKGAGTVVAVIAAG FDKNHEAWRLTDKTKARYQSKEDLEKAKKEHGITYGEWVNDKVA YYHDYSKDGKTAVDQEHGTHVSGILSGNAPSETKEPYRLEGAMP EAQLLLMRVEIVNGLADYARNYAQAIRDAVNLGAKVINMSFGNA ALAYANLPDETKKAFDYAKSKGVSIVTSAGNDSSFGGKTRLPLA DHPDYGVVGTPAAADSTLTVASYSPDKQLTETATVKTADKQDKE MPVLSTNRFEPNKAYDYAYANRGMKEDDFKDVKGKIALIERGDI DFKDKIANAKKAGAVGVLIYDNQDKGFPIELPNVDQMPAAFISR KDGLLLKDNPKKTITFNATPKVLPTASGTKLSRFSSWGLTADGN IKPDIAAPGQDILSSVANNKYAKLSGTAMSAPLVAGIMGLLQKQ YETQYPDMTPSERLDLAKKVLMSSATALYDEDEKAYFSPRQQGA GAVDAKKASAATMYVTDKDNTSSKVHLNNVSDTFEVTVTVHNKS DKPQELYYQATVQTDKVDGKHFALAPKALYETSWQKITIPANSS KQVTVPIDASRFSKDLLAQMKNGYFLEGFVRFKQDPTKEELMSI PYIGFRGDFGNLSALEKPIYDSKDGSSYYHEANSDAKDQLDGDG LQFYALKNNFTALTTESNPWTIIKAVKEGVENIEDIESSEITET IFAGTFAKQDDDSHYYIHRHANGKPYAAISPNGDGNRDYVQFQG TFLRNAKNLVAEVLDKEGNVVWTSEVTEQVVKNYNNDLASTLGS |

-continued

Sequence identifier descriptions

| Seq ID | Name/description | Amino acid sequence |
|---|---|---|
| | | TRFEKTRWDGKDKDGKVVANGTYTYRVRYTPISSGAKEQHTDED<br>VIVDNTTPEVATSATFSTEDRRLTLASKPKTSQPVYRERIAYTY<br>MDEDLPTTEYISPNEDGTFTLPEEAETMEGATVPLKMSDFTYVV<br>EDMAGNITYTPVTKLLEGHSNK |
| 31 | SLO [79-571 fragment] WT w/o leader, with G overhang from cleavage | GAPKEMPLESAEKEEKKSEDKKKSEEDHTEEINDKIYSLNYNEL<br>EVLAKNGETIENFVPKEGVKKADKFIVIERKKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVFDKSVTFKELQRKGVSNEAPPLEVSN<br>VAYGRTVFVKLETSSKSNDVEAAFSAALKGTDVKTNGKYSDILE<br>NSSFTAVVLGGDAAEHNKVVTKDFDVIRNVIKDNATFSRKNPAY<br>PISYTSVFLKNNKIAGVNNRTEYVETTSTEYTSGKINLSHQGAY<br>VAQYEILWDEINYDDKGKEVITKRRWDNNWYSKTSPFSTVIPLG<br>ANSRNIRIMARECTGLAWEWWRKVIDERDVKLSKEINVNISGST<br>LSPYGSITYK |
| 32 | SLO [79-571 fragment] W535A w/o leader, with G overhang from cleavage | GAPKEMPLESAEKEEKKSEDKKKSEEDHTEEINDKIYSLNYNEL<br>EVLAKNGETIENFVPKEGVKKADKFIVIERKKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTFKELQRKGVSNEAPPLFVSN<br>VAYGRTVFVKLETSSKSNDVEAAFSAALKGTDVKINGKYSDILE<br>NSSFTAVVLGGDAAEHNKVVTKDFDVIRNVIKDNATFSRKNPAY<br>PISYTSVFLKNNKIAGVNNRTEYVETTSTEYTSGKINLSHQGAY<br>VAQYEILWDEINYDDKGKEVITKRRWDNNWYSKTSPFSTVIPLG<br>ANSRNIRIMARECTGLAAEWWRKVIDERDVKLSKEINVNISGST<br>LSPYGSITYK |
| 33 | SpyAD [33-849 fragment] WT w/o leader, with G overhang from cleavage | GQVKADDRASGETKASNTHDDSLPKPETIQEAKATIDAVEKTLS<br>QQKAELTELATALTKTTAEINHLKEQQDNEQKALTSAQEIYTNT<br>LASSEETLLAQGAEHQRELTATETELHNAQADQHSKETALSEQK<br>ASISAETTRAQDLVEQVKTSEQNIAKLNAMISNPDAITKAAQTA<br>NDNTKALSSELEKAKADLENQKAKVKKQLTEELAAQKAALAEKE<br>AELSRLKSSAPSTQDSIVGNNTMKAPQGYPLEELKKLEASGYIG<br>SASYNNYYKEHADQIIAKASPGNQLNQYQDIPADRNRFVDPDNL<br>TPEVQNELAQFAAHMINSVRRQLGLPPVTVTAGSQEFARLLSTS<br>YKKTHGNTRPSFVYGQPGVSGHYGVGPHDKTIIEDSAGASGLIR<br>NDDNMYENIGAFNDVHTVNGIKRGIYDSIKYMLFTDHLHGNTYG<br>HAINFLRVDKHNPNAPVYLGFSTSNVGSLNEHFVMFPESNIANH<br>QRFNKTPIKAVGSTKDYAQRVGTVSDTIAAIKGKVSSLENRLSA<br>IHQEADIMAAQAKVSQLQGKLASTLKQSDSLNLQVRQLNDTKGS<br>LRTELLAAKAKQAQLEATRDQSLAKLASLKAALHQTEALAEQAA<br>ARVTALVAKKAHLQYLRDFKLNPNRLQVIRERIDNTKQDLAKTT<br>SSLLNAQEALAALQAKQSSLEATIATTEHQLTLLKTLANEKEYR<br>HLDEDIATVPDLQVAPPLTGVKPLSYSKIDTTPLVQEMVKETKQ<br>LLEASARLAAENTSLVAEALVGQTSEMVASNAIVSKITSSITQP<br>SSKTSYGSGSSTTSNLISDVDESTQR |
| 34 | SpyAD [33-849 fragment] nnAA (e.g., pAMF) w/o leader, with G overhang from cleavage<br><br>X = nnAA (e.g., pAMF) positions K64/K287/K386/K657 - numbered | GQVKADDRASGETKASNTHDDSLPKPETIQEAXATIDAVEKTLS<br>QQKAELTELATALTKTTAEINHLKEQQDNEQKALTSAQEIYTNT<br>LASSEETLLAQGAEHQRELTATETELHNAQADQHSKETALSEQK<br>ASISAETTRAQDLVEQVKTSEQNIAKLNAMISNPDAITKAAQTA<br>NDNTKALSSELEKAKADLENQKAKVKKQLTEELAAQKAALAEKE<br>AELSRLKSSAPSTQDSIVGNNTMKAPQGYPLEELKXLEASGYIG<br>SASYNNYYKEHADQIIAKASPGNQLNQYQDIPADRNRFVDPDNL<br>TPEVQNELAQFAAHMINSVRRQLGLPPVTVTAGSQEFARLLSTS<br>YKXTHGNTRPSFVYGQPGVSGHYGVGPHDKTIIEDSAGASGLIR<br>NDDNMYENIGAFNDVHTVNGIKRGIYDSIKYMLFTDHLHGNTYG<br>HAINFLRVDKHNPNAPVYLGFSTSNVGSLNEHFVMFPESNIANH<br>QRFNKTPIKAVGSTKDYAQRVGTVSDTIAAIKGKVSSLENRLSA<br>IHQEADIMAAQAKVSQLQGKLASTLKQSDSLNLQVRQLNDTKGS<br>LRTELLAAKAKQAQLEATRDQSLAKLASLKAALHQTEALAEQAA<br>ARVTALVAKXAHLQYLRDFKLNPNRLQVIRERIDNTKQDLAKTT<br>SSLLNAQEALAALQAKQSSLEATIATTEHQLTLLKTLANEKEYR<br>HLDEDIATVPDLQVAPPLTGVKPLSYSKIDTTPLVQEMVKETKQ<br>LLEASARLAAENTSLVAEALVGQTSEMVASNAIVSKITSSITQP<br>SSKTSYGSGSSTTSNLISDVDESTQR |

-continued

Sequence identifier descriptions

| Seq ID | Name/description | Amino acid sequence |
| --- | --- | --- |
| 35 | ADI [full length] WT w/o leader, with G overhang from cleavage | GTAQTPIHVYSEIGKLKKVLLHRPGKEIENLMPDYLERLLEDDI<br>PFLEDAQKEHDAFAQALRDEGIEVLYLETLAAESLVTPEIREAF<br>IDEYLSEANIRGRATKKAIRELLMAIEDNQELIEKTMAGVQKSE<br>LPEIPASEKGLTDLVESNYPFAIDPMPNLYFTRDPFATIGTGVS<br>LNHMFSETRNRETLYGKYIFTHHPIYGGGKVPMVYDRNETTRIE<br>GGDELVLSKDVLAVGISQRTDAASIEKLLVNIFKQNLGFKKVLA<br>FEFANNRKFMHLDTVFTMVDYDKFTIHPEIEGDLRVYSVTYDNE<br>ELHIVEEKGDLAELLAANLGVEKVDLIRCGGDNLVAAGREQWND<br>GSNTLTIAPGVVVVYNRNTITNAILESKGLKLIKIHGSELVRGR<br>GGPRCMSMPFEREDI |
| 36 | ADI [full length] D277A w/o leader, with G overhang from cleavage | GTAQTPIHVYSEIGKLKKVLLHRPGKEIENLMPDYLERLLEDDI<br>PFLEDAQKEHDAFAQALRDEGIEVLYLETLAAESLVTPEIREAF<br>IDEYLSEANIRGRATKKAIRELLMAIEDNQELIEKTMAGVQKSE<br>LPEIPASEKGLTDLVESNYPFAIDPMPNLYFTRDPFATIGTGVS<br>LNHMFSETRNRETLYGKYIFTHHPIYGGGKVPMVYDRNETTRIE<br>GGDELVLSKDVLAVGISQRTDAASIEKLLVNIFKQNLGFKKVLA<br>FEFANNRKFMHLATVFTMVDYDKFTIHPEIEGDLRVYSVTYDNE<br>ELHIVEEKGDLAELLAANLGVEKVDLIRCGGDNLVAAGREQWND<br>GSNTLTIAPGVVVVYNRNTITNAILESKGLKLIKIHGSELVRGR<br>GGPRCMSMPFEREDI |
| 37 | ADI [full length] nnAA (e.g., pAMF) w/o leader, with G overhang from cleavage X = nnAA (e.g., pAMF) positions - K15, K193, K316 | GTAQTPIHVYSEIGXLKKVLLHRPGKEIENLMPDYLERLLEDDI<br>PFLEDAQKEHDAFAQALRDEGIEVLYLETLAAESLVTPEIREAF<br>IDEYLSEANIRGRATKKAIRELLMAIEDNQELIEKTMAGVQKSE<br>LPEIPASEKGLTDLVESNYPFAIDPMPNLYFTRDPFATIGTGVS<br>LNHMFSETRNRETLYGXYIFTHHPIYGGGKVPMVYDRNETTRIE<br>GGDELVLSKDVLAVGISQRTDAASIEKLLVNIFKQNLGFKKVLA<br>FEFANNRKFMHLDTVFTMVDYDKFTIHPEIEGDLRVYSVTYDNE<br>ELHIVEEXGDLAELLAANLGVEKVDLIRCGGDNLVAAGREQWND<br>GSNTLTIAPGVVVVYNRNTITNAILESKGLKLIKIHGSELVRGR<br>GGPRCMSMPFEREDI |
| 38 | ADI (mut5) [full length] D277A nnAA (e.g., pAMF) w/o leader, with G overhang from cleavage X = nnAA (e.g., pAMF) positions - K15, K193, K316 | GTAQTPIHVYSEIGXLKKVLLHRPGKEIENLMPDYLERLLEDDI<br>PFLEDAQKEHDAFAQALRDEGIEVLYLETLAAESLVTPEIREAF<br>IDEYLSEANIRGRATKKAIRELLMAIEDNQELIEKTMAGVQKSE<br>LPEIPASEKGLTDLVESNYPFAIDPMPNLYFTRDPFATIGTGVS<br>LNHMFSETRNRETLYGXYIFTHHPIYGGGKVPMVYDRNETTRIE<br>GGDELVLSKDVLAVGISQRTDAASIEKLLVNIFKQNLGFKKVLA<br>FEFANNRKFMHLATVFTMVDYDKFTIHPEIEGDLRVYSVTYDNE<br>ELHIVEEXGDLAELLAANLGVEKVDLIRCGGDNLVAAGREQWND<br>GSNTLTIAPGVVVVYNRNTITNAILESKGLKLIKIHGSELVRGR<br>GGPRCMSMPFEREDI |
| 39 | hFL [full length] WT w/ leader | MHHHHHHGSGSSQIRQNYSTDVEAAVNSLVNLYLQASYTYLSLG<br>FYFDRDDVALEGVSHFFRELAEEKREGYERLLKMQNQRGGRALF<br>QDIKKPAEDEWGKTPDAMKAAMALEKKLNQALLDLHALGSARTD<br>PHLCDFLETHFLDEEVKLIKKMGDHLTNLHRLGGPEAGLGEYLE<br>ERLTLKHD |
| 40 | hFL [full length] WT w/o leader | SSQIRQNYSTDVEAAVNSLVNLYLQASYTYLSLGFYFDRDDVAL<br>EGVSHFFRELAEEKREGYERLLKMQNQRGGRALFQDIKKPAEDE<br>WGKTPDAMKAAMALEKKLNQALLDLHALGSARTDPHLCDFLETH<br>FLDEEVKLIKKMGDHLTNLHRLGGPEAGLGEYLFERLTLKHD |
| 41 | hFL [full length] nnAA (e.g., pAMF) w/ leader X = nnAA (e.g., pAMF) position - I5 | MHHHHHHGSGSSQXRQNYSTDVEAAVNSLVNLYLQASYTYLSLG<br>FYFDRDDVALEGVSHFFRELAEEKREGYERLLKMQNQRGGRALF<br>QDIKKPAEDEWGKTPDAMKAAMALEKKLNQALLDLHALGSARTD<br>PHLCDFLETHFLDEEVKLIKKMGDHLTNLHRLGGPEAGLGEYLF<br>ERLTLKHD |
| 42 | hFL [full length] nnAA (e.g., pAMF) w/o leader X = nnAA (e.g., pAMF) position - I5 | SSQXRQNYSTDVEAAVNSLVNLYLQASYTYLSLGFYFDRDDVAL<br>EGVSHFFRELAEEKREGYERLLKMQNQRGGRALFQDIKKPAEDE<br>WGKTPDAMKAAMALEKKLNQALLDLHALGSARTDPHLCDFLETH<br>FLDEEVKLIKKMGDHLTNLHRLGGPEAGLGEYLFERLTLKHD |
| 43 | eCRM-pAMF6 mutant | GADDVVDSSKSFVMENFSSYHGTKPGYVDSIQXGIQKPKSGTQG<br>NYDDDWKEFYSTDNKYDAAGYSVDNENPLSGKAGGVVKVTYPGL<br>TKVLALKVDNAETIKKELGLSLTEPLMEQVGTEEFIKRFGDGAS<br>RVVLSLPFAEGSSSVEYINNWEQAKALSVELEINFETRGKRGQD<br>AMYEYMAQACAGNRVRNSVGSSLSCINLDWDVIRDXTKTKIESL |

-continued

Sequence identifier descriptions

| Seq ID | Name/description | Amino acid sequence |
|---|---|---|
| | | KEHGPIKNKMSESPNKTVSEEKAXQYLEEFHQTALEHPELSELX TVTGTNPVFAGANYAAWAVNVAQVIDSETADNLEKTTAALSILP GIGSVMGIADGAVHHNTEEIVAQSIALSSLMVAQAIPLVGELVD IGFAAYNFVESIINLFQVVHNSYNRPAYSPGHXTQPFLHDGYAV SWNTVEDSIIRTGFQGESGHDIKITAENTPLPIAGVLLPTIPGK LDVNKSKTHISVNGRKIRMRCRAIDGDVTFCRPKSPVYVGNGVH ANLHVAFHRSSSEKIHSNEISSDSIGVLGYQKTVDHTKVNSXLS LFFEIKS |
| 44 | SLO(ΔC11) W535A w/o leader, with G overhang from cleavage | GAPKEMPLESAEKEEKKSEDKKKSEEDHTEEINDKIYSLNYNEL EVLAKNGETIENFVPKEGVKKADKFIVIERKKKNINTTPVDISI IDSVTDRTYPAALQLANKGFTENKPDAVVTKRNPQKIHIDLPGM GDKATVEVNDPTYANVSTAIDNLVNQWHDNYSGGNTLPARTQYT ESMVYSKSQIEAALNVNSKILDGTLGIDFKSISKGEKKVMIAAY KQIFYTVSANLPNNPADVEDKSVTFKELQRKGVSNEAPPLFVSN VAYGRTVFVKLETSSKSNDVEAAFSAALKGTDVKINGKYSDILE NSSFTAVVLGGDAAEHNKVVTKDEDVIRNVIKDNATFSRKNPAY PISYTSVFLKNNKIAGVNNRTEYVETTSTEYTSGKINLSHQGAY VAQYEILWDEINYDDKGKEVITKRRWDNNWYSKTSPFSTVIPLG ANSRNIRIMARECTGLAAEWWRKVIDERDVKLSKEINVNISGS |
| 45 | SLO(ΔC21) fragment W535A w/o leader, with G overhang from cleavage | GAPKEMPLESAEKEEKKSEDKKKSEEDHTEEINDKIYSLNYNEL EVLAKNGETIENFVPKEGVKKADKFIVIERKKKNINTTPVDISI IDSVTDRTYPAALQLANKGFTENKPDAVVTKRNPQKIHIDLPGM GDKATVEVNDPTYANVSTAIDNLVNQWHDNYSGGNTLPARTQYT ESMVYSKSQIEAALNVNSKILDGTLGIDFKSISKGEKKVMIAAY KQIFYTVSANLPNNPADVEDKSVTFKELQRKGVSNEAPPLEVSN VAYGRTVFVKLETSSKSNDVEAAFSAALKGTDVKINGKYSDILE NSSFTAVVLGGDAAEHNKVVTKDEDVIRNVIKDNATFSRKNPAY PISYTSVFLKNNKIAGVNNRTEYVETTSTEYTSGKINLSHQGAY VAQYEILWDEINYDDKGKEVITKRRWDNNWYSKTSPFSTVIPLG ANSRNIRIMARECTGLAAEWWRKVIDERDVKLS |
| 46 | SLO(ΔC31) fragment W535A w/o leader, with G overhang from cleavage | GAPKEMPLESAEKEEKKSEDKKKSEEDHTEEINDKIYSLNYNEL EVLAKNGETIENFVPKEGVKKADKFIVIERKKKNINTTPVDISI IDSVTDRTYPAALQLANKGFTENKPDAVVTKRNPQKIHIDLPGM GDKATVEVNDPTYANVSTAIDNLVNQWHDNYSGGNTLPARTQYT ESMVYSKSQIEAALNVNSKILDGTLGIDFKSISKGEKKVMIAAY KQIFYTVSANLPNNPADVEDKSVTFKELQRKGVSNEAPPLFVSN VAYGRTVFVKLETSSKSNDVEAAFSAALKGTDVKINGKYSDILE NSSFTAVVLGGDAAEHNKVVTKDFDVIRNVIKDNATFSRKNPAY PISYTSVELKNNKIAGVNNRTEYVETTSTEYTSGKINLSHQGAY VAQYEILWDEINYDDKGKEVITKRRWDNNWYSKTSPFSTVIPLG ANSRNIRIMARECTGLAAEWWRK |
| 47 | SLO(ΔC41) fragment W535A w/o leader, with G overhang from cleavage | GAPKEMPLESAEKEEKKSEDKKKSEEDHTEEINDKIYSLNYNEL EVLAKNGETIENFVPKEGVKKADKFIVIERKKKNINTTPVDISI IDSVTDRTYPAALQLANKGFTENKPDAVVTKRNPQKIHIDLPGM GDKATVEVNDPTYANVSTAIDNLVNQWHDNYSGGNTLPARTQYT ESMVYSKSQIEAALNVNSKILDGTLGIDFKSISKGEKKVMIAAY KQIFYTVSANLPNNPADVEDKSVTFKELQRKGVSNEAPPLEVSN VAYGRTVFVKLETSSKSNDVEAAFSAALKGTDVKINGKYSDILE NSSFTAVVLGGDAAEHNKVVTKDFDVIRNVIKDNATFSRKNPAY PISYTSVFLKNNKIAGVNNRTEYVETTSTEYTSGKINLSHQGAY VAQYEILWDEINYDDKGKEVITKRRWDNNWYSKTSPFSTVIPLG ANSRNIRIMAREC |
| 48 | SLO(ΔC51) fragment W535A w/o leader, with G overhang from cleavage | GAPKEMPLESAEKEEKKSEDKKKSEEDHTEEINDKIYSLNYNEL EVLAKNGETIENFVPKEGVKKADKFIVIERKKKNINTTPVDISI IDSVTDRTYPAALQLANKGFTENKPDAVVTKRNPQKIHIDLPGM GDKATVEVNDPTYANVSTAIDNLVNQWHDNYSGGNTLPARTQYT ESMVYSKSQIEAALNVNSKILDGTLGIDFKSISKGEKKVMIAAY KQIFYTVSANLPNNPADVEDKSVTFKELQRKGVSNEAPPLFVSN VAYGRTVFVKLETSSKSNDVEAAFSAALKGTDVKINGKYSDILE NSSFTAVVLGGDAAEHNKVVTKDEDVIRNVIKDNATFSRKNPAY PISYTSVFLKNNKIAGVNNRTEYVETTSTEYTSGKINLSHQGAY VAQYEILWDEINYDDKGKEVITKRRWDNNWYSKTSPFSTVIPLG ANS |
| 49 | SLO(ΔC61) fragment W535A w/o leader, with G overhang from cleavage | GAPKEMPLESAEKEEKKSEDKKKSEEDHTEEINDKIYSLNYNEL EVLAKNGETIENFVPKEGVKKADKFIVIERKKKNINTTPVDISI IDSVTDRTYPAALQLANKGFTENKPDAVVTKRNPQKIHIDLPGM GDKATVEVNDPTYANVSTAIDNLVNQWHDNYSGGNTLPARTQYT ESMVYSKSQIEAALNVNSKILDGTLGIDFKSISKGEKKVMIAAY |

-continued

Sequence identifier descriptions

| Seq ID | Name/description | Amino acid sequence |
|---|---|---|
| | | KQIFYTVSANLPNNPADVFDKSVTFKELQRKGVSNEAPPLFVSN<br>VAYGRTVFVKLETSSKSNDVEAAFSAALKGTDVKINGKYSDILE<br>NSSFTAVVLGGDAAEHNKVVTKDFDVIRNVIKDNATFSRKNPAY<br>PISYTSVFLKNNKIAGVNNRTEYVETTSTEYTSGKINLSHQGAY<br>VAQYEILWDEINYDDKGKEVITKRRWDNNWYSKTSPF |
| 50 | SLO(ΔC71) fragment W535A w/o leader, with G overhang from cleavage | GAPKEMPLESAEKEEKKSEDKKKSEEDHTEEINDKIYSLNYNEL<br>EVLAKNGETIENFVPKEGVKKADKFIVIERKKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTFKELQRKGVSNEAPPLFVSN<br>VAYGRTVFVKLETSSKSNDVEAAFSAALKGTDVKINGKYSDILE<br>NSSFTAVVLGGDAAEHNKVVTKDEDVIRNVIKDNATFSRKNPAY<br>PISYTSVFLKNNKIAGVNNRTEYVETTSTEYTSGKINLSHQGAY<br>VAQYEILWDEINYDDKGKEVITKRRWD |
| 51 | SLO(ΔC81) fragment W535A w/o leader, with G overhang from cleavage | GAPKEMPLESAEKEEKKSEDKKKSEEDHTEEINDKIYSLNYNEL<br>EVLAKNGETIENFVPKEGVKKADKFIVIERKKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTFKELQRKGVSNEAPPLEVSN<br>VAYGRTVFVKLETSSKSNDVEAAFSAALKGTDVKTNGKYSDILE<br>NSSFTAVVLGGDAAEHNKVVTKDEDVIRNVIKDNATFSRKNPAY<br>PISYTSVFLKNNKIAGVNNRTEYVETTSTEYTSGKINLSHQGAY<br>VAQYEILWDEINYDDKG |
| 52 | SLO(ΔC91) fragment W535A w/o leader, with G overhang from cleavage | GAPKEMPLESAEKEEKKSEDKKKSEEDHTEEINDKIYSLNYNEL<br>EVLAKNGETIENFVPKEGVKKADKFIVIERKKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTFKELQRKGVSNEAPPLEVSN<br>VAYGRTVFVKLETSSKSNDVEAAFSAALKGTDVKINGKYSDILE<br>NSSFTAVVLGGDAAEHNKVVTKDEDVIRNVIKDNATFSRKNPAY<br>PISYTSVFLKNNKIAGVNNRTEYVETTSTEYTSGKINLSHQGAY<br>VAQYEIL |
| 53 | SLO(ΔC101) fragment W535A w/o leader, with G overhang from cleavage | GAPKEMPLESAEKEEKKSEDKKKSEEDHTEEINDKIYSLNYNEL<br>EVLAKNGETIENFVPKEGVKKADKFIVIERKKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTFKELQRKGVSNEAPPLEVSN<br>VAYGRTVFVKLETSSKSNDVEAAFSAALKGTDVKINGKYSDILE<br>NSSFTAVVLGGDAAEHNKVVTKDFDVIRNVIKDNATFSRKNPAY<br>PISYTSVFLKNNKIAGVNNRTEYVETTSTEYTSGKINLSHQ |
| 54 | SLO(ΔC101) fragment W535A w/o leader, with G overhang from cleavage X = nnAA (e.g., pAMF) or native amino acid (e.g.: K98, K112, R151, K189, K272, K323, K357, K375, K407, K464; or K or R.) | GAPKEMPLESAEKEEKKSED**X**KKSEEDHTEEIND**X**IYSLNYNEL<br>EVLAKNGETIENFVPKEGVKKADKFIVIE**X**KKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVEDKSVTE**X**ELQRKGVSNEAPPLFVSN<br>VAYGRTVFVKLETSS**X**SNDVEAAFSAALKGTDV**X**INGKYSDILE<br>NSSFTAVVLGGDAAEHNKVVT**X**DFDVIRNVIKDNATFSRKNPAY<br>PISYTSVELKNNKIAGVNNRTEYVETTSTEYTSG**X**INLSHQ |
| 55 | SLO(ΔC101) fragment W535A - nnAA (e.g., pAMF) 1 - w/o leader, with G overhang from cleavage (420995) X = nnAA (e.g., pAMF) positions - K98, R151 , K272, K357 | GAPKEMPLESAEKEEKKSED**X**KKSEEDHTEEINDKIYSLNYNEL<br>EVLAKNGETIENFVPKEGVKKADKFIVIE**X**KKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVFDKSVTFKELQRKGVSNEAPPLEVSN<br>VAYGRTVFVKLETSS**X**SNDVEAAFSAALKGTDVKINGKYSDILE<br>NSSFTAVVLGGDAAEHNKVVTKDFDVIRNVIKDNATFSRKNPAY<br>PISYTSVFLKNNKIAGVNNRTEYVETTSTEYTSGKINLSHQ |

-continued

Sequence identifier descriptions

| Seq ID | Name/description | Amino acid sequence |
|---|---|---|
| 56 | SLO(ΔC101) fragment W535A - nnAA (e.g., pAMF) 2 - w/o leader, with G overhang from cleavage (420996) X = nnAA (e.g., pAMF) positions - K112, K189, K323, K375 | GAPKEMPLESAEKEEKKSEDKKKSEEDHTEEIND**X**IYSLNYNEL<br>EVLAKNGETIENFVPKEGVKKADKFIVIERKKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTE**X**ELQRKGVSNEAPPLEVSN<br>VAYGRTVFVKLETSSKSNDVEAAFSAALKGTDV**X**INGKYSDILE<br>NSSFTAVVLGGDAAEHNKVVTKDFDVIRNVIKDNATFSRKNPAY<br>PISYTSVFLKNNKIAGVNNRTEYVETTSTEYTSGKINLSHQ |
| 57 | SLO(ΔC101) fragment W535A - nnAA (e.g., pAMF) 3 - w/o leader, with G overhang from cleavage (420997) X = nnAA (e.g., pAMF) positions - R151, K272, K357, K407 | GAPKEMPLESAEKEEKKSEDKKKSEEDHTEEINDKIYSLNYNEL<br>EVLAKNGETIENFVPKEGVKKADKFIVIE**X**KKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVEDKSVTFKELQRKGVSNEAPPLFVSN<br>VAYGRTVFVKLETSS**X**SNDVEAAFSAALKGTDVKTNGKYSDILE<br>NSSFTAVVLGGDAAEHNKVVT**X**DEDVIRNVIKDNATFSRKNPAY<br>PISYTSVFLKNNKIAGVNNRTEYVETTSTEYTSGKINLSHQ |
| 58 | SLO(ΔC101) fragment W535A - nnAA (e.g., pAMF) 4 - w/o leader, with G overhang from cleavage (420998) X = nnAA (e.g., pAMF) positions - R151, K272, K375, K464 | GAPKEMPLESAEKEEKKSEDKKKSEEDHTEEINDKIYSLNYNEL<br>EVLAKNGETIENFVPKEGVKKADKFIVIE**X**KKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVFDKSVTFKELQRKGVSNEAPPLEVSN<br>VAYGRTVFVKLETSSKSNDVEAAFSAALKGTDV**X**TNGKYSDILE<br>NSSFTAVVLGGDAAEHNKVVTKDFDVIRNVIKDNATFSRKNPAY<br>PISYTSVFLKNNKIAGVNNRTEYVETTSTEYTSG**X**INLSHQ |
| 59 | SLO(ΔC101) fragment W535A - nnAA (e.g., pAMF)5 - w/o leader, with G overhang from cleavage (420999) X = nnAA (e.g., pAMF) positions - K112, K272, K357, K464 | GAPKEMPLESAEKEEKKSEDKKKSEEDHTEEIND**X**IYSLNYNEL<br>EVLAKNGETIENFVPKEGVKKADKFIVIERKKKNINTTPVDISI<br>IDSVTDRTYPAALQLANKGFTENKPDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVEDKSVTFKELQRKGVSNEAPPLFVSN<br>VAYGRTVFVKLETSS**X**SNDVEAAFSAALKGTDVKINGKYSDILE<br>NSSFTAVVLGGDAAEHNKVVTKDFDVIRNVIKDNATFSRKNPAY<br>PISYTSVFLKNNKIAGVNNRTEYVETTSTEYTSG**X**INLSHQ |
| 60 | SLO(ΔC101) fragment W535A - nnAA (e.g., pAMF) 6 - w/o leader, with G overhang from cleavage (421000) X = nnAA (e.g., pAMF) positions - K98, K189, K357 | GAPKEMPLESAEKEEKKSED**X**KKSEEDHTEEINDKIYSLNYNEL<br>EVLAKNGETIENFVPKEGVKKADKFIVIERKKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTFKELQRKGVSNEAPPLEVSN<br>VAYGRTVFVKLETSS**X**SNDVEAAFSAALKGTDVKINGKYSDILE<br>NSSFTAVVLGGDAAEHNKVVTKDEDVIRNVIKDNATFSRKNPAY<br>PISYTSVFLKNNKIAGVNNRTEYVETTSTEYTSGKINLSHQ |
| 61 | SLO(ΔC101) fragment W535A - nnAA (e.g., pAMF) 7 - w/o leader, with G overhang from cleavage (421001) X = nnAA (e.g., pAMF) positions - K112, K189, K323 | GAPKEMPLESAEKEEKKSED**X**KKSEEDHTEEIND**X**IYSLNYNEL<br>EVLAKNGETIENFVPKEGVKKADKFIVIERKKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTE**X**ELQRKGVSNEAPPLEVSN<br>VAYGRTVFVKLETSSKSNDVEAAFSAALKGTDVKINGKYSDILE<br>NSSFTAVVLGGDAAEHNKVVTKDFDVIRNVIKDNATFSRKNPAY<br>PISYTSVFLKNNKIAGVNNRTEYVETTSTEYTSGKINLSHQ |
| 62 | SLO(ΔC101) fragment W535A - nnAA (e.g., | GAPKEMPLESAEKEEKKSED**X**KKSEEDHTEEINDKIYSLNYNEL<br>EVLAKNGETIENFVPKEGVKKADKFIVIE**X**KKKNINTTPVDISI<br>IDSVTDRTYPAALQLANKGFTENKPDAVVTKRNPQKIHIDLPGM |

-continued

Sequence identifier descriptions

| Seq ID | Name/description | Amino acid sequence |
|---|---|---|
| | pAMF) 8 - w/o leader, with G overhang from cleavage (421002) X = nnAA (e.g., pAMF) positions - K98, R151, K272 | GDKATVEVNDPTYANVSTAIDNLVNQWHDNYSGGNTLPARTQYTESMVYSKSQIEAALNVNS**X**ILDGTLGIDFKSISKGEKKVMIAAYKQIFYTVSANLPNNPADVEDKSVTFKELQRKGVSNEAPPLEVSNVAYGRTVFVKLETSSKSNDVEAAFSAALKGTDVKINGKYSDILENSSFTAVVLGGDAAEHNKVVTKDEDVIRNVIKDNATFSRKNPAYPISYTSVFLKNNKIAGVNNRTEYVETTSTEYTSGKINLSHQ |
| 63 | SLO(ΔC101) fragment W535A - nnAA (e.g., pAMF) 9 - w/o leader, with G overhang from cleavage (421003) X = nnAA (e.g., pAMF) positions - K112, K272, K375 | GAPKEMPLESAEKEEKKSEDKKKSEEDHTEEIND**X**IYSLNYNELEVLAKNGETIENFVPKEGVKKADKFIVIERKKKNINTTPVDISIIDSVTDRTYPAALQLANKGFTENKPDAVVTKRNPQKIHIDLPGMGDKATVEVNDPTYANVSTAIDNLVNQWHDNYSGGNTLPARTQYTESMVYSKSQIEAALNVNS**X**ILDGTLGIDFKSISKGEKKVMIAAYKQIFYTVSANLPNNPADVEDKSVTFKELQRKGVSNEAPPLEVSNVAYGRTVFVKLETSSKSNDVEAAFSAALKGTDV**X**INGKYSDILENSSFTAVVLGGDAAEHNKVVTKDFDVIRNVIKDNATFSRKNPAYPISYTSVFLKNNKIAGVNNRTEYVETTSTEYTSGKINLSHQ |
| 64 | SLO(ΔC101) fragment W535A - nnAA (e.g., pAMF) 10 - w/o leader, with G overhang from cleavage (421004) X = nnAA (e.g., pAMF) positions - K112, K323, K407 | GAPKEMPLESAEKEEKKSEDKKKSEEDHTEEIND**X**IYSLNYNELEVLAKNGETIENFVPKEGVKKADKFIVIERKKKNINTTPVDISIIDSVTDRTYPAALQLANKGFTENKPDAVVTKRNPQKIHIDLPGMGDKATVEVNDPTYANVSTAIDNLVNQWHDNYSGGNTLPARTQYTESMVYSKSQIEAALNVNSKILDGTLGIDFKSISKGEKKVMIAAYKQIFYTVSANLPNNPADVEDKSVTE**X**ELQRKGVSNEAPPLEVSNVAYGRTVFVKLETSSKSNDVEAAFSAALKGTDVKINGKYSDILENSSFTAVVLGGDAAEHNKVVT**X**DFDVIRNVIKDNATFSRKNPAYPISYTSVFLKNNKIAGVNNRTEYVETTSTEYTSGKINLSHQ |
| 65 | SLO(ΔC101) fragment W535A - nnAA (e.g., pAMF) 10 - w/o leader, with G overhang from cleavage (426507) X = nnAA (e.g., pAMF) positions - K98, R151, K272, K357, K407 | GAPKEMPLESAEKEEKKSED**X**KKSEEDHTEEINDKIYSLNYNELEVLAKNGETIENFVPKEGVKKADKFIVIE**X**KKKNINTTPVDISIIDSVTDRTYPAALQLANKGFTENKPDAVVTKRNPQKIHIDLPGMGDKATVEVNDPTYANVSTAIDNLVNQWHDNYSGGNTLPARTQYTESMVYSKSQIEAALNVNS**X**ILDGTLGIDFKSISKGEKKVMIAAYKQIFYTVSANLPNNPADVEDKSVTFKELQRKGVSNEAPPLFVSNVAYGRTVFVKLETSS**X**SNDVEAAFSAALKGTDVKINGKYSDILENSSFTAVVLGGDAAEHNKVVT**X**DFDVIRNVIKDNATFSRKNPAYPISYTSVFLKNNKIAGVNNRTEYVETTSTEYTSGKINLSHQ |
| 66 | SLO(ΔC101) fragment W535A - nnAA (e.g., pAMF) 10 - w/o leader, with G overhang from cleavage (426508) X = nnAA (e.g., pAMF) positions - K112, K189, K323, K375, K464 | GAPKEMPLESAEKEEKKSEDKKKSEEDHTEEIND**X**IYSLNYNELEVLAKNGETIENFVPKEGVKKADKFIVIERKKKNINTTPVDISIIDSVTDRTYPAALQLANKGFTEN**X**PDAVVTKRNPQKIHIDLPGMGDKATVEVNDPTYANVSTAIDNLVNQWHDNYSGGNTLPARTQYTESMVYSKSQIEAALNVNSKILDGTLGIDFKSISKGEKKVMIAAYKQIFYTVSANLPNNPADVEDKSVTE**X**ELQRKGVSNEAPPLEVSNVAYGRTVFVKLETSSKSNDVEAAFSAALKGTDV**X**TNGKYSDILENSSFTAVVLGGDAAEHNKVVTKDFDVIRNVIKDNATFSRKNPAYPISYTSVFLKNNKIAGVNNRTEYVETTSTEYTSG**X**INLSHQ |
| 67 | SLO(ΔC101) fragment W535A - nnAA (e.g., pAMF) 10 - w/o leader, with G overhang from cleavage (426509) X = nnAA (e.g., pAMF) positions - K112, R151, K272, K357, K407 | GAPKEMPLESAEKEEKKSEDKKKSEEDHTEEIND**X**IYSLNYNELEVLAKNGETIENFVPKEGVKKADKFIVIE**X**KKKNINTTPVDISIIDSVTDRTYPAALQLANKGFTENKPDAVVTKRNPQKIHIDLPGMGDKATVEVNDPTYANVSTAIDNLVNQWHDNYSGGNTLPARTQYTESMVYSKSQIEAALNVNS**X**ILDGTLGIDFKSISKGEKKVMIAAYKQIFYTVSANLPNNPADVEDKSVTFKELQRKGVSNEAPPLEVSNVAYGRTVFVKLETSS**X**SNDVEAAFSAALKGTDVKINGKYSDILENSSFTAVVLGGDAAEHNKVVT**X**DEDVIRNVIKDNATFSRKNPAYPISYTSVFLKNNKIAGVNNRTEYVETTSTEYTSGKINLSHQ |
| 68 | SLO(ΔC101) fragment W535A - nnAA (e.g., pAMF) 10 - w/o leader, with G | GAPKEMPLESAEKEEKKSED**X**KKSEEDHTEEINDKIYSLNYNELEVLAKNGETIENFVPKEGVKKADKFIVIE**X**KKKNINTTPVDISIIDSVTDRTYPAALQLANKGFTENKPDAVVTKRNPQKIHIDLPGMGDKATVEVNDPTYANVSTAIDNLVNQWHDNYSGGNTLPARTQYTESMVYSKSQIEAALNVNS**X**ILDGTLGIDFKSISKGEKKVMIAAYKQIFYTVSANLPNNPADVEDKSVTFKELQRKGVSNEAPPLEVSNVAYGRTVFVKLETSS**X**SNDVEAAFSAALKGTDVKINGKYSDILENSSFTAVVLGGDAAEHNKVVT**X**DEDVIRNVIKDNATFSRKNPAYPISYTSVFLKNNKIAGVNNRTEYVETTSTEYTSGKINLSHQ |

-continued

Sequence identifier descriptions

| Seq ID | Name/description | Amino acid sequence |
|---|---|---|
| | overhang from cleavage (426510) X = nnAA (e.g., pAMF) positions - K98, R151, K272, K357, K407, K464 | KQIFYTVSANLPNNPADVEDKSVTFKELQRKGVSNEAPPLFVSN<br>VAYGRTVFVKLETSS**X**SNDVEAAFSAALKGTDVKINGKYSDILE<br>NSSFTAVVLGGDAAEHNKVVT**X**DFDVIRNVIKDNATFSRKNPAY<br>PISYTSVELKNNKIAGVNNRTEYVETTSTEYTSG**X**INLSHQ |
| 69 | SLO(ΔC101) fragment W535A - nnAA (e.g., pAMF) 10 - w/o leader, with G overhang from cleavage (426511) X = nnAA (e.g., pAMF) positions - K112, R151, K189, K323, K375, K464 | GAPKEMPLESAEKEEKKSEDKKKSEEDHTEEIND**X**IYSLNYNEL<br>EVLAKNGETIENFVPKEGVKKADKFIVIE**X**KKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTE**X**ELQRKGVSNEAPPLFVSN<br>VAYGRTVFVKLETSSKSNDVEAAFSAALKGTDV**X**TNGKYSDILE<br>NSSFTAVVLGGDAAEHNKVVTKDFDVIRNVIKDNATFSRKNPAY<br>PISYTSVFLKNNKIAGVNNRTEYVETTSTEYTSG**X**INLSHQ |
| 70 | SLO(ΔC101) fragment W535A - nnAA (e.g., pAMF) 10 - w/o leader, with G overhang from cleavage (426512) X = nnAA (e.g., pAMF) positions - K98, K112, K189, K323, K375, K464 | GAPKEMPLESAEKEEKKSED**X**KKSEEDHTEEIND**X**IYSLNYNEL<br>EVLAKNGETIENFVPKEGVKKADKFIVIERKKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTF**X**ELQRKGVSNEAPPLFVSN<br>VAYGRTVFVKLETSSKSNDVEAAFSAALKGTDV**X**TNGKYSDILE<br>NSSFTAVVLGGDAAEHNKVVTKDEDVIRNVIKDNATFSRKNPAY<br>PISYTSVFLKNNKIAGVNNRTEYVETTSTEYTSG**X**INLSHQ |
| 71 | SLO(ΔC101) fragment W535A - nnAA (e.g., pAMF) 10 - w/o leader, with G overhang from cleavage (426513) X = nnAA (e.g., pAMF) positions - K112, R151, K189, K272, K357, K407, K464 | GAPKEMPLESAEKEEKKSEDKKKSEEDHTEEIND**X**IYSLNYNEL<br>EVLAKNGETIENFVPKEGVKKADKFIVIE**X**KKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVEDKSVTFKELQRKGVSNEAPPLFVSN<br>VAYGRTVFVKLETSS**X**SNDVEAAFSAALKGTDVKINGKYSDILE<br>NSSFTAVVLGGDAAEHNKVVT**X**DFDVIRNVIKDNATFSRKNPAY<br>PISYTSVELKNNKIAGVNNRTEYVETTSTEYTSG**X**INLSHQ |
| 72 | SLO(ΔC101) fragment W535A - nnAA (e.g., pAMF) 10 - w/o leader, with G overhang from cleavage (426514) X = nnAA (e.g., pAMF) positions - K98, R151, K189, K323, K375, K407, K464 | GAPKEMPLESAEKEEKKSED**X**KKSEEDHTEEINDKIYSLNYNEL<br>EVLAKNGETIENFVPKEGVKKADKFIVIE**X**KKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNSKILDGTLGIDFKSISKGEKKVMIAAY<br>KQIFYTVSANLPNNPADVEDKSVTE**X**ELQRKGVSNEAPPLEVSN<br>VAYGRTVFVKLETSSKSNDVEAAFSAALKGTDV**X**INGKYSDILE<br>NSSFTAVVLGGDAAEHNKVVT**X**DFDVIRNVIKDNATFSRKNPAY<br>PISYTSVFLKNNKIAGVNNRTEYVETTSTEYTSG**X**INLSHQ |
| 73 | SLO(ΔC101) fragment W535A - nnAA (e.g., pAMF) 10 - w/o leader, with G overhang from cleavage (426515) X = nnAA (e.g., pAMF) positions - K112, K189, K272, K357, K375, K407, K464 | GAPKEMPLESAEKEEKKSEDKKKSEEDHTEEIND**X**IYSLNYNEL<br>EVLAKNGETIENFVPKEGVKKADKFIVIERKKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVEDKSVTFKELQRKGVSNEAPPLEVSN<br>VAYGRTVFVKLETSS**X**SNDVEAAFSAALKGTDV**X**INGKYSDILE<br>NSSFTAVVLGGDAAEHNKVVT**X**DEDVIRNVIKDNATFSRKNPAY<br>PISYTSVFLKNNKIAGVNNRTEYVETTSTEYTSG**X**INLSHQ |
| 74 | SLO(ΔC101) fragment W535A - nnAA (e.g., pAMF) 10 - w/o | GAPKEMPLESAEKEEKKSED**X**KKSEEDHTEEIND**X**IYSLNYNEL<br>EVLAKNGETIENFVPKEGVKKADKFIVIE**X**KKKNINTTPVDISI<br>IDSVTDRTYPAALQLANKGFTEN**X**PDAVVIKRNPQKIHIDLPGM<br>GDKATVEVNDPTYANVSTAIDNLVNQWHDNYSGGNTLPARTQYT |

-continued

Sequence identifier descriptions

| Seq ID | Name/description | Amino acid sequence |
|---|---|---|
| | leader, with G overhang from cleavage (426516) X = nnAA (e.g., pAMF) positions - K98, K112, R151, K189, K272, K323, K357, K375, | ESMVYSKSQIEAALNVNS**X**ILDGTLGIDFKSISKGEKKVMIAAY<br>KQIFYTVSANLPNNPADVEDKSVTE**X**ELQRKGVSNEAPPLEVSN<br>VAYGRTVFVKLETSS**X**SNDVEAAFSAALKGTDV**X**INGKYSDILE<br>NSSFTAVVLGGDAAEHNKVVTKDEDVIRNVIKDNATFSRKNPAY<br>PISYTSVFLKNNKIAGVNNRTEYVETTSTEYTSGKINLSHQ |
| 75 | SLO(ΔC101) fragment W535A - nnAA (e.g., pAMF) 10 - w/o leader, with G overhang from cleavage (426510) X = nnAA (e.g., pAMF) positions - K98, R151, K189, K272, K323, K357, K407, K464 | GAPKEMPLESAEKEEKKSED**X**KKSEEDHTEEINDKIYSLNYNEL<br>EVLAKNGETIENFVPKEGVKKADKFIVIE**X**KKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVEDKSVTE**X**ELQRKGVSNEAPPLEVSN<br>VAYGRTVFVKLETSS**X**SNDVEAAFSAALKGTDVKINGKYSDILE<br>NSSFTAVVLGGDAAEHNKVVT**X**DEDVIRNVIKDNATFSRKNPAY<br>PISYTSVFLKNNKIAGVNNRTEYVETTSTEYTSG**X**INLSHQ |
| 76 | SLO(ΔC101) fragment W535A - nnAA (e.g., pAMF) 10 - w/o leader, with G overhang from cleavage (426515) X = nnAA (e.g., pAMF) positions - K112, K189, K272, K323, K357, K375, K407, K464 | GAPKEMPLESAEKEEKKSEDKKKSEEDHTEEIND**X**IYSLNYNEL<br>EVLAKNGETIENFVPKEGVKKADKFIVIERKKKNINTTPVDISI<br>IDSVTDRTYPAALQLANKGFTEN**X**PDAVVTKRNPQKIHIDLPGM<br>GDKATVEVNDPTYANVSTAIDNLVNQWHDNYSGGNTLPARTQYT<br>ESMVYSKSQIEAALNVNS**X**ILDGTLGIDFKSISKGEKKVMIAAY<br>KQIFYTVSANLPNNPADVEDKSVTE**X**ELQRKGVSNEAPPLFVSN<br>VAYGRTVFVKLETSS**X**SNDVEAAFSAALKGTDV**X**INGKYSDILE<br>NSSFTAVVLGGDAAEHNKVVT**X**DEDVIRNVIKDNATFSRKNPAY<br>PISYTSVFLKNNKIAGVNNRTEYVETTSTEYTSG**X**INLSHQ |

What is claimed is:

1. An immunogenic composition comprising a. a first Group A *Streptococcus* (GAS) polypeptide antigen that is a C5a peptidase polypeptide antigen comprising the amino acid sequence set forth in SEQ ID NO: 29 or SEQ ID NO: 30 or a fragment thereof;

b. a second GAS polypeptide antigen that is SLO; and c. at least one polypeptide-polysaccharide conjugate comprising a conjugate polypeptide and a conjugate polysaccharide, wherein the conjugate polypeptide is a third GAS polypeptide antigen or a non-GAS carrier polypeptide and comprises at least one non-natural amino acid (nnAA), and wherein the conjugate polysaccharide is a GAS polysaccharide or a variant thereof that lacks an immunodominant N-acetyl Glucosamine (GlcNAc) side chain.

2. The immunogenic composition of claim 1, wherein the first and second GAS polypeptide antigens are C5a peptidase and SLO.

3. The immunogenic composition of claim 2, wherein the SLO polypeptide antigen comprises an amino acid sequence that is at least 95% identical to SEQ ID NO: 31 or SEQ ID NO: 32.

4. The immunogenic composition of claim 1, wherein the first and second GAS polypeptide antigens are C5a peptidase and SLO, and the SLO polypeptide antigen comprises an amino acid sequence that is at least 95% identical to SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53, or a fragment of any of the foregoing.

5. The immunogenic composition of claim 1, wherein the SLO polypeptide antigen comprises the amino acid sequence of SEQ ID NO: 31 or SEQ ID NO: 32, or a fragment thereof.

6. The immunogenic composition of claim 1, wherein the first and second GAS polypeptide antigens are C5a peptidase and SLO, and the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53, or a fragment of any of the foregoing.

7. The immunogenic composition of claim 1, wherein the third GAS polypeptide antigen or non-GAS polypeptide antigen is selected from *Streptococcus pyogenes* Adhesion and Division (SpyAD) polypeptide, arginine deiminase (ADI), SEQ ID NO: 25, Protein D, and SLO, or a fragment of any of the foregoing.

8. The immunogenic composition of claim 7, wherein the conjugate polypeptide is a third GAS polypeptide antigen, which is a SpyAD polypeptide and comprises an amino acid sequence that is at least 95% identical to SEQ ID NO: 33, or a fragment thereof.

9. The immunogenic composition of claim 8, wherein the SpyAD polypeptide comprises a pAMF substitution at positions K64, K287, K386, and K657 of SEQ ID NO: 33, or a fragment thereof.

10. The immunogenic composition of claim 8, wherein the SpyAD polypeptide comprises the amino acid sequence of SEQ ID NO: 33 or SEQ ID NO: 34, or a fragment thereof.

11. The immunogenic composition of claim 7, wherein the conjugate polypeptide is a third GAS polypeptide antigen, which is an ADI polypeptide and comprises an amino acid sequence that is at least 95% identical to SEQ ID NO: 35 or SEQ ID NO: 36, or a fragment thereof.

12. The immunogenic composition of claim 11, wherein the ADI polypeptide comprises the amino acid sequence of SEQ ID NO: 27, SEQ ID NO: 37 or SEQ ID NO: 38, or a fragment thereof.

13. The immunogenic composition of claim 7, wherein the conjugate polypeptide is a third GAS polypeptide antigen, which is a SLO polypeptide and comprises an amino acid sequence that is at least 95% identical to SEQ ID NO: 31, SEQ ID NO: 32, or SEQ ID NO: 53, or a fragment of any of the foregoing.

14. The immunogenic composition of claim 13, wherein the SLO polypeptide comprises 3 or 4 pAMF substitutions at positions selected from K98, Kll2, RISI, KI 89, K272, K323, K357, K375, K407, or K464.

15. The immunogenic composition of claim 14, wherein the SLO polypeptide comprises the amino acid sequence of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, or SEQ ID NO: 64, or a fragment of any of the foregoing.

16. The immunogenic composition of claim 13, wherein the SLO polypeptide comprises the amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, or SEQ ID NO: 76, or a fragment of any of the foregoing.

17. The immunogenic composition of claim 1, wherein the nnAA comprises a click chemistry reactive group.

18. The immunogenic composition of claim 17, wherein the conjugate polypeptide is a ferritin polypeptide and comprises an amino acid sequence that is at least 95% identical to SEQ ID NO: 21, or a fragment thereof.

19. The immunogenic composition of claim 18, wherein the ferritin polypeptide comprises a pAMF substitution at position 15 of SEQ ID NO: 21, or a fragment thereof.

20. The immunogenic composition of claim 1, wherein the nnAA is selected from 2-amino-3-(4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl) propanoic acid, 2-amino-3-(6-(azidomethyl)pyridin-3-yl)propanoic acid, and 2-amino-5-azidopentanoic acid.

21. The immunogenic composition of claim 20, wherein the nnAA is PAMF.

22. The immunogenic composition of claim 1, wherein the conjugate polysaccharide is a GAS polysaccharide that lacks the immunodominant GlcNAc side chain.

23. The immunogenic composition of claim 1, wherein the conjugate polysaccharide has an average molecular weight of about 10 kDa to about 45 kDa.

24. The immunogenic composition of claim 1, comprising a C5a peptidase polypeptide antigen of SEQ ID NO: 30 or a fragment thereof; a SLO polypeptide antigen of SEQ ID NO: 53 or a fragment thereof; and a polypeptide-polysaccharide conjugate comprising a SpyAD conjugate polypeptide of SEQ ID NO: 34 or a fragment thereof and a GAS conjugate polysaccharide.

25. The immunogenic composition of claim 1, comprising a C5a peptidase polypeptide antigen of SEQ ID NO: 30 or a fragment thereof; a SLO polypeptide antigen of SEQ ID NO: 52 or a fragment thereof; and a polypeptide-polysaccharide conjugate comprising a SpyAD conjugate polypeptide of SEQ ID NO: 34 or a fragment thereof and a GAS conjugate polysaccharide.

26. The immunogenic composition of claim 1, comprising a C5a peptidase polypeptide antigen of SEQ ID NO: 30 or a fragment thereof; a SLO polypeptide antigen of SEQ ID NO: 32 or a fragment thereof; and a polypeptide-polysaccharide conjugate comprising a SpyAD conjugate polypeptide of SEQ ID NO: 34 or a fragment thereof and a GAS conjugate polysaccharide.

27. The immunogenic composition of claim 1, comprising a C5a peptidase polypeptide antigen of SEQ ID NO: 29 or a fragment thereof; a SLO polypeptide antigen of SEQ ID NO: 53 or a fragment thereof; and a polypeptide-polysaccharide conjugate comprising a SpyAD conjugate polypeptide of SEQ ID NO: 34 or a fragment thereof and a GAS conjugate polysaccharide.

28. The immunogenic composition of claim 1, wherein the polypeptide-polysaccharide conjugate has an average molecular mass of about 10 kDa to about 5000 kDa.

29. A method of inducing a protective immune response against a *Shigella* bacterium in a subject comprising administering the immunogenic composition of claim 1.

30. The immunogenic composition of claim 1, wherein one or more of the first or second GAS polypeptide antigens is a fragment of the first or second polypeptide antigen.

31. The immunogenic composition of claim 1, wherein the third GAS polypeptide antigen is a fragment of the third GAS polypeptide antigen.

32. An immunogenic composition comprising a. a Group A *Streptococcus* (GAS) C5a peptidase polypeptide antigen;

b. a GAS streptolysin O (SLO) polypeptide antigen, wherein the SLO polypeptide antigen comprises the amino acid sequence of SEQ ID NO: 31, SEQ ID NO: 32, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53 or a fragment of any of the foregoing; and c. a polypeptide-polysaccharide conjugate comprising a *Streptococcus pyogenes* Adhesion and Division (SpyAD) conjugate polypeptide and a GAS conjugate polysaccharide or a variant thereof that lacks an immunodominant N-acetyl Glucosamine (GlcNAc) side chain.

33. The immunogenic composition of claim 32, wherein the SpyAD protein comprises an amino acid sequence that is at least 95% identical to SEQ ID NO: 33, or a fragment thereof, and comprises a pAMF substitution at positions K64, K287, K386, and K657.

34. An immunogenic composition comprising a. a Group A *Streptococcus* (GAS) C5a peptidase polypeptide antigen;

b. a GAS streptolysin O (SLO) polypeptide antigen; and c. a polypeptide-polysaccharide conjugate comprising an arginine deiminase (ADI) conjugate polypeptide and a GAS conjugate polysaccharide or a variant thereof that lacks an immunodominant N-acetyl Glucosamine (GlcNAc) side chain.

35. The immunogenic composition of claim 34, wherein the ADI polypeptide comprises an amino acid sequence that is at least 95% identical to SEQ ID NO: 35 or SEQ ID NO: 36, or a fragment thereof, and comprises a pAMF substitution at positions K15, K193, and K316.

36. A method of inducing a protective immune response against a Group A *Streptococcus* (GAS) bacterium in a subject comprising administering the immunogenic composition of claim 1 to the subject.

37. The method of claim 36, wherein the immunogenic composition induces an antibody response in the subject against the Group A *Streptococcus* (GAS) bacterium and does not induce an antibody response in the subject against human tissue.

38. The method of claim 36, wherein the immunogenic composition induces a protective immune response against a *Shigella* bacterium in the subject, wherein the *Shigella* bacterium comprises a polysaccharide with a polyrhamnose backbone.

* * * * *